(12) United States Patent
Nolan et al.

(10) Patent No.: US 9,902,986 B2
(45) Date of Patent: Feb. 27, 2018

(54) ENTEROBACTIN CONJUGATES AND USES THEREOF

(71) Applicant: Massachusetts Institute of Technology, Cambridge, MA (US)

(72) Inventors: Elizabeth Marie Nolan, Cambridge, MA (US); Tengfei Zheng, Cambridge, MA (US); Phoom Chairatana, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 147 days.

(21) Appl. No.: 14/516,440

(22) Filed: Oct. 16, 2014

(65) Prior Publication Data

US 2015/0105337 A1 Apr. 16, 2015

Related U.S. Application Data

(60) Provisional application No. 61/953,642, filed on Mar. 14, 2014, provisional application No. 61/891,741, filed on Oct. 16, 2013.

(51) Int. Cl.
| | | |
|---|---|---|
| *C07H 7/04* | (2006.01) | |
| *A61K 31/7042* | (2006.01) | |
| *A61K 31/7048* | (2006.01) | |
| *A61K 31/7052* | (2006.01) | |
| *C12Q 1/06* | (2006.01) | |
| *A61K 31/496* | (2006.01) | |
| *A61K 47/54* | (2017.01) | |

(52) U.S. Cl.
CPC ............ *C12Q 1/06* (2013.01); *A61K 31/496* (2013.01); *A61K 47/545* (2017.08); *A61K 47/549* (2017.08); *C07H 7/04* (2013.01)

(58) Field of Classification Search
None
See application file for complete search history.

(56) References Cited

U.S. PATENT DOCUMENTS

2013/0202616 A1* 8/2013 Spellberg ............ C07K 16/1203
424/158.1

OTHER PUBLICATIONS

Barry et al., Current Opinion in Chemical Biology, vol. 13, No. 2, pp. 205-215, 2009.*
Budzikiewicz, Current Topics in Medicinal Chemistry, 2001, (1), pp. 73-82.*
International Preliminary Report on Patentability, dated Apr. 28, 2016, in connection with PCT/US2014/060890.
Ballouche et al., Iron metabolism: a promising target for antibacterial strategies. Recent Pat Antiinfect Drug Discov. Nov. 2009;4(3):190-205.
Barry et al., Recent advances in siderophore biosynthesis. Curr Opin Chem Biol. Apr. 2009;13(2):205-15. doi: 10.1016/j.cbpa.2009.03.008.
Bernhardt, Coordination chemistry and biology of chelators for the treatment of iron overload disorders. Dalton Trans. Aug. 14, 2007;(30):3214-20. Epub Jul. 5, 2007.
Braun et al., Sideromycins: tools and antibiotics. Biometals. Feb. 2009;22(1):3-13. doi: 10.1007/s10534-008-9199-7. Epub Jan. 7, 2009.
Braun, Active transport of siderophore-mimicking antibacterials across the outer membrane. Drug Resist Updat. Dec. 1999;2(6):363-369.
Budzikiewicz, Siderophore-antibiotic conjugates used as trojan horses against Pseudomonas aeruginosa. Curr Top Med Chem. May 2001;1(1):73-82.
Bugdahn et al., Direct identification of a siderophore import protein using synthetic petrobactin ligands. Angew Chem Int Ed Engl. Dec. 27, 2010;49(52):10210-3. doi: 10.1002/anie.201005527.

(Continued)

*Primary Examiner* — Traviss C McIntosh, III
(74) *Attorney, Agent, or Firm* — Wolf, Greenfield & Sacks, P.C.

(57) ABSTRACT

The present invention provides novel enterobactin-cargo conjugates, such as compounds of Formula (I), and salts thereof, where X is the cargo and may be an antibiotic, a fluorophore, or biotin. The present invention also provides complexes, compositions, kits, and methods that involve the compounds of Formula (I) and are useful in delivering a cargo to a bacterium, treating a bacterial infection, cystic fibrosis, and/or inflammatory bowel disease in a subject, preventing a bacterial infection, cystic fibrosis, and/or inflammatory bowel disease in a subject, inhibiting the growth of or killing a bacterium, or determining the concentration of a bacterium in a biological sample. In certain embodiments, the bacterium is a Gram-negative bacterium.

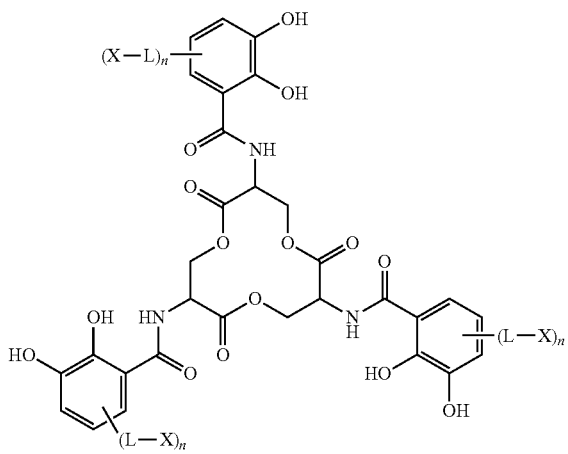

45 Claims, 80 Drawing Sheets

(56) References Cited

OTHER PUBLICATIONS

Chung et al., Fluorescence-based siderophore biosensor for the determination of bioavailable iron in oceanic waters. Anal Chem. Jul. 15, 2006;78(14):5040-5.

Doorneweerd et al., Selective capture and identification of pathogenic bacteria using an immobilized siderophore. Langmuir. Oct. 5, 2010;26(19):15424-9. doi: 10.1021/la101962w.

Espósito et al., A review of fluorescence methods for assessing labile iron in cells and biological fluids. Anal Biochem. May 1, 2002;304(1):1-18.

Hider et al., Chemistry and biology of siderophores. Nat Prod Rep. May 2010;27(5):637-57. doi: 10.1039/b906679a.

Ji et al., Exploiting bacterial iron acquisition: siderophore conjugates. Future Med Chem. Mar. 2012;4(3):297-313. doi:10.4155/fmc.11.191.

Kim et al., Label-free detection of a bacterial pathogen using an immobilized siderophore, deferoxamine. Lab Chip. Mar. 7, 2012;12(5):971-6. doi: 10.1039/c2lc20904g. Epub Jan. 25, 2012.

Manning et al., Iron chelators in medicinal applications—chemical equilibrium considerations in pharmaceutical activity. Curr Med Chem. 2009;16(19):2416-29.

Miethke et al., Siderophore-based iron acquisition and pathogen control. Microbiol Mol Biol Rev. Sep. 2007;71(3):413-51.

Miller et al., Utilization of microbial iron assimilation processes for the development of new antibiotics and inspiration for the design of new anticancer agents. Biometals. Feb. 2009;22(1):61-75. doi:10.1007/s10534-008-9185-0. Epub Jan. 7, 2009.

Miller, Syntheses and therapeutic potential of hydroxamic acid based siderophores and analogs. Chem. Rev. 1989;89(7):1563-1579.

Möllmann et al., Siderophores as drug delivery agents: application of the "Trojan Horse" strategy. Biometals. Aug. 2009;22(4):615-24. doi: 10.1007/s10534-009-9219-2. Epub Feb. 12, 2009.

Noël et al., Synthesis of fluorescent probes based on the pyochelin siderophore scaffold. Org Lett. Mar. 4, 2011;13(5):844-7. doi:10.1021/ol1028173. Epub Feb. 4, 2011.

Rajkumar et al., Potential of siderophore-producing bacteria for improving heavy metal phytoextraction. Trends Biotechnol. Mar. 2010;28(3):142-9. doi: 10.1016/j.tibtech.2009.12.002. Epub Jan. 13, 2010.

Roosenberg et al., Studies and syntheses of siderophores, microbial iron chelators, and analogs as potential drug delivery agents. Curr Med Chem. Feb. 2000;7(2):159-97.

Zheng et al., Siderophore-based detection of Fe(III) and microbial pathogens. Metallomics. Aug. 2012;4(9):866-80. doi: 10.1039/c2mt20082a.

Zheng et al., Siderophore-mediated cargo delivery to the cytoplasm of *Escherichia coli* and Pseudomonas aeruginosa: syntheses of monofunctionalized enterobactin scaffolds and evaluation of enterobactin-cargo conjugate uptake. J Am Chem Soc. Nov. 7, 2012;134(44):18388-400. doi: 10.1021/ja3077268. Epub Oct. 25, 2012.

Zheng et al., Enterobactin-mediated delivery of β-lactam antibiotics enhances antibacterial activity against pathogenic *Escherichia coli* . J Am Chem Soc. Jul. 9, 2014;136(27):9677-91. doi: 10.1021/ja503911p. Epub Jun. 27, 2014.

Bieler et al., Bactericidal activity of both secreted and nonsecreted microcin E492 requires the mannose permease. J Bacteriol. Oct. 2006;188(20):7049-61.

Chairatana et al., Targeting virulence: salmochelin modification tunes the antibacterial activity spectrum of β-lactams for pathogen-selective killing of *Escherichia coli*. Chem. Sci. May 22, 2015;6:4458-71.

Nolan et al., Biosynthetic tailoring of microcin E492m: post-translational modification affords an antibacterial siderophore-peptide conjugate. J Am Chem Soc. Nov. 21, 2007;129(46):14336-47.

Thomas et al., Siderophore peptide, a new type of post-translationally modified antibacterial peptide with potent activity. J Biol Chem. Jul. 2, 2004;279(27):28233-42.

PCT/US2014/060890, dated Feb. 4, 2015, Invitation to Pay Additional Fees.

PCT/US2014/060890, dated Jun. 1, 2015, International Search Report and Written Opinion.

\* cited by examiner

MGE-Amp (R = H)
MGE-Amx (R = OH)

DGE-Amp (R = H)
DGE-Amx (R = OH)

ENTEROBACTIN CONJUGATES AND USES THEREOF

RELATED APPLICATIONS

The present application claims priority under 35 U.S.C. §119(e) to U.S. provisional patent applications, U.S. Ser. No. 61/891,741, filed Oct. 16, 2013, and U.S. Ser. No. 61/953,642, filed Mar. 14, 2014, each of which is incorporated herein by reference.

BACKGROUND OF THE INVENTION

Siderophores are low-molecular-weight high-affinity Fe(III) chelators that are biosynthesized and exported by bacteria, fungi, and plants during periods of nutrient limitation for acquiring this essential metal ion from the extracellular milieu.[1,2] Both naturally-occurring siderophores and synthetic siderophore mimics are useful for bioremediation,[3] iron chelation therapies,[4,5] antibiotic drug-delivery strategies,[6-14] Fe(III) detection,[15-18] protein identification,[19] and pathogen capture.[20,21] These types of applications benefit from or require siderophores amenable to facile and site-specific synthetic modification.

SUMMARY OF THE INVENTION

There remains a need for such siderophore derivatives. For example, antibiotic resistance is a global problem and new strategies to combat resistant bacteria are needed. Moreover, the outer membrane of Gram-negative pathogens, such as *Escherichia coli*, *Klebsiella*, and *Salmonella*, is a barrier and prevents the influx of many antibiotics in clinical use. Thus, new antibiotics to treat resistant microbes, including Gram-negatives, are needed.

The present invention provides novel enterobactin-cargo conjugates, such as compounds of Formula (I), and salts, hydrates, solvates, polymorphs, co-crystals, tautomers, stereoisomers, and isotopically labeled derivatives thereof:

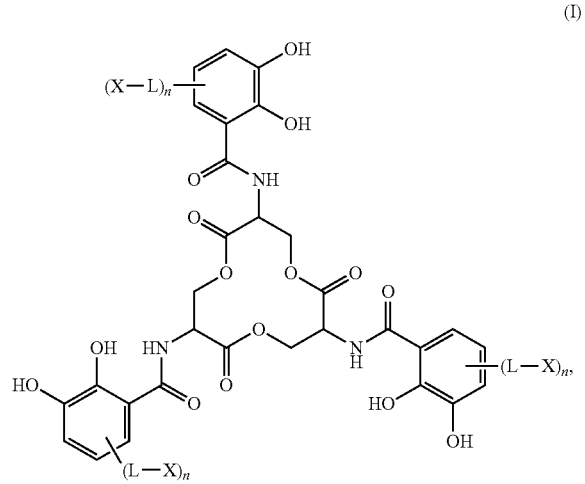

(I)

wherein X (hydrogen or a cargo, e.g., an antibiotic, a fluorophore, or biotin), L, and n are as described herein.

In another aspect, the present invention provides complexes including a compound of Formula (I), and iron (e.g., Fe(III)) or gallium (e.g., Ga(III)).

The compounds of Formula (I) and complexes of the invention are amenable to facile and site-specific synthetic modification and are able to deliver various cargos (e.g., antibiotics, fluorophores, and biotin) into a bacterium (e.g., a Gram-negative bacterium, such as *Escherichia coli* and *Pseudomonas aeruginosa*). Without wishing to be bound by any particular theory, the cargos may be transported into the intracellular space (e.g., the cytoplasm or periplasm) of a bacterium by the enterobactin uptake machinery. The present invention also provides compositions, kits, and methods involving the compounds of Formula (I) and/or complexes of the invention in treating and/or preventing in a subject in need thereof an infection caused by a bacterium, cystic fibrosis, and/or inflammatory bowel disease (IBD), in inhibiting the growth and/or reproduction of a bacterium, and/or in killing a bacterium, where the cargo delivered into the bacterium is an antibiotic. Also provided in the present invention are compositions, kits, and methods that involve the compounds of Formula (I) and/or complexes of the invention and are useful in determining the concentration of or detecting the presence of a bacterium, where the cargo delivered into the bacterium is a fluorophore or biotin.

Enterobactin (Ent, 1, FIG. 1A) is a canonical siderophore biosynthesized by Gram-negative species of Enterobacteriaceae that include *Escherichia coli*, *Salmonella*, and *Klebsiella*.[22] Decades of exploration pertaining to enterobactin biosynthesis and coordination chemistry, in addition to investigations of the proteins involved in its cellular transport and processing, provide a detailed molecular and physiological understanding of how this chelate contributes to bacterial iron homeostasis and colonization.[22] The enterobactin synthetase is comprised of four proteins, EntBDEF, and is responsible for the production of enterobactin from L-serine and 2,3-dihydroxybenzoic acid (DHB).[23] Following biosynthesis, Ent is exported into the extracellular space where it scavenges Fe(III). Enterobactin coordinates Fe(III) by its three catecholate groups with $K_a \sim 10^{49}$ M$^{-1}$.[24] In *E. coli*, the outer membrane transporter FepA (and to a lesser extent Cir and Fiu) recognizes and binds ferric enterobactin with sub-nanomolar affinity,[25,26] and provides periplasmic entry where the siderophore forms a complex with the periplasmic binding protein FepB.[27] Subsequently, [Fe(Ent)]$^{3-}$ is transported into the cytosol, which requires the action of ExbBD, TonB, and FepCDG, the latter of which constitute the inner-membrane ATP-binding cassette (ABC) transporter system (FIG. 1B).[28-32] Fes, the cytosolic enterobactin esterase, catalyzes the hydrolysis of the [Fe(Ent)]$^{3-}$ macrolactone,[33] and the ferric reductase YgjH may subsequently assist in Fe(III) release such that the metal ion can be used metabolically.[34] Several pathogenic Gram-negative species harbor gene clusters (e.g., iroA, MccE492) responsible for post-assembly line modifications of the enterobactin scaffold to provide the salmochelins.[33,35-38] Salmochelins are a family of glucosylated enterobactin derivatives where the sugar moieties are attached to the 5-position of one or more catecholate rings (e.g., MGE 2 and DGE 3, FIG. 1A).[39]

In another aspect, the present invention provides compounds of Formula (A1) or (A2), and salts thereof:

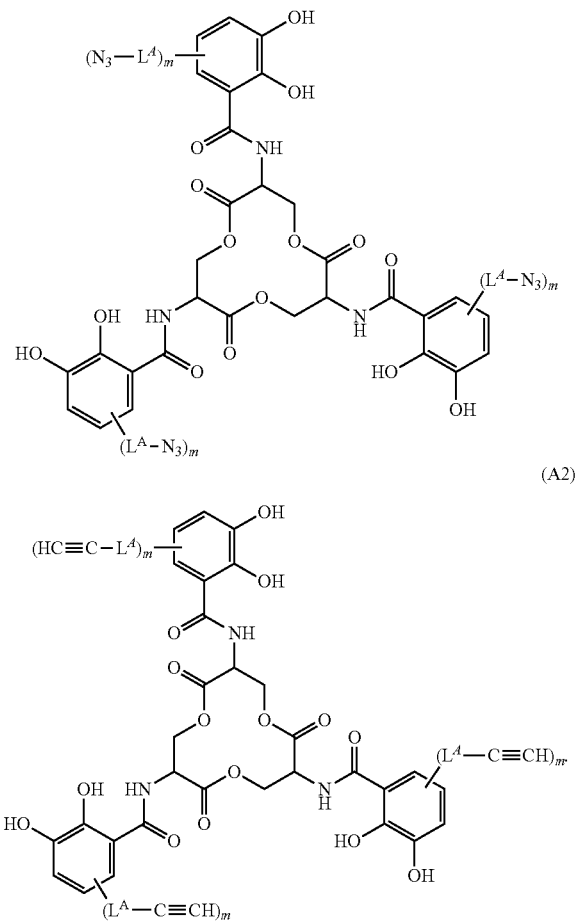

Compounds of Formula (A1) or (A2) are useful in preparing compounds of Formula (I) and complexes of the invention.

In another aspect, the present invention provides methods of preparing compounds of Formula (I). In certain embodiments, the methods of preparing compounds of Formula (I) includes contacting a compound of Formula (A1), or a salt thereof, with a compound of Formula (B1), or a salt thereof, or contacting a compound of Formula (A2), or a salt thereof, with a compound of Formula (B2), or a salt thereof:

$$X\text{-}L^B\text{-}C\equiv CH \quad (B1)$$

$$X\text{-}L^BN_3 \quad (B2).$$

In another aspect, the present invention provides compositions (e.g., pharmaceutical compositions or diagnostic compositions) including a compound of Formula (I) or a complex of the invention, and optionally an excipient. In certain embodiments, the inventive composition is useful in delivering a cargo described herein to a bacterium.

An inventive composition may be a pharmaceutical composition. In certain embodiments, a pharmaceutical composition of the invention includes a therapeutically or prophylactically effective amount of a compound of Formula (I) or a complex of the invention, or a pharmaceutically acceptable salt thereof, wherein at least one instance of X is an antibiotic. The pharmaceutical composition may be useful for treating and/or preventing a bacterial infection, cystic fibrosis, and/or IBD in a subject in need thereof, inhibiting the growth of a bacterium, and/or killing a bacterium.

An inventive composition may be a diagnostic composition. In certain embodiments, a diagnostic composition of the invention includes an effective amount of a compound of Formula (I), or a salt thereof, or a complex of the invention, wherein at least one instance of X is a fluorophore or biotin. The diagnostic composition may be useful for determining the concentration, presence, and/or absence of a bacterium in a biological sample.

Another aspect of the present invention relates to methods of treating a bacterial infection, cystic fibrosis, and/or IBD in a subject in need thereof, the method including administering to the subject a therapeutically effective amount of a compound of Formula (I), or a pharmaceutically acceptable salt thereof, a complex, or a pharmaceutical composition of the invention, wherein at least one instance of X is an antibiotic.

Another aspect of the present invention relates to methods of preventing a bacterial infection, cystic fibrosis, and/or IBD in a subject in need thereof, the method including administering to the subject a prophylactically effective amount of a compound of Formula (I), or a pharmaceutically acceptable salt thereof, a complex, or a pharmaceutical composition of the invention, wherein at least one instance of X is an antibiotic.

In yet another aspect, the present invention provides methods of inhibiting the growth of a bacterium or killing a bacterium, the method including contacting the bacterium with a therapeutically effective amount of a compound of Formula (I), or a pharmaceutically acceptable salt thereof, a complex, or a pharmaceutical composition of the invention, wherein at least one instance of X is an antibiotic.

In certain embodiments, the subject is a human. In certain embodiments, the subject is a non-human mammal. In certain embodiments, the bacterium is a Gram-negative bacterium. In certain embodiments, the bacterial infection is an infection caused by a Gram-negative bacterium.

Another aspect of the invention relates to methods of screening a library of compounds or complexes to identify a compound or complex that is useful in the methods of the invention.

Another aspect of the present invention relates to kits comprising a container with a compound, complex, or composition of the invention. The kits of the invention may include a single dose or multiple doses of the compound, complex, or composition. The provided kits may be useful in delivering a cargo described herein to a bacterium, treating a bacterial infection, cystic fibrosis, and/or IBD in a subject in need thereof, preventing a bacterial infection, cystic fibrosis, and/or IBD in a subject in need thereof, inhibiting the growth of a bacterium, killing a bacterium, or determining the concentration, presence, or absence of a bacterium. In certain embodiments, a kit further includes instructions for using the kit.

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, the Figures, the Examples, and the Claims.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987.

It is to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers," and those that are non-superimposable mirror images of each other are termed "enantiomers". When a compound has an asymmetric center, for example, a carbon atom of the compound is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates plane polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Where an isomer/enantiomer is preferred, it may, in some embodiments, be provided substantially free of the corresponding enantiomer, and may also be referred to as "optically enriched" or "enantiomerically enriched." "Optically enriched" and "enantiomerically enriched" means that a provided compound is made up of a significantly greater proportion of one enantiomer. In certain embodiments, a compound of the present invention is made up of at least about 70% by weight of a preferred enantiomer. In certain embodiments, a compound of the present invention is made up of at least about 80% by weight of a preferred enantiomer. In certain embodiments, a compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

Unless otherwise stated, structures depicted herein are also meant to include compounds that differ only in the presence of one or more isotopically enriched atoms. For example, compounds having the depicted structures that differ only in the replacement of hydrogen by deuterium or tritium, or the replacement of a carbon by $^{13}C$ or $^{14}C$ are within the scope of this invention. Such compounds are useful, for example, as analytical tools, as probes in biological assays, or as therapeutic agents in accordance with the present invention.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The terms "purified," "substantially purified," and "isolated" refer to a compound useful in the present invention being free of other, dissimilar compounds with which the compound is normally associated in its natural state, so that the compound comprises at least 0.5%, 1%, 5%, 10%, 20%, 50%, 75%, 80%, 85%, 90%, 95%, 96%, 97%, 98%, 99%, 99.5%, 99.9% of the mass, by weight, of a given sample or composition. In one embodiment, these terms refer to the compound comprising at least 95%, 98%, 99%, or 99.9% of the mass, by weight, of a given sample or composition.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula (—$OR^i$), wherein $R^i$ is an optionally substituted acyl group, as defined herein, and the oxygen moiety is directly attached to the parent molecule.

The term "aliphatic" includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl" refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl" denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl" refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(=O)$R^{aa}$, —$CO_2H$, —CHO, —C($OR^{cc}$)$_2$, —$CO_2R^{aa}$, —OC(=O)$R^{aa}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —C(=$NR^{bb}$)$R^{aa}$, —C(=$NR^{bb}$)$OR^{aa}$, —OC(=$NR^{bb}$)$R^{aa}$, —OC(=$NR^{bb}$)OR—, —C(=$NR^{bb}$)N($R^{bb}$)$_2$, —OC(=$NR^{bb}$)N($R^{bb}$)$_2$, —$NR^{bb}$C(=$NR^{bb}$)N($R^{bb}$)$_2$, —C(=O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(=O)$R^{aa}$, —OS(=O)$R^{aa}$, —Si($R^{aa}$)$_3$, —OSi($R^{aa}$)$_3$ —C(=S)N($R^{bb}$)$_2$, —C(=O)$SR^{aa}$, —C(=S)$SR^{aa}$, —SC(=S) $SR^{aa}$, —SC(=O)$SR^{aa}$, —OC(=O)$SR^{aa}$, —SC(=O)$OR^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

The term "amino" refers to a group of the formula (—NH$_2$). A "substituted amino" refers either to a mono-substituted amine (—NHR$^h$) of a disubstituted amine (—NR$^h{}_2$), wherein the R$^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the R$^h$ substituents of the di-substituted amino group (—NR$^h{}_2$) form a 5- to 6-membered heterocyclic ring.

The term "alkoxy" refers to a "substituted hydroxyl" of the formula (—OR$^i$), wherein R$^i$ is an optionally substituted alkyl group as defined herein, and the oxygen moiety is directly attached to the parent molecule.

The term "alkylthioxy" refers to a "substituted thiol" of the formula (—SR$^r$), wherein R$^r$ is an optionally substituted alkyl group as defined herein, and the sulfur moiety is directly attached to the parent molecule.

The term "alkylamino" refers to a "substituted amino" of the formula ($-NR^h_2$), wherein $R^h$ is, independently, a hydrogen or an optionally substituted alkyl group as defined herein, and the nitrogen moiety is directly attached to the parent molecule.

The term "aryl" refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylalkyl" refers to an aryl substituted alkyl group, wherein the terms "aryl" and "alkyl" are defined herein, and wherein the aryl group is attached to the alkyl group, which in turn is attached to the parent molecule. Exemplary arylalkyl groups are benzyl and phenethyl.

The term "aryloxy" refers to a "substituted hydroxyl" of the formula ($-OR^i$), wherein $R^i$ is an optionally substituted aryl group as defined herein, and the oxygen moiety is directly attached to the parent molecule.

The term "arylamino," refers to a "substituted amino" of the formula ($-NR^h_2$), wherein $R^h$ is, independently, a hydrogen or an optionally substituted aryl group as defined herein, and the nitrogen moiety is directly attached to the parent molecule.

The term "arylthioxy" refers to a "substituted thiol" of the formula ($-SR^r$), wherein $R^r$ is an optionally substituted aryl group as defined herein, and the sulfur moiety is directly attached to the parent molecule.

The terms "halo" and "halogen" refer to an atom selected from fluorine (fluoro, $-F$), chlorine (chloro, $-Cl$), bromine (bromo, $-Br$), and iodine (iodo, $-I$).

The term "heteroaliphatic" refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, the terms "heteroalkyl", "heteroalkenyl", "heteroalkynyl", and the like encompass both substituted and unsubstituted groups. In certain embodiments, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" refers to an alkyl moiety, as defined herein, which contain one or more oxygen, sulfur, nitrogen, phosphorus, or silicon atoms, e.g., in place of carbon atoms.

The term "heteroalkenyl" refers to an alkenyl moiety, as defined herein, which contain one or more oxygen, sulfur, nitrogen, phosphorus, or silicon atoms, e.g., in place of carbon atoms.

The term "heteroalkynyl" refers to an alkynyl moiety, as defined herein, which contain one or more oxygen, sulfur, nitrogen, phosphorus, or silicon atoms, e.g., in place of carbon atoms.

The term "heteroalkylamino" refers to a "substituted amino" of the formula ($-NR^h_2$), wherein $R^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula ($-OR^i$), wherein $R^i$ is an optionally substituted heteroalkyl group, as defined herein, and the oxygen moiety is directly attached to the parent molecule.

The term "heteroalkylthioxy" refers to a "substituted thiol" of the formula ($-SR^r$), wherein $R^r$ is an optionally substituted heteroalkyl group, as defined herein, and the sulfur moiety is directly attached to the parent molecule.

The term "heterocyclic," "heterocycles," or "heterocyclyl" refers to a cyclic heteroaliphatic group. A heterocyclic group refers to a non-aromatic, partially unsaturated or fully saturated, 3- to 12-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocyclyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl" refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene" refers to a divalent moiety formed by removing two hydrogen atoms from a heteroaryl compound, which is not a monovalent moiety, or by removing one hydrogen atom from a heteroaryl monovalent moiety.

The term "heteroarylamino" refers to a "substituted amino" of the ($-NR^h{}_2$), wherein $R^h$ is, independently, hydrogen or an optionally substituted heteroaryl group, as defined herein, and the nitrogen moiety is directly attached to the parent molecule.

The term "heteroaryloxy" refers to a "substituted hydroxyl" of the formula ($-OR^i$), wherein $R^i$ is an optionally substituted heteroaryl group, as defined herein, and the oxygen moiety is directly attached to the parent molecule.

The term "heteroarylthioxy" refers to a "substituted thiol" of the formula ($-SR^r$), wherein $R^r$ is an optionally substituted heteroaryl group, as defined herein, and the sulfur moiety is directly attached to the parent molecule.

The term "hydroxy" or "hydroxyl" refers to a group of the formula ($-OH$). A "substituted hydroxyl" refers to a group of the formula ($-OR^i$), wherein $R^i$ can be any substituent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino" refers to a group of the formula ($=NR^r$), wherein $R^r$ corresponds to hydrogen or any substituent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted). In certain embodiments, imino refers to $=NH$ wherein $R^r$ is hydrogen.

The term "nitro" refers to a group of the formula ($-NO_2$).

The term "oxo" refers to a group of the formula ($=O$).

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$, (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group ($-OH$), with the exception of the first and last carbons, is asymmetric, making the carbon atom a stereocenter with two possible configurations (R or S). Because of this asymmetry, a number of isomers may exist for any given monosaccharide formula. The aldohexose d-glucose, for example, has the formula $C_6H_{12}O_6$, of which all but two of its six carbons atoms are stereogenic, making d-glucose one of the 16 (i.e., $2^4$) possible stereoisomers. The assignment of d or l is made according to the orientation of the asymmetric carbon furthest from the carbonyl group: in a standard Fischer projection if the hydroxyl group is on the right the molecule is a d sugar, otherwise it is an l sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an α anomer, the —OH substituent on the anomeric carbon rests on the opposite side (trans) of the ring from the —CH₂OH side branch. The alternative form, in which the —CH₂OH substituent and the anomeric hydroxyl are on the same side (cis) of the plane of the ring, is called a β anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, trehalose, and cellobiose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

A "monovalent radical" or "monovalent moiety" is a moiety formed by removing one hydrogen atom from a molecule. For example, a monovalent carbohydrate radical is a moiety formed by removing one hydrogen atom from a carbohydrate. A "divalent radical" or "divalent moiety" is a moiety formed by removing two hydrogen atoms from a molecule. For example, a divalent carbohydrate radical is a moiety formed by removing two hydrogen atoms from a carbohydrate. A divalent peptide radical is a moiety formed by removing two hydrogen atoms from a peptide. The atom from which a hydrogen atom is removed is a point of attachment.

A "hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —C$^A$H(C$^B$H₂C$^C$H₃)— includes only one carbon unit C$^A$. The term "C$_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —CH(C₂H₅)— is a C₁ hydrocarbon chain, and

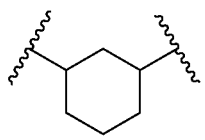 [SMILES: *C1CCCC(*)C1]

is a C₃ hydrocarbon chain. When a range of values is used, e.g., a C$_{1-6}$ hydrocarbon chain, the meaning of the range is as described herein. A hydrocarbon chain may be saturated (e.g., —(CH₂)₄—). A hydrocarbon chain may also be unsaturated and include one or more C═C and/or C≡C bonds anywhere in the hydrocarbon chain. For instance, —CH═CH—(CH₂)₂—, —CH₂—C≡C—CH₂—, and —C≡C—CH═CH— are all examples of a unsubstituted and unsaturated hydrocarbon chain. In certain embodiments, the hydrocarbon chain is unsubstituted (e.g., —(CH₂)₄—). In certain embodiments, the hydrocarbon chain is substituted (e.g., —CH(C₂H₅)— and —CF₂—). Any two substituents on the hydrocarbon chain may be joined to form an optionally substituted carbocyclyl, optionally substituted heterocyclyl, optionally substituted aryl, or optionally substituted heteroaryl ring. For instance,

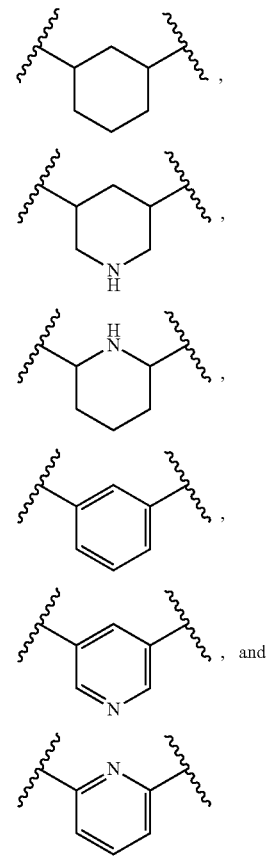

are all examples of a hydrocarbon chain. Hydrocarbon chains also include a divalent carbohydrate radical (wherein one or two oxygen atoms at the points of attachment may be present or absent), such as a divalent glucose radical (e.g., 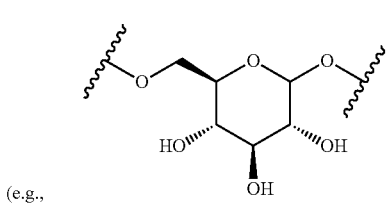 [SMILES: *OC[C@H]1OC(O*)[C@H](O)[C@@H](O)[C@@H]1O]

(both two oxygen atoms at the points of attachment are present) and

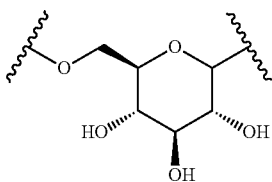 [SMILES: *OC[C@H]1OC(*)[C@H](O)[C@@H](O)[C@@H]1O]

(only one of the two oxygen atom at the points of attachment is present)). In contrast, in certain embodiments

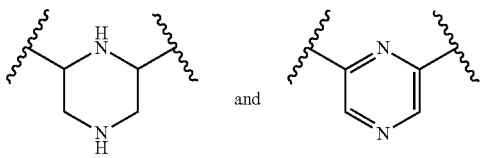 [SMILES: *C1CNCC(*)N1 ; *c1cncc(*)n1]

are not within the scope of the hydrocarbon chains described herein.

A "protecting group" is well known in the art and include those described in detail in *Greene's Protective Groups in Organic Synthesis*, P. G. M. Wuts and T. W. Greene, 4$^{th}$ edition, Wiley-Interscience, 2006, the entirety of which is incorporated herein by reference. Suitable "amino-protecting groups" (also referred to as "nitrogen protecting groups") include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (oMoz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "hydroxyl protecting group" (also referred to as an "oxygen protecting group") is well known in the art and includes those described in detail in Greene (1999). Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis (4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

The term "pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylpropionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable salts include inorganic acids such as hydrochloric acid, hydrobromic acid, sulfuric acid, and phosphoric acid; and organic acids such as oxalic acid, maleic acid, succinic acid, and citric acid. "Basic addition salts" refer to salts derived from appropriate bases, these salts including alkali metal, alkaline earth metal, and quaternary amine salts. Hence, the present invention contemplates sodium, potassium, magnesium, and calcium salts of the compounds disclosed herein, and the like. Basic addition salts can be prepared during the final isolation and purification of the compounds, often by reacting a carboxyl group with a suitable base such as the hydroxide, carbonate, or bicarbonate of a metal cation or with ammonia or an organic primary, secondary, or tertiary amine. The cations of therapeutically acceptable salts include lithium, sodium (by using, e.g., NaOH), potassium (by using, e.g., KOH), calcium (by using, e.g., Ca(OH)$_2$), magnesium (by using, e.g., Mg(OH)$_2$ and magnesium acetate), zinc, (by using, e.g., Zn(OH)$_2$ and zinc acetate), and aluminum, as well as non-toxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N,N'-dibenzylethylenediamine, N,N'-diethylethanolamine, N,N'-dimethylethanolamine, triethanolamine, and tromethamine. Basic amino acids (e.g., 1-glycine and 1-arginine) and amino acids which may be zwitterionic at neutral pH (e.g., betaine (N,N,N-trimethylglycine)) are also contemplated.

The term "tautomer" refers to a particular isomer of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, lactam-lactim forms, ketene-ynol forms, enamine-enamine forms, and pyridione-hydroxypyridine forms.

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of the invention may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.xH$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

The term "intracellular conditions" refers to conditions of the internal milieu that occur in a subject (e.g., a human) naturally, as opposed to artificial laboratory conditions. In certain embodiments, intracellular conditions include a temperature range of about 20 to about 40° C. (e.g., about 37° C.), pressure of about 1 atmosphere, pH of about 6 to about 8 (e.g., about 7), glucose concentration of about 1 to about 20 mM, atmospheric oxygen concentration, and earth gravity. In certain embodiments, intracellular conditions are conditions that occur in a bacterium (e.g., a bacterium described herein).

The term "stable under intracellular conditions" refers to a compound or a moiety of a compound (e.g., linker L of a compound of Formula (I)) showing a long half-life under intracellular conditions. The concentration of the compound or the moiety at the inception of the half-life measurement is a concentration effective for the intended use of the compound. In certain embodiments, the concentration of the compound or the moiety at the inception of the half-life measurement is the half maximal inhibitory concentration (IC$_{50}$) of the compound in inhibiting the growth of a bacterium (e.g., a bacterium described herein). In certain embodiments, a long half-life is at least about 20 min, 1 hour, 3 hours, 6 hours, at least about 12 hours, or at least about 24 hours.

The term "hydrophobic" or "non-polar" refers to the ability of a compound to dissolve, or the ability of a moiety of a compound to assist the compound in dissolving in fats, oils, lipids, and/or non-polar solvents (e.g., hexane or toluene). Hydrophobic moieties include, but are not limited to, substituted or unsubstituted, branched or unbranched alkyl or alkylene groups having 1 to 50 carbon atoms. In certain embodiments, the hydrophobic moiety is an alkyl or alkylene group including at least 1, at least 6, at least 12, at least 18, at least 24, at least 36, or at least 50 carbon atoms. In certain embodiments, the hydrophobic moiety is unsubstituted alkyl or alkylene. In certain embodiments, the hydrophobic moiety is unsubstituted alkyl or alkylene. In certain embodiments, the hydrophobic moiety is unsubstituted C$_{1-24}$ alkyl or alkylene.

The term "hydrophilic" or "polar" refers to the ability of a compound to dissolve, or the ability of a moiety of a compound to assist the compound in dissolving in water. A hydrophilic compound or moiety typically includes one or more heteroatoms (e.g., atoms that are not carbon or hydrogen). In certain embodiments, the water solubility of a hydrophilic compound is at least about 1 mg/ml, at least about 3 mg/ml, or at least about 10 mg/ml at 25° C. and 1 atmosphere. A hydrophilic compound or moiety is not hydrophobic.

The term "conjugate" refers to a compound or complex formed by covalently attaching directly or indirectly (e.g., through a divalent linker) one compound or complex to another compound or complex. In certain embodiments, a conjugate (e.g., an enterobactin-cargo conjugate, which includes an enterobactin derivative-cargo conjugate, such as a salmochelin-cargo conjugate) is a compound of Formula (I), or a salt, hydrate, solvate, polymorph, co-crystal, tautomer, or isotopically labeled derivative thereof, or a complex described herein. A salmochelin-cargo conjugate (including a salmochelin derivative-cargo conjugate) is a compound of Formula (I), or a salt, hydrate, solvate, polymorph, co-crystal, tautomer, or isotopically labeled derivative thereof, or a complex described herein, wherein at least one instance of L is of the formula:

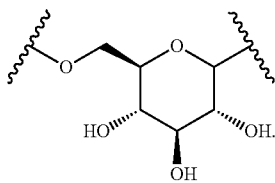 [SMILES: *OC[C@H]1OC(*)[C@H](O)[C@@H](O)[C@@H]1O]

In certain embodiments, a conjugate is a compound of Formula (I), or a salt (e.g., pharmaceutically acceptable salt) thereof. In certain embodiments, a conjugate is a complex described herein.

The term "PEG" refers to a -poly(ethylene glycol)-divalent moiety. The term "$PEG_x$" refers to a -(poly(ethylene glycol))$_x$-divalent moiety, wherein x is an integer from 1 to 10, inclusive.

The term "fluorophore" refers to a fluorescent compound that can emit light upon light excitation. Fluorophores typically contain several combined aromatic groups, or plane or cyclic molecules with several π bonds. Exemplary fluorophores include xanthene derivatives (e.g., fluorescein, rhodamine, Oregon green, eosin, and Texas red), cyanine derivatives (e.g., cyanine, indocarbocyanine, oxacarbocyanine, thiacarbocyanine, and merocyanine), naphthalene derivatives (e.g., dansyl and prodan derivatives), coumarin derivatives, oxadiazole derivatives (e.g., pyridyloxazole, nitrobenzoxadiazole, and benzoxadiazole), Pyrene derivatives (e.g., cascade blue), oxazine derivatives (e.g., Nile red, Nile blue, cresyl violet, oxazine 170), acridine derivatives (e.g., proflavin, acridine orange, acridine yellow), arylmethine derivatives (e.g., auramine, crystal violet, malachite green), and tetrapyrrole derivatives (e.g., porphin, phthalocyanine, bilirubin).

A "counterion" or "anionic counterion" is a negatively charged group associated with a positively charged group in order to maintain electronic neutrality. An anionic counterion may be monovalent (i.e., including one formal negative charge). An anionic counterion may also be multivalent (e.g., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, ethanoate, propanoate, benzoate, glycerate, lactate, tartrate, glycolate), BF$_4^-$, PF$_4^-$, PF$_6^-$, AsF$_6^-$, SbF$_6^-$, B[3,5-(CF$_3$)$_2$C$_6$H$_3$]$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$).

The term "complex" or "coordination complex" refers to an association of at least one atom or ion (which is referred to as a "central atom," "central ion," or "acceptor," and is usually a metallic cation) and a surrounding array of bound ligands or donors). Ligands are generally bound to a central atom or central ion by a coordinate covalent bond (e.g., ligands may donate electrons from a lone electron pair into an empty orbital of the central atom or central ion) and are referred to as being "coordinated" to the central atom or central ion. There are also organic ligands such as alkenes whose π-bonds can coordinate to empty orbitals of an acceptor. A complex may include one or more donors, which can be the same or different. A complex may also include one or more acceptors, which can be the same or different.

The term "subject" refers to any animal. In certain embodiments, the subject is a mammal. In certain embodiments, the subject is a human (e.g., a man, a woman, or a child). The human may be of either sex and may be at any stage of development. In certain embodiments, the subject has been diagnosed with the condition or disease to be treated. In other embodiments, the subject is at risk of developing the condition or disease. In certain embodiments, the subject is an experimental animal (e.g., mouse, rat, rabbit, dog, pig, or primate). The experimental animal may be genetically engineered. In certain embodiments, the subject is a domesticated animal (e.g., dog, cat, bird, horse, cow, goat, sheep, or chicken).

The terms "administer," "administering," or "administration" refers to implanting, absorbing, ingesting, injecting, or inhaling a compound, complex, or pharmaceutical composition described herein, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound or complex of the present invention or a pharmaceutical composition thereof refers to an amount sufficient to elicit the desired biological response, i.e., treating the condition. As will be appreciated by those of ordinary skill in this art, the effective amount of a compound or complex of the invention may vary depending on such factors as the desired biological endpoint, the pharmacokinetics of the compound or complex, the condition being treated, the mode of administration, and the age and health of the subject. An effective amount encompasses therapeutically and prophylactically effective amounts.

A "therapeutically effective amount" of a compound or complex of the present invention or a pharmaceutical composition thereof is an amount sufficient to provide a therapeutic benefit in the treatment of a disease or to delay or minimize one or more symptoms associated with the condition. A therapeutically effective amount of a compound or complex means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

A "prophylactically effective amount" of a compound or complex of the present invention is an amount sufficient to prevent a disease or one or more symptoms associated with the condition or prevent its recurrence. A prophylactically effective amount of a compound or complex means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

BRIEF DESCRIPTION OF THE DRAWINGS

(FIG. 1A) Structures of enterobactin 1 and the salmochelins 2 (monoglucosylated enterobactin (MGE) and 3 (diglucosylated enterobactin, DGE). (FIG. 1B) A cartoon depiction of the enterobactin transport and processing machinery in $E.$ $coli.$ FIG. 2 is an unlimited example and shows enterobactin substituted at the 5-position of the catecholate moiety.

(FIG. 3A) L-Ent promotes growth recovery of $E.$ $coli.$ (FIG. 3B) Enterobactin conjugate 30 housing a cyclohexyl cargo affords growth recovery of $E.$ $coli.$ (FIG. 3C) Enterobactin conjugate 34 housing a coumarin moiety affords little-to-no growth recovery of $E.$ $coli.$ (FIG. 3D) L-Ent promotes growth recovery of $P.$ $aeruginosa.$ (FIG. 3E) Enterobactin conjugate 30 housing a cyclohexyl cargo affords growth recovery of $P.$ $aeruginosa.$ (FIG. 3F) Enterobactin conjugate 34 housing a coumarin moiety affords growth recovery of $P.$ $aeruginosa.$ Each bar indicates the average of three independent replicates (two wells per replicate) and the error bars are the standard deviation of the mean.

(FIG. 4A) $E.$ $coli$ ATCC 33475 (ent-) and the DP concentration was 200 µM. (FIG. 4B) $P.$ $aeruginosa$ PAO1 (pvd-, pch-) and the DP concentration was 600 µM. NC refers to a no-conjugate control.

(FIG. 6A) Antibacterial activity against the non-pathogenic laboratory strain $E.$ $coli$ K-12. (FIG. 6B) Antibacterial activity against the human pathogen $E.$ $coli$ CFT073. (FIG. 6C) Antibacterial activity against the Gram-positive laboratory strain $S.$ $aureus$ ATCC 25923.

(FIG. 11A) Antibacterial activity against the non-pathogenic laboratory strain $E.$ $coli$ K-12 (FepA only). Ent-Amp provided complete growth inhibition at 100 nM, whereas DGE-Amp was inactive at this concentration. The growth inhibition observed for DGE-Amp at 10 µM is attributed to iron deprivation. Because DGE-Amp is cell impermeable, the DGE moiety sequesters iron that is in the growth media. (FIG. 11B) Antibacterial activity against the human pathogen $E.$ $coli$ CFT073 (FepA and IroN). Ent-Amp and DGE-Amp exhibited similar activities against this pathogenic strain, indicating DGE-Amp entry via IroN.

(FIG. 12A) Antibacterial activity of Amp and the Amp-containing conjugates (Ent-Amp, MGE-Amp, and DGE-Amp). Ent-Amp, MGE-Amp, and DGE-Amp all provided enhanced antibacterial activity relative to unmodified Amp. (FIG. 12B) Antibacterial activity of Amx and the Amx-containing conjugates (Ent-Amx, MGE-Amx, and DGE-Amx). Ent-Amx, MGE-Amx, and DGE-Amx all provided enhanced antibacterial activity relative to unmodified Amx.

(FIG. 20A) Images showing three cultures untreated with any antibiotics: *E. coli* CFT073, *S. aureus* 25923, and *E. coli* CFT073 and *S. aureus* 25923 co-culture (in a 1:1 ratio). (FIG. 20B) Images showing co-cultures of *E. coli* CFT073 and *S. aureus* 25923 (in a 1:1 ratio), in the absence of any antibiotics or in the presence of Amp, Amx, Ent-Amp, or Ent-Amx.

FIG. 21A: Ent-Amp, MGE-Amp, and DGE-Amp, in the presence of 2,2'-dipyridyl (DP). FIG. 21B: Ent-Amp, MGE-Amp, and DGE-Amp, in the absence of DP. FIG. 21C: Ent-Amx, MGE-Amx, and DGE-Amx, in the presence of DP. FIG. 21D: Ent-Amx, MGE-Amx, and DGE-Amx, in the absence of DP.

FIG. 22A: Ent-Amp, MGE-Amp, and DGE-Amp, in the presence of 2,2'-dipyridyl (DP). FIG. 22B: Ent-Amp, MGE-Amp, and DGE-Amp, in the absence of DP. FIG. 22C: Ent-Amx, MGE-Amx, and DGE-Amx, in the presence of DP. FIG. 22D: Ent-Amx, MGE-Amx, and DGE-Amx, in the absence of DP.

FIG. 23A: Ent-Amp, MGE-Amp, and DGE-Amp, in the presence of 2,2'-dipyridyl (DP). FIG. 23B: Ent-Amp, MGE-Amp, and DGE-Amp, in the absence of DP. FIG. 23C: Ent-Amx, MGE-Amx, and DGE-Amx, in the presence of DP. FIG. 23D: Ent-Amx, MGE-Amx, and DGE-Amx, in the absence of DP.

FIG. 24A: Ent-Amp, MGE-Amp, and DGE-Amp, in the presence of 2,2'-dipyridyl (DP). FIG. 24B: Ent-Amp, MGE-Amp, and DGE-Amp, in the absence of DP. FIG. 24C: Ent-Amx, MGE-Amx, and DGE-Amx, in the presence of DP. FIG. 24D: Ent-Amx, MGE-Amx, and DGE-Amx, in the absence of DP.

FIG. 25A: Ent-Amp, MGE-Amp, and DGE-Amp, in the presence of 2,2'-dipyridyl (DP). FIG. 25B: Ent-Amp, MGE-Amp, and DGE-Amp, in the absence of DP. FIG. 25C: Ent-Amx, MGE-Amx, and DGE-Amx, in the presence of DP. FIG. 25D: Ent-Amx, MGE-Amx, and DGE-Amx, in the absence of DP.

FIG. 26A: Ent-Amp, MGE-Amp, and DGE-Amp, in the presence of 2,2'-dipyridyl (DP). FIG. 26B: Ent-Amp, MGE-Amp, and DGE-Amp, in the absence of DP. FIG. 26C: Ent-Amx, MGE-Amx, and DGE-Amx, in the presence of DP. FIG. 26D: Ent-Amx, MGE-Amx, and DGE-Amx, in the absence of DP.

FIG. 27A: the bacteria were treated with 50 µM Amp, Ent-Amp, MGE-Amp, or DGE-Amp in the presence of DP. FIG. 27B: the bacteria were treated with 50 µM Amp, Ent-Amp, MGE-Amp, or DGE-Amp in the absence of DP. FIG. 27C: the bacteria were treated with 50 µM Amx, Ent-Amx, MGE-Amx, or DGE-Amx in the presence of DP. FIG. 27D: the bacteria were treated with 50 µM Amx, Ent-Amx, MGE-Amx, or DGE-Amx in the absence of DP.

FIG. 28A: the bacteria were treated with 50 µM Amp, Ent-Amp, MGE-Amp, and DGE-Amp in the presence of DP. FIG. 28B: the bacteria were treated with 50 µM Amp, Ent-Amp, MGE-Amp, and DGE-Amp in the absence of DP. FIG. 28C: the bacteria were treated with 50 µM Amx, Ent-Amx, MGE-Amx, and DGE-Amx in the presence of DP. FIG. 28D: the bacteria were treated with 50 µM Amx, Ent-Amx, MGE-Amx, and DGE-Amx in the absence of DP.

FIG. 29A: the bacteria were treated with 50 µM Amp, or 5 µM Ent-Amp, MGE-Amp, and DGE-Amp in the presence of DP. FIG. 29B: the bacteria were treated with 50 µM Amp, or 5 µM Ent-Amp, MGE-Amp, and DGE-Amp in the absence of DP. FIG. 29C: the bacteria were treated with 50 µM Amx, or 5 µM Ent-Amx, MGE-Amx, and DGE-Amx in the presence of DP. FIG. 29D: the bacteria were treated with 50 µM Amx, or 5 µM Ent-Amx, MGE-Amx, and DGE-Amx in the absence of DP.

FIG. 30A: the bacteria were treated with 50 µM Amp, 5 µM Ent-Amp, MGE-Amp, and DGE-Amp in the presence of DP. FIG. 30B: the bacteria were treated with 50 µM Amp, 5 µM Ent-Amp, MGE-Amp, and DGE-Amp in the absence of DP. FIG. 30C: the bacteria were treated with 50 µM Amx, or 5 µM Ent-Amx, MGE-Amx, and DGE-Amx in the presence of DP. FIG. 30D: the bacteria were treated with 50 µM Amx, or 5 µM Ent-Amx, MGE-Amx, and DGE-Amx in the absence of DP.

FIG. 31A: the bacteria were treated with Ent-Amp, MGE-Amp, and DGE-Amp in the presence and absence of Lcn2 or BSA. FIG. 31B: the bacteria were treated with Ent-Amx, MGE-Amx, and DGE-Amx in the presence and absence of Lcn2 or BSA.

FIG. 36A: Ent-Amp, MGE-Amp, and DGE-Amp in the presence of 2,2'-dipyridyl (DP). FIG. 36B: Ent-Amp, MGE-Amp, and DGE-Amp in the absence of DP. FIG. 36C: Ent-Amx, MGE-Amx, and DGE-Amx in the presence of DP. FIG. 36D: Ent-Amx, MGE-Amx, and DGE-Amx in the absence of DP.

FIG. 37A: Ent-Amp, MGE-Amp, and DGE-Amp in the presence of DP. FIG. 37B: Ent-Amx, MGE-Amx, and DGE-Amx in the presence of DP.

FIG. 38A: Ent-Amp, MGE-Amp, and DGE-Amp in the presence of 2,2'-dipyridyl (DP). FIG. 38B: Ent-Amp, MGE-Amp, and DGE-Amp in the absence of DP. FIG. 38C: Ent-Amx, MGE-Amx, and DGE-Amx in the presence of DP. FIG. 38D: Ent-Amx, MGE-Amx, and DGE-Amx in the absence of DP.

FIG. 39A: Ent-Amp, MGE-Amp, and DGE-Amp in the presence of DP. FIG. 39B: Ent-Amp, MGE-Amp, and DGE-Amp in the absence of DP. FIG. 39C: Ent-Amx, MGE-Amx, and DGE-Amx in the presence of DP. FIG. 39D: Ent-Amx, MGE-Amx, and DGE-Amx in the absence of DP.

FIG. 41A: Amp in the presence of Ent, MGE, or DGE, and in the presence of DP. FIG. 41B: Amp in the presence of Ent, MGE, or DGE, and in the absence of DP. FIG. 41C: Amx in the presence of Ent, MGE, or DGE, and in the presence of DP. FIG. 41D: Amx in the presence of Ent, MGE, or DGE, and in the absence of DP.

FIG. 42A: Amp in the presence of Ent, MGE, or DGE, and in the presence of DP. FIG. 42B: Amp in the presence of Ent, MGE, or DGE, and in the absence of DP. FIG. 42C: Amx in the presence of Ent, MGE, or DGE, and in the presence of DP. FIG. 42D: Amx in the presence of Ent, MGE, or DGE, and in the absence of DP.

FIG. 43A: Ent-Amp, MGE-Amp, and DGE-Amp, in the presence or absence of Fe(III). FIG. 43B: Ent-Amx, MGE-Amx, and DGE-Amx, in the presence or absence of Fe(III).

DETAILED DESCRIPTION OF CERTAIN EMBODIMENTS OF THE INVENTION

The present invention provides novel enterobactin-cargo conjugates, such as compounds of Formula (I), and salts thereof, where at least one instance of X is the cargo and may be an antibiotic, a fluorophore, or biotin. The present invention also provides complexes including a compound of the invention, and iron (e.g., Fe(III)) or gallium (e.g., Ga(III)). The present invention further provides compositions, kits, and methods that involve the compounds of Formula (I) and/or complexes of the invention and are useful in delivering a cargo to a bacterium, treating a bacterial infection, cystic fibrosis, and/or inflammatory bowel disease (IBD) in a subject, preventing a bacterial infection, cystic fibrosis, and/or IBD in a subject, inhibiting the growth of or killing a bacterium, or determining the concentration of a bacterium in a biological sample. In certain embodiments, the bacterium is a Gram-negative bacterium.

Compounds

Figure 2:
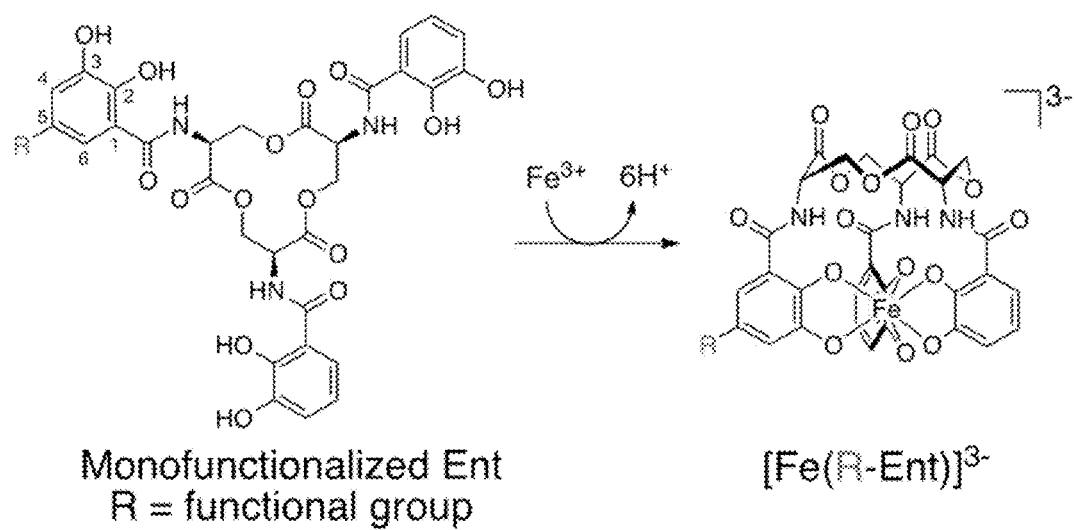

In one aspect, the present invention provides a family of enterobactin-cargo conjugates that are based on a functionalized (e.g., mono-functionalized or multi-functionalized) enterobactin scaffold. Enterobactin may be derivatized at the 4-, 5-, or 6-position of the catecholate moiety (FIG. 2). For example, enterobactin may be derivatized at the 5-position of the catecholate moiety, which provides a point for site-specific modification without compromising the Fe(III)-binding groups or the macrolactone (FIG. 2). Moreover, the ferric enterobactin uptake machineries of bacteria (e.g., Escherichia coli and Pseudomonas aeruginosa PAO1) deliver enterobactin-derivatized cargo to the intracellular space (e.g., the cytoplasm or periplasm) of the bacteria. In certain embodiments, the inventive enterobactin-cargo conjugates deliver the cargo into a bacterium under iron deficient conditions. The size of a cargo may affect the delivery of the cargo into a bacterium by an enterobactin-cargo conjugate of the invention and may be bacterial species/strain-specific.

In one aspect, the present invention provides enterobactin-cargo conjugates of Formula (I):

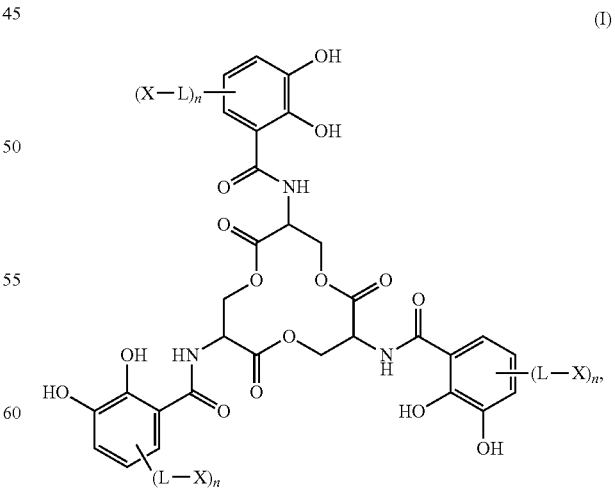

(I)

and salts, hydrates, solvates, polymorphs, co-crystals, tautomers, stereoisomers, and isotopically labeled derivatives thereof, wherein:

each instance of L is independently a bond or a divalent linker;

one instance of X is an antibiotic, a fluorophore, or a biotin moiety of the formula:

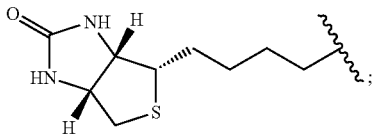 [SMILES: *CCCC[C@@H]1SC[C@@H]2NC(=O)N[C@@H]21]

all other instances of X are independently selected from the group consisting of hydrogen, an antibiotic, a fluorophore, and a biotin moiety of the formula:

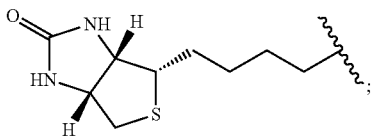

one instance of n is 1, 2, or 3; and
the other two instances of n are independently 0, 1, 2, or 3.

In certain embodiments, the compounds of Formula (I) includes salts and stereoisomers thereof. In certain embodiments, the compounds of Formula (I) includes salts thereof. In certain embodiments, the compounds of Formula (I) includes pharmaceutically acceptable salts thereof. In certain embodiments, a compound of Formula (I) is a mixture of stereoisomers. In certain embodiments, a compounds of Formula (I) is a racemic mixture of stereoisomers. In certain embodiments, a compounds of Formula (I) is a substantially pure stereoisomer.

A compound of Formula (I) includes an enterobactin moiety; one or more linker moieties L; and one or more cargo moieties (e.g., antibiotic, fluorophore, and/or biotin moieties). In certain embodiments, at least one instance of L is stable under intracellular conditions. In certain embodiments, the half-life of at least one instance of L under physiological conditions is at least about 6 hours, at least about 12 hours, at least about 1 day, at least about 2 days, at least about 3 days, at least about 5 days, or at least about 1 week. In certain embodiments, at least one instance of L is unstable under intracellular conditions. In certain embodiments, the half-life of at least one instance of L under physiological conditions is less than about 6 hours, less than about 3 hours, less than about 1 hour, or less than about 20 min. In certain embodiments, at least one instance of L is hydrophilic. In certain embodiments, at least one instance of L is hydrophobic. In certain embodiments, the molecular weight of at least one instance of L is less than about 600 Da, less than about 500 Da, less than about 400 Da, less than about 300 Da, or less than about 200 Da. In certain embodiments, the molecular weight of at least one instance of L is at least about 600 Da, at least about 500 Da, at least about 400 Da, at least about 300 Da, or at least about 200 Da. In certain embodiments, at least one instance of L consists of less than about 150 atoms, less than about 100 atoms, less than about 70 atoms, less than about 50 atoms, or less than about 30 atoms. In certain embodiments, at least one instance of L consists of at least about 150 atoms, at least about 100 atoms, at least about 70 atoms, at least about 50 atoms, or at least about 30 atoms. In certain embodiments, at least one instance of L consists of less than about 10, less than about 8, less than about 6, or less than about 4 unsaturated bonds. In certain embodiments, at least one instance of L consists of 0, 1, or 2 unsaturated bonds. In certain embodiments, at least one instance of L consists of at least about 10, at least about 8, at least about 6, or at least about 4 unsaturated bonds. In certain embodiments, the distance between the two points of attachment of at least one instance of L is less than about 15 Å, less than about 20 Å, less than about 30 Å, less than about 40 Å, less than about 50 Å, less than about 70 Å, or less than about 100 Å, when L is under the minimum-energy conformation. In certain embodiments, the distance between the two points of attachment of at least one instance of L is at least about 15 Å, at least about 20 Å, at least about 30 Å, at least about 40 Å, at least about 50 Å, at least about 70 Å, or at least about 100 Å, when L is under the minimum-energy conformation. Combinations of the ranges described herein (e.g., the molecular weight of at least one instance of L being at least about 200 Da and less than about 1.4 kDa) are also with the scope of the present invention.

In certain embodiments, each instance of L is independently a bond or a substituted or unsubstituted $C_{1-100}$ hydrocarbon chain, optionally wherein one or more carbon units of the hydrocarbon chain are independently replaced with —O—, —S—, —NR$^L$—, —S(=O)—, —S(=O)$_2$—, or substituted or unsubstituted heteroarylene; and each instance of R$^L$ is independently hydrogen, substituted or unsubstituted $C_{1-6}$ alkyl, or a nitrogen protecting group.

In certain embodiments, at least one instance of L is a bond. In certain embodiments, at least one instance of L is a divalent linker. Either one of the two points of attachment of L may be attached to a phenyl ring of a conjugate described herein. In certain embodiments, at least one instance of L is a substituted or unsubstituted $C_{1-100}$ hydrocarbon chain, optionally wherein one or more carbon units of the hydrocarbon chain are independently replaced with —O—, —S—, —NR$^L$—, —S(=O)—, —S(=O)$_2$—, or substituted or unsubstituted heteroarylene. In certain embodiments, at least one instance of L is a substituted or unsubstituted $C_{1-100}$ hydrocarbon chain, optionally wherein one or more carbon units of the hydrocarbon chain are independently replaced with —O—, —S—, —NR$^L$—, —S(=O)—, —S(=O)$_2$—, or substituted or unsubstituted heteroarylene. In certain embodiments, at least one instance of L is a substituted or unsubstituted $C_{6-36}$ hydrocarbon chain, optionally wherein one or more carbon units of the hydrocarbon chain are independently replaced with —O—, —S—, —NR$^L$—, —S(=O)—, —S(=O)$_2$—, or substituted or unsubstituted heteroarylene. In certain embodiments, at least one instance of L is a substituted or unsubstituted $C_{12-36}$ hydrocarbon chain, optionally wherein one or more carbon units of the hydrocarbon chain are independently replaced with —O—, —S—, —NR$^L$—, —S(=O)—, —S(=O)$_2$—, or substituted or unsubstituted heteroarylene. In certain embodiments, 1 to 10 carbon units of at least one instance of L are independently replaced with —O—, —S—, —NR$^L$—, —S(=O)—, —S(=O)$_2$—, or substituted or unsubstituted heteroarylene. In certain embodiments, 3 to 8 carbon units of at least one instance of L are independently replaced with —O—, —S—, —NR$^L$—, —S(=O)—, —S(=O)$_2$—, or substituted or unsubstituted heteroarylene. In certain embodiments, at least one instance of L is a divalent peptide radical. In certain embodiments, at least one instance of L is a divalent peptide radical consisting of between 2 and 80 amino acid residues, inclusive. In certain embodiments, at least one instance of L is a divalent peptide radical consisting of between 2 and 6 amino acid residues, inclusive. In certain embodiments, at least one instance of L is a divalent peptide radical consisting of between 7 and 15 amino acid residues, inclusive. In certain embodiments, at least one instance of L is a divalent peptide radical consisting of between 16 and 80 amino acid residues, inclusive. In certain embodiments, two carbon units of at least one instance of L are independently replaced with substituted or unsubstituted heteroarylene. In certain embodiments, one carbon unit of at least one instance of L is replaced with substituted or unsubstituted heteroarylene. In certain embodiments, at least one instance of the substituted or unsubstituted heteroarylene of at least one instance of L is substituted or unsubstituted, 5- to 6-membered, monocyclic heteroaryl, wherein one, two, three, or four atoms in the heteroaryl ring system are independently selected from the group consisting of nitrogen, oxygen, and sulfur. In certain embodiments, at least one instance of the substituted or unsubstituted heteroarylene of at least one instance of L is substituted or unsubstituted, 5-membered, monocyclic heteroaryl, wherein one atom in the heteroaryl ring system is nitrogen, oxygen, or sulfur. In certain embodiments, at least one instance of the substituted or unsubstituted heteroarylene of at least one instance of L is substituted or unsubstituted, 5-membered, monocyclic heteroaryl, wherein two atoms in the heteroaryl ring system are independently selected from the group consisting of nitrogen, oxygen, and sulfur. In certain embodiments, at least one instance of the substituted or unsubstituted heteroarylene of at least one instance of L is substituted or unsubstituted, 5-membered, monocyclic heteroaryl, wherein three atoms in the heteroaryl ring system are independently selected from the group consisting of nitrogen, oxygen, and sulfur. In certain embodiments, at least one instance of the substituted or unsubstituted heteroarylene of at least one instance of L is of the formula:

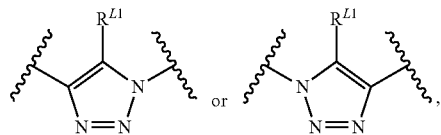

wherein $R^{L1}$ is hydrogen, halogen, unsubstituted $C_{1-6}$ alkyl, or $C_{1-6}$ alkyl substituted with at least one halogen. In certain embodiments, at least one instance of the substituted or unsubstituted heteroarylene of at least one instance of L is of the formula:

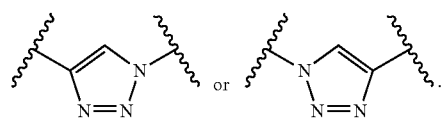 [SMILES: *c1cn(*)nn1 ; "or" ; *c1cn(*)nn1 ; "."]

In certain embodiments, at least one instance of the substituted or unsubstituted heteroarylene of at least one instance of L is substituted or unsubstituted, 5-membered, monocyclic heteroaryl, wherein four atoms in the heteroaryl ring system are independently selected from the group consisting of nitrogen, oxygen, and sulfur. In certain embodiments, at least one instance of the substituted or unsubstituted heteroarylene of at least one instance of L is substituted or unsubstituted, 6-membered, monocyclic heteroaryl, wherein one atom in the heteroaryl ring system is nitrogen. In certain embodiments, at least one instance of the substituted or unsubstituted heteroarylene of at least one instance of L is substituted or unsubstituted, 6-membered, monocyclic heteroaryl, wherein two atoms in the heteroaryl ring system are nitrogen. In certain embodiments, at least one instance of the substituted or unsubstituted heteroarylene of at least one instance of L is substituted or unsubstituted, 6-membered, monocyclic heteroaryl, wherein three atoms in the heteroaryl ring system are nitrogen.

In certain embodiments, at least one instance of L is a divalent hydrocarbon radical. In certain embodiments, at least one instance of L is a divalent monosaccharide radical. In certain embodiments, at least one instance of L is a divalent hexose radical. In certain embodiments, at least one instance of L is a divalent aldohexose radical. In certain embodiments, at least one instance of L is a divalent glucose radical (e.g., a divalent radical of α-D-, β-D-, α-L-, or β-L-glucose). In certain embodiments, at least one instance of L is a divalent dextrose radical. In certain embodiments, at least one instance of L is a divalent glucopyranose radical. In certain embodiments, at least one instance of L is of the formula:

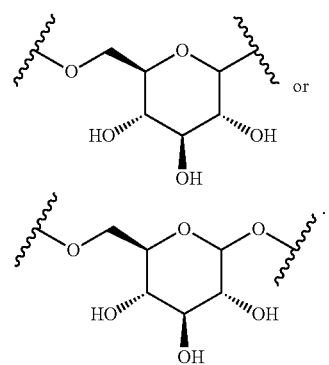

In certain embodiments, at least one instance of L is of the formula:

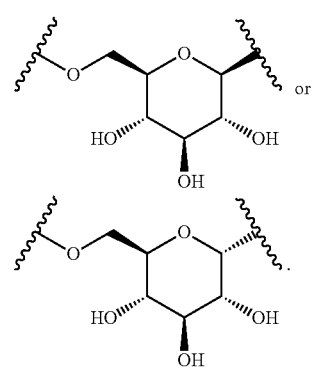

In certain embodiments, at least one instance of L is of the formula:

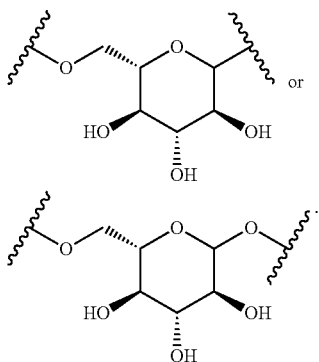

or

In certain embodiments, at least one instance of L is a divalent glucofuranose radical. In certain embodiments, at least one instance of L is a divalent radical of mannose, galactose, allose, altrose, talose, gulose, or idose. In certain embodiments, at least one instance of L is a divalent ketohexose radical (e.g., a divalent radical of fructose, psicose, sorbose, or tagatose). In certain embodiments, at least one instance of L is a divalent aldopentose radical (e.g., a divalent radical of ribose, arabinose, xylose, or lyxose) or a divalent ketopentose radical (e.g., a divalent radical of ribulose, arabulose, xylulose, or lyxulose). In certain embodiments, at least one instance of L is a divalent disaccharide radical or divalent polysaccharide radical.

In certain embodiments, at least one instance of L is a combination of two or more divalent radicals described herein, wherein any two divalent radicals are independently the same or different.

In certain embodiments, no instance of L comprises a divalent peptide radical (e.g., a divalent radical of a peptide consisting of between 7 and 15 amino acid residues, inclusive, or a divalent radical of a peptide consisting of 81 or more amino acid residues). In certain embodiments, no instance of L comprises a divalent radical formed by removing two hydrogen atoms from a peptide of the sequence: SSSGSGS (SEQ ID NO: 1), SATSSSGSGS (SEQ ID NO: 2), GYNSATSSSGSGS (SEQ ID NO: 3), SSGYNSATSSSGSGS (SEQ ID NO: 4), SATSSSGSGG (SEQ ID NO: 5), SATSSSGSGA (SEQ ID NO: 6), SATSSSGSGT (SEQ ID NO: 7), SASSSAGGGS (SEQ ID NO: 8), SSTSSAVSGS (SEQ ID NO: 9), or SASSSAGSGS (SEQ ID NO: 10). In certain embodiments, no instance of L comprises a divalent radical formed by removing two hydrogen atoms from a peptide of the sequence GETDPNTQLLNDL-GNNMAWGAALGAPGGLGSAALGAAGGALQT-VGQGLIDHGPVNVPIP VLIGPSWNGSSSGYN-SATSSSGSGS (SEQ ID NO: 11). In certain embodiments, no instance of L comprises both a divalent peptide radical and a divalent carbohydrate radical (e.g., a divalent glucose radical). In certain embodiments, no instance of L is (divalent peptide radical)(divalent carbohydrate radical)-. In certain embodiments, no instance of L is -(divalent peptide radical)-(divalent glucose radical)-. In certain embodiments, no instance of L is of the formula:

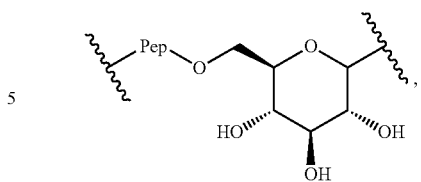

wherein -Pep- is a divalent peptide radical. In certain embodiments, the carbonyl moiety of the C-terminus of -Pep- is attached to the oxygen atom at C6 of the glucose moiety, and the nitrogen atom of the N-terminus of -Pep- is attached to X. In certain embodiments, -Pep- is a divalent radical of a peptide of the sequence SSSGSGS (SEQ ID NO: 1), SATSSSGSGS (SEQ ID NO: 2), GYNSATSSSGSGS (SEQ ID NO: 3), SSGYNSATSSSGSGS (SEQ ID NO: 4), SATSSSGSGG (SEQ ID NO: 5), SATSSSGSGA (SEQ ID NO: 6), SATSSSGSGT (SEQ ID NO: 7), SASSSAGGGS (SEQ ID NO: 8), SSTSSAVSGS (SEQ ID NO: 9), or SASSSAGSGS (SEQ ID NO: 10). In certain embodiments, -Pep- is a divalent radical of a peptide of the sequence:

```
                                            (SEQ ID NO: 11)
GETDPNTQLLNDLGNNMAWGAALGAPGGLGSAALGAAGGAL

QTVGQGLIDHGPVNVPIPVLIGPSWNGSSSGYNSATSSSGSGS.
```

In certain embodiments, at least one instance of $R^L$ is hydrogen. In certain embodiments, at least one instance of $R^L$ is substituted alkyl. In certain embodiments, at least one instance of $R^L$ is unsubstituted alkyl. In certain embodiments, at least one instance of $R^L$ is $C_{1-12}$ alkyl. In certain embodiments, at least one instance of $R^L$ is $C_{1-6}$ alkyl. In certain embodiments, at least one instance of $R^L$ is unsubstituted methyl. In certain embodiments, at least one instance of $R^L$ is substituted methyl. In certain embodiments, at least one instance of $R^L$ is —$CH_2F$, —$CHF_2$, or —$CF_3$. In certain embodiments, at least one instance of $R^L$ is Bn. In certain embodiments, at least one instance of $R^L$ is ethyl, propyl, butyl, pentyl, or hexyl. In certain embodiments, at least one instance of $R^L$ is a nitrogen protecting group. In certain embodiments, at least one instance of $R^L$ is Bn, Boc, Cbz, Fmoc, trifluoroacetyl, triphenylmethyl, acetyl, or Ts. In certain embodiments, at least one instance of $R^L$ is hydrogen, unsubstituted $C_{1-6}$ alkyl, and $C_{1-6}$ alkyl substituted with one or more substituents independently selected from the group consisting of halogen and —O(unsubstituted $C_{1-6}$ alkyl).

In the divalent linker L, each instance of the carbon units of the $C_{1-100}$ hydrocarbon chain and each instance of the heteroarylene may be independently substituted. In certain embodiments, at least one instance of the carbon units of the $C_{1-100}$ hydrocarbon chain or at least one instance of the heteroarylene is substituted with hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, =O, —$OR^{L1}$, —$N(R^{L1})_2$, —$SR^{L1}$, —CN, —SCN, —C(=$NR^{L1}$)$R^{L1}$, —C(=$NR^{L1}$)$OR^{L1}$, —C(=$NR^{L1}$)N($R^{L1}$)$_2$, —C(=O)$R^{L1}$, —C(=O)$OR^{L1}$, —C(=O)N($R^{L1}$)$_2$, —S(=O)$R^{L1}$, —S(=O)$OR^{L1}$, —S(=O)N($R^{L1}$)$_2$, —S(=O)$_2R^{L1}$, —S(=O)$_2OR^{L1}$, —S(=O)$_2$N($R^{L1}$)$_2$, —$NO_2$, —$NR^{L1}$C(=O)$R^{L1}$, —$NR^{L1}$C(=O)$OR^{L1}$, —$NR^{L1}$C(=O)N($R^{L1}$)$_2$, —$NR^{L1}$S(=O)$R^{L1}$, —$NR^{L1}$S —(=O)OR$^{L1}$, —NR$^{L1}$S(=O)N(R$^{L1}$)$_2$, —NR$^{L1}$S(=O)$_2$R$^{L1}$, —NR$^{L1}$S(=O)$_2$OR$^{L1}$, —NR$^{L1}$S(=O)$_2$N(R$^{L1}$)$_2$, —OC(=O)R$^{L1}$, —OC(=O)OR$^{L1}$, —OC(=O)N(R$^{L1}$)$_2$, —OS(=O)R$^{L1}$, —OS(=O)OR$^{L1}$, —OS(=O)N(R$^{L1}$)$_2$, —OS(=O)$_2$R$^{L1}$, OS(=O)$_2$OR$^{L1}$, —OS(=O)$_2$N(R$^{L1}$)$_2$, wherein each occurrence of R$^{L1}$ is independently selected from the group consisting of hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, and a sulfur protecting group when attached to a sulfur atom, or two R$^{L1}$ groups are joined to form an substituted or unsubstituted heterocyclic ring, provided that no instance of the heteroarylene is substituted with =O. In certain embodiments, at least one instance of the carbon units of the C$_{1-100}$ hydrocarbon chain is substituted with halogen, =O, or substituted or unsubstituted alkyl. In certain embodiments, at least one instance of the carbon units of the C$_{1-100}$ hydrocarbon chain is substituted with halogen, =O, unsubstituted C$_{1-6}$ alkyl, or C$_{1-6}$ alkyl substituted with at least one halogen. In certain embodiments, at least one instance of the heteroarylene is substituted with halogen or substituted or unsubstituted alkyl. In certain embodiments, at least one instance of the heteroarylene is substituted with halogen, unsubstituted C$_{1-6}$ alkyl, or C$_{1-6}$ alkyl substituted with at least one halogen. In certain embodiments, no instance of the carbon units of the C$_{1-100}$ hydrocarbon chain and no instance of the heteroarylene is substituted with substituted or unsubstituted alkenyl or substituted or unsubstituted alkynyl. In certain embodiments, at least one instance of L is of the formula:

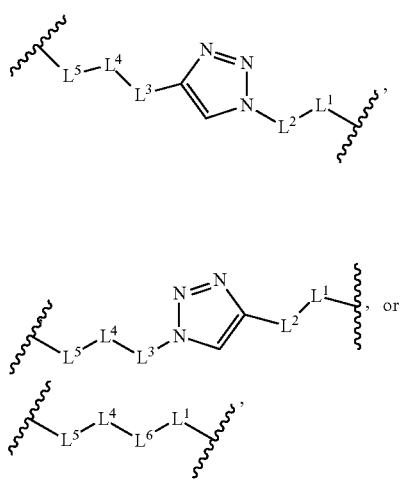

wherein: L$^1$ and L$^4$ are independently —NR$^L$C(=O)— or —C(=O)NR$^L$—; L$^2$ and L$^3$ are independently unsubstituted C$_{1-50}$ alkylene or C$_{1-50}$ alkylene substituted with at least one halogen, optionally wherein one to six carbon units of the C$_{1-50}$ alkylene are replaced with —O—; L$^5$ is a bond, unsubstituted C$_{1-6}$ alkylene, or C$_{1-6}$ alkylene substituted with at least one halogen, optionally wherein one or two carbon units of the C$_{1-6}$ alkylene are replaced with —O—; and L$^6$ is unsubstituted C$_{2-90}$ alkylene, or C$_{2-90}$ alkylene substituted with at least one halogen, optionally wherein one to eight carbon units of the C$_{2-90}$ alkylene are replaced with —O—. In certain embodiments, at least one instance of L is of the formula:

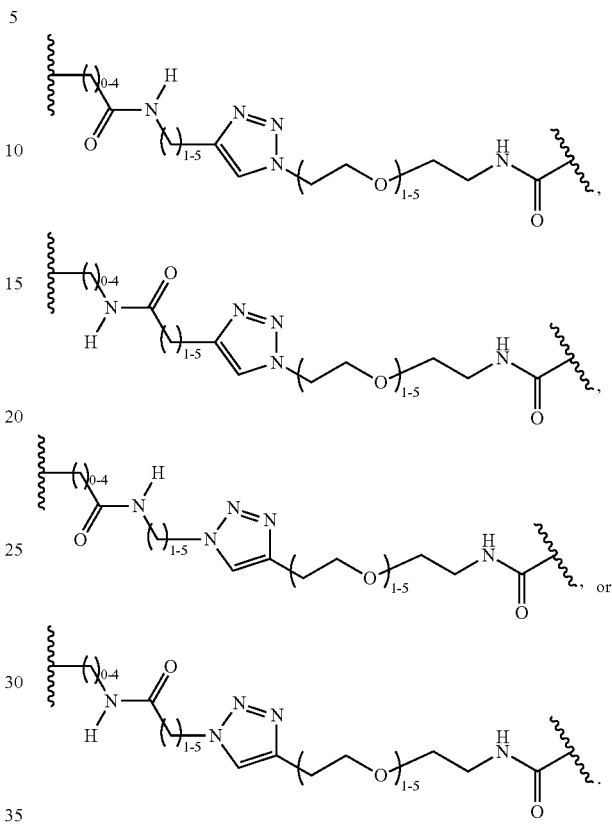

In certain embodiments, at least one instance of L is of the formula:

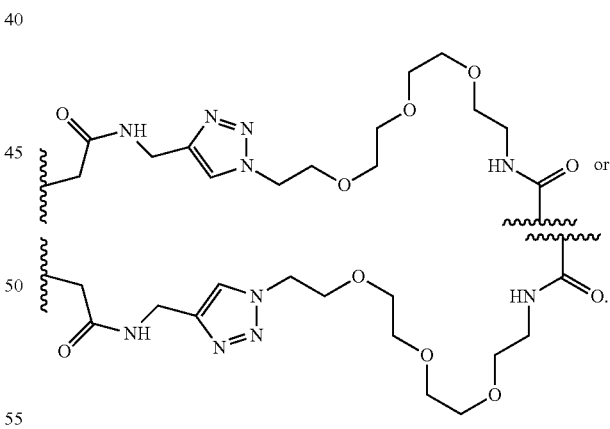

In certain embodiments, at least one instance of L is of the formula:

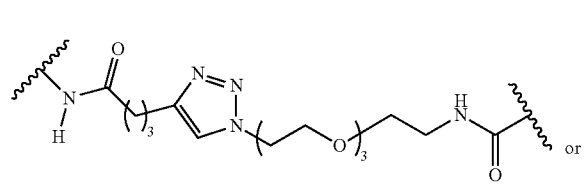

-continued

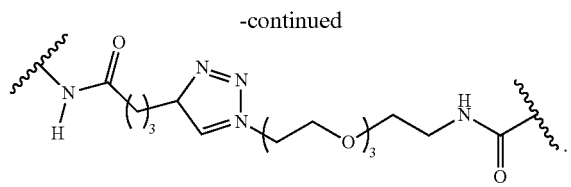

In certain embodiments, at least one instance of L is of the formula:

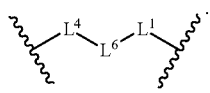

In certain embodiments, at least one instance of L is —NHC(=O)—(CH$_2$)$_{2-8}$—NHC(=O)— or —C(=O)NH—(CH$_2$)$_{2-8}$—C(=O)NH—. In certain embodiments, at least one instance of L is —NHC(=O)—(CH$_2$)$_5$—NHC(=O)— or —C(=O)NH—(CH$_2$)$_5$—C(=O)NH—. In certain embodiments, at least one instance of L is of the formula:

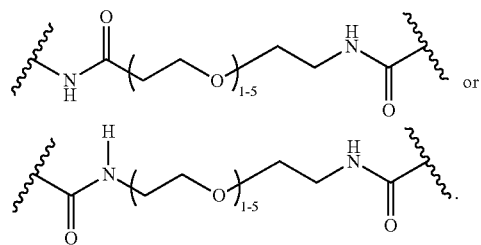

In certain embodiments, at least one instance of L is of the formula:

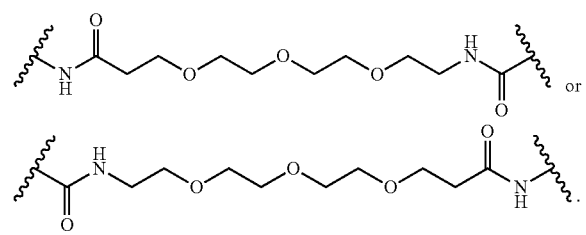

A compounds of Formula (I) includes one or more moieties X. At least one instance of X is a cargo (e.g., an antibiotic, a fluorophore, or biotin). In certain embodiments, at least one instance of X is an antibiotic. In certain embodiments, one of the hydrogen atoms of the antibiotic is removed, the rest of the antibiotic forms a monovalent radical, and the monovalent radical is attached to L. In certain embodiments, the antibiotic is effective against a Gram-negative bacterium. In certain embodiments, the antibiotic is effective at inhibiting the growth of a Gram-negative bacterium. In certain embodiments, the antibiotic is effective at inhibiting the reproduction of a Gram-negative bacterium. In certain embodiments, the antibiotic is effective at killing a Gram-negative bacterium. In certain embodiments, the antibiotic is a β-lactam antibiotic. In certain embodiments, the antibiotic is a penicillin (i.e., a penam, such as an aminopenicillin (e.g., amoxicillin, an ampicillin (e.g., pivampicillin, hetacillin, bacampicillin, metampicillin, talampicillin), epicillin), a carboxypenicillin (e.g., a carbenicillin (e.g., carindacillin), ticarcillin, temocillin), a ureidopenicillin (e.g., azlocillin, piperacillin, mezlocillin), a mecillinam (e.g, pivmecillinam), sulbenicillin, benzylpenicillin, clometocillin, benzathine benzylpenicillin, procaine benzylpenicillin, azidocillin, penamecillin, phenoxymethylpenicillin, propicillin, benzathine phenoxymethylpenicillin, pheneticillin, a cloxacillin (e.g., dicloxacillin, flucloxacillin), oxacillin, methicillin, nafcillin). In certain embodiments, the antibiotic is a penem (e.g., faropenem). In certain embodiments, the antibiotic is a carbapenem (e.g., biapenem, ertapenem, an antipseudomonal (e.g., doripenem, imipenem, meropenem), panipenem). In certain embodiments, the antibiotic is a cephalosporin (i.e., a cephem, such as cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, a cephamycin (e.g, cefoxitin, cefotetan, cefmetazole), a carbacephem (e.g., loracarbef), cefixime, ceftriaxone, an antipseudomonal (e.g., ceftazidime, cefoperazone), cefcapene, cefdaloxime, cefdinir, cefditoren, cefetamet, cefmenoxime, cefodizime, cefotaxime, cefpimizole, cefpiramide, cefpodoxime, cefsulodin, cefteram, ceftibuten, ceftiolene, ceftizoxime, an oxacephem (e.g., flomoxef, latamoxef), cefepime, cefozopran, cefpirome, cefquinome, ceftobiprole, ceftaroline fosamil, ceftiofur, cefquinome, cefovecin). In certain embodiments, the antibiotic is a monobactam (e.g., aztreonam, tigemonam, carumonam, nocardicin A). In certain embodiments, the antibiotic is an aminoglycoside (e.g., amikacin, gentamicin, kanamycin, neomycin, netilmicin, tobramycin, paromomycin, spectinomycin). In certain embodiments, the antibiotic is an ansamycin (e.g., geldanamycin, herbimycin, rifaximin). In certain embodiments, the antibiotic is a glycopeptide (e.g., teicoplanin, vancomycin, telavancin). In certain embodiments, the antibiotic is a lincosamide (e.g., clindamycin, lincomycin). In certain embodiments, the antibiotic is a lipopeptide (e.g., daptomycin). In certain embodiments, the antibiotic is a macrolide (e.g., azithromycin, clarithromycin, dirithromycin, erythromycin, roxithromycin, troleandomycin, telithromycin, spiramycin). In certain embodiments, the antibiotic is a nitrofuran (e.g., furazolidone, nitrofurantoin). In certain embodiments, the antibiotic is an oxazolidonone (e.g., linezolid, posizolid, radezolid, torezolid). In certain embodiments, the antibiotic is a polypeptide (e.g., bacitracin, colistin, polymyxin B). In certain embodiments, the antibiotic is a quinolone (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin). In certain embodiments, the antibiotic is a sulfonamide (e.g., mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim, sulfonamidochrysoidine). In certain embodiments, the antibiotic is a tetracycline (e.g., demeclocycline, doxycycline, minocycline, oxytetracycline, tetracycline). In certain embodiments, the antibiotic is clofazimine, dapsone, capreomycin, cycloserine, ethambutol, ethionamide, isoniazid, pyrazinamide, rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, or trimethoprim. In certain embodiments, the antibiotic is vancomycin (shown below). In certain embodiments, the antibiotic is ciprofloxacin.

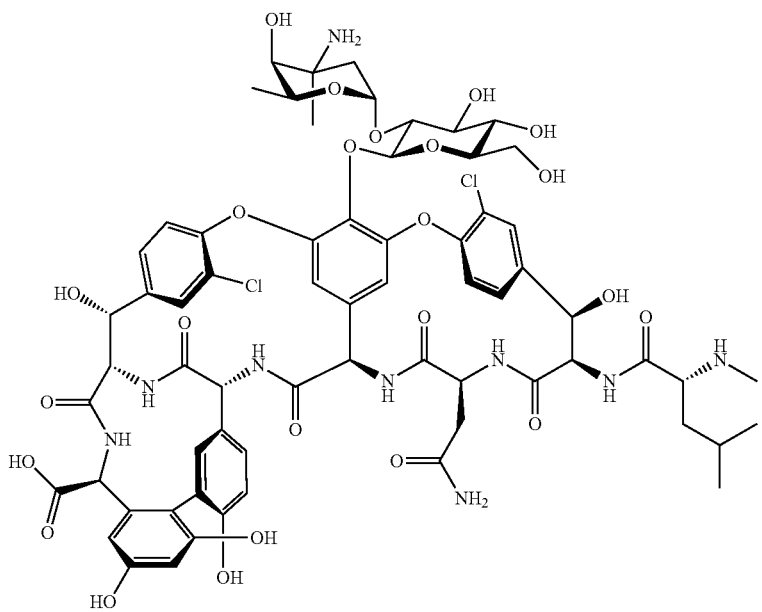

vancomycin

In certain embodiments, at least one instance of X is a fluorophore. In certain embodiments, one of the hydrogen atoms of the fluorophore is removed, the rest of the fluorophore forms a monovalent radical, and the monovalent radical is attached to L. In certain embodiments, the fluorophore is a non-protein organic fluorophore. In certain embodiments, the fluorophore is a coumarin derivative (e.g., coumarin 343, coumarin 1, coumarin 6, coumarin 30, coumarin 153, coumarin 314, coumarin 334, coumarin 545t, 6,8-difluoro-7-hydroxy-4-methylcoumarin, 7-amino-4-methyl-6-sulfocoumarin-3-acetic acid (Alexa Fluor® 350), 7-methoxycoumarin-4-acetic acid, 7-hydroxy-4-methylcoumarin). in certain embodiments, the fluorophore is coumarin 343. In certain embodiments, the fluorophore is a xanthene derivative (e.g., fluorescein, rhodamine, Oregon green, eosin, Texas red). In certain embodiments, the fluorophore is a naphthalene derivative (e.g., dansyl, a prodan derivative). In certain embodiments, the fluorophore is a cyanine derivative (e.g., cyanine, indocarbocyanine, oxacarbocyanine, thiacarbocyanine, merocyanine). In certain embodiments, the fluorophore is an oxadiazole derivative (e.g., pyridyloxazole, nitrobenzoxadiazole, benzoxadiazole). In certain embodiments, the fluorophore is a pyrene derivative (e.g., cascade blue). In certain embodiments, the fluorophore is an oxazine derivative (e.g., Nile red, Nile blue, cresyl violet, oxazine 170). In certain embodiments, the fluorophore is an acridine derivative (e.g., proflavin, acridine orange, acridine yellow). In certain embodiments, the fluorophore is an arylmethine derivative (e.g., auramine, crystal violet, malachite green). In certain embodiments, the fluorophore is a tetrapyrrole derivative (e.g., porphin, phthalocyanine, bilirubin).

In certain embodiments, at least one instance of X is a biotin moiety of the formula:

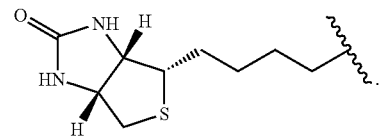

In certain embodiments, at least one instance of X is hydrogen. In certain embodiments, no instance of X is hydrogen.

In certain embodiments, the molecular weight of at least one instance of X is less than about 1,000 kDa, less than about 300 kDa, less than about 100 kDa, less than about 30 kDa, less than about 10 kDa, less than about 1.5 kDa, less than about 1.4 kDa, less than about 1.2 kDa, less than about 1 kDa, less than about 600 Da, less than about 300 Da, less than about 250 Da, or less than about 200 Da. In certain embodiments, the molecular weight of at least one instance of X is less than about 1.4 kDa. In certain embodiments, the molecular weight of at least one instance of X is less than about 300 Da. In certain embodiments, the molecular weight of at least one instance of X is less than about 250 Da. In certain embodiments, the molecular weight of at least one instance of X is at least about 1.4 kDa, at least about 1 kDa, at least about 600 Da, at least about 350 Da, at least about 300 Da, or at least about 200 Da. In certain embodiments, the molecular weight of at least one instance of X is at least about 1.4 kDa. In certain embodiments, the molecular weight of at least one instance of X is at least about 350 Da. In certain embodiments, the molecular weight of at least one instance of X is at least about 300 Da. Combinations of the ranges described herein (e.g., the molecular weight of at least one instance of X being at least about 200 Da and less than about 1.4 kDa) are also with the scope of the present invention.

A compound of Formula (I) may include one or more -L-X moieties. When a compound of Formula (I) include two or more -L-X moieties, the -L-X moieties may be the same or different. When two X moieties are different, they may be of different types of cargos (e.g., one instance of X is an antibiotic, and another instance of X is a fluorophore), may be structurally different but of the same type of cargo (e.g., two instances of X are two different antibiotics), or may be hydrogen and a cargo, respectively. In certain embodiments, one instance of n is 1; and the other two instances of n are 0. In certain embodiments, one instance of n is 0; and the other two instances of n are 1. In certain embodiments, two instances of n are 1; one instance of n is 0; and both instances of L are the same. In certain embodiments, two instances of n are 1; one instance of n is 0; and both instances of L are different. In certain embodiments, two instances of n are 1; one instance of n is 0; and both instances of X are the same. In certain embodiments, two instances of n are 1; one instance of n is 0; and two instances of X are different. In certain embodiments, two instances of n are 1; one instance of n is 0; and both instances of -L-X are the same. In certain embodiments, two instances of n are 1; one instance of n is 0; and two instances of -L-X are different. In certain embodiments, all instances of n are 1. In certain embodiments, all instances of n are 1; and all instances of L are the same. In certain embodiments, all instances of n are 1; and at least two instances of L are different. In certain embodiments, all instances of n are 1; and all instances of X are the same. In certain embodiments, all instances of n are 1; and at least two instances of X are different. In certain embodiments, all instances of n are 1; and all instances of -L-X are the same. In certain embodiments, all instances of n are 1; and at least two instances of -L-X are different. In certain embodiments, one instance of n is 2 or 3; and two instances of n are 0. In certain embodiments, at least one instance of -L-X is -(divalent carbohydrate radical)-H. In certain embodiments, at least one instance of -L-X is -(divalent glucose radical)-H. In certain embodiments, at least one instance of -L-X is of the formula:

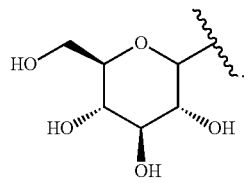 [SMILES: *C1O[C@H](CO)[C@@H](O)[C@H](O)[C@H]1O]

In certain embodiments, at least one instance of -L-X is of the formula:

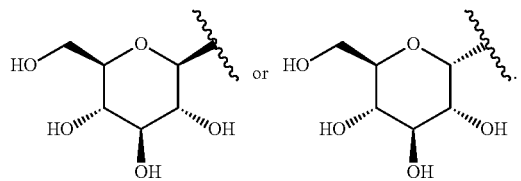 [SMILES: *[C@@H]1O[C@H](CO)[C@@H](O)[C@H](O)[C@H]1O ; *[C@H]1O[C@H](CO)[C@@H](O)[C@H](O)[C@H]1O]

In certain embodiments, a compound of Formula (I) is of the formula:

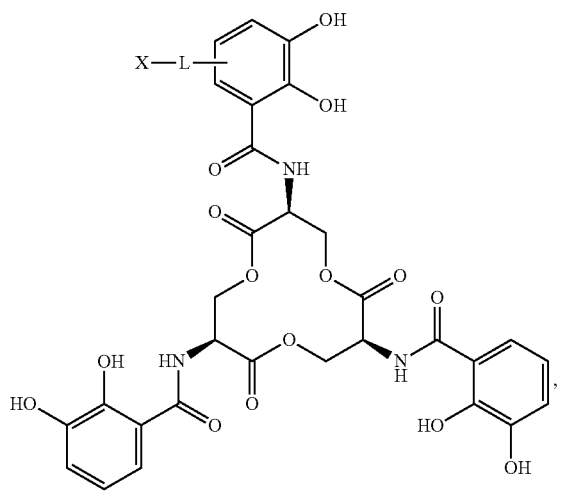

or a salt, hydrate, solvate, polymorph, co-crystal, tautomer, or isotopically labeled derivative thereof.

In certain embodiments, a compound of Formula (I) is of the formula:

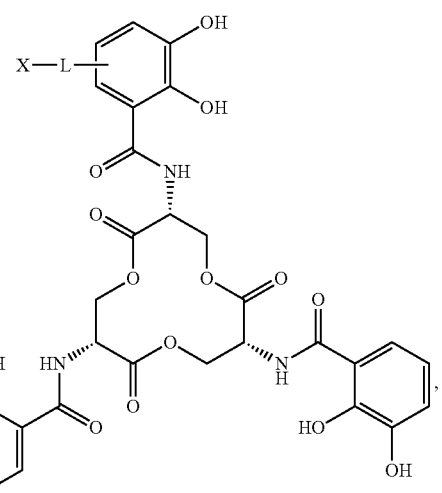

or a salt, hydrate, solvate, polymorph, co-crystal, tautomer, or isotopically labeled derivative thereof.

In certain embodiments, a compound of Formula (I) is of the formula:

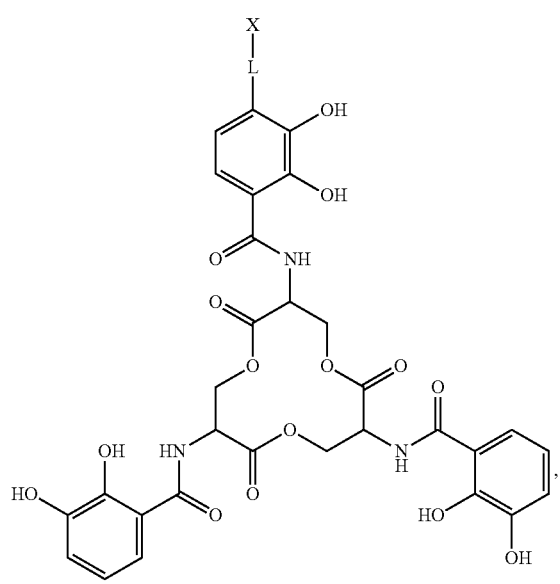
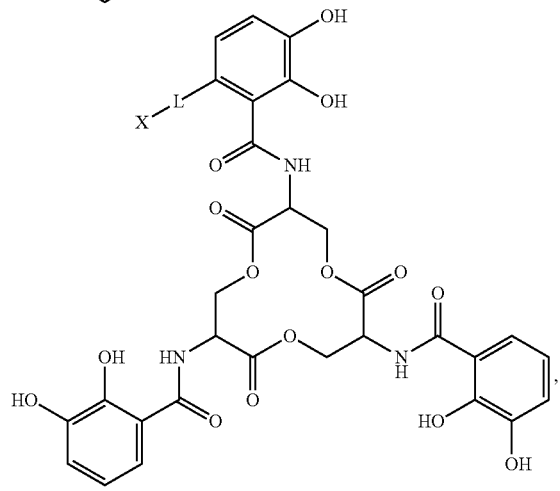
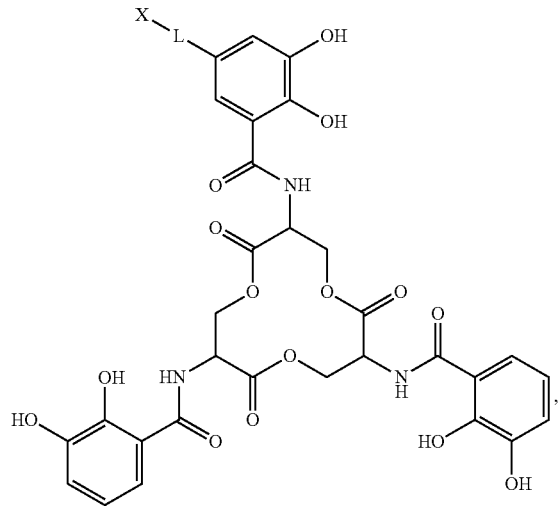
or a salt, hydrate, solvate, polymorph, co-crystal, tautomer, stereoisomer, or isotopically labeled derivative thereof.
In certain embodiments, a compound of Formula (I) is of the formula:
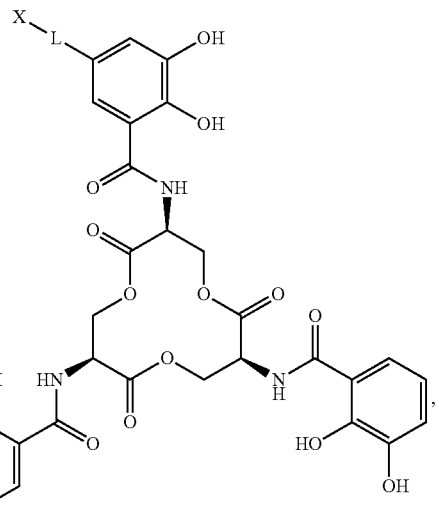
or a salt, hydrate, solvate, polymorph, co-crystal, tautomer, or isotopically labeled derivative thereof.
In certain embodiments, a compound of Formula (I) is of the formula:
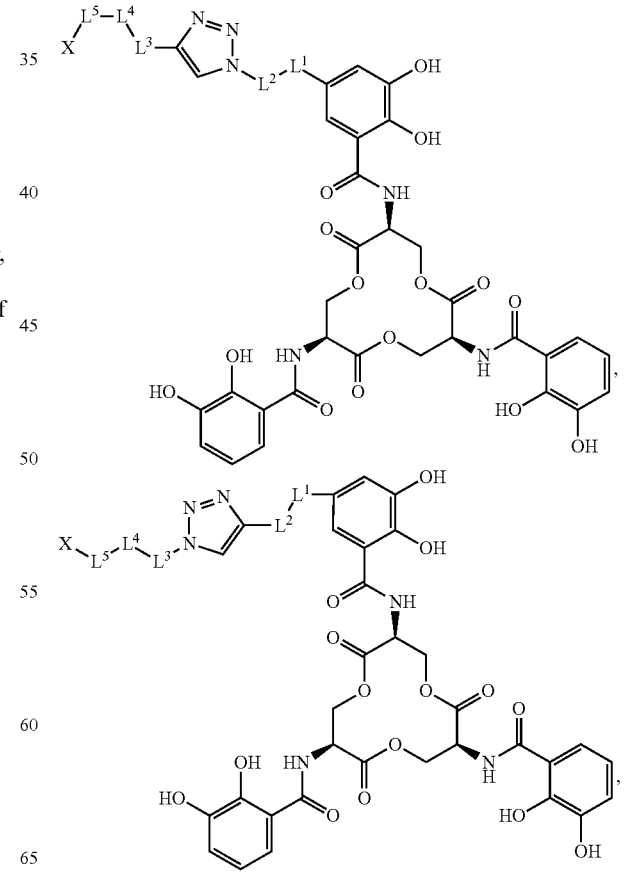

or a salt, hydrate, solvate, polymorph, co-crystal, tautomer, or isotopically labeled derivative thereof.

In certain embodiments, a compound of Formula (I) is of the formula:

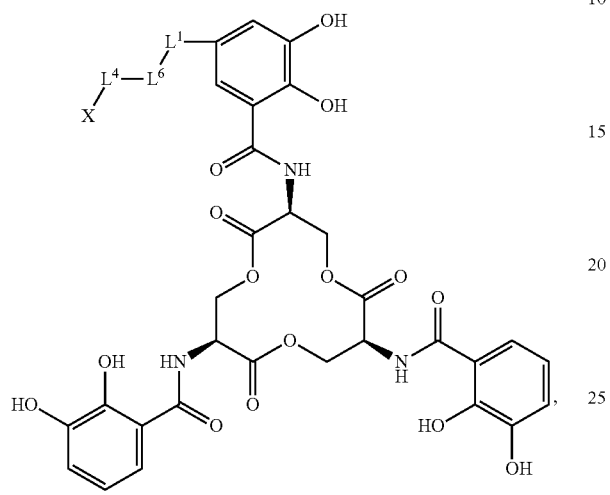

or a salt, hydrate, solvate, polymorph, co-crystal, tautomer, or isotopically labeled derivative thereof.

In certain embodiments, a compound of Formula (I) is of the formula:

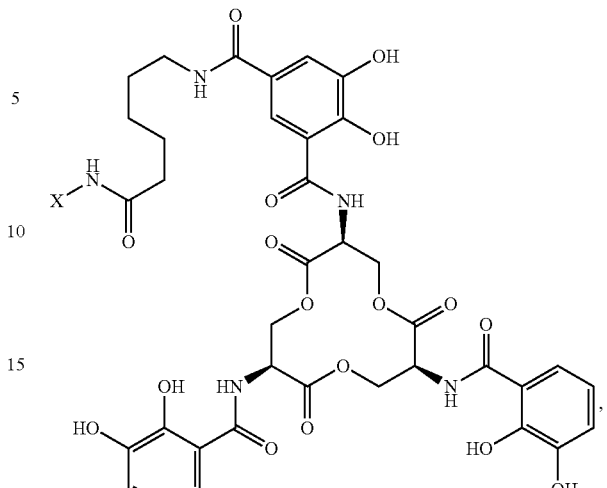

or a salt, hydrate, solvate, polymorph, co-crystal, tautomer, or isotopically labeled derivative thereof.

In certain embodiments, a compound of Formula (I) is of the formula:

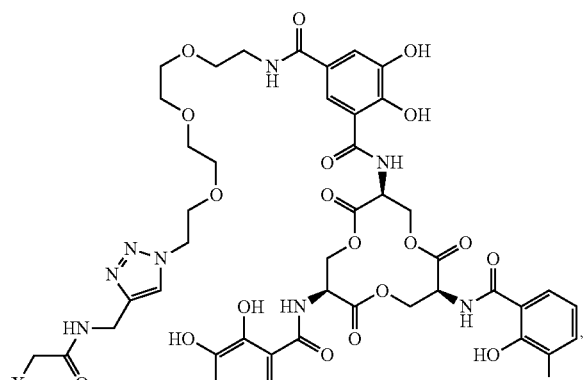

or a salt, hydrate, solvate, polymorph, co-crystal, tautomer, or isotopically labeled derivative thereof.

In certain embodiments, a compound of Formula (I) is of the formula:

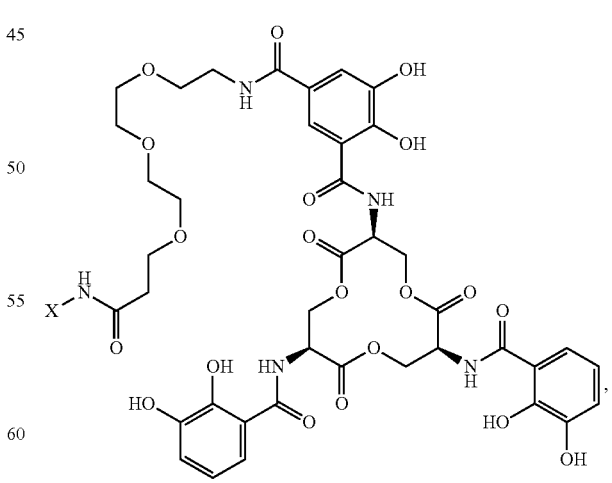

or a salt, hydrate, solvate, polymorph, co-crystal, tautomer, or isotopically labeled derivative thereof.

In certain embodiments, a compound of Formula (I) is of the formula:

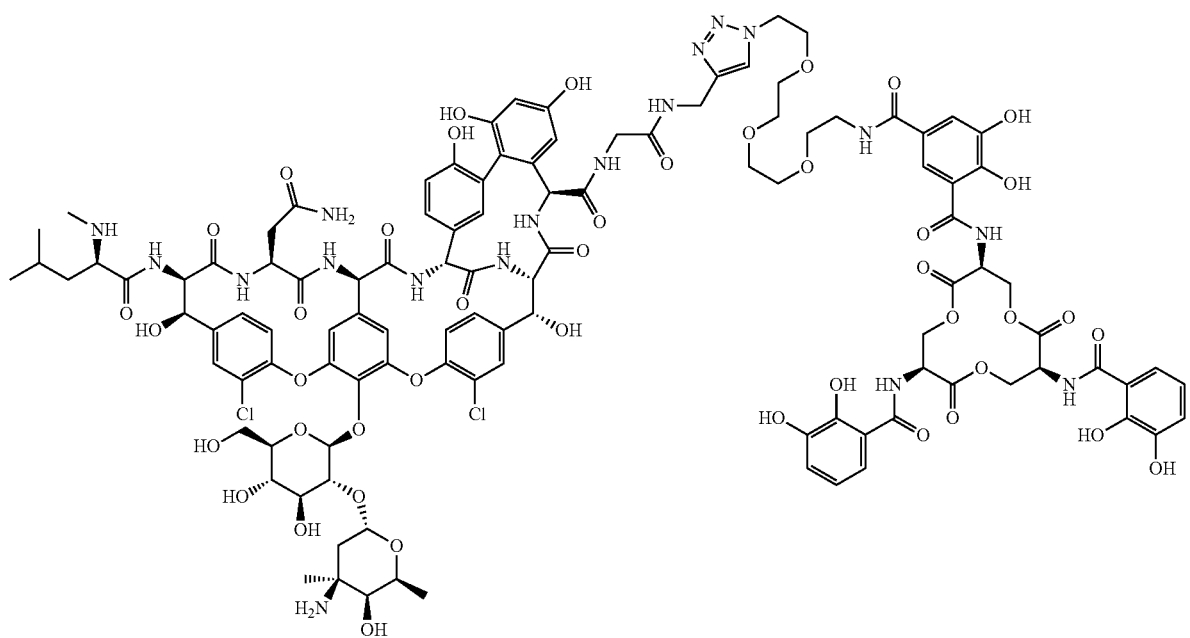
or a salt, hydrate, solvate, polymorph, co-crystal, tautomer, or isotopically labeled derivative thereof.
In certain embodiments, a compound of Formula (I) is of the formula:
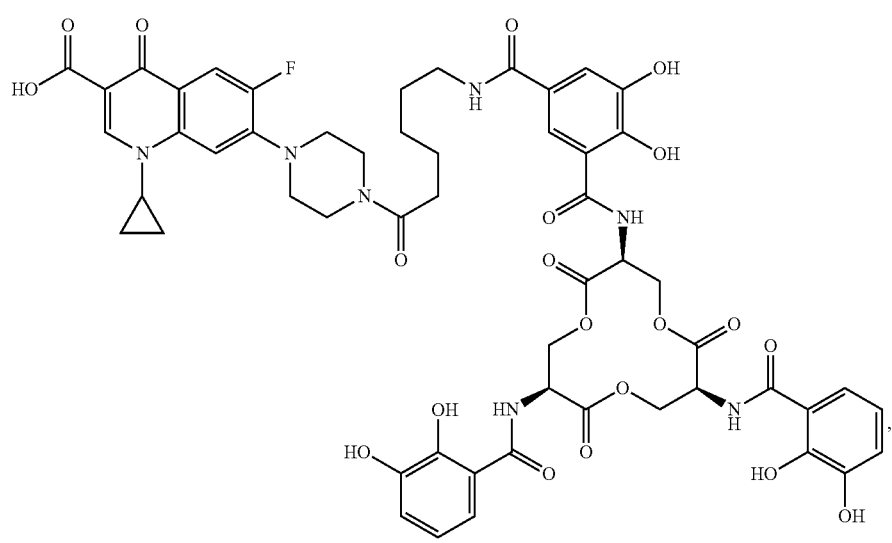

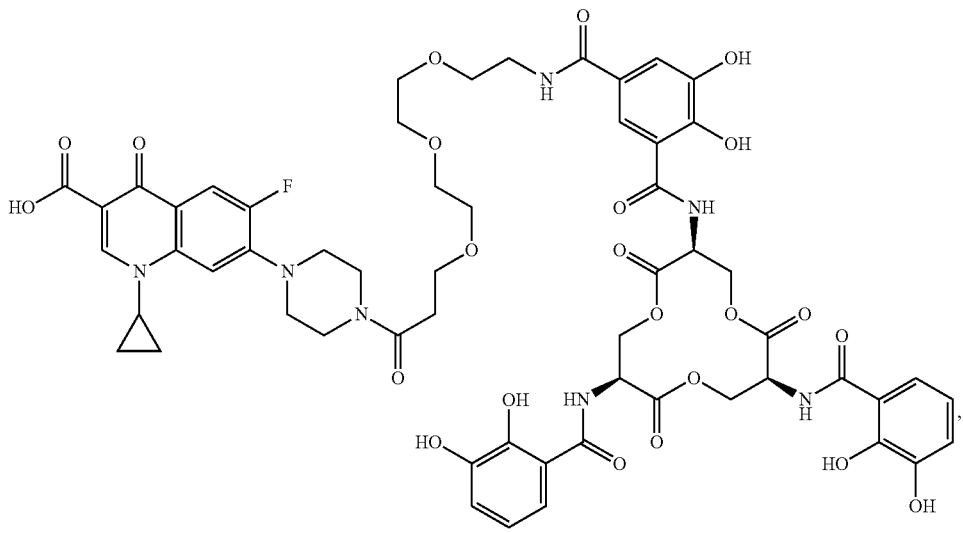

or a salt, hydrate, solvate, polymorph, co-crystal, tautomer, or isotopically labeled derivative thereof.

In certain embodiments, a compound of Formula (I) is of the formula:

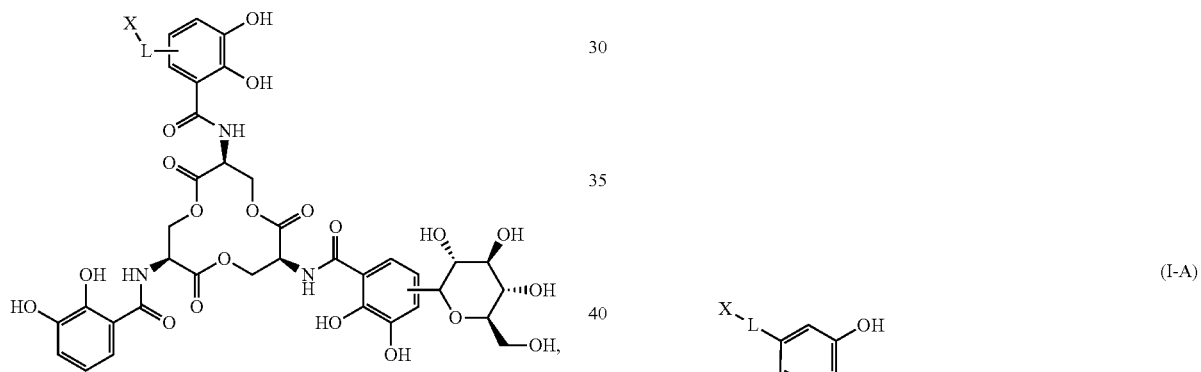

or a salt, hydrate, solvate, polymorph, co-crystal, tautomer, or isotopically labeled derivative thereof.

In certain embodiments, a compound of Formula (I) is of the formula:

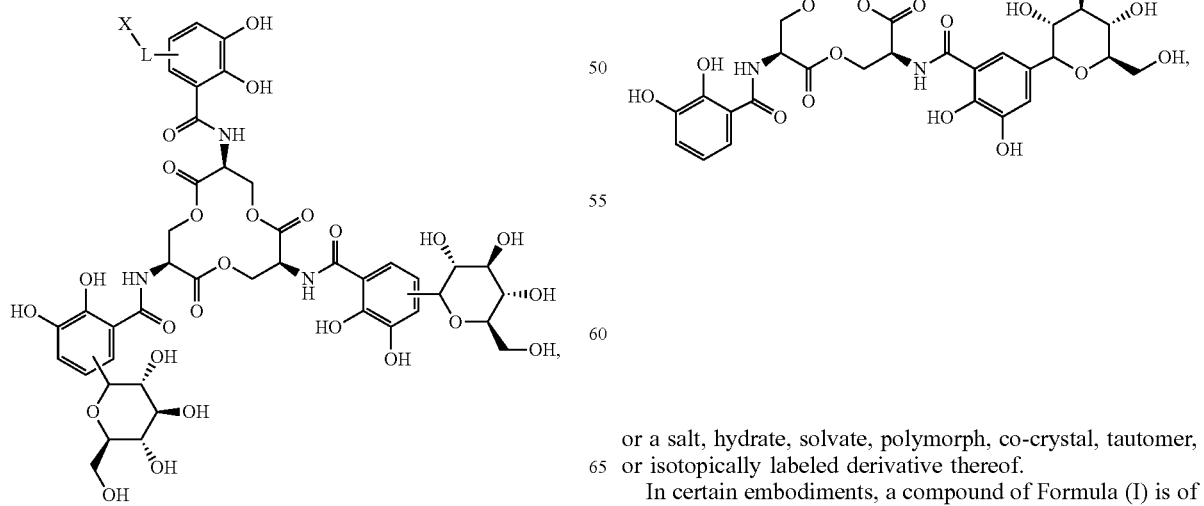

or a salt, hydrate, solvate, polymorph, co-crystal, tautomer, or isotopically labeled derivative thereof.

In certain embodiments, a compound of Formula (I) is of Formula (I-A):

(I-A)

or a salt, hydrate, solvate, polymorph, co-crystal, tautomer, or isotopically labeled derivative thereof.

In certain embodiments, a compound of Formula (I) is of Formula (I-B):

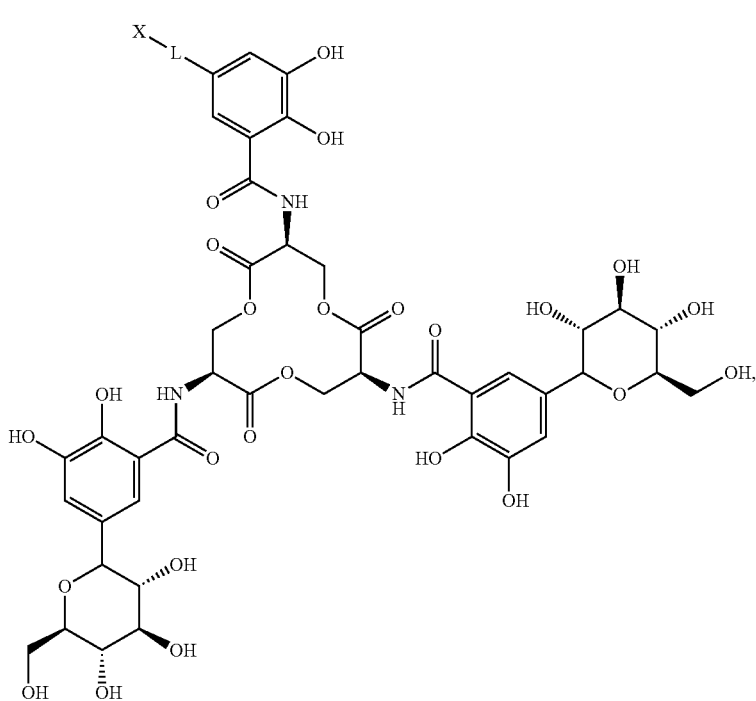

(I-B)

or a salt, hydrate, solvate, polymorph, co-crystal, tautomer, or isotopically labeled derivative thereof.

In certain embodiments, a compound of Formula (I) is of Formula (I-A) or (I-B), or a salt, hydrate, solvate, polymorph, co-crystal, tautomer, or isotopically labeled derivative thereof, wherein L is of the formula:

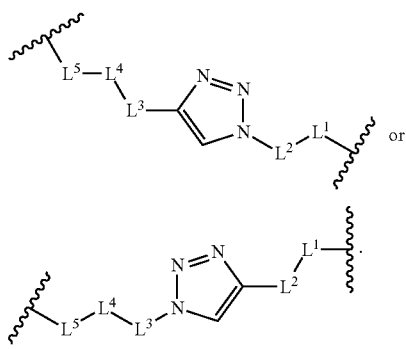

In certain embodiments, a compound of Formula (I) is of Formula (I-A) or (I-B), or a salt, hydrate, solvate, polymorph, co-crystal, tautomer, or isotopically labeled derivative thereof, wherein L is of the formula:

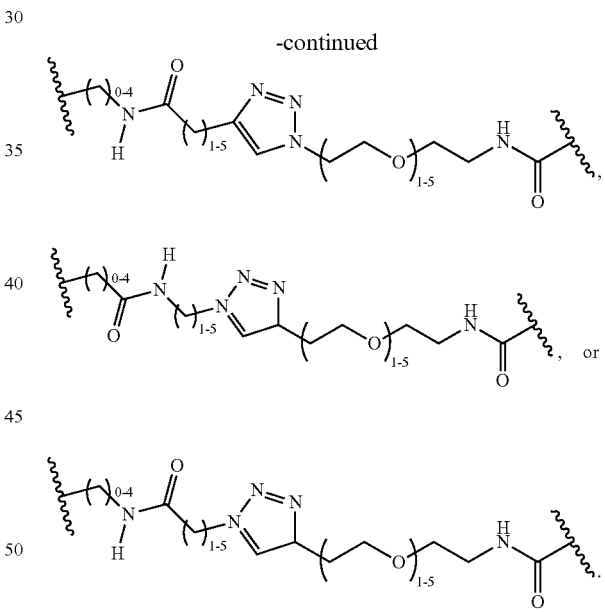

In certain embodiments, a compound of Formula (I) is of Formula (I-A) or (I-B), or a salt, hydrate, solvate, polymorph, co-crystal, tautomer, or isotopically labeled derivative thereof, wherein L is of the formula:

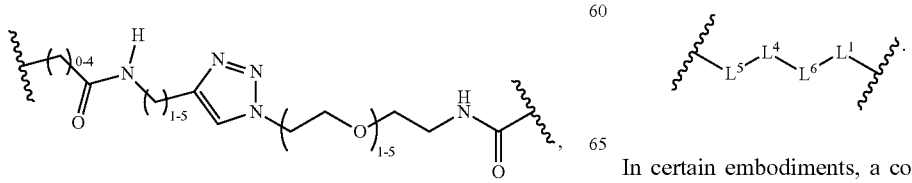

In certain embodiments, a compound of Formula (I) is of Formula (I-A) or (I-B), or a salt, hydrate, solvate, polymorph, co-crystal, tautomer, or isotopically labeled derivative thereof, wherein L is of the formula:

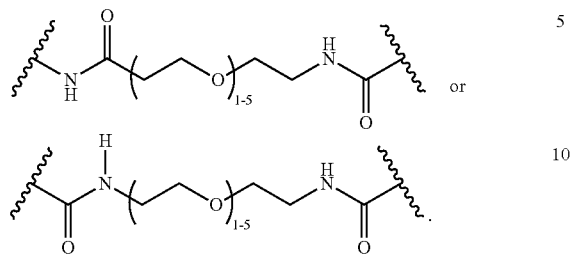

In certain embodiments, a compound of Formula (I) is MGE-Amp or MGE-Amx, or a salt, hydrate, solvate, polymorph, co-crystal, tautomer, or isotopically labeled derivative thereof.

In certain embodiments, a compound of Formula (I) is DGE-Amp or DGE-Amx, or a salt, hydrate, solvate, polymorph, co-crystal, tautomer, or isotopically labeled derivative thereof.

In certain embodiments, a compound of Formula (I) is not of the formula:

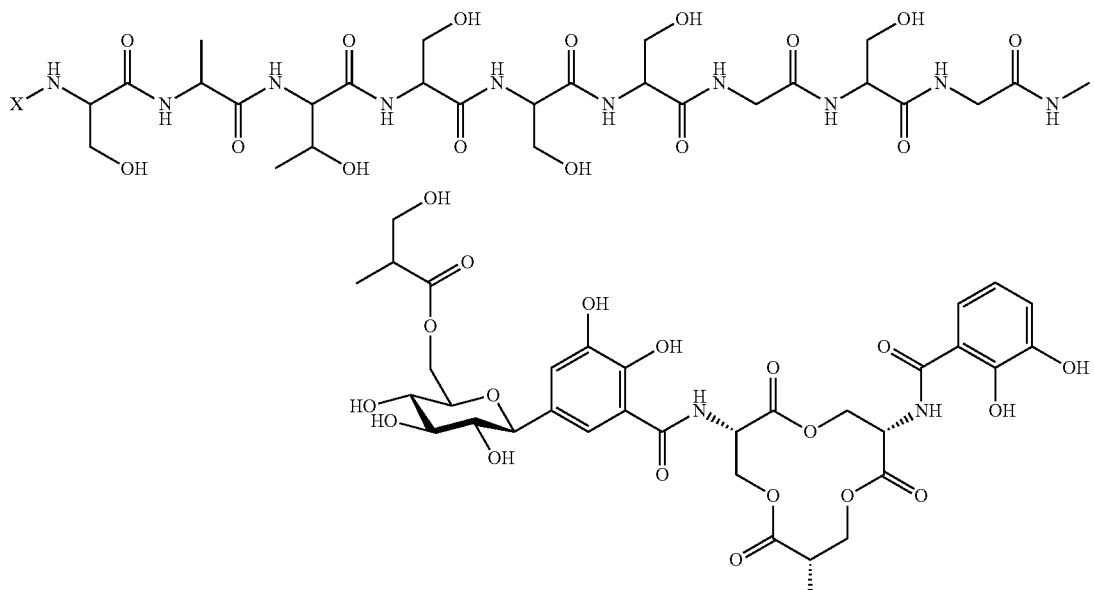

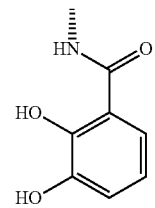

or a salt, hydrate, solvate, polymorph, co-crystal, tautomer, or isotopically labeled derivative thereof.

In certain embodiments, a compound of Formula (I) is not of the formula:

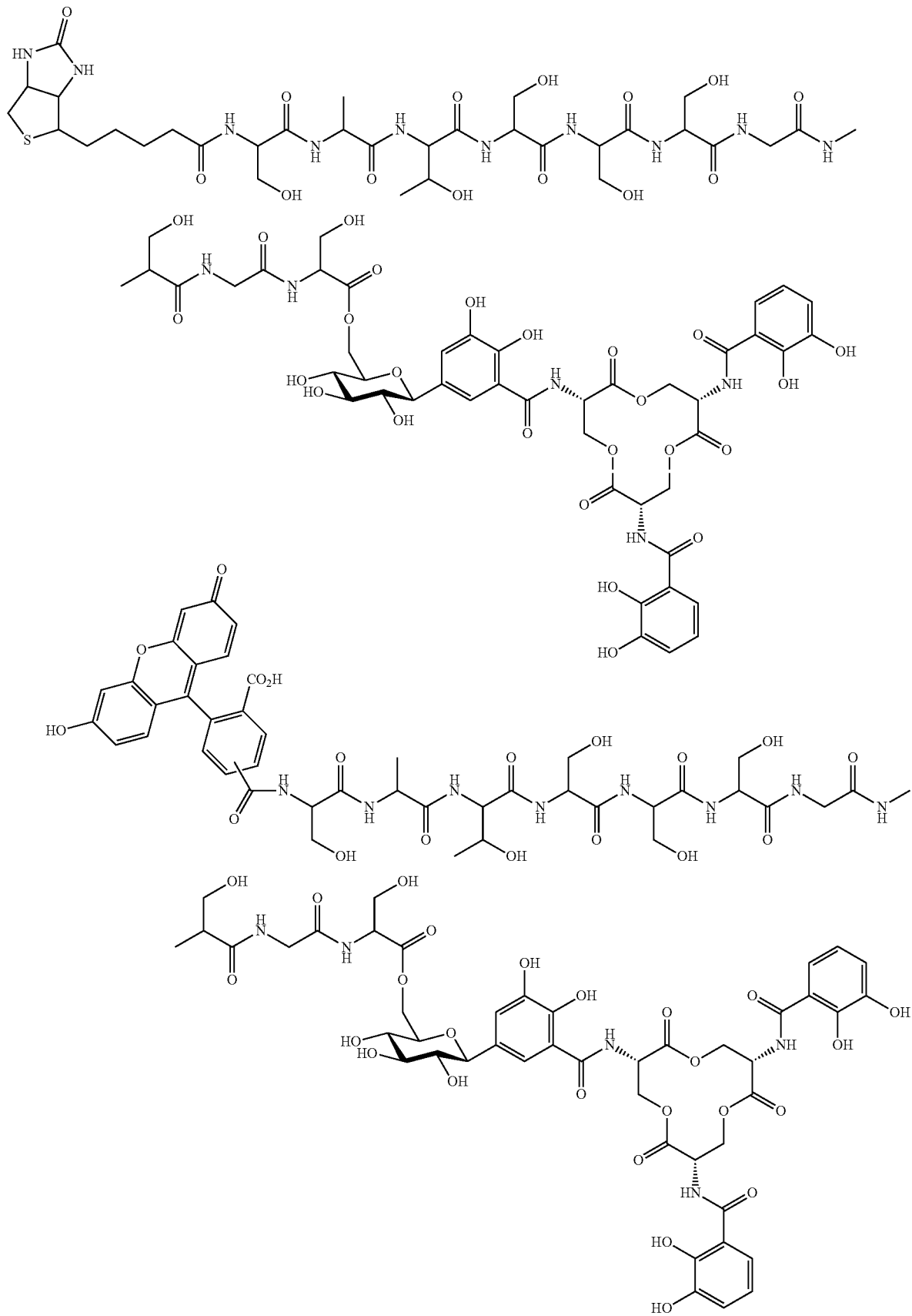

or a salt, hydrate, solvate, polymorph, co-crystal, tautomer, or isotopically labeled derivative thereof.

In certain embodiments, a compound of Formula (I) is not of the formula:

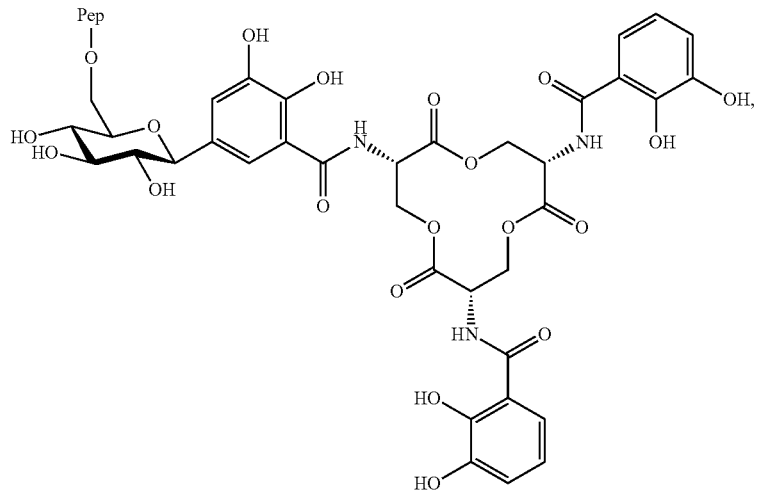

or a salt, hydrate, solvate, polymorph, co-crystal, tautomer, or isotopically labeled derivative thereof, wherein -Pep is a monovalent radical of a peptide of the sequence: GETD-PNTQLLNDLGNNMAWGAALGAPGGLGSAAL-GAAGGALQTVGQGLIDHGPVNVPIP VLIGPSWNGSSSGYNSATSSSGSGS (SEQ ID NO: 11), wherein the carbonyl moiety of the C-terminus of Pep- is attached to the oxygen atom at C6 of the glucose moiety.

Complexes

In another aspect, the present invention provides complexes comprising a compound of Formula (I), or a salt, hydrate, solvate, polymorph, co-crystal, tautomer, stereoisomer, or isotopically labeled derivative thereof, and iron or gallium. In certain embodiments, a complex of the invention consists essentially of a compound of the invention, and iron or gallium. In certain embodiments, the iron is Fe(III), e.g., a ferric salt or ferric ion. In certain embodiments, the iron is Fe(II), e.g., a ferrous salt or ferrous ion. In certain embodiments, the gallium is Ga(III), e.g., a Ga(III) salt or Ga(III) ion. In a complex of the invention, the molar ratio of the iron or gallium to the compound may be about 1:1. The iron or gallium may be associated (e.g., complexed) with the compound through non-covalent interactions (e.g., electrostatic interactions). In certain embodiments, in a complex of the invention, one catechol moiety of the compound forms at least one coordinate bond with iron or gallium. A complex of the invention may further comprise an anionic counterion. In certain embodiments, a complex of the invention is substantially electrically neutral. In certain embodiments, a complex of the invention consists of a compound of the invention, iron or gallium, and anionic counterion. In certain embodiments, a complex of the invention is a complex of Ent-Amp and Fe(III), a complex of Ent-Amx and Fe(III), a complex of MGE-Amp and Fe(III), a complex of MGE-Amx and Fe(III), a complex of DGE-Amp and Fe(III), or a complex of DGE-Amx and Fe(III).

The compounds of Formula (I) and complexes of the invention may be useful in delivering a cargo (e.g., an antibiotic, a fluorophore, or biotin (e.g., a moiety of the formula:

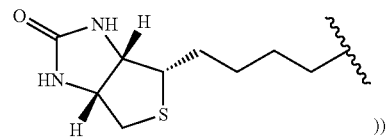 [SMILES: *CCCC[C@@H]1SC[C@@H]2NC(=O)N[C@@H]21]

into a bacterium. In certain embodiments, the compounds of Formula (I) and complexes of the invention are useful in delivering an antibiotic into a bacterium and are thus useful in treating a bacterial infection, cystic fibrosis, and/or inflammatory bowel disease (IBD) in a subject in need thereof, in preventing a bacterial infection, cystic fibrosis, and/or IBD in a subject in need thereof, in inhibiting the growth and/or reproduction of a bacterium, and/or in killing a bacterium. In certain embodiments, the compounds of Formula (I) and complexes of the invention are useful in delivering a fluorophore or biotin into a bacterium and are thus useful in determining the concentration of a bacterium in a biological sample.

The delivery of an antibiotic, fluorophore, or biotin to a bacterium may be characterized in various ways, such as the concentration or exposure of the antibiotic, fluorophore, or biotin. The concentration of the antibiotic, fluorophore, or biotin, and, when appropriate, metabolite(s) thereof, in a bacterium, may be measured as a function of time. The concentration of the antibiotic, fluorophore, or biotin in a bacterium may be determined by HPLC, LC/MS, fluorescence, and streptavidin- or avidin-binding analysis. In certain embodiments, the concentration of the antibiotic, fluorophore, or biotin is the total concentration of (1) a compound of Formula (I) or a complex of the invention; and (2) a fragment of a compound of Formula (I) or a complex of the invention, wherein the fragment includes the antibiotic, fluorophore, or biotin. The exposure of the antibiotic, fluorophore, or biotin in a bacterium may be defined as the area under the curve (AUC) of the concentration of the antibiotic, fluorophore, or biotin in the bacterium at certain point of time after contacting the bacterium with a compound of Formula (I) or a complex of the invention.

In some embodiments, the delivery of an antibiotic, fluorophore, or biotin into a bacterium increases when the bacterium is contacted with a compound of Formula (I) or a complex of the invention, compared with when the bacterium is contacted with the antibiotic, fluorophore, or biotin in the absence of a compound of Formula (I) or a complex of the invention. In some embodiments, a compound of Formula (I) or a complex of the invention increases the delivery of an antibiotic, fluorophore, or biotin to a bacterium by at least about 10%, at least about 20%, at least about 30%, at least about 40%, at least about 50%, at least about 100%, at least about 2-fold, at least about 3-fold, at least about 10-fold, at least about 30-fold, at least about 100-fold, at least about 300-fold, at least about 1000-fold, or at least about 10,000-fold.

A compound of Formula (I) or a complex of the invention may selectively deliver an antibiotic, fluorophore, or biotin into a bacterium. In certain embodiments, a compound of Formula (I) or a complex of the invention delivers more amount of the antibiotic, fluorophore, or biotin into a bacterial cell than into a non-bacterial cell. In certain embodiments, a compound of Formula (I) or a complex of the invention delivers more amount of the antibiotic, fluorophore, or biotin into a bacterium than into a different type of bacterium. In certain embodiments, the compositions deliver at least about 10%, at least about 20%, at least about 30%, at least about 40%, at least about 50%, at least about 70%, at least about 100%, at least about 3-fold, at least about 10-fold, at least about 30-fold, at least about 100-fold, at least about 300-fold, or at least about 1000-fold more amount of the antibiotic, fluorophore, or biotin into a bacterial cell than into a non-bacterial cell. In certain embodiments, the compositions deliver at least about 10%, at least about 20%, at least about 30%, at least about 40%, at least about 50%, at least about 70%, at least about 100%, at least about 3-fold, at least about 10-fold, at least about 30-fold, at least about 100-fold, at least about 300-fold, or at least about 1000-fold more amount of the antibiotic, fluorophore, or biotin into a bacterium than into a different type of bacterium. In certain embodiments, a compound of Formula (I) or a complex of the invention selectively delivers an antibiotic, fluorophore, or biotin into a Gram-negative bacterium.

In another aspect, the present invention provides compounds of Formula (A1) or (A2):

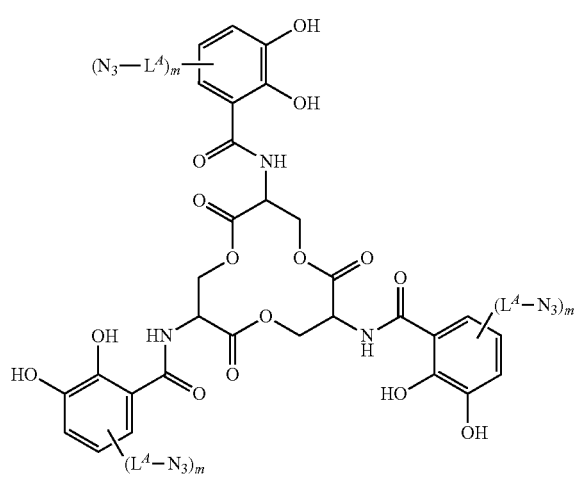

(A1)

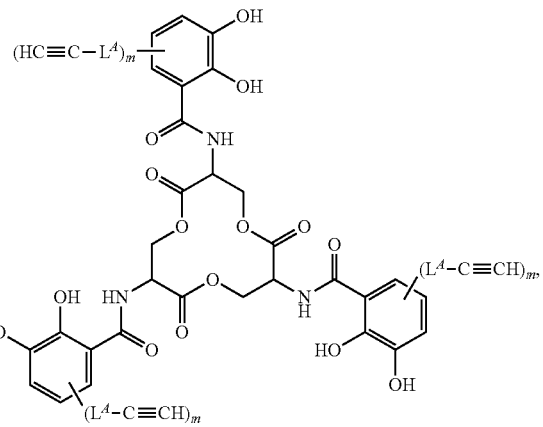

(A2)

or a salt, hydrate, solvate, polymorph, co-crystal, tautomer, stereoisomer, or isotopically labeled derivative thereof, wherein:

each instance of $L^A$ is independently a bond or substituted or unsubstituted $C_{1-17}$ hydrocarbon chain, optionally wherein one or more carbon units of the hydrocarbon chain are independently replaced with —O—, —S—, —NR$^{LA}$—, —S(=O)—, or —S(=O)$_2$—; and each instance of $R^{LA}$ is independently hydrogen, unsubstituted $C_{1-6}$ alkyl, $C_{1-6}$ alkyl substituted with at least one halogen, or a nitrogen protecting group; and one instance of m is 1, 2, or 3; and two instances of m are independently 0, 1, 2, or 3.

Compounds of Formula (A1) or (A2), and salts, hydrates, solvates, polymorphs, co-crystals, tautomers, stereoisomers, or isotopically labeled derivatives thereof, are useful in preparing compounds of Formula (I) and complexes of the invention. In certain embodiments, one instance of m is 1; and two instances of m are 0. In certain embodiments, one instance of m is 2 or 3; and two instances of m are 0. In certain embodiments, one instance of m is 0; and two instances of m are 1. In certain embodiments, all instance of m are 1. When two or more instances of m are independently 1, 2, or 3, the two or more $(N_3-L^A)_m$- moieties of a compound of Formula (A1) may be the same or different, and the two or more (HC≡C-$L^A$)$_m$- moieties of a compound of Formula (A2) may be the same or different. In certain embodiments, at least one instance of $L^A$ is -$L^{A2}$-$L^{A1}$-; each instance of $L^{A1}$ is independently —NR$^{LA1}$C(=O)— or —C(=O)NR$^{LA1}$—; each instance of $L^{A2}$ is independently unsubstituted $C_{1-50}$ alkylene or $C_{1-50}$ alkylene substituted with at least one halogen, optionally wherein one to six carbon units of the $C_{1-50}$ alkylene are replaced with —O—; and each instance of $R^{LA1}$ is independently hydrogen, unsubstituted $C_{1-6}$ alkyl, $C_{1-6}$ alkyl substituted with at least one halogen, or a nitrogen protecting group. In certain embodiments, each instance of $L^{A1}$ is independently —NHC(=O)— or —C(=O)NH—. In certain embodiments, each instance of $L^{A2}$ is independently —(CH$_2$CH$_2$O)$_{1-6}$—(CH$_2$CH$_2$)—. In certain embodiments, at least one instance of $L^{A2}$ is —(CH$_2$CH$_2$O)$_3$—(CH$_2$CH$_2$)—.

In certain embodiments, each instance of $L^{A2}$ is independently —(CH$_2$)$_{1-17}$—. In certain embodiments, at least one instance of $L^{A2}$ is —(CH$_2$)$_5$—.

In certain embodiments, the compound of Formula (A1) is of the formula:

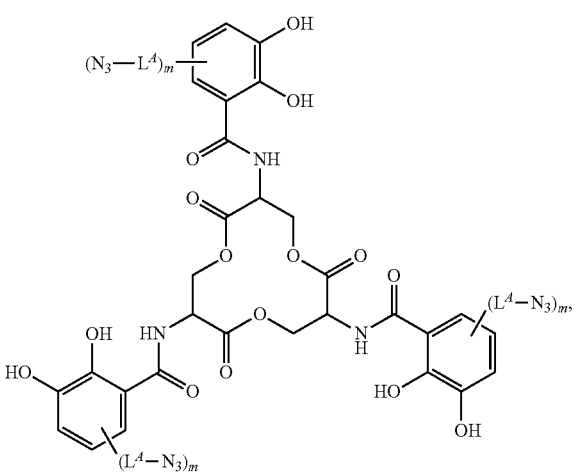

or a salt, hydrate, solvate, polymorph, co-crystal, tautomer, stereoisomer, or isotopically labeled derivative thereof, wherein:

each instance of $L^A$ is independently -$L^{A2}$-$L^{A1}$-;

each instance of $L^{A1}$ is independently —NR$^{LA1}$C(=O)— or —C(=O)NR$^{LA1}$—;

each instance of $L^{A2}$ is independently unsubstituted $C_{1-50}$ alkylene or $C_{1-50}$ alkylene substituted with at least one halogen, optionally wherein one to six carbon units of the $C_{1-50}$ alkylene are replaced with —O—; and each instance of R$^{LA1}$ is independently hydrogen, unsubstituted $C_{1-6}$ alkyl, $C_{1-6}$ alkyl substituted with at least one halogen, or a nitrogen protecting group.

In certain embodiments, the compound of Formula (A1) is compound 41, or a salt thereof. In certain embodiments, the compound of Formula (A1) is a stereoisomer of compound 41, or a salt thereof. In certain embodiments, the compound of Formula (A1) is the opposite enantiomer of compound 41, or a salt thereof.

In certain embodiments, the compound of Formula (A2) is of the formula:

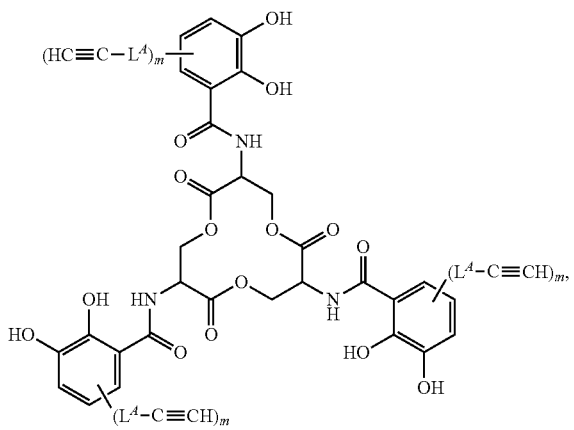

or a salt, hydrate, solvate, polymorph, co-crystal, tautomer, stereoisomer, or isotopically labeled derivative thereof, wherein:

each instance of $L^A$ is independently -$L^{A2}$-$L^{A1}$-;

each instance of $L^{A1}$ is independently —NR$^{LA1}$C(=O)— or —C(=O)NR$^{LA1}$—;

each instance of $L^{A2}$ is independently unsubstituted $C_{1-50}$ alkylene or $C_{1-50}$ alkylene substituted with at least one halogen, optionally wherein one to six carbon units of the $C_{1-50}$ alkylene are replaced with —O—; and each instance of R$^{LA1}$ is independently hydrogen, unsubstituted $C_{1-6}$ alkyl, $C_{1-6}$ alkyl substituted with at least one halogen, or a nitrogen protecting group.

Methods of Preparing Compounds of Formula (I) and Complexes of the Invention

Another aspect of the present invention relates to methods of preparing a compound of Formula (I), or a pharmaceutically acceptable salt, hydrate, solvate, polymorph, co-crystal, tautomer, stereoisomer, or isotopically labeled derivative thereof, the method comprising:

contacting a compound of Formula (A1), or a salt thereof, with a compound of Formula (B1), or a salt thereof, or contacting a compound of Formula (A2), or a salt thereof, with a compound of Formula (B2), or a salt thereof:

$$X\text{-}L^B\text{-}C\equiv CH \quad (B1)$$

$$X\text{-}L^B\text{-}N_3 \quad (B2),$$

wherein:

each instance of $L^B$ is independently a bond or substituted or unsubstituted $C_{1-17}$ hydrocarbon chain, optionally wherein one or more carbon units of the hydrocarbon chain are independently replaced with —O—, —S—, —NR$^{LB}$—, —S(=O)—, or —S(=O)$_2$—; and each instance of R$^{LB}$ is independently hydrogen, unsubstituted $C_{1-6}$ alkyl, $C_{1-6}$ alkyl substituted with at least one halogen, or a nitrogen protecting group.

In certain embodiments, all -L-X moieties of a compound of Formula (I), or a salt thereof, prepared by the inventive methods are the same. In certain embodiments, $L^B$ is —(CH$_2$)$_{1-4}$—NHC(=O)—(CH$_2$)$_{1-4}$—. In certain embodiments, $L^B$ is —(CH$_2$)$_{1-4}$—C(=O)NH—(CH$_2$)$_{1-4}$—.

Figure 10:
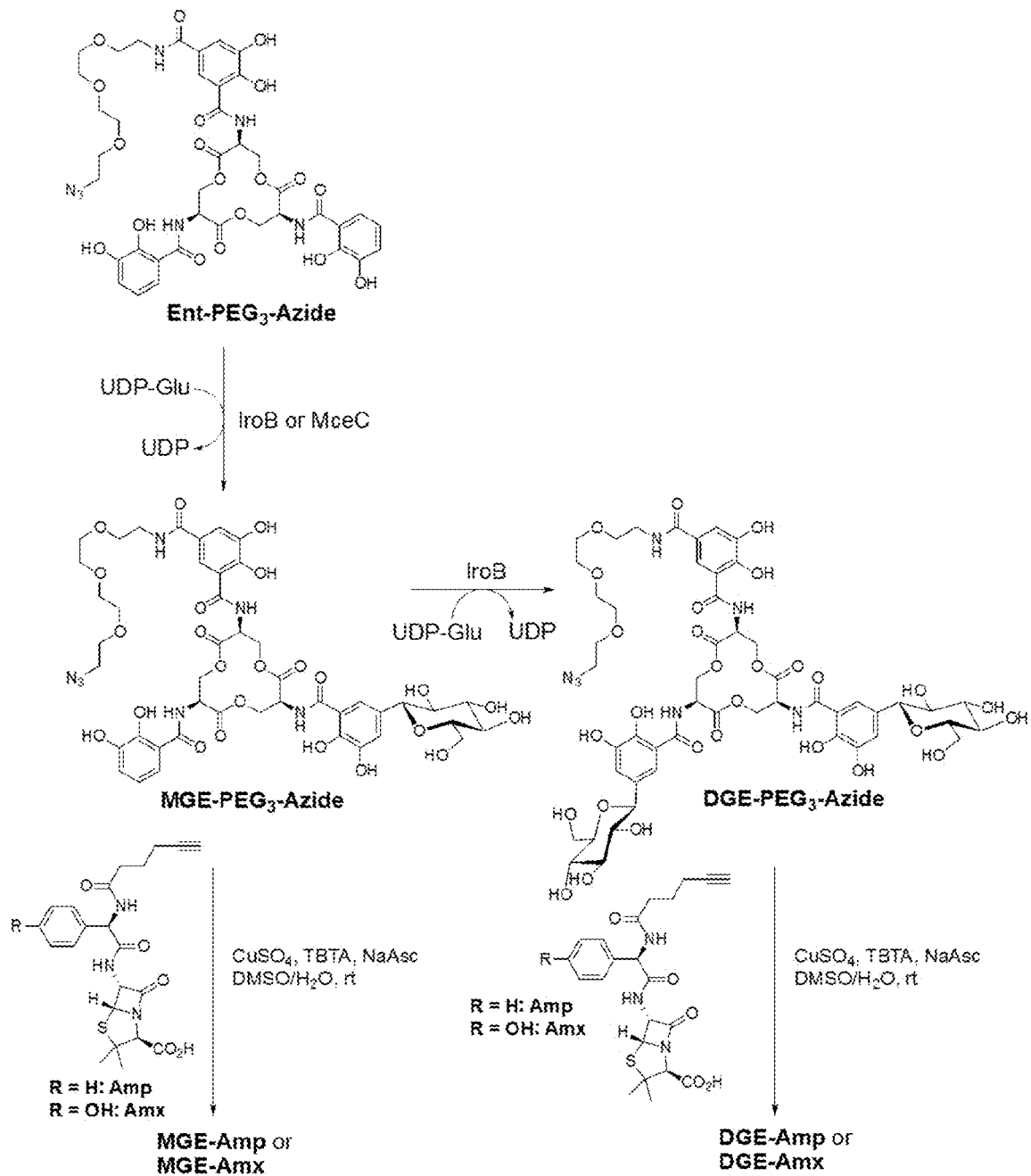
FIG. 10 shows an exemplary synthesis of MGE-Amp, MGE-Amx, DGE-Amp, and DGE-Amx.

Salmochelin-cargo conjugates described herein (e.g., MGE-Amp, MGE-Amx, DGE-Amp, and DGE-Amx) may be prepared by similar "click chemistry" described herein using azide intermediates and alkyne intermediates. See, e.g., FIG. 10. MGE-PEG$_3$-Azide and DGE-PEG$_3$-Azide intermediates may be synthesized from a precursor, enterobactin-PEG$_3$-Azide, using either IroB or MceC. MceC is a C-glucosyltransferase expressed by *Klebsiella pneumoniae* RYC492 and, like IroB, C-glucosylates enterobactin.

A conjugate described herein may be purified by semi-preparative HPLC and characterized by analytical HPLC, mass spectrometry, and optical absorption spectroscopy.

The present invention also provides methods of preparing a complex of the invention, the methods comprising contacting (e.g., complexing) a compound of the invention with an iron-containing substance (e.g., iron-containing inorganic compound or iron-containing organic compound) or a gallium-containing substance (e.g., gallium-containing inorganic compound or gallium-containing organic compound). In certain embodiments, the iron-containing substance is a ferric salt or ferrous salt. In certain embodiments, the gallium-containing substance is a Ga(III) salt.

Compositions, Kits, and Administration

The present invention provides compositions comprising a compound of Formula (I) (e.g., a compound of Formula (I), or a salt, hydrate, solvate, polymorph, co-crystal, tautomer, stereoisomer, or isotopically labeled derivative thereof) and/or a complex of the invention, and optionally an excipient. In certain embodiments, a composition of the invention comprises a compound of Formula (I), or a salt or stereoisomer thereof, and optionally an excipient. In certain embodiments, a composition of the invention comprises a compound of Formula (I), or a salt thereof, and an excipient. In certain embodiments, a composition of the invention further comprises an iron chelator. In certain embodiments, a composition of the invention further comprises iron (e.g., Fe(III)). In certain embodiments, a composition of the invention further comprises an iron chelator and iron (e.g., Fe(III)). In certain embodiments, a composition of the invention further comprises gallium (e.g., Ga(III)). In certain embodiments, a composition of the invention comprises a complex of the invention, and optionally an excipient. In certain embodiments, a composition of the invention is a pharmaceutical composition. In certain embodiments, a pharmaceutical composition of the invention comprises a compound of Formula (I), or a pharmaceutically acceptable salt, hydrate, solvate, polymorph, co-crystal, tautomer, stereoisomer, or isotopically labeled derivative thereof, and optionally a pharmaceutically acceptable excipient. In certain embodiments, a pharmaceutical composition of the invention comprises a compound of Formula (I), or a pharmaceutically acceptable salt or stereoisomer thereof, and optionally a pharmaceutically acceptable excipient. In certain embodiments, a pharmaceutical composition of the invention comprises a compound of Formula (I), or a pharmaceutically acceptable salt thereof, and a pharmaceutically acceptable excipient. In certain embodiments, a pharmaceutical composition of the invention further comprises an iron chelator. In certain embodiments, a pharmaceutical composition of the invention further comprises iron (e.g., Fe(III)). In certain embodiments, a pharmaceutical composition of the invention further comprises an iron chelator and iron (e.g., Fe(III)). In certain embodiments, a pharmaceutical composition of the invention further comprises gallium (e.g., Ga(III)). In certain embodiments, a pharmaceutical composition of the invention comprises a complex of the invention, and optionally a pharmaceutically acceptable excipient.

In certain embodiments, the compound of Formula (I) or complex of the invention is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a bacterial infection (e.g., a bacterial infection described herein). In certain embodiments, the effective amount is an amount effective for preventing a bacterial infection. In certain embodiments, the effective amount is an amount effective for treating an infection caused by a Gram-negative bacterium (e.g., a Gram-negative bacterium described herein). In certain embodiments, the effective amount is an amount effective for preventing an infection caused by a Gram-negative bacterium. In certain embodiments, the effective amount is an amount effective for determining the concentration of a bacterium in a biological sample. In certain embodiments, the effective amount is an amount effective for detecting the presence of a bacterium in a biological sample. In certain embodiments, the effective amount is an amount effective for treating cystic fibrosis. In certain embodiments, the effective amount is an amount effective for preventing cystic fibrosis. In certain embodiments, the effective amount is an amount effective for treating inflammatory bowel disease (IBD). In certain embodiments, the effective amount is an amount effective for preventing IBD.

An effective amount of a compound or complex may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An effective amount of a compound of Formula (I) or complex of the invention may be an amount effective for inhibiting the growth and/or reproduction of a bacterium or killing a bacterium. In certain embodiments, the effective amount is an amount effective for inhibiting the growth or reproduction of a bacterium or killing a bacterium by at least about 10%, at least about 20%, at least about 30%, at least about 40%, at least about 50%, at least about 60%, at least about 70%, at least about 80%, or at least about 90%. In certain embodiments, the growth or reproduction of a bacterium is inhibited by a percentage described herein by an effective amount of a compound of Formula (I) or a complex of the invention.

Pharmaceutical compositions described herein can be prepared by any method known in the art of pharmacology. In general, such preparatory methods include the steps of bringing the compound of Formula (I) or complex of the invention (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound or complex of this invention may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound or complex in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds and complexes provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds, complexes, and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound, complex, or pharmaceutical composition of the invention is suitable for topical administration to the eye of a subject.

The exact amount of a compound or complex required to achieve an effective amount will vary from subject to subject, depending, for example, on species, age, and general condition of a subject, severity of the side effects or disorder, identity of the particular compound or complex, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound or complex for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound or complex per unit dosage form.

In certain embodiments, the compounds of Formula (I) or complex of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound, complex, or composition, as described herein, can be administered in combination with one or more additional agents (e.g., pharmaceutical agents (e.g., therapeutically and/or prophylactically active agents) or diagnostic agents (e.g., imaging agents). The compounds, complexes, or compositions can be administered in combination with additional agents that improve their activity (e.g., potency and/or efficacy) in treating a bacterial infection, cystic fibrosis, and/or IBD in a subject in need thereof, in preventing a bacterial infection, cystic fibrosis, and/or IBD in a subject in need thereof, in inhibiting the growth and/or reproduction of a bacterium, and/or in killing a bacterium, bioavailability, and/or safety, reduce drug resistance, reduce and/or modify their metabolism, inhibit their excretion, and/or modify their distribution within the body of a subject. It will also be appreciated that the therapy employed may achieve a desired effect for the same disorder, and/or it may achieve different effects. In certain embodiments, an inventive composition including a compound of Formula (I) or complex of the invention, and an additional agent, shows a synergistic effect that is absent in a composition including one of the compound or complex, and the additional agent, but not both.

The compound, complex, or composition can be administered concurrently with, prior to, or subsequent to one or more additional agents, which may be useful as, e.g., combination therapies. Additional agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional agent is a pharmaceutical agent useful in treating a bacterial infection, cystic fibrosis, and/or IBD, in preventing a bacterial infection, cystic fibrosis, and/or IBD in a subject in need thereof, in inhibiting the growth and/or reproduction of a bacterium, and/or in killing a bacterium. Each additional agent may be employed (e.g., administered) at a dose and/or on a time schedule determined for that agent. The additional agents may also be employed together with each other and/or with the compound, complex, or composition described herein in a single dose or employed separately in different doses. The particular combination to employ in a regimen will take into account compatibility of the compound of Formula (I) or complex of the invention with the additional agent(s) and/or the desired effect (e.g., therapeutic and/or prophylactic effect) to be achieved. In general, it is expected that the additional agent(s) utilized in combination be utilized at levels that do not exceed the levels at which they are utilized individually. In some embodiments, the levels utilized in combination will be lower than those utilized individually.

In certain embodiments, the additional agent is a pharmaceutical agent. Additional pharmaceutical agents include, but are not limited to, anti-bacterial agents, anti-viral agents, anti-proliferative agents, anti-cancer agents, anti-angiogenesis agents, anti-inflammatory agents, immunosuppressants, anti-diabetic agents, anti-allergic agents, pain-relieving agents, and iron chelators. In certain embodiments, the additional pharmaceutical agent is an antibiotic. In certain embodiments, the additional pharmaceutical agent is an antibiotic effective against a Gram-negative bacterium. In certain embodiments, the additional pharmaceutical agent is an antibiotic effective against a Gram-positive bacterium. In certain embodiments, the additional pharmaceutical agent is a β-lactam antibiotic. In certain embodiments, the additional pharmaceutical agent is a penicillin (i.e., a penam, such as an aminopenicillin (e.g., amoxicillin, an ampicillin (e.g., pivampicillin, hetacillin, bacampicillin, metampicillin, talampicillin), epicillin), a carboxypenicillin (e.g., a carbenicillin (e.g., carindacillin), ticarcillin, temocillin), a ureidopenicillin (e.g., azlocillin, piperacillin, mezlocillin), a mecillinam (e.g, pivmecillinam), sulbenicillin, benzylpenicillin, clometocillin, benzathine benzylpenicillin, procaine benzylpenicillin, azidocillin, penamecillin, phenoxymethylpenicillin, propicillin, benzathine phenoxymethylpenicillin, pheneticillin, a cloxacillin (e.g., dicloxacillin, flucloxacillin), oxacillin, methicillin, nafcillin), a penem (e.g., faropenem), a carbapenem (e.g., biapenem, ertapenem, an antipseudomonal (e.g., doripenem, imipenem, meropenem), panipenem), a cephalosporin (i.e., a cephem, such as cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, a cephamycin (e.g, cefoxitin, cefotetan, cefmetazole), a carbacephem (e.g., loracarbef), cefixime, ceftriaxone, an antipseudomonal (e.g., ceftazidime, cefoperazone), cefcapene, cefdaloxime, cefdinir, cefditoren, cefetamet, cefmenoxime, cefodizime, cefotaxime, cefpimizole, cefpiramide, cefpodoxime, cefsulodin, cefteram, ceftibuten, ceftiolene, ceftizoxime, an oxacephem (e.g., flomoxef, latamoxef), cefepime, cefozopran, cefpirome, cefquinome, ceftobiprole, ceftaroline fosamil, ceftiofur, cefquinome, cefovecin), a monobactam (e.g., aztreonam, tigemonam, carumonam, nocardicin A), an aminoglycoside (e.g., amikacin, gentamicin, kanamycin, neomycin, netilmicin, tobramycin, paromomycin, spectinomycin), an ansamycin (e.g., geldanamycin, herbimycin, rifaximin), a glycopeptide (e.g., teicoplanin, vancomycin, telavancin), a lincosamide (e.g., clindamycin, lincomycin), a lipopeptide (e.g., daptomycin), a macrolide (e.g., azithromycin, clarithromycin, dirithromycin, erythromycin, roxithromycin, troleandomycin, telithromycin, spiramycin), a nitrofuran (e.g., furazolidone, nitrofurantoin), an oxazolidonone (e.g., linezolid, posizolid, radezolid, torezolid), a polypeptide (e.g., bacitracin, colistin, polymyxin B), a quinolone (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin), a sulfonamide (e.g., mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim, sulfonamidochrysoidine), a tetracycline (e.g., demeclocycline, doxycycline, minocycline, oxytetracycline, tetracycline), clofazimine, dapsone, capreomycin, cycloserine, ethambutol, ethionamide, isoniazid, pyrazinamide, rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, or trimethoprim. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the compounds of Formula (I), complexes, or compositions of the invention, can be administered in combination with an anti-cancer therapy including, but not limited to, surgery, radiation therapy, and chemotherapy. In certain embodiments, the additional agent is an iron chelator (e.g., 2,2'-dipyridyl, desferrioxamine (DFO, Desferal®), deferasirox (Exjade®), deferiprone (L1, Ferriprox®), Feralex-G, $CaNa_3DTPA$, dexrazoxane, a phosphorothioate-oligonucleotide, desferrithiocin, desazadesferrithiocin, or a derivative thereof). In certain embodiments, the additional agent is a Fe(III) chelator. In certain embodiments, the additional agent is a Fe(II) chelator. In certain embodiments, the additional agent is an iron-containing substance (e.g., iron-containing inorganic compound or iron-containing organic compound) or a gallium-containing substance (e.g., gallium-containing inorganic compound or gallium-containing organic compound). In certain embodiments, the additional agent is a ferric salt. In certain embodiments, the additional agent is a ferrous salt. In certain embodiments, the additional agent is a Ga(III) salt.

Also encompassed by the invention are kits (e.g., pharmaceutical packs). The kits provided may comprise a compound of Formula (I), complex, or composition (e.g., pharmaceutical or diagnostic composition) of the invention, and a container (e.g., a vial, ampule, bottle, syringe, and/or dispenser package, or other suitable container). In some embodiments, provided kits may optionally further include a second container comprising an excipient (e.g., pharmaceutically acceptable excipient) for dilution or suspension of an inventive compound, complex, or composition. In some embodiments, the compound of Formula (I), complex, or composition provided in the first container and the second container are combined to form one unit dosage form.

Thus, in one aspect, the present invention provides kits including a first container comprising a compound of Formula (I), or a salt, solvate, hydrate, polymorph, co-crystal, tautomer, stereoisomer, or isotopically labeled derivative thereof, a complex, or a composition of the invention. In certain embodiments, a provide kit includes a first container comprising a compound of Formula (I), or a salt or stereoisomer thereof, a complex, or a composition of the invention. In certain embodiments, a provide kit includes a first container comprising a compound of Formula (I), or a pharmaceutically acceptable salt thereof, a complex, or a pharmaceutical composition of the invention.

In certain embodiments, the kits are useful in treating and/or preventing a bacterial infection (e.g., a bacterial infection described herein) in a subject in need thereof. In certain embodiments, the bacterial infection is an infection caused by a Gram-negative bacterium. In certain embodiments, the kits are useful in inhibiting the growth and/or reproduction of a bacterium (e.g., a Gram-negative bacterium). In certain embodiments, the kits are useful in killing a bacterium (e.g., a Gram-negative bacterium). In certain embodiments, the kits are useful in determining the concentration of a bacterium in a biological sample. In certain embodiments, the kits are useful in treating and/or preventing cystic fibrosis. In certain embodiments, the kits are useful in treating and/or preventing IBD. In certain embodiments, the kits are useful for screening a library of compounds and/or complexes to identify a compound or complex that is useful in the methods of the invention. In certain embodiments, the kits further include instructions for using the kit (e.g., for administering to a subject in need of treatment and/or prevention of a bacterial infection, cystic fibrosis, and/or IBD a compound of Formula (I), complex, or composition of the invention, or for contacting a bacterium with a compound of Formula (I), complex, or composition of the invention). The kits may also include information as required by a regulatory agency such as the U.S. Food and Drug Administration (FDA). In certain embodiments, the information included in the kits is prescribing information. In certain embodiments, the kits and instructions provide for treating and/or preventing a bacterial infection in a subject in need thereof. In certain embodiments, the kits and instructions provide for treating and/or preventing cystic fibrosis in a subject in need thereof. In certain embodiments, the kits and instructions provide for treating and/or preventing IBD in a subject in need thereof. In certain embodiments, the kits and instructions provide for inhibiting the growth and/or reproduction of a bacterium. In certain embodiments, the kits and instructions provide for killing a bacterium. In certain embodiments, the kits and instructions provide for determining the concentration of a bacterium in a biological sample. In certain embodiments, the kits and instructions provide for screening a library of compounds and/or complexes to identify a compound or complex that is useful in the methods of the invention. The kit of the invention may include one or more additional agents described herein as a separate composition.

Methods of Use

Another aspect of the present invention relates to methods of using the compounds and complexes of the invention, which are enterobactin-cargo conjugates, and compositions of the invention, in pharmaceutical and non-pharmaceutical applications.

Enterobactin (Ent, 1, FIG. 1A) is a canonical siderophore biosynthesized by Gram-negative species of Enterobacteriaceae that include *Escherichia coli* (*E. coli*), *Salmonella*, and *Klebsiella*.[22] Decades of exploration pertaining to enterobactin biosynthesis and coordination chemistry, in addition to investigations of the proteins involved in its cellular transport and processing, provide a detailed molecular and physiological understanding of how this chelate contributes to bacterial iron homeostasis and colonization.[22] The enterobactin synthetase is comprised of four proteins, EntBDEF, and is responsible for the production of enterobactin from L-serine and 2,3-dihydroxybenzoic acid (DHB).[23] Following biosynthesis, Ent is exported into the extracellular space where it scavenges Fe(III). Enterobactin coordinates Fe(III) by its three catecholate groups with $K_a \sim 10^{49}$ $M^{-1}$.[24] In *E. coli*, the outer membrane transporter FepA (and to a lesser extent Cir and Fiu) recognizes and binds ferric enterobactin with sub-nanomolar affinity,[25,26] and provides periplasmic entry where the siderophore forms a complex with the periplasmic binding protein FepB.[27] Subsequently, $[Fe(Ent)]^{3-}$ is transported into the cytosol, which requires the action of ExbBD, TonB, and FepCDG, the latter of which constitute the inner-membrane ATP-binding cassette (ABC) transporter system (FIG. 1B).[28-32] Fes, the cytosolic enterobactin esterase, catalyzes the hydrolysis of the $[Fe(Ent)]^{3-}$ macrolactone,[33] and the ferric reductase YqjH may subsequently assist in Fe(III) release such that the metal ion can be used metabolically.[34] Several pathogenic Gram-negative species harbor gene clusters (e.g., iroA, MccE492) responsible for post-assembly line modifications of the enterobactin scaffold to provide the salmochelins.[33,35-38]

Figure 1A:
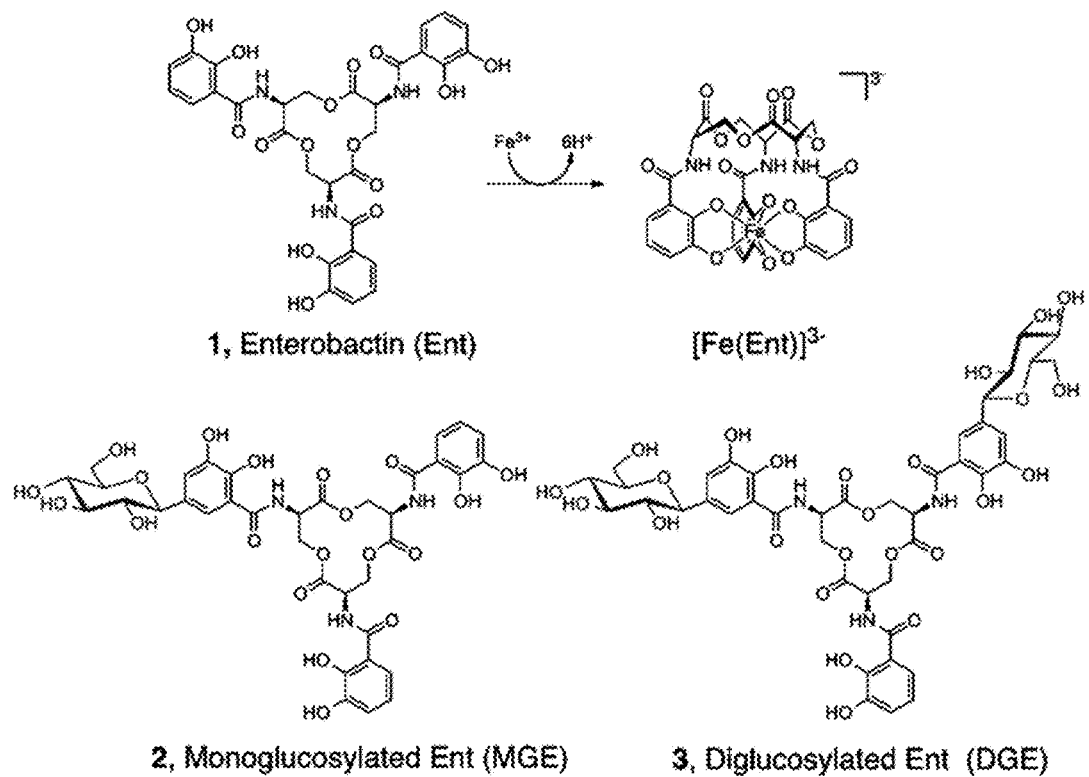
FIGS. 1A and 1B is an unlimited example and shows exemplary siderophores and siderophore transport machinery.
Figure 1B:
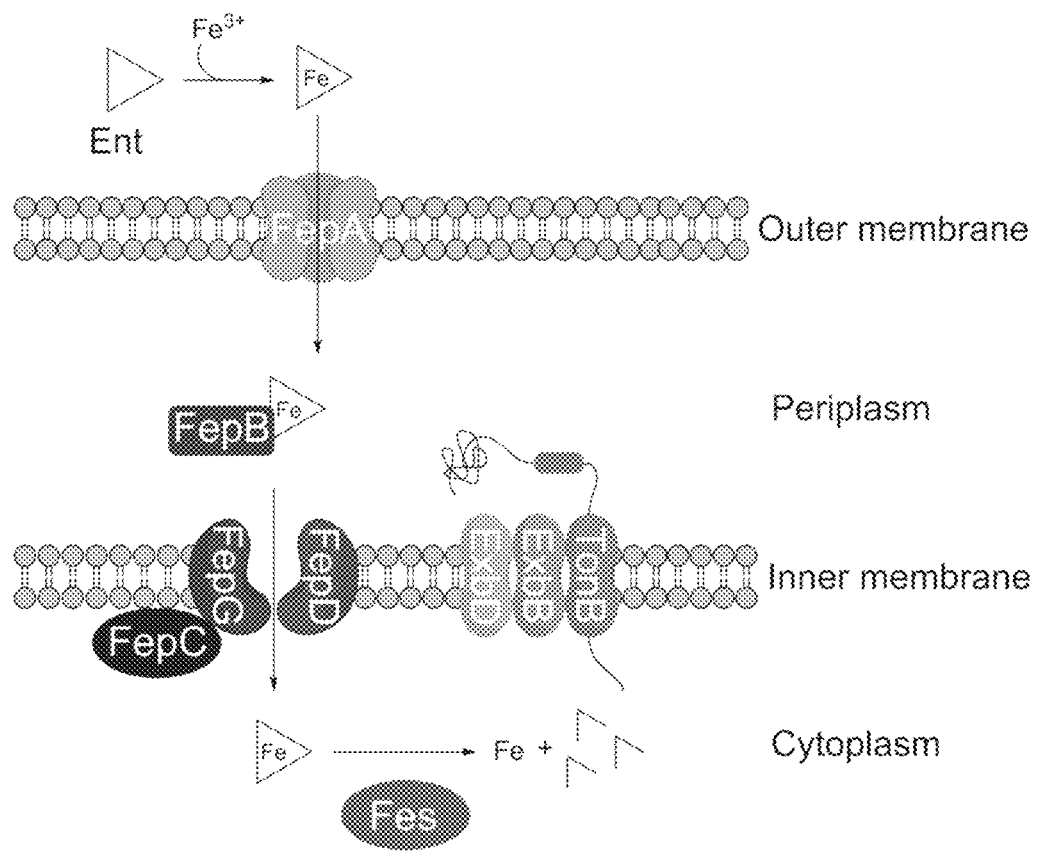
Figure 7:
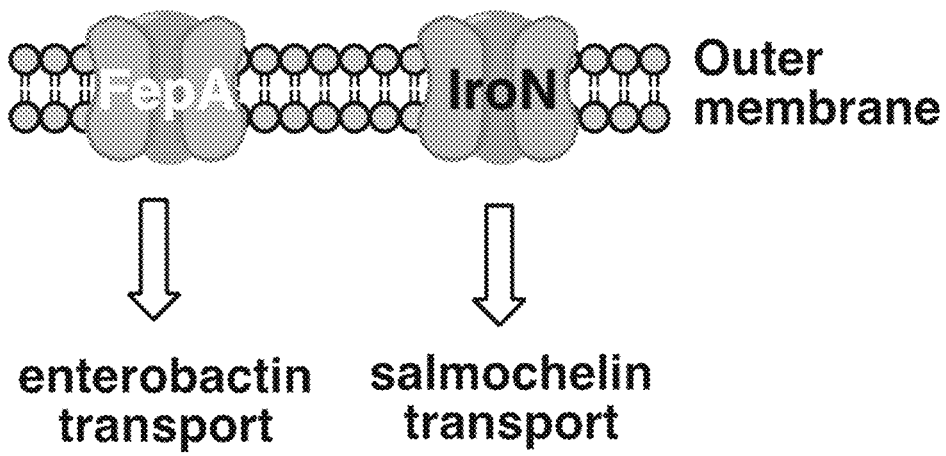
FIG. 7 is an exemplary cartoon showing the outer membrane receptors FepA and IroN. FepA is the enterobactin transporter and it is utilized by non-pathogenic and pathogenic bacterial strains. IroN is the salmochelin transporter and it is only expressed by pathogenic strains such as $E.$ $coli$ CFT073 (uropathogen) and $Salmonella$ spp. (food-borne pathogen) that harbor the iroA gene cluster. Targeting IroN therefore provides a means to target pathogenicity.
Figure 8:
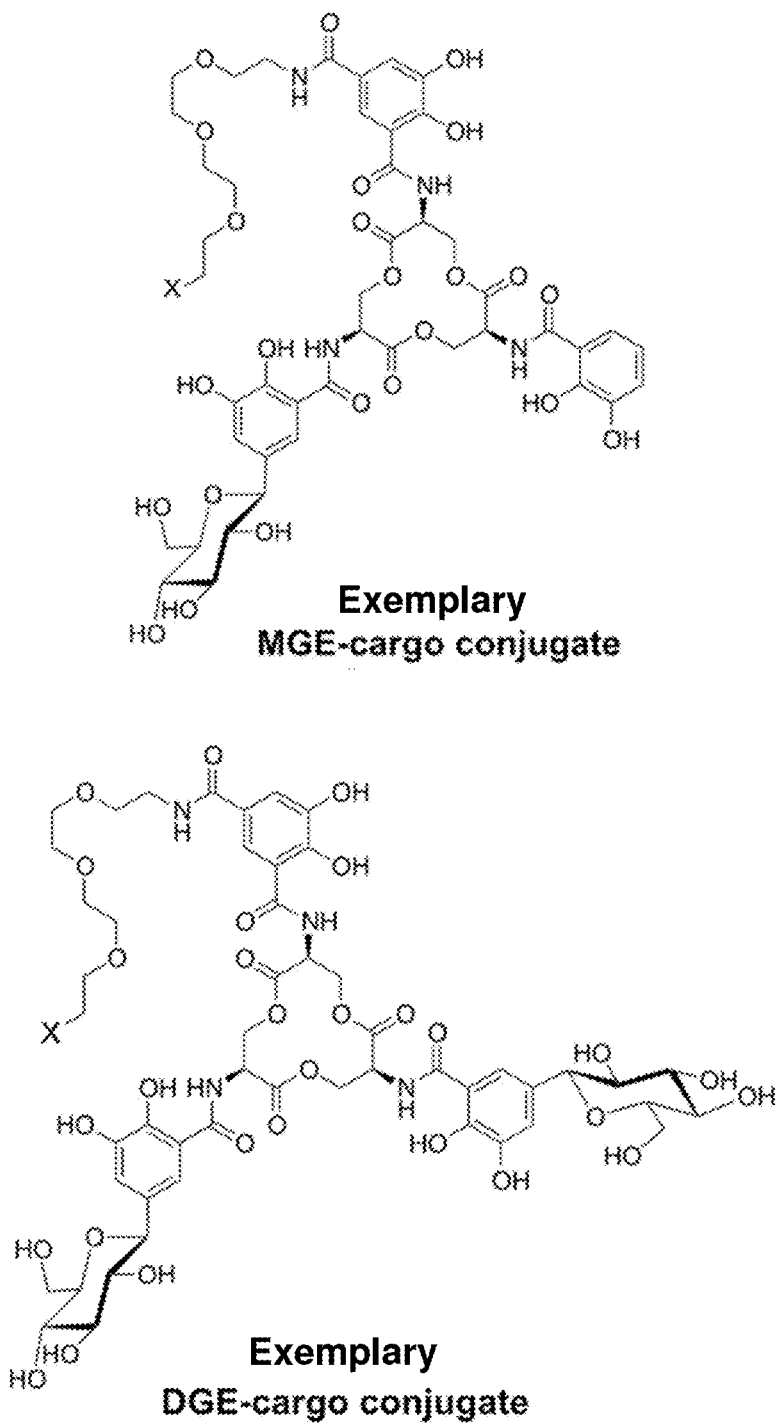
FIG. 8 shows the generalized chemical structures of exemplary antibiotic-salmochelin conjugates: exemplary MGE-cargo conjugates and exemplary DGE-cargo conjugates, based on the current design strategy (where X is a cargo). The catechol hydroxy groups may be the iron-binding groups.
Figure 9:
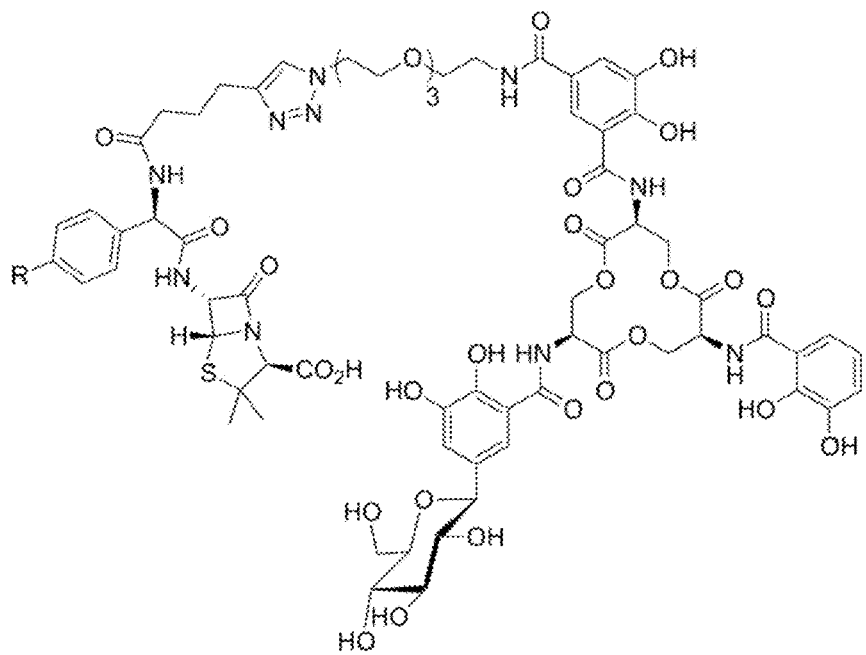
FIG. 9 shows the chemical structures of exemplary antibiotic-salmochelin conjugates: MGE-Amp, MGE-Amx, DGE-Amp, and DGE-Amx. Ampicillin (Amp) and amoxicillin (Amx) are β-lactam antibiotics that have periplasmic targets and inhibit cell wall biosynthesis. The catechol hydroxy groups may be the iron-binding groups.
Figure 9:
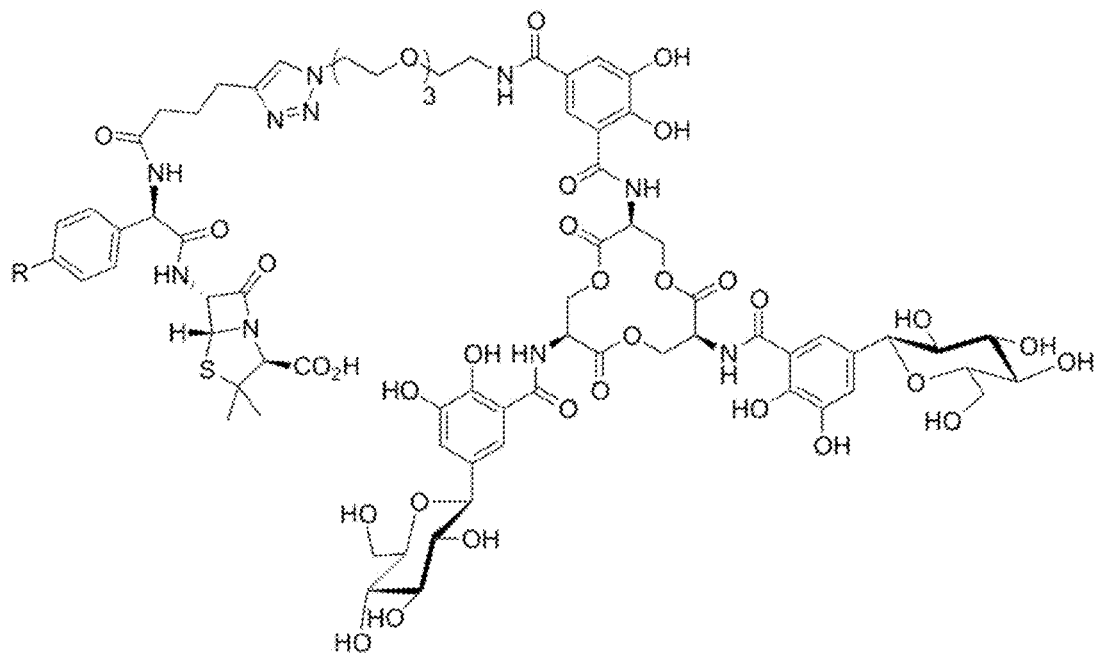

Salmochelins are a family of glucosylated enterobactin derivatives where the sugar moieties are attached to the C5 position of one or more catecholate rings (e.g., compounds 2 (MGE) and 3 (DGE), FIG. 1A).[39] A cartoon of the salmochelin uptake machinery is provided in FIG. 7. Many pathogenic strains have the capacity to biosynthesize salmochelins, C-glucosylated analogs of enterobactin. Many biological and animal studies have demonstrated that salmochelin biosynthesis and acquisition are essential for the establishment of infection in mouse models of infection. Thus, salmochelin-antibiotic conjugates may be useful to human disease and bacterial pathogenesis. Salmochelins harbor the iroA gene cluster (iroBCDEN). This gene cluster contains genes encoding enterobactin modification enzymes (IroBDE) and transport machinery (IroCN). IroB is a C-glucosyltransferase that attaches a glucose moiety to one or more of the enterobactin catechol rings via a C-glucosidic bond to afford salmochelins. IroB is expressed by *Salmonella* spp. and certain pathogenic *E. coli* strains, such as *E. coli* CFT073. IroN is the outer membrane receptor for the salmochelins. Similar to FepA, IroN allows the transport of ferric salmochelins (and also ferric enterobactin) into the bacterial cell. In certain embodiments, a salmochelin-cargo conjugate described herein is delivered to an intracellular space (e.g., a cytoplasm or periplasm) via IroN (used by pathogens) and not FepA (used by commensals and pathogens).

The salmochelins are virulence factors. In addition to providing the pathogens with additional siderophores for iron acquisition, the salmochelins allow pathogens to subvert the host innate immune response. Lipocalin-2 (lcn2) is a host protein that is released by neutrophils and epithelial cells at sites of infection. This protein captures ferric enterobactin (low-nanomolar affinity) and thereby prevents enterobactin-utilizing bacteria from acquiring iron via this siderophore. Enterobactin can also bind gallium (e.g., Ga(III)) and be imported. In contrast, lcn2 cannot capture the salmochelins because the glucose moieties are bulky and prevent lcn2 binding, and also confer increase hydrophilicity to the siderophore scaffold (the lcn2 binding pocket is hydrophobic). Therefore, a salmochelin-cargo conjugate may be targeted to pathogenic bacterium and leave the commensals unaffected. For example, a salmochelin-antibiotic conjugate described herein (e.g., a compound of Formula (I), wherein at least one instance of X is an antibiotic, and at least one instance of L is of the formula:

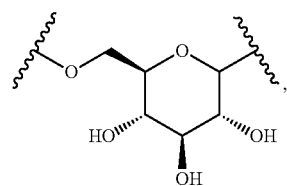 [SMILES: *OC[C@H]1OC(*)[C@H](O)[C@@H](O)[C@@H]1O]

or a complex comprising such a compound, and iron or gallium) may be able to selectively inhibit a first bacterium that expresses the salmochelin receptor IroN over a second bacterium that does not express the IroN. An unlimiting example of the first bacterium is a pathogenic *E. coli* strain (e.g., uropathogenic *E. coli* CFT073), and an unlimiting example of the second bacterium is a non-pathogenic *E. coli* strain (e.g., *E. coli* K-12, which lacks the iroA cluster and cannot utilize salmochelins).

Gram-negative bacteria have an outer membrane that serves as a permeability barrier and prevents cellular entry of many molecules, including antibiotics (e.g., vancomycin). Siderophore uptake machinery provides one route to overcome this permeability barrier,[6-14] and enterobactin and its transporter FepA have been identified as a desirable siderophore/receptor pair for cargo delivery to Gram-negative bacterial species.[13,37] FepA-mediated uptake of the ribosomal peptide antibiotics colicin B[40] and MccE492m,[41] in addition to bacteriophage,[42] indicates that this receptor has the capacity to transport large molecules. Moreover, the catecholate siderophore transporters of *E. coli* (e.g., Fiu, Cir) recognize synthetic catechol-modified β-lactam antibiotics;[43-46] these serendipitous observations motivated early "Trojan horse" delivery strategies. Indeed, small-molecule antibiotics appended to siderophore-inspired di- and tricatecholate platforms have been evaluated for antibacterial activity with mixed results.[47-51] Most recently, amoxicillin and ampicillin, β-lactam antibiotics that act in the periplasm and target bacterial cell wall biosynthesis, were covalently linked to a tripodal catecholate platform and remarkably afforded ca. $10^2$- to $10^3$-fold enhanced activity against *P. aeruginosa* PAO1 compared to the free drug.[49]

Certain antibiotics, such as β-lactams, have periplasmic targets and form covalent adducts with penicillin binding proteins (PBPs) involved in cell wall biosynthesis. Without wishing to be bound by any particular theory, a compound or complex of the invention, wherein at least one instance of X is an antibiotic (e.g., a β-lactam) may be captured by PBPs in the periplasm. Such compounds include, but are not limited to, Ent-Amp and Ent-Amx, and salts, hydrates, solvates, polymorphs, co-crystals, tautomers, stereoisomers, and isotopically labeled derivatives thereof.

The ability of FepABCDG and the TonB-ExbB-ExbD system of *E. coli*, as well as the enterobactin transport machinery of other bacterial species, to recognize and provide cytosolic transport of unnatural cargo appended to the native ligand remains unexplored. Enterobactin exhibits $C_3$ symmetry and houses no unique functional group for site-specific synthetic modification. Total syntheses of enterobactin,[52-56] hydrolytically stable enterobactin analogs,[57-60] and salmochelins[61] have been reported. However, no enterobactin scaffold housing a site-specific synthetic handle has been presented. Such scaffolds are a pre-requisite for employing enterobactin in a variety of paradigms that include cargo delivery, iron detection, gallium detection, siderophore detection, and bacterial capture.

In one aspect, the present invention provides methods of delivering a cargo (e.g., an antibiotic, a fluorophore, or biotin) to a bacterium (e.g., to the intracellular space (e.g., the cytoplasm or periplasm) of a bacterium) using a compound of Formula (I) or complex of the invention (which is an enterobactin-cargo conjugate), or a composition (e.g., a pharmaceutical composition or diagnostic composition) of the invention. In certain embodiments, the inventive methods include contacting a bacterium with a compound of Formula (I), or a salt, hydrate, solvate, polymorph, co-crystal, tautomer, stereoisomer, or isotopically labeled derivative thereof, a complex, or a composition of the invention. In certain embodiments, the cargo is delivered to the bacterium (e.g., to the intracellular space (e.g., the cytoplasm or periplasm) of the bacterium) by the inventive methods.

In certain embodiments, the bacterium is a Gram-negative bacterium. In certain embodiments, the bacterium is a pathogenic Gram-negative bacterium. In certain embodiments, the Gram-negative bacterium is a Gram-negative bacterium described herein. In certain embodiments, the Gram-negative bacterium is an *Escherichia* species. In certain embodiments, the Gram-negative bacterium is an *Escherichia coli* (*E. coli*) strain (e.g., ATCC 33475, K-12, CFT073, ATCC 43895). In certain embodiments, the Gram-negative bacterium is a pathogenic *E. coli* strain. In certain embodiments, the Gram-negative bacterium is a uropathogenic *E. coli* strain (e.g., *E. coli* CFT073). In certain embodiments, the Gram-negative bacterium is a non-pathogenic *E. coli* strain (e.g., *E. coli* K-12). In certain embodiments, the Gram-negative bacterium is not a non-pathogenic *E. coli* strain (e.g., *E. coli* K-12). In certain embodiments, the Gram-negative bacterium is an *Escherichia albertii* strain, *Escherichia blattae* strain, *Escherichia fergusonii* strain, *Escherichia hermannii* strain, or *Escherichia vulneris* strain.

In certain embodiments, the Gram-negative bacterium is a *Pseudomonas* species. In certain embodiments, the Gram-negative bacterium is a *Pseudomonas aeruginosa* (*P. aeruginosa*) strain (e.g., PAO1, ATCC 10145, CCUG 551, CFBP 2466, CIP 100720, DSM 50071, JCM 5962, LMG 1242, NBRC 12689, NCCB 76039, NCIMB 8295, NCTC 10332, NRRL B-771, VKM). In certain embodiments, the Gram-negative bacterium is *Pseudomonas aeruginosa* PAO1. In certain embodiments, the Gram-negative bacterium is a *Pseudomonas alcaligenes* strain, *Pseudomonas anguilliseptica* strain, *Pseudomonas argentinensis* strain, *Pseudomonas borbori* strain, *Pseudomonas citronellolis* strain, *Pseudomonas flavescens* strain, *Pseudomonas mendocina* strain, *Pseudomonas nitroreducens* strain, *Pseudomonas oleovorans* strain, *Pseudomonas pseudoalcaligenes* strain, *Pseudomonas resinovorans* strain, *Pseudomonas straminea* strain, *Pseudomonas chlororaphis* strain, *Pseudomonas fluorescens* strain, *Pseudomonas pertucinogena* strain, *Pseudomonas putida* strain, *Pseudomonas stutzeri* strain, or *Pseudomonas syringae* strain.

In certain embodiments, the Gram-negative bacterium is a *Klebsiella* species. In certain embodiments, the Gram-negative bacterium is a *Klebsiella granulomatis* strain, *Klebsiella oxytoca* strain, *Klebsiella pneumoniae* strain, *Klebsiella terrigena* strain, or *Klebsiella planticola* strain.

In certain embodiments, the Gram-negative bacterium is a *Salmonella* species. In certain embodiments, the Gram-negative bacterium is a *Salmonella bongori* strain or *Salmonella enterica* strain, e.g., *Salmonella typhi*.

In certain embodiments, the Gram-negative bacterium is an *Acinetobacter* species.

In certain embodiments, the Gram-negative bacterium is an *Acinetobacter baumannii* strain, *Acinetobacter baylyi* strain, *Acinetobacter bouvetii* strain, *Acinetobacter calcoaceticus* strain, *Acinetobacter gerneri* strain, *Acinetobacter grimontii* strain, *Acinetobacter haemolyticus* strain, *Acinetobacter johnsonii* strain, *Acinetobacter junii* strain, *Acinetobacter lwoffii* strain, *Acinetobacter parvus* strain, *Acinetobacter pittii* strain, *Acinetobacter radioresistens* strain, *Acinetobacter schindleri* strain, *Acinetobacter tandoii* strain, *Acinetobacter tjernbergiae* strain, *Acinetobacter towneri* strain, *Acinetobacter ursingii* strain, or *Acinetobacter gyllenbergii* strain.

In certain embodiments, the Gram-negative bacterium is resistant to an antibiotic. In certain embodiments, the Gram-negative bacterium is resistant to an antibiotic described herein. In certain embodiments, the Gram-negative bacterium is resistant to a β-lactam antibiotic. In certain embodiments, the Gram-negative bacterium is resistant to more than one antibiotics.

In certain embodiments, the bacterium described herein (e.g., a Gram-negative bacterium) is in vivo. In certain embodiments, the bacterium is in vitro. In certain embodiments, the bacterium is ex vivo.

An compound of Formula (I), complex, composition, or method of the invention may improve or increase the delivery of a cargo described herein to a bacterium. In certain embodiments, the delivery of the cargo to the bacterium by a compound of Formula (I), complex, composition, or method of the invention is increased compared to the delivery of the cargo to the bacterium in the absence of a compound of Formula (I), complex, or composition, or method of the invention.

The delivery of a cargo described herein into a bacterium may be characterized in various ways, such as the concentration and/or exposure of the cargo in the bacterium. Concentration of a cargo, and, when appropriate, of its metabolite(s), in bacterium, may be measured as a function of time. The concentration of the cargo in a bacterium may be determined by a fluorescence, chromatography, or mass spectroscopy analysis, blotting, or a combination thereof. In certain embodiments, when at least one instance of X is a fluorophore, the concentration of the cargo in a bacterium is determined by a fluorescence analysis.

The exposure of a cargo in a bacterium may be defined as the area under the curve (AUC) of the concentration of the cargo in the bacterium after contacting a compound of Formula (I) or complex of the invention with the bacterium. In general, an increase in exposure may be calculated by taking the difference in the AUC measured in a bacterium between those of a compound of Formula (I), complex, or composition of the invention, and a control compound, complex, or composition, and dividing the difference by the exposure of the control compound, complex, or composition. Exposure of a cargo may be measured in an appropriate animal model.

In some embodiments, the delivery of the cargo into a bacterium increases due to the presence of the enterobactin moiety and/or the L moiety in a compound of Formula (I) or a complex of the invention. In some embodiments, a compound, complex, composition, or method of the invention increase the delivery of the cargo into a bacterium by at least about 1-fold, at least about 3-fold, at least about 10-fold, at least about 30-fold, at least about 100-fold, at least about 300-fold, at least about 1,000-fold, at least about 3,000-fold, or at least about 10,000-fold.

After being delivered into a bacterium, a cargo may detach from a compound of Formula (I) or a complex of the invention to which the cargo attaches before being delivered into the bacterium. In certain embodiments, a cargo detaches from the compound of Formula (I) or a complex of the invention because at least one instance of L is hydrolyzed under intracellular conditions into at least moieties A and B, wherein: moiety A is not connected to moiety B; the cargo is directly or indirectly connected to moiety A; and the enterobactin moiety of the compound of Formula (I) or complex of the invention is directly or indirectly connected to moiety B. In other embodiments, after being delivered into a bacterium, a cargo does not detach from a compound of Formula (I) or complex of the invention to which the cargo attaches before being delivered into the bacterium.

In another aspect, the present invention provides methods of treating a bacterial infection, cystic fibrosis, or inflammatory bowel disease (IBD) in a subject in need thereof using a compound of Formula (I) (e.g., an enterobactin-cargo conjugate of Formula (I)), a complex, or a pharmaceutical composition of the invention. In certain embodiments, the methods of the invention include administering to a subject in need thereof an effective amount of a compound of Formula (I), or a pharmaceutically acceptable salt, hydrate, solvate, polymorph, co-crystal, tautomer, stereoisomer, or isotopically labeled derivative thereof, a complex, or a pharmaceutical composition of the invention, wherein at least one instance of X is an antibiotic. In certain embodiments, the methods of the invention include administering to a subject in need thereof an effective amount of a compound of Formula (I), or a pharmaceutically acceptable salt thereof, a complex, or a pharmaceutical composition of the invention, wherein at least one instance of X is an antibiotic. In certain embodiments, the methods of the invention include administering to a subject in need thereof a therapeutically effective amount of a compound of Formula (I), a complex, or a pharmaceutical composition of the invention, wherein at least one instance of X is an antibiotic.

In certain embodiments, the present invention provides methods of treating a bacterial infection in a subject thereof. In certain embodiments, the bacterial infection is treated by the methods. In certain embodiments, the bacterial infection is a bacterial infection described herein. In certain embodiments, the bacterial infection is caused by a Gram-negative bacterium (e.g., a Gram-negative bacterium described herein). In certain embodiments, the bacterial infection is a respiratory tract infection. In certain embodiments, the bacterial infection is pneumonia. In certain embodiments, the bacterial infection is a bloodstream infection. In certain embodiments, the bacterial infection is hemolytic uremic syndrome. In certain embodiments, the bacterial infection is a gastrointestinal tract infection. In certain embodiments, the bacterial infection is diarrhea. In certain embodiments, the bacterial infection is a urinary tract infection. In certain embodiments, the bacterial infection is a food-borne illness. In certain embodiments, the bacterial infection is an ear infection. In certain embodiments, the bacterial infection is a skin rash. In certain embodiments, the bacterial infection is meningitis (e.g., neonatal meningitis). In certain embodiments, the bacterial infection is a wound or surgical site infection.

In certain embodiments, the present invention provides methods of treating cystic fibrosis in a subject thereof. In certain embodiments, the cystic fibrosis is treated by the methods.

In certain embodiments, the present invention provides methods of treating IBD in a subject thereof. In certain embodiments, the IBD is treated by the methods.

In certain embodiments, the subject described herein is a human. In certain embodiments, the subject is an animal. The animal may be of either sex and may be at any stage of development. In certain embodiments, the subject is a fish. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal. In certain embodiments, the subject is a human with cystic fibrosis. In certain embodiments, the subject is non-human mammal with cystic fibrosis.

In another aspect, the present invention provides methods of preventing a bacterial infection, cystic fibrosis, and/or IBD in a subject in need thereof using a compound of Formula (I) (e.g., an enterobactin-cargo conjugate of Formula (I)), a complex, or a pharmaceutical composition of the invention. In certain embodiments, the methods of the invention include administering to a subject in need thereof an effective amount of a compound of Formula (I), or a pharmaceutically acceptable salt, hydrate, solvate, polymorph, co-crystal, tautomer, stereoisomer, or isotopically labeled derivative thereof, a complex, or a pharmaceutical composition of the invention, wherein at least one instance of X is an antibiotic. In certain embodiments, the methods of the invention include administering to a subject in need thereof an effective amount of a compound of Formula (I), or a pharmaceutically acceptable salt thereof, a complex, or a pharmaceutical composition of the invention, wherein at least one instance of X is an antibiotic. In certain embodiments, the methods of the invention include administering to a subject in need thereof a prophylactically effective amount of a compound of Formula (I), a complex, or a pharmaceutical composition of the invention, wherein at least one instance of X is an antibiotic. In certain embodiments, the bacterial infection, cystic fibrosis, and/or IBD is prevented by the methods.

Another aspect of the present invention relates to methods of inhibiting the growth of a bacterium using a compound of Formula (I), a complex, or a pharmaceutical composition of the invention. In certain embodiments, an inventive method specifically inhibits the growth of a bacterium, compared to a bacterium of a different type. In certain embodiments, the growth of a bacterium is inhibited by the inventive methods. In certain embodiments, the growth of a bacterium is specifically inhibited by the inventive methods, compared to a bacterium of a different type. In certain embodiments, the specificity is at least about 1-fold, at least about 2-fold, at least about 4-fold, at least about 10-fold, at least about 30-fold, at least about 100-fold, or at least about 1,000 fold. In certain embodiments, the methods of the invention include contacting a bacterium with an effective amount of a compound of Formula (I), or a pharmaceutically acceptable salt, hydrate, solvate, polymorph, co-crystal, tautomer, stereoisomer, or isotopically labeled derivative thereof, a complex, or a pharmaceutical composition of the invention, wherein at least one instance of X is an antibiotic. In certain embodiments, the methods of the invention include contacting a bacterium with a therapeutically effective amount of a compound of Formula (I), a complex, or a pharmaceutical composition of the invention, wherein at least one instance of X is an antibiotic.

Another aspect of the present invention relates to methods of killing a bacterium using a compound of Formula (I), a complex, or a pharmaceutical composition of the invention. In certain embodiments, an inventive method specifically kills a bacterium, compared to a bacterium of a different type. In certain embodiments, a bacterium is killed by the inventive methods. In certain embodiments, a bacterium is specifically killed by the inventive methods, compared to a bacterium of a different type. In certain embodiments, the methods of the invention include contacting a bacterium with an effective amount of a compound of Formula (I), or a pharmaceutically acceptable salt, hydrate, solvate, polymorph, co-crystal, tautomer, stereoisomer, or isotopically labeled derivative thereof, a complex, or a pharmaceutical composition of the invention, wherein at least one instance of X is an antibiotic. In certain embodiments, the methods of the invention include contacting a bacterium with a therapeutically effective amount of a compound of Formula (I), a complex, or a pharmaceutical composition of the invention, wherein at least one instance of X is an antibiotic.

Still another aspect of the present invention relates to determining the concentration of a bacterium in a biological sample. In certain embodiments, provided are methods of detecting the presence or absence of a bacterium in a biological sample. In certain embodiments, the biological sample is a biological sample described herein. In certain embodiments, the inventive methods include contacting a biological sample with an effective amount of a compound of Formula (I), or a salt, hydrate, solvate, polymorph, co-crystal, tautomer, stereoisomer, or isotopically labeled derivative thereof, a complex, or a composition (e.g., a diagnostic composition) of the invention, wherein at least one instance of X is a fluorophore. In certain embodiments, the inventive methods include contacting a biological sample with an effective amount of a compound of Formula (I), or a salt, hydrate, solvate, polymorph, co-crystal, tautomer, stereoisomer, or isotopically labeled derivative thereof, a complex, or a composition (e.g., diagnostic composition) of the invention, wherein at least one instance of X is biotin (e.g., a moiety of the formula

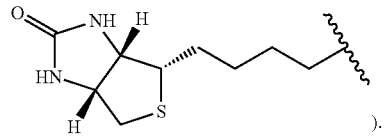 [SMILES: *CCCC[C@@H]1SC[C@@H]2NC(=O)N[C@@H]21]

).

When at least one instance of X is a fluorophore, the concentration, presence, or absence of the bacterium in the biological sample may be determined by measuring the fluorescence of the fluorophore in the biological sample. When at least one instance of X is biotin, the concentration, presence, or absence of the bacterium in the biological sample may be determined by a biotin binding assay on the biological sample. In certain embodiments, the biotin binding assay is a streptavidin-biotin binding assay. In certain embodiments, the biotin binding assay is an avidin-biotin binding assay. In certain embodiments, the biotin binding assay is a neutravidin-biotin binding assay.

Another aspect of the invention relates to methods of screening a library of compounds or complexes to identify one or more compounds or complexes that are useful in the methods of the invention. In certain embodiments, the one or more compounds or complexes identified are useful for delivering a cargo described herein to a bacterium. In certain embodiments, the one or more compounds or complexes identified are useful for treating a bacterial infection, cystic fibrosis, and/or IBD in a subject in need thereof. In certain embodiments, the one or more compounds or complexes identified are useful for preventing a bacterial infection, cystic fibrosis, and/or IBD in a subject in need thereof. In certain embodiments, the one or more compounds or complexes identified are useful for inhibiting the growth of a bacterium. In certain embodiments, the one or more compounds or complexes identified are useful for killing a bacterium.

In certain embodiments, the one or more compounds identified are useful for determining the concentration, presence, or absence of a bacterium in a biological sample. In certain embodiments, the library of compounds or complexes is a library of compounds of Formula (I) and/or complexes of the invention. In certain embodiments, the methods of screening a library include providing at least two different compounds of Formula (I) and/or complexes of the invention; and performing at least one assay using the different compounds of Formula (I) and/or complexes, to identify one or more compounds or complexes that are useful in the inventive methods.

Typically, the methods of screening a library of compounds or complexes involve at least one assay. In certain embodiments, the assay is performed to detect one or more characteristics associated with the treatment of a bacterial infection, cystic fibrosis, and/or IBD, with the prevention of a bacterial infection, cystic fibrosis, and/or IBD, with the inhibition of the growth of a bacterium, and/or with the killing of a bacterium. The characteristics may be desired (e.g., a cargo being delivered to a bacterium, a bacterial infection, cystic fibrosis, and/or IBD being treated and/or prevented, the growth of a bacterial being inhibited, or a bacterium being killed) or undesired (e.g., a cargo not being delivered to a bacterium, a bacterial infection, cystic fibrosis, and/or IBD not being treated and/or prevented, the growth of a bacterial not being inhibited, or a bacterium not being killed) characteristics. The step of performing at least one assay may be performed robotically or manually.

In another aspect, the present invention provides the compounds of Formula (I), and salts thereof, complexes, and compositions of the invention, for use in delivering a cargo described herein into a bacterium.

In still another aspect, the present invention provides the compounds of Formula (I), and pharmaceutically acceptable salts thereof, complexes, and pharmaceutical compositions of the invention, for use in the treatment of a bacterial infection in a subject in need thereof, wherein at least one instance of X is an antibiotic.

In still another aspect, the present invention provides the compounds of Formula (I), and pharmaceutically acceptable salts thereof, complexes, and pharmaceutical compositions of the invention, for use in the treatment of cystic fibrosis in a subject in need thereof, wherein at least one instance of X is an antibiotic.

In still another aspect, the present invention provides the compounds of Formula (I), and pharmaceutically acceptable salts thereof, complexes, and pharmaceutical compositions of the invention, for use in the treatment of IBD in a subject in need thereof, wherein at least one instance of X is an antibiotic.

In still another aspect, the present invention provides the compounds of Formula (I), and pharmaceutically acceptable salts thereof, complexes, and pharmaceutical compositions of the invention, for use in the prevention of a bacterial infection, cystic fibrosis, and/or IBD in a subject in need thereof, wherein at least one instance of X is an antibiotic.

In still another aspect, the present invention provides the compounds of Formula (I), and pharmaceutically acceptable salts thereof, complexes, and pharmaceutical compositions of the invention, for use in inhibiting the growth of a bacterium, wherein at least one instance of X is an antibiotic.

In yet another aspect, the present invention provides the compounds of Formula (I), and pharmaceutically acceptable salts thereof, complexes, and pharmaceutical compositions of the invention, for use in killing a bacterium, wherein at least one instance of X is an antibiotic.

In yet another aspect, the present invention provides the compounds of Formula (I), and salts thereof, complexes, and compositions (e.g., diagnostic compositions) of the invention, for use in determining the concentration, presence, or absence of a bacterium in a biological sample, wherein at least one instance of X is a fluorophore.

In yet another aspect, the present invention provides the compounds of Formula (I), and salts thereof, complexes, and compositions (e.g., diagnostic compositions) of the invention, for use in determining the concentration, presence, or absence of a bacterium in a biological sample, wherein at least one instance of X is biotin (e.g., a moiety of the formula:

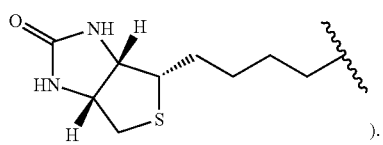 [SMILES: *CCCC[C@@H]1SC[C@@H]2NC(=O)N[C@@H]21]

).

EXAMPLES

In order that the invention described herein may be more fully understood, the following examples are set forth. The synthetic and biological examples described in this application are offered to illustrate the compounds, complexes, pharmaceutical compositions, and methods provided herein and are not to be construed in any way as limiting their scope.

Example 1. Preparation of the Compounds

The compounds provided herein can be prepared from readily available starting materials using the following general methods and procedures. See, e.g., Schemes 1 to 5 below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Reagents.

Dimethylformamide (DMF) and dichloromethane ($CH_2Cl_2$) were dried over 4 Å molecular sieves or by using a VAC solvent purification system (Vacuum Atmospheres). Anhydrous dimethyl sulfoxide (DMSO) was purchased from Sigma-Aldrich and used as received. HPLC-grade acetonitrile (MeCN) was purchased from EMD. The triserine lactone 4 and its D-isomer 5 were synthesized according to a literature procedure.[55] 2,3-Bis(benzyloxy)benzoic acid 6,[62] vancomycin-alkyne 7,[63] and tert-butyl (2-oxo-2-(prop-2-yn-1-ylamino)ethyl)carbamate 8,[63] were synthesized according to literature procedures. L-Ent 1 and its D-isomer 9 were synthesized as reported elsewhere.[55,56] Tert-butyl 3-(2-(2-(2-aminoethoxy)ethoxy)ethoxy)propanoate 10 was purchased from BOC Sciences (Shirley, N.Y.), 11-azido-3,6,9-trioxaundecan-1-amine 11 was purchased from Fluka, 6-((tert-butyoxycarbonyl)amino)hexanoic acid 12 was purchased from Advanced Chem Tech, and Fmoc-PEG-$CO_2$H 13 was purchased from Chem-Impex International, Inc. The PEG-derivatized cargos 14-18 were synthesized according to methods described herein. Methyl-5-allyl-3-methoxysalicylate 19 was obtained from Sigma Aldrich. All other chemicals were purchased from Sigma-Aldrich, Alfa Aesar, or TCI in the highest available purity and used as received.

General Synthetic Materials and Methods.

EMD TLC silica gel 60 $F_{254}$ plates were used for analytical thin-layer chromatography. EMD PLC silica gel 60 $F_{254}$ plates of 1-mm thickness were used for preparative TLC. Zeoprep 60HYD silica gel (40-63 μm) obtained from Zeochem was used for flash chromatography. $^1$H, $^{19}$F, and $^{13}$C NMR spectra were collected on a Varian 300 or 500 MHz spectrophotometer, which were operated at ambient probe temperature (283 K) and housed in the Department of Chemistry Instrumentation Facility. The $^1$H and $^{13}$C NMR spectra were referenced to internal standards and $^{19}$F spectra were referenced to an external $CF_3Cl$ standard. An Avatar FTIR instrument was used to acquire IR spectra. Optical absorption spectra were recorded on an Agilent 8453 diode array spectrophotometer (1-cm quartz cuvettes, Starna).

Analytical and semi-preparative high-performance liquid chromatography (HPLC) were performed using an Agilent 1200 series HPLC system outfitted with a CLIPEUS reverse-phase $C_{18}$ column (5-μm pore size, 4.6×250 mm; Higgins Analytical, Inc.) at a flow rate of 1 mL/min and an Agilent Zorbax reverse-phase $C_{18}$ column (5-μm pore size, 9.4×250 mm) at a flow rate of 4 mL/min, respectively. The multi-wavelength detector was set to read the absorbance at 220, 280, and 316 (catecholate absorption) nm. For HPLC analyses, solvent A was 0.1% TFA in $H_2O$ and solvent B was 0.1% TFA in MeCN, unless stated otherwise. Each run began with a five-minute equilibration with the % B used for the start of the gradient, followed by a liner gradient of increasing % B. The HPLC solvents were prepared with HPLC-grade MeCN and TFA, and MILLI-Q water (18.2 mΩcm$^{-1}$), and filtered through a 0.2-μm filter before use. For analytical HPLC to evaluate conjugate purity, the entire portion of each HPLC-purified compound was dissolved in a mixture of 1:1 MeCN/$H_2O$ and an aliquot was taken for HPLC analysis, and the remaining solution was subsequently lyophilized.

High-resolution mass spectrometry was performed by using an Agilent LC-MS system comprised of an Agilent 1260 series LC system outfitted with an Agilent POROSHELL 120 EC-$C_{18}$ column (2.7-μm pore size) and an Agilent 6230 TOF system housing an Agilent JETSTREAM ESI source. For all LC-MS analyses, solvent A was 0.1% formic acid in $H_2O$ and solvent B was 0.1% formic acid in MeCN. The samples were analyzed using a solvent gradient of 5-95% B over 5 min with a flow rate of 0.4 mL/min. Optical absorption spectra were recorded on an Beckman Coulter DU800 spectrophotometer (1-cm quartz cuvettes, Starna).

Methyl-5-allyl-2,3-dihydroxybenzoate (20)

Methyl-5-allyl-3-methoxysalicylate (19, 2.22 g, 10.0 mmol) and anhydrous N,N-diisopropylethylamine (DIPEA, 1.94 g, 15.0 mmol) were dissolved in 125 mL of dry $CH_2Cl_2$ and stirred at room temperature (rt) for five min. The solution was cooled to −78° C. in an acetone/dry ice bath, and boron tribromide ($BBr_3$, 1M solution in $CH_2Cl_2$, 30 mL, 30 mmol) was added slowly over ca. 10 min via a syringe to afford a yellow solution. The reaction was stirred at −78° C. for 1 h, warmed to −30° C. over the course of 1 h, and subsequently warmed to rt and stirred for another 4.5 h. Water (200 mL) was added slowly to quench the reaction, and the organic phase was washed with saturated aqueous potassium bicarbonate ($K_2CO_3$, 3×100 mL). The organic phase was dried over sodium sulfate ($Na_2SO_4$), and the solvent was removed under reduced pressure to afford a brown oil. Flash chromatography on silica gel with a solvent gradient (100% hexanes to 20% EtOAc/hexanes) gave the product as a white solid (1.09 g, 53%). TLC $R_f$=0.5 (silica, $CH_2Cl_2$); mp=55-56° C. $^1$H NMR (CDCl$_3$, 500 MHz) δ 3.29 (2H, d, J=7.0 Hz), 3.95 (3H, s), 5.05-5.10 (2H, m), 5.80 (1H, s), 5.91 (1H, m), 6.97 (1H, s), 7.18 (1H, s), 10.76 (1H, s) ppm. $^{13}$C NMR (CDCl$_3$, 125 MHz) δ 39.4, 52.3, 111.9, 116.0, 119.8, 120.4, 131.1, 137.0, 144.8, 147.2, 170.7 ppm. HRMS (DART): [M+Na]$^+$ m/z calcd., 231.0628. found, 231.0637.

5-Allyl-2,3-bis(benzyloxy)benzoic acid (21)

Alkene 20 (2.18 g, 10.5 mmol), benzyl bromide (10.8 g, 60.3 mmol), and $K_2CO_3$ (24.5 g, 17.8 mmol) were combined in 200 mL of acetone at rt. The reaction was refluxed under $N_2$ for 16 h, which provided a yellow solution with white solids, and the mixture was cooled to rt and filtered. The filtrate was concentrated under reduced pressure to afford a yellow oil. The oil was dissolved in a 375-mL mixture of 4:1 MeOH/5 M NaOH (aq). The resulting solution was refluxed for 3.5 h and concentrated under reduced pressure to afford a white-yellow oil. Water (300 mL) was added to the oil, and the aqueous phase was washed with hexanes (4×100 mL). The pH of the aqueous phase was adjusted to ca. 1 by addition of 12 M HCl and the product precipitated as a white solid. A 100-mL portion of $CH_2Cl_2$ was added, and the resulting mixture was partitioned. The aqueous phase was extracted with additional $CH_2Cl_2$ (2×100 mL) and the combined organic layers were dried over $Na_2SO_4$ and concentrated under reduced pressure to yield 21 as a white solid (3.91 g, 99%). TLC $R_f$=0.55 (silica, 100% $CH_2Cl_2$); mp=135-136° C. $^1$H NMR (CDCl$_3$, 300 MHz) δ 3.38 (2H, d, J=6.6 Hz), 5.06-5.14 (2H, m), 5.17 (2H, s), 5.22 (2H, s), 5.92 (1H, m), 7.09 (1H, d, J=2.1 Hz), 7.31-7.50 (10H, m), 7.58 (1H, m) ppm. $^{13}$C NMR (CDCl$_3$, 125 MHz) δ 39.6, 71.4, 76.9, 116.7, 119.3, 122.6, 123.9, 127.8, 128.4, 128.7, 128.7, 129.1, 129.2, 134.8, 135.8, 136.2, 137.2, 145.5, 151.2, 165.6 ppm. HRMS (DART): [M−H]$^-$ m/z calcd., 373.1445. found, 373.1439.

(E)-2,3-Bis(benzyloxy)-5-(prop-1-en-1-yl)benzoic acid (22)

A 30-mL portion of methanol (MeOH) was degassed with $N_2$ for 4 h at rt and 21 (750 mg, 2.00 mmol) was subsequently added. The mixture was stirred at rt until 21 dissolved and PdCl$_2$ (58 mg, 0.32 mmol) was added to give a cloudy brown solution. The reaction was stirred at rt for 24 h and filtered. The filtrate was concentrated and purified by column chromatography using silica gel (1:4:5 EtOAc/hexanes/$CH_2Cl_2$) to yield 22 as a light yellow solid (666 mg, 89%). TLC $R_f$=0.4 (40% EtOAc/hexanes); mp=140-142° C. $^1$H NMR (CDCl$_3$, 300 MHz) δ 1.88-1.90 (3H, m), 5.19 (2H, s), 5.23 (2H, s), 6.25 (1H, dq, J=15.9, 6.0 Hz), 6.32-6.38

(1H, m), 7.22 (1H, d, J=2.1 Hz), 7.32-7.51 (10H, m), 7.69 (1H, d, J=2.1 Hz) ppm. $^{13}$C NMR (CDCl$_3$, 125 MHz) δ 18.3, 71.4, 77.0, 115.8, 121.6, 122.7, 127.4, 127.7, 128.4, 128.7, 129.1, 129.2, 129.3, 134.7, 135.0, 135.9, 145.7, 151.3, 165.5 ppm. HRMS (DART): [M–H]$^-$ m/z calcd., 373.1445. found, 373.1457.

N,N'-((3S,7S,11S)-11-(2,3-Bis(benzyloxy)-5-((E)-prop-1-en-1-yl)benzamido)-2,6,10-trioxo-1,5,9-trioxacyclododecane-3,7-diyl)bis(2,3-bis(benzyloxy)benzamide) (23)

Trilactone 4 (740 mg, 2.00 mmol) and DIPEA (2.58 g, 20 mmol) were mixed in dry DMSO (8 mL) and stirred for 10 min at rt to give a clear solution. PyAOP (3.13 g, 6.07 mmol), 22 (748 mg, 2.00 mmol) and 6 (1.00 g, 2.99 mmol) were dissolved in dry DMSO (10 mL) and added to the solution containing 4, and the reaction turned yellow and became orange after stirring for 2 h at rt. The orange solution was mixed with EtOAc (50 mL) and water (50 mL) and partitioned. The organic phase was washed with brine (3×50 mL), dried over Na$_2$SO$_4$, and concentrated to afford a yellow oil. Flash chromatography on silica gel with a solvent gradient (10% EtOAc/hexanes to 55% EtOAc/hexanes) yielded the product as a white foam (931 mg, 37%). TLC R$_f$=0.3 (50% EtOAc/hexanes); mp=100-102° C. (decomposed). $^1$H NMR (CDCl$_3$, 300 MHz) δ 1.88-1.91 (3H, m), 4.01-4.11 (3H, m), 4.16-4.22 (3H, m), 4.91-4.98 (3H, m), 5.03-5.19 (12H, m), 6.17-6.40 (2H, m), 7.10-7.47 (32H, m), 7.66-7.71 (3H, m), 8.51-8.53 (3H, m) ppm. $^{13}$C NMR (CDCl$_3$, 125 MHz) δ 18.2, 40.6, 51.2, 63.9, 70.9, 76.0, 76.1, 114.2, 117.3, 120.4, 122.8, 124.1, 125.7, 126.1, 126.3, 127.4, 127.5, 127.9, 128.0, 128.2, 128.4, 128.4, 128.4, 128.7, 128.7, 129.6, 134.1, 135.8, 135.8, 136.0, 136.0, 145.5, 146.7, 151.4, 151.4, 164.7, 168.8, 168.8 ppm. HRMS (DART): [M+H]$^+$ m/z calcd., 1250.4645. found, 1250.4653.

N,N'-((3S,7S,11S)-11-(2,3-Bis(benzyloxy)-5-formylbenzamido)-2,6,10-trioxo-1,5,9-trioxacyclododecane-3,7-diyl)bis(2,3-bis(benzyloxy)benzamide) (24)

A portion of compound 23 (285 mg, 0.228 mmol) was dissolved in 1,4-dioxane (9 mL) at rt, and water (3 mL) was added to give a colorless solution. Osmium tetraoxide (OsO$_4$, 68 μL of 2.5% wt solution in 2-methyl-2 propanol, 6.7 μmol) was added and the reaction was stirred for 0.5 h at rt, which afforded a light brown solution. Sodium periodate (NaIO$_4$, 76.5 mg, 0.570 mmol) was then added and the reaction was stirred for another 2 h at rt. The suspension was partitioned in water (20 mL) and EtOAc (50 mL). The organic phase was washed with 0.1 M sodium thiosulfate (Na$_2$S$_2$O$_3$, 3×20 mL) and brine (2×20 mL), and dried over Na$_2$SO$_4$. Flash chromatography on silica gel with a solvent gradient (20% EtOAc/hexanes to 65% EtOAc/hexanes) yielded the product as white solid (165 mg, 58%). TLC R$_f$=0.6 (70% EtOAc/hexanes); mp=74° C. (decomposed). $^1$H NMR (CDCl$_3$, 300 MHz) δ 4.03-4.11 (3H, m), 4.18-4.26 (3H, m), 4.90-4.96 (3H, m), 5.05-5.28 (12H, m), 7.09-7.44 (31H, m), 7.65-7.67 (2H, m), 8.14-8.15 (1H, m), 8.46-8.52 (3H, m), 9.86 (1H, s) ppm. $^{13}$C NMR (CDCl$_3$, 125 MHz) δ 51.4, 51.4, 51.7, 64.1, 64.2, 71.0, 71.2, 76.2, 76.2, 76.5, 113.1, 117.3, 117.4, 122.9, 123.0, 124.2, 126.2, 126.3, 126.5, 127.5, 127.6, 127.8, 128.1, 128.3, 128.4, 128.4, 128.5, 128.5, 128.6, 128.8, 128.9, 132.1, 135.2, 135.3, 135.9, 135.9, 136.0, 146.7, 146.8, 151.5, 151.5, 151.7, 152.2, 163.7, 164.9, 164.9, 168.7, 168.9, 169.1, 190.6 ppm. HRMS (DART): [M+H]$^+$ m/z calcd., 1238.4287. found, 1238.4279.

3,4-Bis(benzyloxy)-5-(((3S,7S,11S)-7,11-bis(2,3-bis(benzyloxy)benzamido)-2,6,10-trioxo-1,5,9-trioxacyclododecan-3-yl)carbamoyl)benzoic acid (25)

A portion of 24 (112 mg, 0.0903 mmol) was dissolved in 1,4-dioxane (3 mL) at rt. Sulfamic acid (NH$_3$SO$_3$, 15.8 mg, 0.162 mmol) was dissolved in water (0.75 mL) and added to the dioxane solution. Sodium chlorite (NaClO$_2$, 14.7 mg, 0.163 mmol) dissolved in 0.2 mL of water and the resulting solution was added to the reaction over the course of 10 min, and the reaction turned yellow. After stirring for 0.5 h at rt, the reaction was partitioned in water (10 mL) and EtOAc (20 mL), the aqueous phase was extracted with EtOAc (2×10 mL), and the combined organic phases were dried over Na$_2$SO$_4$. Flash chromatography on silica gel with a solvent gradient (CH$_2$Cl$_2$ to 10% MeOH/CH$_2$Cl$_2$) yielded the product as white solid (87 mg, 76%). TLC R$_f$=0.5 (10% MeOH/CH$_2$Cl$_2$); mp=128-129° C. (decomposed). $^1$H NMR (CDCl$_3$, 500 MHz) δ 4.05-4.08 (3H, m), 4.22-4.25 (3H, m), 4.93-4.98 (3H, m), 5.06-5.25 (12H, m), 7.06-7.47 (31H, m), 7.67-7.69 (2H, m), 7.86 (1H, s), 8.44-8.47 (2H, m), 8.54-8.57 (2H, m) ppm. $^{13}$C NMR (CDCl$_3$, 125 MHz) δ 51.4, 51.5, 51.6, 64.1, 71.1, 71.2, 76.2, 76.4, 117.5, 117.6, 123.0, 124.2, 125.4, 125.6, 126.2, 127.5, 127.6, 127.8, 128.1, 128.3, 128.4, 128.4, 128.5, 128.6, 128.7, 128.8, 128.9, 135.4, 135.6, 135.9, 136.1, 146.8, 150.7, 151.4, 151.5, 164.1, 165.0, 168.8, 168.9, 169.0, 169.3 ppm. HRMS (DART): [M+H]$^+$ m/z calcd., 1254.4230. found, 1254.4204.

Enantiomers 26-28.

The D-isomers of the enterobactin alkene 23, aldehyde 24, and acid 25 were synthesized as described for the L-isomers except that triserine lactone 5 was employed instead of 4.

Tert-butyl(1-(3-(((3S,7S,11S)-7,11-bis(2,3-dihydroxybenzamido)-2,6,10-trioxo-1,5,9-trioxacyclodecan-3-yl)carbamoyl)-4,5-dihydroxyphenyl)-1-oxo-5,8,11-trioxa-2-azatridecan-13-yl)carbamate (29)

Compound 25 (50 mg, 40 mol), PyAOP (34 mg, 60 μmol) and DIPEA (15.2 μL, 160 μmol) were mixed in 2 mL of dry CH$_2$Cl$_2$ at rt. A portion of 7 (15 mg, 48 μmol) was then added and the resulting yellow solution was stirred for 4 h at rt. The crude reaction was washed with 0.01 N HCl (2×10 mL), dried over Na$_2$SO$_4$, and concentrated. The benzyl-protected product was purified by preparative TLC (10% MeOH/CH$_2$Cl$_2$) and obtained as a white viscous solid (46 mg, 75%). TLC R$_f$=0.7 (10% MeOH/CH$_2$Cl$_2$). $^1$H NMR (CDCl$_3$, 500 MHz) δ 1.42 (9H, s), 3.27-3.28 (2H, m), 3.50-3.52 (2H, m), 3.59-3.66 (12H, m), 4.02-4.07 (3H, m), 4.15-4.18 (3H, m), 4.90-4.94 (3H, m), 5.03-5.20 (12H, m), 7.10-7.45 (36H, m), 7.65-7.67 (2H, m), 7.85-7.85 (1H, m), 7.99 (1H, bs), 8.49-8.54 (3H, m) ppm. $^{13}$C NMR (CDCl$_3$, 125 MHz) δ 28.3, 39.9, 40.2, 51.3, 51.4, 63.9, 64.1, 69.7, 70.0, 70.2, 70.3, 70.4, 71.1, 71.2, 76.2, 76.3, 79.0, 116.7, 117.5, 120.3, 123.0, 124.2, 125.4, 126.1, 126.2, 127.6, 127.6, 127.8, 128.2, 128.3, 128.4, 128.4, 128.4, 128.5, 128.6, 128.6, 128.7, 128.8, 128.8, 129.0, 130.2, 135.4, 135.7, 135.9, 135.9, 136.1, 146.8, 146.9, 149.0, 151.5, 151.8, 155.9, 164.2, 164.8, 164.9, 165.8, 168.9, 169.0, 169.1 ppm. HRMS (ESI): [M+Na]$^+$ m/z calcd., 1550.5942. found, 1550.5977.

This benzyl-protected product was dissolved in 2 mL of 1:1 EtOAc/EtOH, the reaction flask was purged with N$_2$, and 45 mg Pd/C (10% wt) was added. The reaction was stirred under $H_2$ (1 atm) for 6 h at rt, and the Pd/C was removed by centrifugation (13,000 rpm, 10 min). The clear supernatant was decanted, concentrated, and re-dissolved in a 4:2:1 mixture of 1,4-dioxane/$H_2O$/MeOH, and purified by semi-preparative HPLC (20% B for 5 min followed by 20-70% B over 15 min, 4 mL/min). The product eluted at 15.8 min and was lyophilized to give 29 as white solid (15 mg, 50%). HRMS (ESI): $[M+Na]^+$ m/z calcd., 1010.3125. found, 1010.3173.

$N^3$-((3S,7S,11S)-7,11-Bis(2,3-dihydroxybenzamido)-2,6,10-trioxo-1,5,9-trioxacyclododecan-3-yl)-$N^1$-(1-cyclohexyl-1-oxo-5,8,11-trioxa-2-azatridecan-13-yl)-4,5-dihydroxyisophthalamide (30)

Compound 30 was synthesized as described for 29 except that 14 (13.6 mg, 45.0 μmol) was used instead of 7. After purification by preparative TLC (10% MeOH/$CH_2Cl_2$), the benzyl-protected precursor of 30 was obtained as a white viscous solid (37 mg, 60%). TLC $R_f$=0.6 (10% MeOH/$CH_2Cl_2$). $^1$H NMR (CDCl$_3$, 500 MHz) δ 1.17-1.21 (3H, m), 1.37-1.43 (2H, m), 1.62-1.63 (1H, m), 1.72-1.74 (2H, m), 1.78-1.81 (2H, m), 2.00-2.06 (1H, m), 3.39-3.42 (2H, m), 3.51-3.53 (2H, m), 3.59-3.61 (2H, m), 3.64-3.65 (10H, m), 4.01-4.06 (3H, m), 4.13-4.17 (3H, m), 4.88-4.93 (3H, m), 5.04-5.21 (12H, m), 6.23-6.25 (1H, m), 7.09-7.45 (35H, m), 7.64-7.66 (2H, m), 7.86 (1H, d, J=2.0 Hz), 8.02 (1H, d, J=2.0 Hz), 8.49-8.54 (3H, m) ppm. $^{13}$C NMR (CDCl$_3$, 125 MHz) δ 25.6, 29.5, 38.8, 40.0, 45.3, 51.3, 51.4, 63.9, 64.1, 69.8, 69.8, 70.0, 70.3, 70.4, 70.4, 71.2, 71.2, 76.2, 76.3, 116.8, 117.5, 120.4, 123.0, 124.3, 125.4, 126.1, 126.2, 127.6, 127.6, 127.9, 128.2, 128.3, 128.4, 128.4, 128.5, 128.5, 128.6, 128.6, 128.8, 128.8, 128.9, 129.0, 130.1, 135.4, 135.7, 135.9, 136.0, 136.1, 146.8, 146.9, 149.1, 151.6, 151.8, 164.3, 164.9, 164.9, 165.8, 168.9, 169.0, 169.1, 176.2 ppm. HRMS (ESI): $[M+Na]^+$ m/z calcd., 1560.6150. found, 1560.6269. Compound 30 was purified by semi-preparative HPLC (20% B for 5 min followed by 20-70% B over 15 min, 4 mL/min). The product eluted at 15.1 min and was obtained as white solid (20 mg, 58%). HRMS (ESI): $[M+Na]^+$ m/z calcd., 1020.3333. found, 1020.3346.

$N^3$-((3R,7R,11R)-7,11-Bis(2,3-dihydroxybenzamido)-2,6,10-trioxo-1,5,9-trioxacyclodo-decan-3-yl)-$N^1$-(1-cyclohexyl-1-oxo-5,8,11-trioxa-2-azatridecan-13-yl)-4,5-dihydroxyiso-phthalamide (31)

Compound 31 was synthesized as described for 30 except that 28 (36 mg, 29 μmol) was used instead of 25. After purification by preparative TLC (10% MeOH/$CH_2Cl_2$), the benzyl-protected precursor of 31 was obtained as a white oily solid (29 mg, 65%). TLC $R_f$=0.6 (10% MeOH/$CH_2Cl_2$). $^1$H NMR (CDCl$_3$, 500 MHz) δ 1.17-1.25 (3H, m), 1.38-1.44 (2H, m), 1.63 (1H, m), 1.72-1.81 (4H, m), 2.01-2.06 (1H, m), 3.40-3.41 (2H, m), 3.39-3.42 (2H, m), 3.51-3.53 (2H, m), 3.58-3.65 (12H, m), 4.01-4.06 (3H, m), 4.13-4.16 (3H, m), 4.87-4.95 (3H, m), 5.03-5.21 (12H, m), 6.22-6.23 (1H, m), 7.09-7.45 (35H, m), 7.65-7.66 (2H, m), 7.86 (1H, s), 8.02 (1H, s), 8.49-8.54 (3H, m) ppm. $^{13}$C NMR (CDCl$_3$, 125 MHz) δ 25.6, 29.5, 38.8, 40.0, 45.3, 51.3, 51.4, 63.9, 64.1, 69.8, 69.8, 70.0, 70.3, 70.4, 70.4, 71.2, 71.2, 76.2, 76.3, 116.8, 117.5, 120.4, 123.0, 124.3, 125.4, 126.1, 126.2, 127.6, 127.6, 127.9, 128.2, 128.3, 128.4, 128.4, 128.5, 128.5, 128.6, 128.6, 128.8, 128.8, 128.9, 129.0, 130.1, 135.4, 135.7, 135.9, 136.0, 136.1, 146.8, 146.9, 149.1, 151.6, 151.8, 164.3, 164.9, 164.9, 165.8, 168.9, 169.0, 169.1, 176.2 ppm. HRMS (ESI): $[M+Na]^+$ m/z calcd., 1560.6150. found, 1560.6141. Compound 31 was purified by semi-preparative HPLC (20% B for 5 min followed by 20-70% B over 15 min, 4 mL/min). The product eluted at 14.8 min and was obtained as white solid (5.1 mg, 27% yield). HRMS (ESI): $[M+Na]^+$ m/z calcd., 1020.3333. found, 1020.3328.

$N^3$-((3S,7S,11S)-7,11-Bis(2,3-dihydroxybenzamido)-2,6,10-trioxo-1,5,9-trioxacyclododecan-3-yl)-4,5-dihydroxy-$N^1$-(1-(naphthalen-2-yl)-1-oxo-5,8,11-trioxa-2-azatridecan-13-yl)isophthalamide (32)

Compound 32 was synthesized as described for 29 except that 15 (20 mg, 44 μmol) was used instead of 7. After purification by preparative TLC (5% MeOH/$CH_2Cl_2$), the benzyl-protected precursor of 32 was obtained as a white-yellow oily solid (37 mg, 59%). TLC $R_f$=0.6 (10% MeOH/$CH_2Cl_2$). $^1$H NMR (CDCl$_3$, 500 MHz) δ 3.44-3.74 (16H, m), 3.94-4.08 (4H, m), 4.12-4.16 (2H, m), 4.78-4.82 (1H, m), 4.87-4.92 (2H, m), 5.02-5.17 (12H, m), 7.01-7.52 (39H, m), 7.58-7.59 (1H, m), 7.64-7.66 (2H, m), 7.79-7.84 (3H, m), 7.94-7.94 (1H, m), 8.29-8.31 (1H, m), 8.47-8.50 (3H, m) ppm. $^{13}$C NMR (CDCl$_3$, 125 MHz) δ 39.6, 39.9, 51.4, 51.4, 63.9, 64.1, 69.6, 69.7, 70.2, 70.4, 71.1, 71.2, 71.2, 76.2, 76.3, 76.3, 116.7, 117.5, 120.3, 123.1, 124.3, 124.6, 125.0, 125.2, 125.4, 126.1, 126.2, 126.2, 126.9, 127.6, 127.6, 127.9, 128.1, 128.2, 128.4, 128.4, 128.5, 128.6, 128.6, 128.8, 128.9, 128.9, 129.0, 130.0, 130.1, 130.3, 133.5, 134.5, 135.4, 135.7, 135.9, 136.0, 136.2, 146.9, 146.9, 149.0, 151.6, 151.7, 164.2, 164.9, 164.9, 165.7, 168.9, 169.0, 169.1, 169.6 ppm. HRMS (ESI): $[M+Na]^+$ m/z calcd., 1604.5837. found, 1604.5964. Compound 32 was purified by semi-preparative HPLC (20% B for 5 min followed by 30-55% B over 10 min, 4 mL/min) and eluted at 12.7 min. The isolated product was lyophilized and obtained as a white solid (4.4 mg, 18%). HRMS (ESI): $[M+Na]^+$ m/z calcd., 1064.3020. found, 1064.3084. Mass spectrometric analysis of the crude reaction indicated M+4 in addition to the desired product 32 and suggested partial reduction of the naphthalene cargo under the deprotection conditions. From analysis of HPLC peak areas, the ratio between 32 and the partial reduction product is ca. 4:1.

$N^1$-(1-(3-Benzylphenyl)-1-oxo-5,8,11-trioxa-2-azatridecan-13-yl)-$N^3$-((3S,7S,11S)-7,11-bis(2,3-dihydroxybenzamido)-2,6,10-trioxo-1,5,9-trioxacyclodo-decan-3-yl)-4,5-dihydroxyisophthalamide (33)

Compound 33 was synthesized as described for 29 except that 16 (24 mg, 62 μmol) was used instead of 7. Partial purification by preparative TLC (10% MeOH/$CH_2Cl_2$) afforded the benzyl-protected precursor of 33 as a white-yellow solid with a grease contamination (43 mg, 67%). TLC $R_f$=0.6 (10% MeOH/$CH_2Cl_2$). $^1$H NMR (CDCl$_3$, 500 MHz) δ 3.57-3.61 (12H, m), 3.94-3.95 (2H, d, J=6.0) 3.97-4.05 (3H, m), 4.07-4.15 (3H, m), 4.85-4.90 (3H, m), 5.01-5.17 (12H, m), 7.01-7.40 (30H, m) 7.62-7.70 (3H, m), 7.82 (1H, d, J=2.0), 7.99-8.00 (1H, d, J=2.0), 8.47-8.51 (3H, m) ppm. HRMS (ESI): $[M+Na]^+$ m/z calcd., 1644.6150. found, 1644.6105. A portion (32.5 mg, 20.0 μmol) of this material was carried on without further purification or characterization. Compound 33 was purified by semi-preparative HPLC (20% B for 5 min followed by 20-70% B over 15 min, 4 mL/min). The product eluted at 15.8 min and was obtained as white solid (13.5 mg, 62%). HRMS (ESI): [M+Na]$^+$ m/z calcd., 1104.3333. found, 1104.3305.

N$^3$-((3S,7S,11S)-7,11-Bis(2,3-dihydroxybenzamido)-2,6,10-trioxo-1,5,9-trioxacyclododecan-3-yl)-4,5-dihydroxy-N$^1$-(1-oxo-1-(11-oxo-2,3,5,6,7,1-hexahydro-1H-pyrano[2,3-f]pyrido[3,2,1-ij]quinolin-10-yl)-5,8,11-trioxa-2-azatridecan-13-yl) isophthalamide (34)

Compound 34 was synthesized as described for 29 except that 17 (18 mg, 39 μmol) was used instead of 7. After purification by preparative TLC (10% MeOH/CH$_2$Cl$_2$) the benzyl-protected precursor of 34 was obtained as an orange oily solid (18 mg, 26%). TLC R$_f$=0.7 (10% MeOH/CH$_2$Cl$_2$). $^1$H NMR (CDCl$_3$, 500 MHz) δ 1.93-1.95 (4H, m), 2.71-2.83 (4H, m), 3.26-3.32 (4H, m), 3.56-3.69 (16H, m), 3.99-4.18 (6H, m), 4.88-4.94 (3H, m), 5.01-5.18 (12H, m), 6.94 (1H, s), 7.06-7.43 (35H, m), 7.62-7.66 (2H, m), 7.80-7.80 (1H, m), 7.97-7.97 (1H, m), 8.47-8.53 (4H, m), 9.02-9.03 (1H, m) ppm. $^{13}$C NMR (CDCl$_3$, 125 MHz) δ 19.9, 20.0, 21.0, 27.3, 39.4, 40.1, 49.7, 50.2, 51.5, 64.1, 69.9, 71.1, 71.2, 76.3, 105.4, 108.1, 115.9, 117.5, 119.8, 123.0, 124.3, 125.7, 126.3, 127.2, 127.6, 127.6, 127.8, 128.1, 128.2, 128.5, 128.5, 128.6, 128.9, 128.9, 129.0, 130.0, 135.7, 136.0, 136.2, 146.9, 148.2, 148.3, 149.0, 151.6, 151.7, 152.6, 162.9, 164.4, 165.0, 165.0, 168.9, 169.1 ppm. HRMS (ESI): [M+Na]$^+$ m/z calcd., 1717.6313. found, 1717.6287. Compound 34 was purified by semi-preparative HPLC (20% B for 5 min followed by 20-70% B over 15 min, 4 mL/min). The product eluted at 17.1 min and was obtained as an orange solid (4.5 mg, 48%). HRMS (ESI): [M+Na]$^+$ m/z calcd., 1177.3496. found, 1177.3540.

7-(4-(1-(3-(((3S,7S,11S)-7,11-Bis(2,3-dihydroxybenzamido)-2,6,10-trioxo-1,5,9-trioxacyclododecan-3-yl)carbamoyl)-4,5-dihydroxyphenyl)-1-oxo-5,8,11-trioxa-2-azatetradecan-14-oyl)piperazin-1-yl)-1-cyclopropyl-6-fluoro-4-oxo-1,4-dihydroquinoline-3-carboxylic acid (35)

Compound 35 was synthesized as described for 29 except that 18 (26 mg, 48 μmol) was used instead of 7, and TMSCl (10 μL, 79 μmol) and DIPEA (15 μL, 160 μmol) was mixed with 18 before addition to the solution containing 25. After purification by preparative TLC (10% MeOH/CH$_2$Cl$_2$), the benzyl-protected precursor of 35 was obtained as a yellow oily solid (46 mg, 65%). TLC R$_f$=0.65 (10% MeOH/CH$_2$Cl$_2$). $^1$H NMR (CDCl$_3$, 500 MHz) δ 1.13 (2H, bs), 1.33 (2H, bs), 2.64 (2H, bs), 3.23-3.30 (4H, m), 3.51 (1H, bs), 3.63 (14H, bs), 3.79 (4H, bs), 3.99-4.04 (3H, m), 4.11-4.14 (3H, m), 4.86-4.91 (3H, m), 5.01-5.19 (12H, m), 7.06-7.43 (39H, m), 7.59-7.61 (2H, m), 7.83 (1H, s), 7.97-7.99 (2H, m), 8.45-8.49 (3H, m), 8.69 (1H, s) ppm. $^{13}$C NMR (CDCl$_3$, 125 MHz) δ 8.2, 33.4, 35.4, 40.0, 41.1, 45.3, 49.3, 50.0, 51.3, 51.4, 51.4, 63.9, 64.1, 67.1, 69.7, 70.2, 70.3, 70.4, 70.5, 71.2, 71.3, 76.2, 76.3, 105.2, 108.0, 112.3, 112.4, 116.7, 117.5, 120.0, 120.0, 120.5, 123.0, 124.3, 125.6, 126.1, 126.1, 127.6, 127.6, 127.8, 128.2, 128.3, 128.4, 128.4, 128.5, 128.6, 128.6, 128.8, 128.8, 128.8, 129.0, 130.2, 135.5, 135.7, 135.9, 136.0, 136.1, 138.9, 145.2, 145.3, 146.8, 146.8, 147.4, 149.0, 151.6, 151.6, 151.8, 152.4, 154.4, 164.2, 164.9, 164.9, 165.8, 166.9, 168.9, 169.0, 169.1, 169.7, 176.9 ppm. $^{19}$F NMR (CDCl$_3$, 282 MHz) δ −121.3 ppm. HRMS (ESI): [M+Na]$^+$ m/z calcd., 1792.6434. found, 1792.6337. Compound 35 was purified by semi-preparative HPLC (20% B for 5 min followed by 20-70% B over 10 min, 4 mL/min) and eluted at 15.2 min. The isolated product was lyophilized and obtained as a white solid (2.5 mg, 9%). HRMS (ESI): [M+Na]$^+$ m/z calcd., 1252.3617. found, 1252.3633.

7-(4-(6-Aminohexanoyl)piperazin-1-yl)-1-cyclopropyl-6-fluoro-4-oxo-1,4-dihydro-quinoline-3-carboxylic acid (36)

Ciprofloxacin (37, 331 mg, 1.00 mmol) and DIPEA (1.0 mL, 5.7 mmol) were mixed in 6 mL of dry CH$_2$Cl$_2$, and TMSCl (370 μL, 2.91 mmol) was added to give a clear yellow solution. 6-((Tert-butoxycarbonyl)amino)hexanoic acid (12, 346 mg, 1.50 mmol), PyAOP (834 mg, 1.60 mmol), and DIPEA (700 μL, 4.02 mmol) were dissolved in 4 mL of dry CH$_2$Cl$_2$, and the two solutions were combined and stirred overnight at rt. The reaction was quenched with MeOH (10 mL), and the resulting solution was concentrated to dryness, and the crude product was redissolved in 40 mL of EtOAc. The organic phase was washed with 10 mM HCl (2×40 mL) and saturated aqueous NaHCO$_3$ (2×40 mL), dried over Na$_2$SO$_4$, and purified by flash chromatography on silica gel (3% MeOH/CH$_2$Cl$_2$) to give 38 as yellow solid (243 mg, 45%). TLC R$_f$=0.7 (5% MeOH/CH$_2$Cl$_2$). $^1$H NMR (CDCl$_3$, 300 MHz) δ 1.14-1.20 (2H, m), 1.32-1.53 (13H, m), 1.59-1.69 (2H, m), 2.36 (2H, t, J=6.0 Hz), 3.08 (2H, dt, J=6.3, 6.3 Hz), 3.26-3.56 (4H, m), 3.51-3.59 (1H, m), 3.69-3.82 (4H, m), 4.68 (1H, bs), 7.32 (1H, d, J=7.2 Hz), 7.82 (1H, d, J=12.9 Hz), 8.60 (1H, s), 14.9 (1H, bs). $^{13}$C NMR (CDCl$_3$, 125 MHz) δ 8.1, 24.7, 26.4, 28.3, 29.8, 32.9, 35.3, 40.2, 41.0, 45.1, 49.3, 49.9, 78.9, 105.0, 107.7, 111.9, 112.1, 119.6, 119.7, 138.8, 145.2, 145.3, 147.3, 152.4, 154.4, 155.9, 166.6, 171.4, 176.7. $^{19}$F NMR (CDCl$_3$, 282 MHz) δ −121.1 ppm. HRMS (ESI): [M+H]$^+$ m/z calcd., 545.2775. found, 545.2768.

The TFA salt of 36 (202 mg, 98%) was obtained as a yellow solid from 38 (201 mg, 0.369 mmol) by stirring 38 in 40% TFA/CH$_2$Cl$_2$ at rt for 3 h and removing the solvent. TLC R$_f$=0.1 (10% MeOH/CH$_2$Cl$_2$). $^1$H NMR (CD$_3$OD, 300 MHz) δ 1.41-1.52 (4H, m), 1.65-1.77 (4H, m), 2.52 (2H, t, J=7.2 Hz), 2.96 (2H, t, J=7.2 Hz), 3.34-3.43 (4H, m), 3.82 (5H, m), 7.57 (1H, d, J=7.5 Hz), 7.85 (1H, d, J=13.2 Hz), 8.76 (1H, s). $^{13}$C NMR (CDCl$_3$, 125 MHz) δ 7.8, 23.8, 25.4, 26.5, 26.6, 32.2, 35.4, 39.0, 39.1, 41.0, 45.0, 48.1, 48.3, 48.5, 48.6, 48.8, 49.0, 49.1, 49.5, 105.0, 107.0, 111.6, 111.8, 119.3, 119.4, 138.8, 145.1, 145.2, 147.4, 152.3, 154.3, 167.3, 171.8, 176.5 ppm. $^{19}$F NMR (CDCl$_3$, 282 MHz) δ −76.0, −120.9 ppm. HRMS (ESI): [M+H]$^+$ m/z calcd., 445.2251. found, 445.2255.

7-(4-(6-(3-(((3S,7S,11S)-7,11-Bis(2,3-dihydroxybenzamido)-2,6,10-trioxo-1,5,9-trioxacyclododecan-3-yl)carbamoyl)-4,5-dihydroxybenzamido)hexanoyl)piperazin-yl)-1-cyclopropyl-6-fluoro-4-oxo-1,4-dihydroquinoline-3-carboxylic acid (40)

Compound 40 was synthesized as described for 35 except that DMSO (1.5 mL) was used as the solvent and compound 36 (19.4 mg, 34.8 μmol) was used instead of 18. After preparative TLC purification (10% MeOH/CH$_2$Cl$_2$), 39 was obtained as white viscous solid (17 mg, 74%). TLC R$_f$=0.6 (10% MeOH/CH$_2$Cl$_2$). $^1$H NMR (CDCl$_3$, 300 MHz) δ 1.17-1.83 (10H, m), 2.40 (2H, bs), 3.29-3.44 (6H, m), 3.70-3.86 (5H, m), 4.02-4.17 (6H, m), 4.86-4.93 (3H, m), 5.04-5.21 (12H, m), 7.07-7.42 (33H, m), 7.60-7.64 (2H, m), 7.85-8.05 (3H, m), 8.47-8.50 (3H, m), 8.74 (1H, bs), 15.0 (1H, bs) ppm. $^{13}$C NMR (CDCl$_3$, 125 MHz) δ 8.1, 12.3, 17.2, 18.6, 24.4, 26.3, 26.4, 26.5, 29.0, 32.8, 34.7, 39.7, 41.2, 45.3, 46.2, 46.3, 51.4, 51.5, 51.5, 52.0, 54.8, 63.9, 64.1, 64.2, 71.1, 71.2, 71.2, 76.2, 76.3, 76.3, 105.2, 109.5, 113.0, 113.2, 116.6, 117.5, 120.1, 123.0, 124.3, 125.5, 126.1, 127.6, 127.8, 128.2, 128.3, 128.4, 128.4, 128.5, 128.6, 128.6, 128.6, 128.8, 128.9, 128.9, 129.0, 130.3, 135.5, 135.8, 135.9, 136.0, 136.1, 138.1, 145.4, 146.8, 148.4, 149.0, 151.6, 151.8, 152.3, 164.4, 164.9, 165.0, 165.8, 166.1, 168.8, 169.0, 169.1, 171.5 ppm. HRMS (ESI): [M+H]$^+$ m/z calcd., 1680.6303. found, 1680.6352. Compound 40 was purified by semi-preparative HPLC (20% B for 5 min followed by 20-70% B over 15 min, 4 mL/min) and eluted at 16.1 min. The isolated product was lyophilized and obtained as a white-yellow solid (6.7 mg, 59%). HRMS (ESI): [M+H]$^+$ m/z calcd., 1140.3486. found, 1140.3482.

$N_1$-(2-(2-(2-(2-Azidoethoxy)ethoxy)ethoxy)ethyl)-4, 5-bis(benzyloxy)-$N_3$-((3S,7S,11S)-7,11-bis(2,3-bis (benzyloxy)benzamido)-2,6,10-trioxo-1,5,9-triox-acyclododecan-3-yl)isophthalamide (41)

11-Azido-3,6,9-trioxaundecan-1-amine (11, 8.2 µL, 42 µmol) and 25 (40 mg, 32 µmol) were dissolved in 1 mL of dry $CH_2Cl_2$. PyAOP (33.2 mg, 63.8 µmol) and DIPEA (22.2 µL, 128 µmol) were added to give a light yellow solution. The reaction was stirred for 4 h at rt and concentrated, and the crude product was purified by preparative TLC (50% EtOAc/$CH_2Cl_2$) to afford 41 as a light yellow oil (31 mg, 68%). TLC $R_f$=0.3 (50% EtOAc/$CH_2Cl_2$). $^1$H NMR (CDCl$_3$, 300 MHz) δ 3.34 (2H, t, J=5.1 Hz), 3.61-3.69 (14H, m), 3.97-4.18 (6H, m), 4.88-4.94 (3H, m), 5.02-5.22 (12H, m), 7.08-7.46 (34H, m), 7.64-7.67 (2H, m), 7.85 (1H, d, J=1.8 Hz), 7.99 (1H, d, J=2.1 Hz), 8.48-8.52 (3H, m) ppm. $^{13}$C NMR (CDCl$_3$, 125 MHz) δ 40.0, 50.6, 51.4, 64.0, 64.1, 69.7, 69.9, 70.3, 70.6, 71.2, 71.2, 76.3, 116.7, 117.5, 120.4, 123.1, 124.3, 125.5, 126.2, 126.2, 127.6, 127.6, 127.9, 128.3, 128.4, 128.4, 128.5, 128.6, 128.7, 128.8, 128.9, 129.0, 130.2, 135.5, 135.8, 136.0, 136.0, 136.2, 146.9, 146.9, 149.1, 151.6, 151.8, 164.2, 164.9, 164.9, 165.9, 168.9, 169.1, 169.1 ppm. HRMS (ESI): [M+Na]$^+$ m/z calcd., 1476.5323. found, 1476.5345.

Vancomycin-PEG-Ent (42).

A DMSO solution of 41 (19 mg/mL, 1.3 mM, 250 µL), an aqueous solution of 8 (20 mg/mL, 1.3 mM, 250 µL), a DMF solution of benzoic acid (49 mg/mL, 450 mM, 50 µL), and an aqueous solution of CuSO$_4$ (10 mg/mL, 45 mM, 50 µL) were mixed together, and an additional 400 µL of DMSO was added to yield a clear light blue solution. An aqueous solution of sodium ascorbate (NaAsc, 18 mg/mL, 90 mM, 50 µL) was subsequently added. The reaction become colorless to yellow and was stirred at rt for 15 min, at which time another 50 µL of aqueous NaAsc was added. After stirring for 15 min, the crude reaction was frozen and lyophilized to give a brown oil. The oil was dissolved in a 2:1:1 ratio of dioxane/MeOH/H$_2$O and purified by semi-preparative HPLC (50% B for 5 min followed by 50-100% B over 11 min, 4 mL/min). The benzyl-protected precursor of 42 eluted at 13 min and was obtained as white solid after lyophilization (3.5 mg, 36%). HRMS (ESI): [M+2Na]$^{2+}$/2 m/z calcd., 1520.5030. found, 1520.5171.

A portion of this precursor (14 mg, 4.7 µmol; obtained from four 250-µL scale Click reactions) was dissolved in 30% H$_2$O/MeOH, the flask was purged with N$_2$, and 16 mg Pd/C (10% wt) was added. The reaction was stirred under H$_2$ (1 atm) for 24 h at rt, and the Pd/C was removed by centrifugation (13,000 rpm, 10 min). The supernatant was concentrated by lyophilization and the resulting residue was dissolved in a 2:1:1 mixture of dioxane/MeOH/H$_2$O. HPLC purification (20% B for 5 min followed by 20-46% B over 8 min, 4 mL/min) gave 43 as white solid (6.3 mg, 55%). HRMS (ESI): [M+2H]$^{2+}$/2 m/z calcd., 1228.37960. found, 1228.37961.

tert-Butyl(2-(((1-(1-(3-(((3S,7S,11S)-7,11-bis(2,3-dihydroxybenzamido)-2,6,10-trioxo-1,5,9-trioxacy-clododecan-3-yl)carbamoyl)-4,5-dihydroxyphenyl)-1-oxo-5,8,11-trioxa-2-azatridecan-13-yl)-1H-1,2,3-triazol-4-yl)methyl)amino)-2-oxoethyl)carbamate (43)

Compound 43 was synthesized as described for 42 except that a DMSO solution of 7 (2.8 mg/mL, 13 mM, 25 µL) was used instead of 8. HPLC purification gave 3.3 mg of the benzyl-protected precursor of 43 as a white solid (58%). HRMS (ESI): [M+H]$^+$ m/z calcd., 1688.6489. found, 1688.6421. Compound 43 (3.3 mg, 33%) was obtained from the precursor (13.3 mg, 7.88 µmol; obtained from four 25-µL scale Click reactions) following the same procedure as synthesizing 42. HPLC purification (0% B for 5 min followed by 0-45% B over 8 min, 4 mL/min) afforded 43 as a white solid with a retention time of 12.8 min. HRMS (ESI): [M+H]$^+$ m/z calcd., 1126.3853. found, 1126.3832.

Amp-alkyne, Amx-alkyne, Ent-PEG$_3$-Azide (Ent-PEG$_3$-N$_3$), Ent-Amp, and Ent-Amx may be prepared according to the methods reported in Zheng, T.; Nolan, E. J. Am. Chem. Soc. 2014, 136, 9677-9691. Salmochelin-cargo conjugates described herein (e.g., MGE-Amp, MGE-Amx, DGE-Amp, and DGE-Amx) were prepared by similar "click chemistry" described herein using azide intermediates and alkyne intermediates. See, e.g., FIG. 10. MGE-PEG$_3$-Azide (MGE-PEG$_3$-N$_3$) and DGE-PEG$_3$-Azide (DGE-PEG$_3$-N$_3$) intermediates were synthesized from a precursor, enterobactin-PEG$_3$-Azide, using either IroB or MceC.

MGE-PEG$_3$-N$_3$ and DGE-PEG$_3$-N$_3$.

The enzymes MceC and IroB were over-expressed as His$_6$-fusion proteins in E. coli BL21 (DE3) and purified as reported (Nolan, E. M.; Fischbach, M. A.; Koglin, A.; Walsh, C. T. Biosynthetic Tailoring of Microcin E492m: Post-Translational Modification Affords an Antibacterial Siderophore-Peptide Conjugate. J. Am. Chem. Soc. 2007, 129, 14336-14347; Fischbach, M. A.; Lin, H.; Liu, D. R.; Walsh, C. T. In vitro characterization of IroB, a pathogen-associated C-glycosyltransferase. Proc. Natl. Acad. Sci. USA. 2005, 102, 571-576). A 6.3-mL solution containing Ent-PEG$_3$-N$_3$ (500 µM), uridine diphosphoglucose (UDP-glucose, 3 mM), and MgCl$_2$ (5 mM) was prepared in 75 mM Tris-HCl buffer at pH 8.0 and divided into seven 900-µL aliquots. MceC or IroB was added to each aliquot in 100-µL volume to a final concentration of 5 µM. The 1-mL aliquots were incubated at room temperature and quenched by adding 100 µL of 6% TFA (aqueous) after 15 min (MceC reaction) or 3 h (IroB reaction). The quenched reaction aliquots were combined, lyophilized, redissolved in 3 mL of 1:1 MeCN/water, and centrifuged (13,000 rpm, 10 min). MGE-PEG$_3$-N$_3$ and DGE-PEG$_3$-N$_3$ were purified from the supernatant by using semi-preparative HPLC (20-45% B over 8.5 min, 4 mL/min). Both compounds were obtained as white powders (MGE-PEG$_3$-N$_3$ 0.66 mg, 41%; DGE-PEG$_3$-N$_3$, 0.85 mg, 45%). HRMS (ESI): MGE-PEG$_3$-N$_3$, [M+H]$^+$ m/z calcd. 1076.3215. found 1076.3214; DGE-PEG$_3$-N$_3$, [M+H]$^+$ m/z calcd. 1238.3743. found 1238.3744.

MGE-Amp.

Figure 44A:
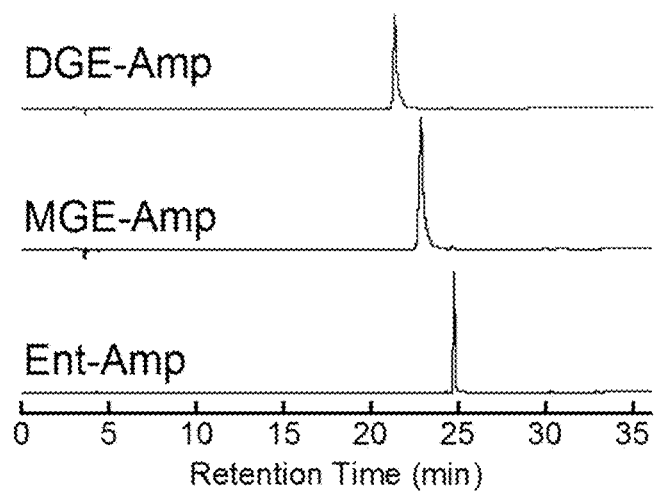
FIGS. 44A to 44B show exemplary HPLC traces of select conjugates: Ent-Amp, MGE-Amp, and DGE-Amp (FIG. 44A); and Ent-Amx, MGE-Amx, and DGE-Amx (FIG. 44B). The conjugates were dissolved in MILLI-Q water. Absorbance at 220 nm was monitored with a reference wavelength of 500 nm. Method: 0% B for 5 min then 0-100% B over 30 min at 1 mL/min.

Amp-alkyne (50 µL of an 50 mM solution in DMSO, 2.5 mol) and MGE-PEG$_3$-N$_3$ (73 µL of an 11.3-mM solution in DMSO, 0.825 µmol) were combined, and 100 µL of DMSO was added. CuSO$_4$ (50 µL of a 90-mM solution in water, 4.5 µmol) and tris[(1-benzyl-1H-1,2,3-triazol-4-yl)methyl]amine (TBTA, 100 µL of a 50-mM solution in DMSO, 5 µmol) were combined to give a blue-green solution, to which sodium ascorbate (NaAsc, 100 µL of a 180-mM solution in water, 18.0 µmol) was added. This solution became light yellow and was immediately added to the alkyne/azide solution. The resulting mixture was gently mixed on a bench-top rotator for 2 h at room temperature and purified by semi-preparative HPLC (20% B for 5 min and 20%-50% B over 11 min, 4 mL/min; 0.005% instead of 0.1% TFA was used in solvents A and B because of the acid-sensitive β-lactam moiety). The title compound was obtained as white powder (0.75 mg, 59%). HRMS (ESI): [M+H]$^+$ m/z calcd., 1519.4730. found, 1519.4639. An exemplary analytical HPLC trace is shown in FIG. 44A.

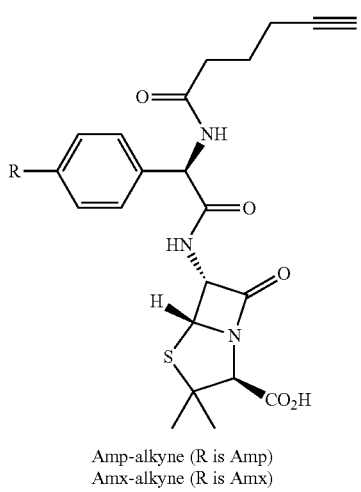

Amp-alkyne (R is Amp)
Amx-alkyne (R is Amx)

DGE-Amp.

DGE-Amp was synthesized as described for MGE-Amp except that DGE-PEG$_3$-N$_3$ was used instead of MGE-PEG$_3$-N$_3$. The title compound was purified by semi-preparative HPLC (0% B for 5 min and 0%-50% B over 13 min, 4 mL/min) and obtained as white powder (0.67 mg, 48%). HRMS (ESI): [M+Na]$^+$ m/z calcd., 1703.5077. found, 1703.5069. An exemplary analytical HPLC trace is shown in FIG. 44A.

MGE-Amx.

Figure 44B:
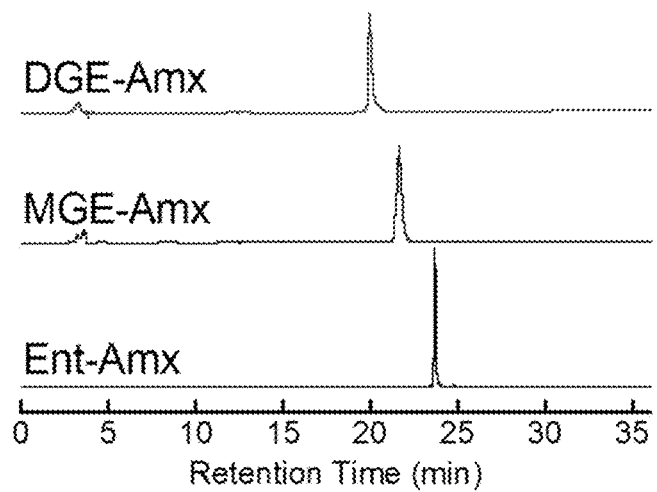

MGE-Amx was synthesized as described for MGE-Amp except that Amx-alkyne was used instead of Amp-alkyne. The product was purified by semi-preparative HPLC (20% B for 5 min and 20%-42% B over 11 min, 4 mL/min) and obtained as white powder (0.49 mg, 31%). HRMS (ESI): [M+H]$^+$ m/z calcd., 1535.4679. found, 1535.4685. An exemplary analytical HPLC trace is shown in FIG. 44B.

DGE-Amx.

DGE-Amx was synthesized as describe for MGE-Amp except that Amx-alkyne and DGE-PEG$_3$-N$_3$ were used instead of Amp-alkyne and MGE-PEG$_3$-N$_3$. The title compound was purified by semi-preparative HPLC (0% B for 5 min and 0%-50% B over 13 min, 4 mL/min) and obtained as white powder (0.36 mg, 26%). HRMS (ESI): [M+H]$^+$ m/z calcd., 1697.5207. found, 1697.5235. An exemplary analytical HPLC trace is shown in FIG. 44B.

Example 2. Design and Synthesis of Monofunctionalized Enterobactin Platforms

An exemplary synthesis of monofunctionalized enterobactin scaffolds is presented in Scheme 1. Functional groups were installed at the 5-position of one enterobactin catechol ring, the 5-position being amenable to synthetic modification. This position is remote from the iron- or gallium-binding hydroxyl groups in addition to the macrolactone (FIG. 2). Prior studies of the salmochelins indicate that modification at this site compromises neither Fe(III) complexation nor the esterase-catalyzed hydrolysis of the macrolactone.[33,64] The structure of the antibiotic-siderophore conjugate MccE492 m[65] exhibits a monoglucosylated enterobactin derivative attached to a ribosomal peptide. Methyl-5-allyl-3-methoxysalicylate 19 was selected as a starting material. This precursor was demethylated using BBr$_3$ in the presence of DIPEA to prevent HBr addition to the alkene moiety, and 20 was obtained in 53% yield as a white powder. Benzyl protection of 20 and subsequent hydrolysis of the methyl ester in refluxing sodium hydroxide was performed following a literature protocol[62] for catecholate protection of 2,3-dihydroxybenzoic acid and 21 was obtained in 99% yield as a white powder. Palladium-catalyzed isomerization of the alkene was achieved by using PdCl$_2$ in degassed methanol and 22 was obtained in 89% yield as a light yellow solid following workup. Next, a one-pot coupling reaction between the enterobactin trilactone 4, 6 and 22 was performed with a 1:1.5:1 ratio and PyAOP as the coupling reagent. This reaction provided a mixture of 23, its di- and tri-substituted analogs, and unmodified Ent. These products were separated by flash chromatography and afforded 23 in 37% yield as a white foam. The 1:1.5:1 ratio of 4/6/22 was chosen based on several optimization trails and this ratio provided the highest yield of the desired monosubstituted product. Oxidation of alkene 23 by using OsO$_4$ and NaIO$_4$ in mixed 1,4-dioxane/water afforded 24 as a white foam in 58% yield. Further oxidation of 24 under mild conditions provided carboxylic acid 25 in 76% yield as a white powder. This step-wise synthesis provides gram quantities of 23-25 (L-isomers) in high purity, and these molecules are stable when stored as dry solids at 4° C. The stepwise coupling and oxidations were also performed using triserine lactone 5 to afford the D-enantiomers alkene 26, aldehyde 27, and acid 28. The D-enantiomer of Ent is transported into E. coli by FepA, but it is not a substrate for the enterobactin esterase Fes.[66] It was therefore reasoned that conjugates based on D-Ent would provide useful controls for conjugate uptake studies, and that this enantiomer may also be advantageous in antibacterial drug delivery applications because it provides an iron-starvation effect.

Scheme 1. Exemplary syntheses of 22 and monofunctionalized enterobactin scaffolds (e.g., compounds 23 to 28).

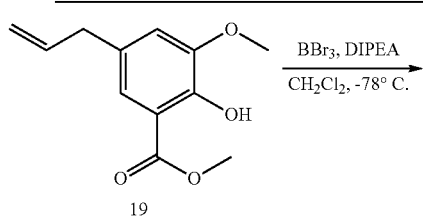

19

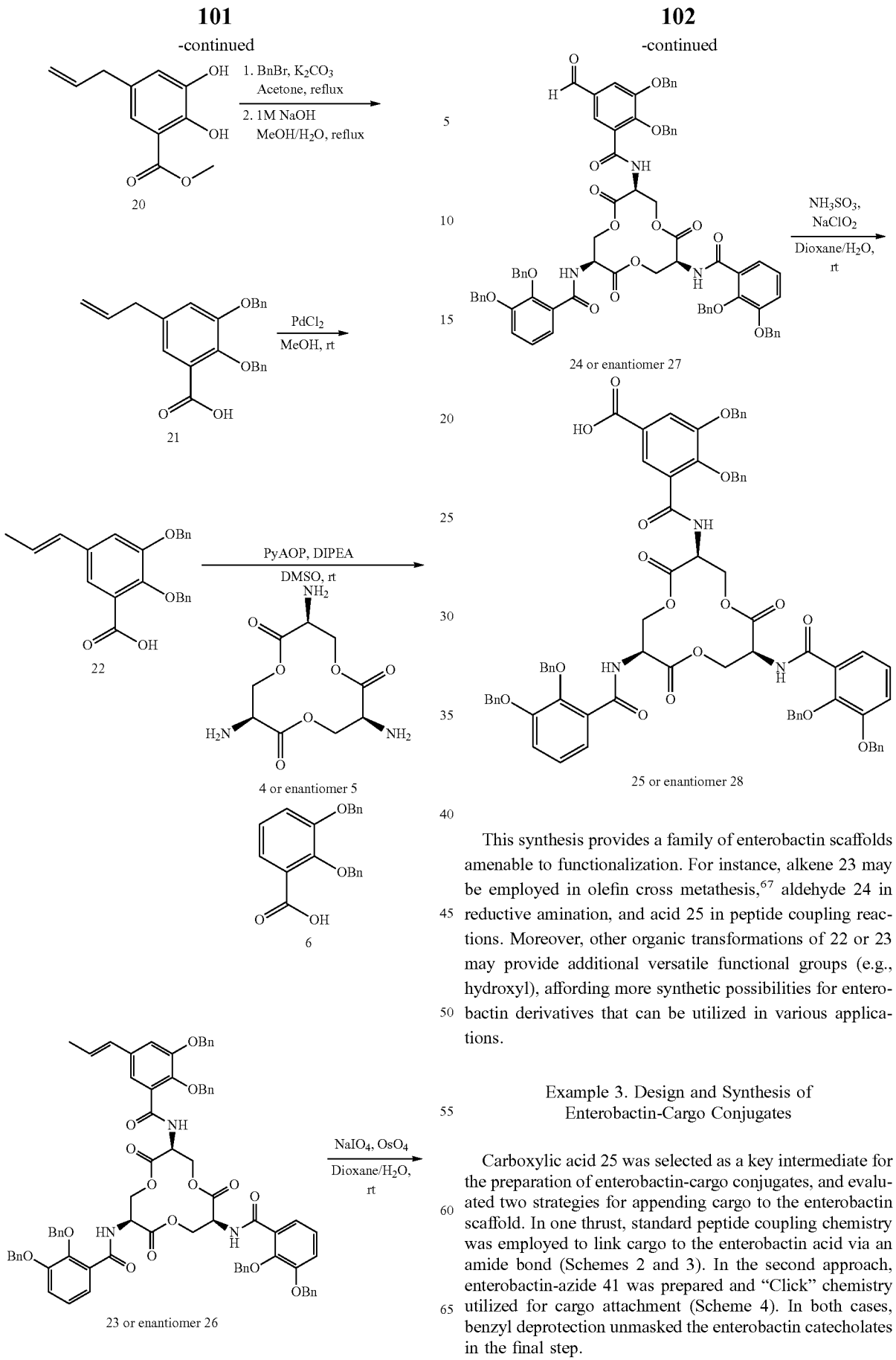

This synthesis provides a family of enterobactin scaffolds amenable to functionalization. For instance, alkene 23 may be employed in olefin cross metathesis,[67] aldehyde 24 in reductive amination, and acid 25 in peptide coupling reactions. Moreover, other organic transformations of 22 or 23 may provide additional versatile functional groups (e.g., hydroxyl), affording more synthetic possibilities for enterobactin derivatives that can be utilized in various applications.

Example 3. Design and Synthesis of Enterobactin-Cargo Conjugates

Carboxylic acid 25 was selected as a key intermediate for the preparation of enterobactin-cargo conjugates, and evaluated two strategies for appending cargo to the enterobactin scaffold. In one thrust, standard peptide coupling chemistry was employed to link cargo to the enterobactin acid via an amide bond (Schemes 2 and 3). In the second approach, enterobactin-azide 41 was prepared and "Click" chemistry utilized for cargo attachment (Scheme 4). In both cases, benzyl deprotection unmasked the enterobactin catecholates in the final step.

Scheme 2. Exemplary syntheses of enterobactin-cargo conjugates 29-35.

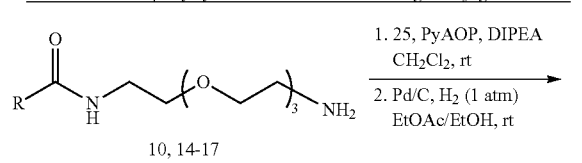

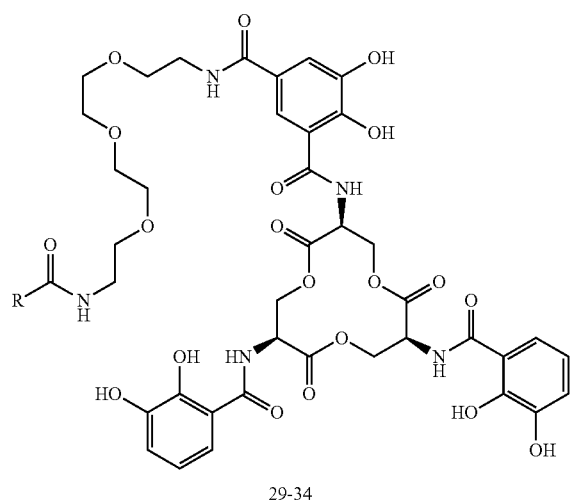

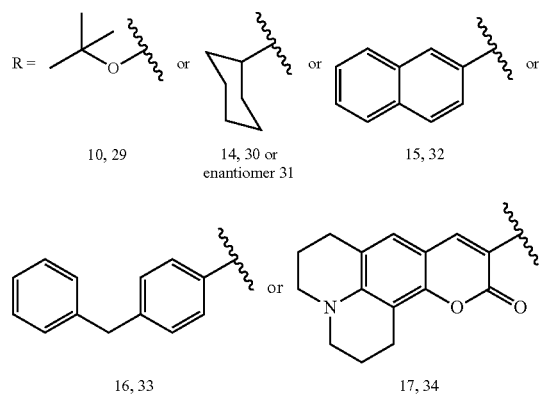

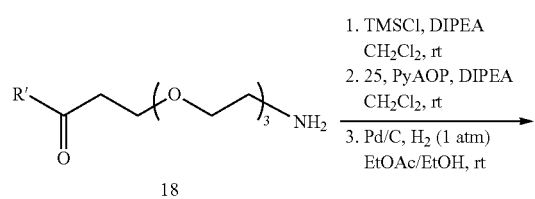

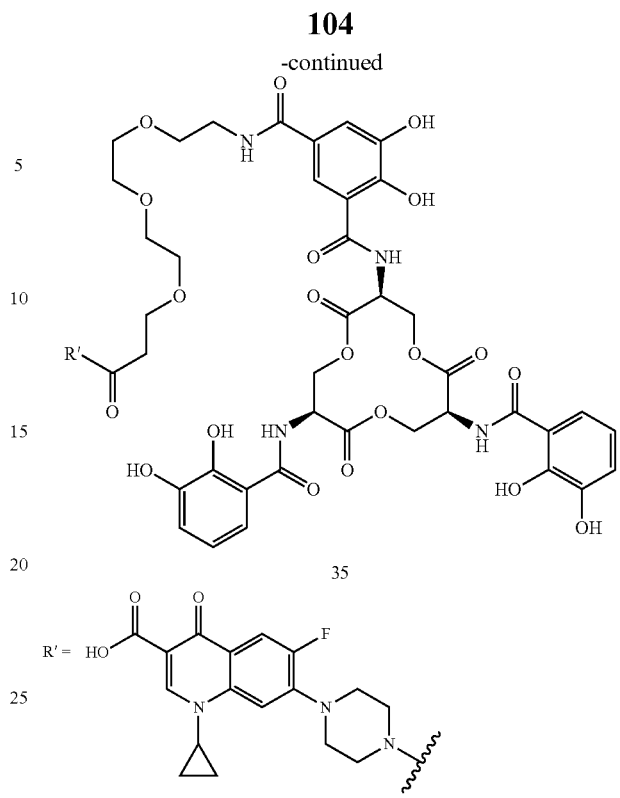

A variety of commercially available molecules housing carboxylic acids were selected as cargos. The cargos presented in Scheme 2 vary in size and shape and include a simple Boc protecting group, cyclohexane, naphthalene, phenylmethylbenzene, ciprofloxacin, and coumarin 343 (shown below). This selection includes cargo expected to be non-toxic (e.g., Boc, cyclohexane) in addition to an antibiotic (e.g., ciprofloxacin) and a fluorophore (e.g., coumarin 343). Next, PEG$_3$ was selected as a stable and water-compatible (e.g., hydrophilic) linker. It provides ca. 14-Å separation between enterobactin and the cargo. The conjugates depicted in Scheme 2 were prepared by coupling the PEG-derivatized cargo 10, 14-18 to 25 using PyAOP as the coupling reagent. The resulting benzyl-protected conjugates were purified by preparative TLC and obtained in yields ranging from 26% (Bn-34) to 75% (Bn-29). Benzyl deprotection reactions were performed by hydrogenation over Pd/C and the resulting enterobactin-cargo conjugates were purified by reverse-phase semi-preparative HPLC. Conjugates 29-35 were obtained in milligram quantities and high purity judging by analytical HPLC and LC/MS analysis. Conjugate 31 houses D-Ent and was prepared to probe the role of Fes-mediated hydrolysis in the bacterial growth recovery assays (vide infra).

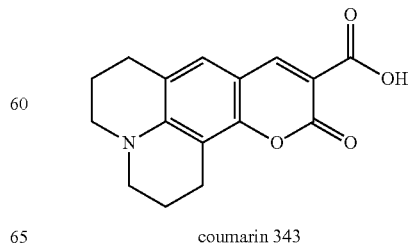

coumarin 343

Scheme 3 exhibits an exemplary synthesis of enterobactin-ciprofloxacin 40 where the PEG linker is substituted by a $C_5$ alkyl chain to probe the consequences of variable linker composition and hydrophilicity. The synthesis of 40 was carried out by reacting ciprofloxacin with 6-Boc-aminohexanoic acid 12 followed by Boc deprotection, coupling of the resulting free amine to 25, and benzyl deprotection. The carboxylic acid of ciprofloxacin was protected in situ by using trimethylsilyl chloride (TMSCl) to prevent self-coupling in the syntheses of both 35 and 40. In this general approach of attaching a carboxylic acid cargo, the linkers were first coupled to the cargo rather than to the Ent scaffold because the Ent macrolactone degrades in the presence of primary amines and under highly acidic conditions such as those required to remove Boc protecting groups.

wall biosynthesis by binding to the D-Ala-D-Ala of lipid II and blocking peptidoglycan cross-linking.[68] It exhibits poor activity against Gram-negative bacteria because it is too large to cross the outer membrane. Because modification of the C-terminal carboxylic acid with a PEG chain did not perturb its antibacterial activity,[69] this site was selected as a point of attachment. Moreover, it was surprisingly found that Click chemistry employed for the conjugate assembly is able to avoid complications with the various functional groups exhibited by vancomycin. First, the azide-functionalized PEG linker 11 was coupled to 25 to afford the enterobactin-azide 41 in 68% yield. Copper(I)-catalyzed azide-alkyne cycloaddition of 41 with alkyne 8[63] subsequently afforded enterobactin-vancomycin 42 in 55% yield following hydrogenation and purification. This synthetic approach was

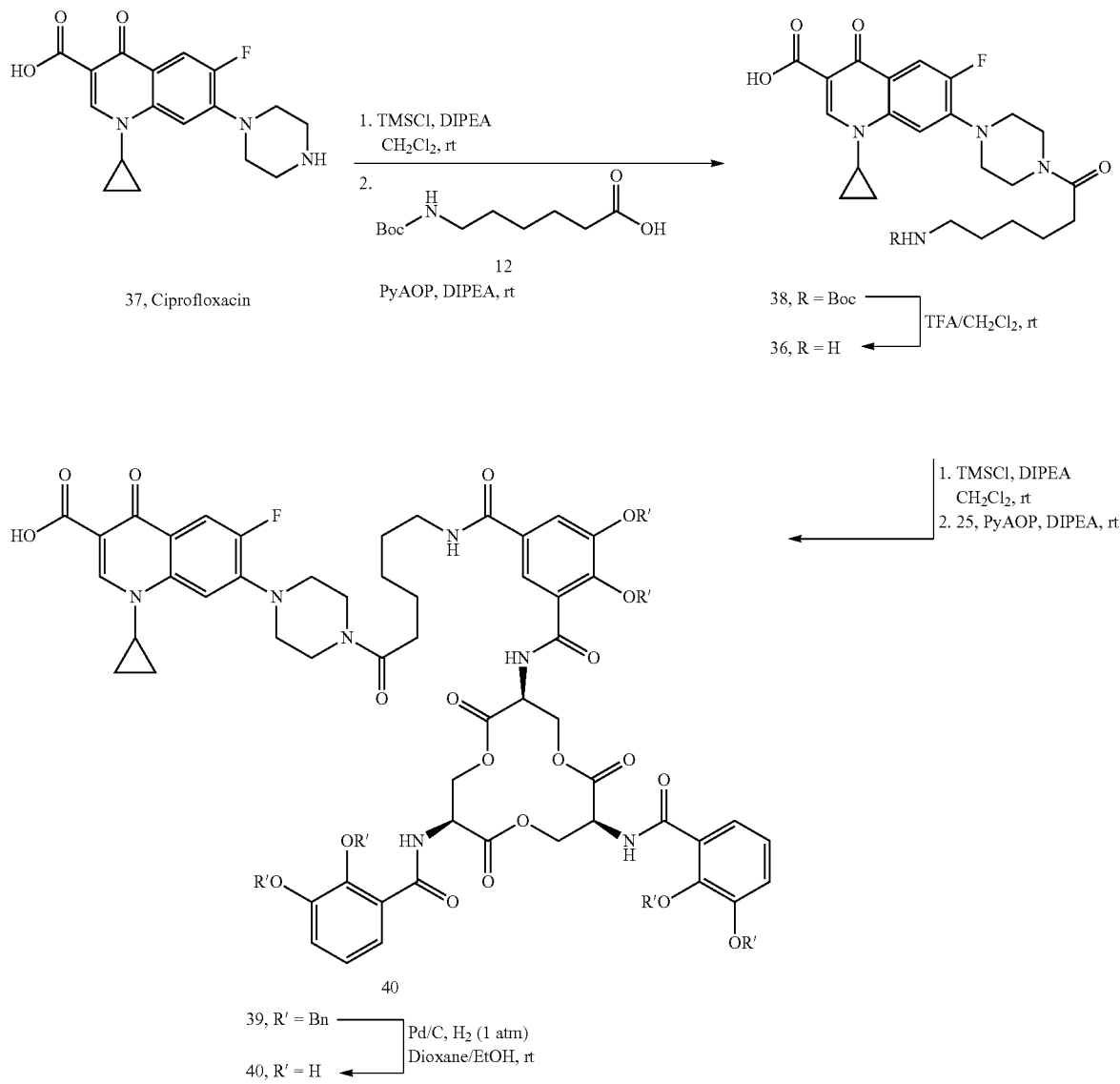

Scheme 3. Exemplary synthesis of enterobactin-ciprofloxacin conjugate 40.

Presented in Scheme 4 is an exemplary synthesis of 43, an enterobactin-vancomycin conjugate assembled via Click chemistry. Vancomycin is a nonribosomal peptide antibiotic active against Gram-positive organisms that inhibits cell extended to 43, a small analog of 42 that houses a tert-butyl cargo, and the strategy is also applicable to other alkyne-substituted cargos that are compatible with the benzyl deprotection conditions.

Scheme 4. Exemplary syntheses of enterobactin-cargo conjugates by Click chemistry.
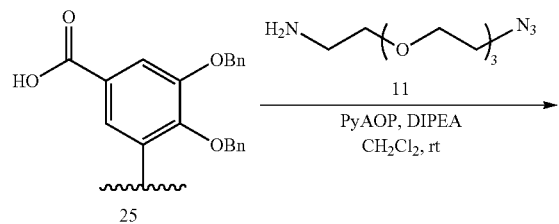
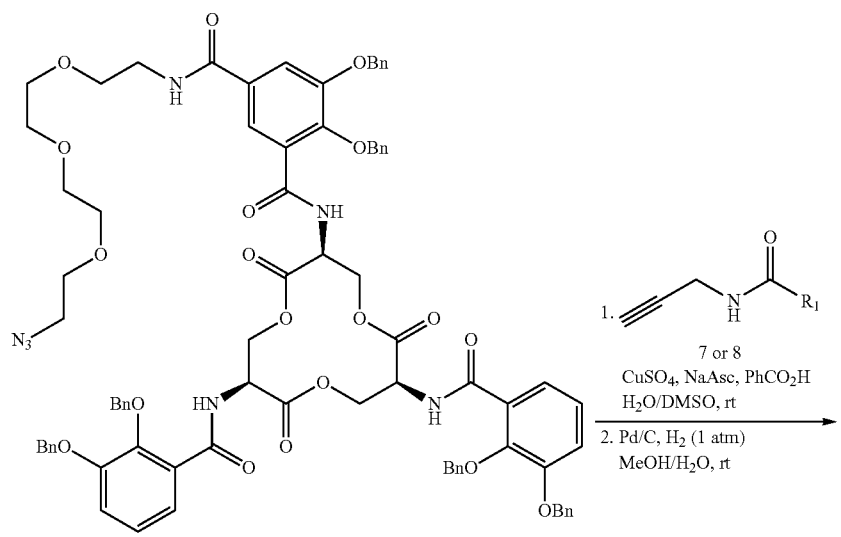
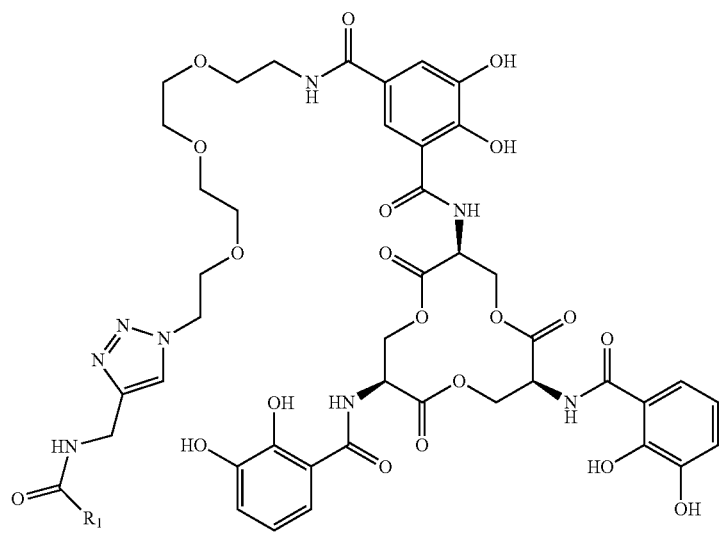

-continued

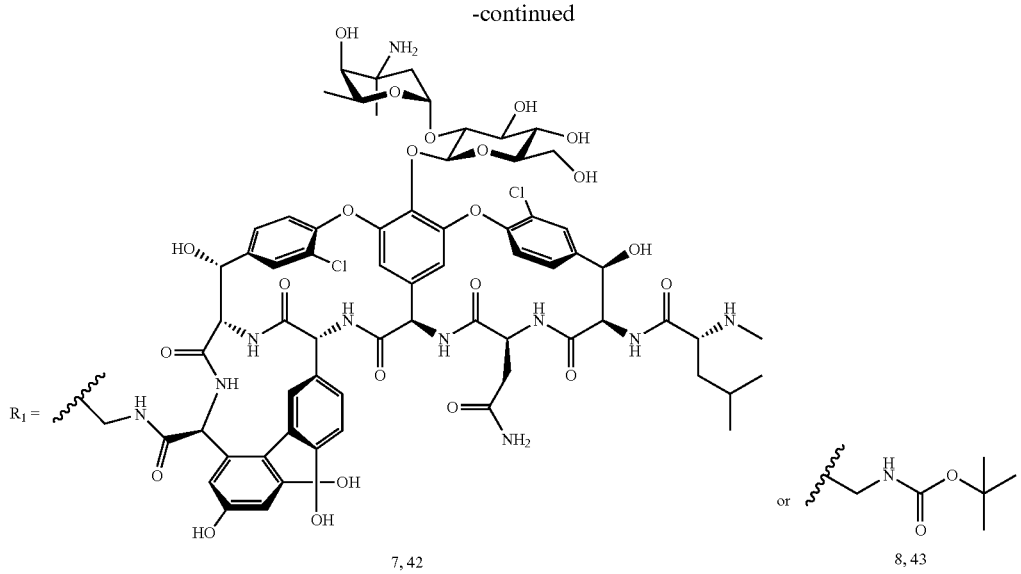

7, 42

8, 43

(L-Ent)-ampicillin conjugate 44 and (L-Ent)-amoxicillin conjugate 45 were prepared from (Bn-protected L-Ent)-PEG$_3$-azide 41 and alkyne-modified ampicillin or alkyne-modified amoxicillin by using the synthetic methods (e.g., Click chemistry) described herein, such as the method shown in Scheme 5. (D-Ent)-ampicillin conjugate 44a and (D-Ent)-amoxicillin conjugate 45a were also prepared, by a method of Scheme 5 using (Bn-protected D-Ent)-PEG$_3$-azide 41a. Each conjugate was purified by semi-preparative HPLC and characterized by analytical HPLC, mass spectrometry, and optical absorption spectroscopy.

Scheme 5. Exemplary syntheses of enterobactin-cargo conjugates by Click chemistry.

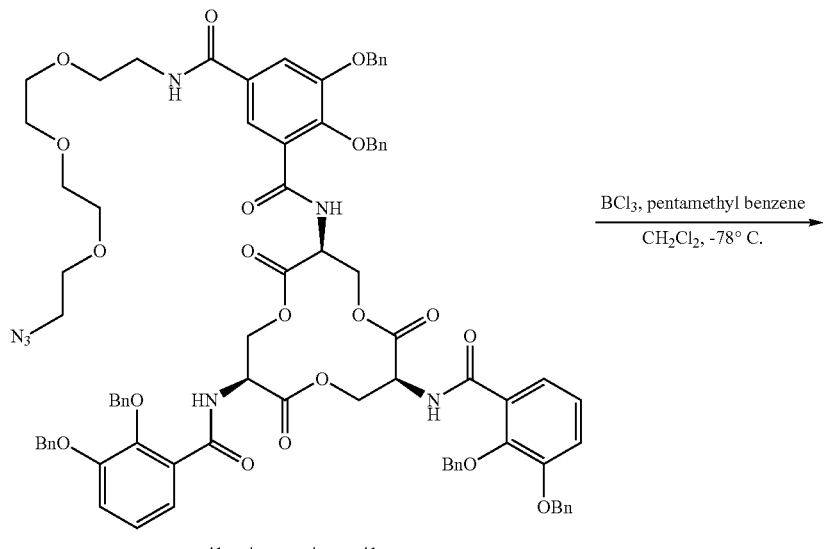

41 or its enantiomer 41a

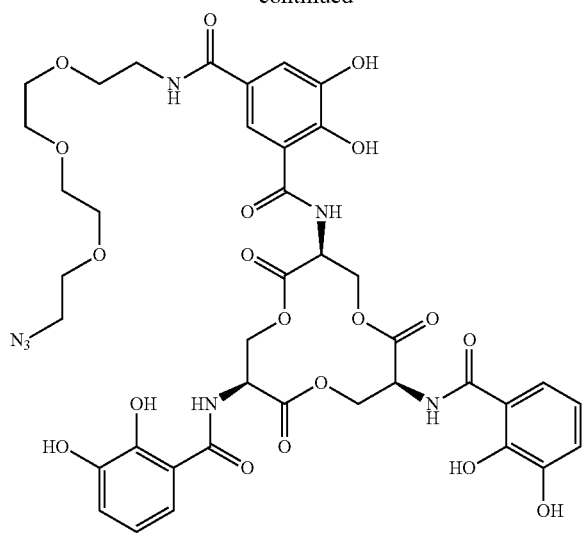
46 or its enantiomer 46a
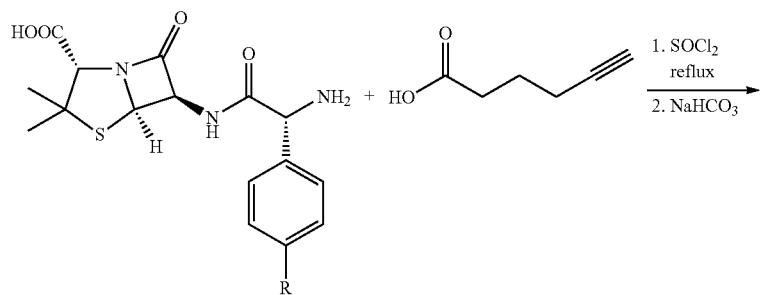
Ampcillin (Amp): R = H
Amoxicillin (Amx): R = OH
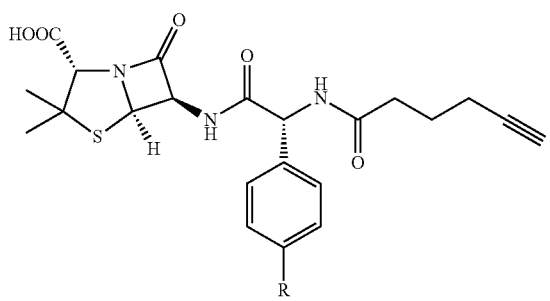
47: R = H
48: R = OH
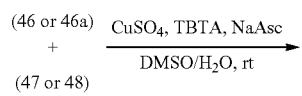

-continued

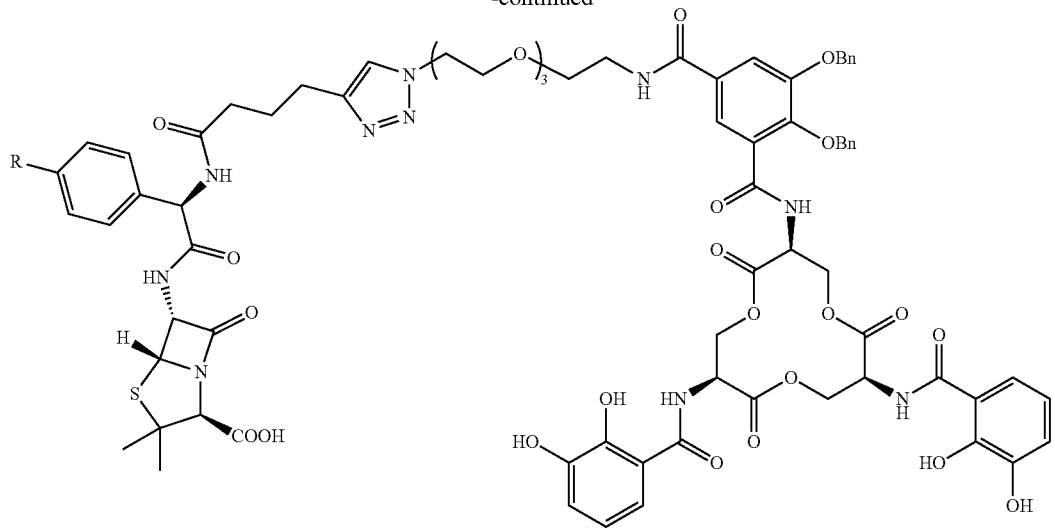

44 (Ent-Amp) or 44a (D-Ent-Amp): R = H
45 (Ent-Amx) or 45a (D-Ent-Amx): R = OH

Example 4. Enterobactin-Cargo Conjugates Coordinate Fe(III)

The optical absorption spectrum of each enterobactin-cargo conjugate exhibited catecholate absorption at ca. 316 nm (MeOH, rt). With the exception of 34, which afforded a yellow solution because of the coumarin moiety, methanolic solutions of each conjugate turned from colorless to wine-colored following the addition of ca. one equivalent of aqueous Fe(III), and the expected ligand-to-metal charge transfer (LMCT) bands were observed, indicating Fe(III) coordination to the enterobactin catecholates.[70]

Example 5. Enterobactin-Cargo Conjugate Delivery to the E. coli Cytoplasm

General Microbiology Materials and Methods (Independently Applicable to any One of Examples 5 to 16).

Information pertaining to all bacterial strains used in this study is listed in Table 1. Freezer stocks of select Escherichia coli strains (E. coli K-12, E. coli B, E. coli 25922 (ATCC 25922), E. coli CFT073, E. coli UTI89, and E. coli H9049) were prepared from single colonies in 25% glycerol/Luria Broth (LB) medium. Luria Broth and agar were purchased from BD. 5×M9 minimal medium was purchased from Sigma-Aldrich. Mueller Hinton Broth (MHB) was purchased from Fluka. Recombinant human Lcn2 was purchased from R&D System (Minneapolis, Minn.). The iron chelator 2,2'-dipyridyl (DP) was purchased from Sigma-Aldrich. All growth medium and MILLI-Q water used for bacterial cultures or for preparing solutions of the enterobactin-antibiotic conjugates were sterilized by using an autoclave. A DP stock solution (200 mM) was prepared in DMSO and used in the bacteria growth assays requiring iron-dependent conditions. All siderophore-antibiotic conjugates and Ent were stored as DMSO stock solutions at −20° C. The stock solution concentrations for tested Ent-, MGE-, and DGE-conjugates were determined by using the reported extinction coefficient for enterobactin in MeOH (316 nm, 9,500 $M^{-1}$ $cm^{-1}$) (Scarrow, R. C.; Ecker, D. J.; Ng, C.; Liu, S.; Raymond, K. N. Iron(III) Coordination Chemistry of Linear Dihydroxyserine Compounds Derived from Enterobactin. Inorg. Chem. 1991, 30, 900-906). Working dilutions of the tested compounds were prepared in 10% DMSO/$H_2O$. For all assays, the final cultures contained 1% v/v DMSO. Sterile polypropylene culture tubes and sterile polystyrene 96-well plates used for culturing were purchased from VWR and Corning Incorporated, respectively. The optical density at 600 nm ($OD_{600}$) was recorded on a Beckman Coulter DU800 spectrophotometer or by using a BIOTEK SYNERGY HT plate reader.

TABLE 1

| Bacterial strains employed. | | |
|---|---|---|
| Strain | Source | Comment |
| E. coli K-12 | ATCC | Common lab strain, BL1 |
| E. coli B | ATCC | Common lab strain, BL1 |
| E. coli 25922 | ATCC | FDA strain Seattle 1946 Clinical isolate |
| E. coli H9049 | C. T. Walsh (Harvard Medical School) | Clinical isolate |
| E. coli CFT073 | ATCC | Clinical isolate, uropathogenic Salmochelin production |
| E. coli UTI89 | L. Cegelski (Stanford University) | Clinical isolate, uropathogenic Salmochelin production |

General Procedure for Antimicrobial Activity Assays (Independently Applicable to any One of Examples 5 to 16).

Overnight cultures of the bacterial strains were prepared by inoculating 5 mL of LB with the bacterial freezer stocks and the cultures were incubated at 37° C. in a tabletop incubator shaker set at 150 rpm. The overnight culture grew to saturation and was diluted 1:100 into 5 mL of fresh LB medium containing DP (200 μM) and incubated at 37° C. with shaking at 150 rpm until $OD_{600}$ reached 0.6. The cultures were subsequently diluted to an $OD_{600}$ value of 0.001 in 50% MHB medium (11.5 g/L) with or without DP (200 μM). No antibiotic marker was included in these cultures. A 90-μL aliquot of the diluted culture was combined with a 10-μL aliquot of a 10× solution of the tested compounds in a 96-well plate, which was wrapped in PARAFILM and incubated at 30° C. with shaking at 150 rpm for 19 h. Bacterial growth was determined by measuring $OD_{600}$ using a BIOTEK SYNERGY HT plate reader. Each well condition was prepared in duplicate, and at least three independent replicates were conducted on different days. The resulting mean $OD_{600}$ are reported and the error bars are the standard deviation.

Growth Recovery Assays.

General microbiology methods are as described herein or according to processes known in the art. Overnight cultures were prepared by inoculating 5 mL of LB (*E. coli*) or LB base supplemented with 2.5 g/L NaCl (*P. aeruginosa*) with the appropriate freezer stocks and the cultures were incubated at 37° C. in a tabletop incubator shaker set at 150 rpm. The overnight culture was diluted 1:100 into 5 mL of fresh media with or without 200 µM 2,2'-dipyridyl (DP) and incubated at 37° C. with shaking at 150 rpm until the optical density at 600 nm ($OD_{600}$) reached 0.6. The cultures were diluted to an $OD_{600}$ value of 0.001 in 50% reduced MHB medium (10.5 g/L) with or without 200 µM (*E. coli*) or 600 µM DP (*P. aeruginosa*). A 90-µL aliquot of the diluted culture was mixed with a 10-µL aliquot of a 10× solution of the siderophore or siderophore-cargo conjugate in a 96-well plate, which was wrapped in PARAFILM and incubated at 30° C. with shaking at 150 rpm for 19 h. Bacterial growth was assayed by measuring $OD_{600}$ using a BioTek Synergy HT plate reader. Each well condition was prepared in duplicate and three independent replicates of each assay were conducted on different days. The resulting mean $OD_{600}$ are reported and the error bars are the standard deviation of the mean obtained from the three independent replicates.

Three non-pathogenic *E. coli* strains were employed that are defective in enterobactin synthesis, enterobactin transport, or ferric enterobactin utilization in growth recovery assays. *E. coli* ATCC 33475 (ent-) cannot biosynthesize enterobactin, but retains the capacity to import and metabolize the siderophore.[71] *E. coli* H1187 (fepA-) lacks the outer membrane enterobactin receptor. *E. coli* K-12 JW0576 (fes-) can accumulate ferric enterobactin, but cannot release the iron because it is deficient in the enterobactin esterase Fes. As a result of these defects in iron metabolism, all three strains grow poorly under conditions of iron limitation.[71] The iron chelator 2,2'-dipyridyl (dipyridyl, DP) was used to generate iron-deficient conditions and promote expression of siderophore transport machinery in the growth recovery assays.

Figures 3A, 3B:
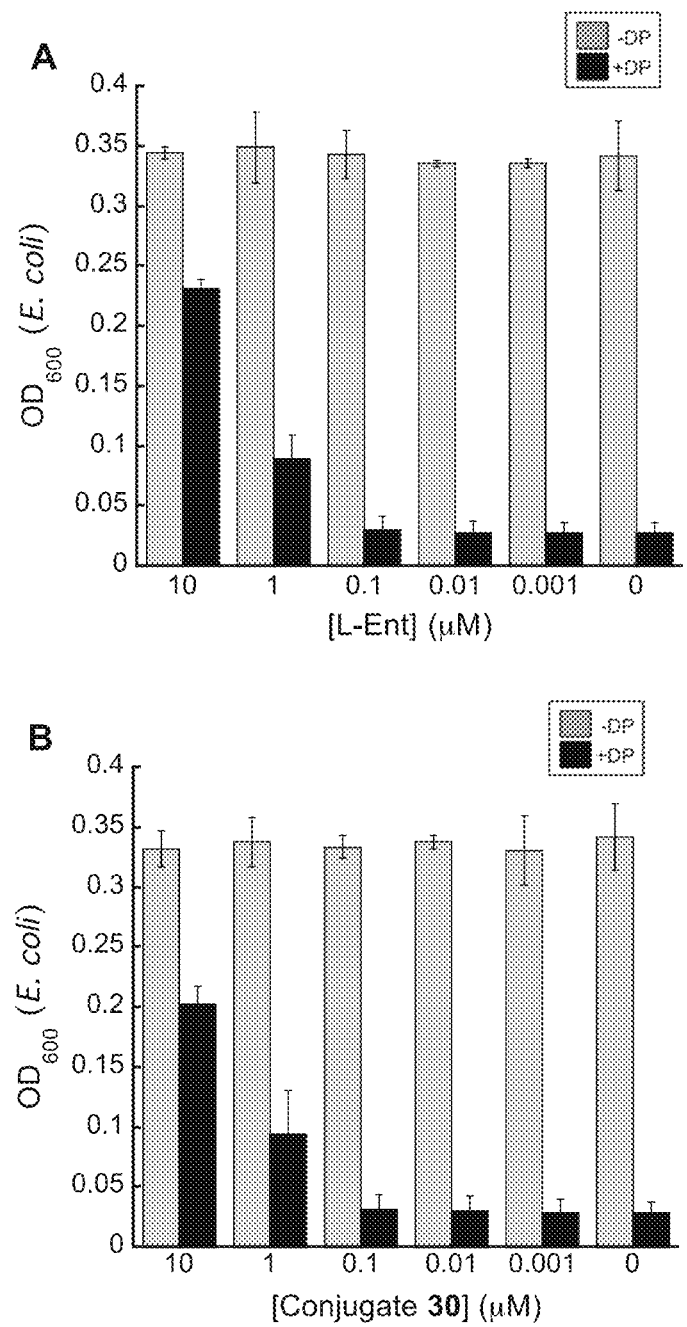
FIGS. 3A-3F is an unlimited example. $E.$ $coli$ ATCC 33475 (ent-) and $P.$ $aeruginosa$ PAO1 (pvd-, pch-) growth recovery assays employing L-Ent and select enterobactin-cargo conjugates (50% MHB, ±200 or 600 µM DP, t=19 h, 30° C.). Grey bars: $OD_{600}$ of bacteria cultured in the absence of DP. Black bars: $OD_{600}$ of bacteria cultured in the presence of 200 ($E.$ $coli$) or 600 ($P.$ $aeruginosa$) µM DP.
Figures 4A, 4B:
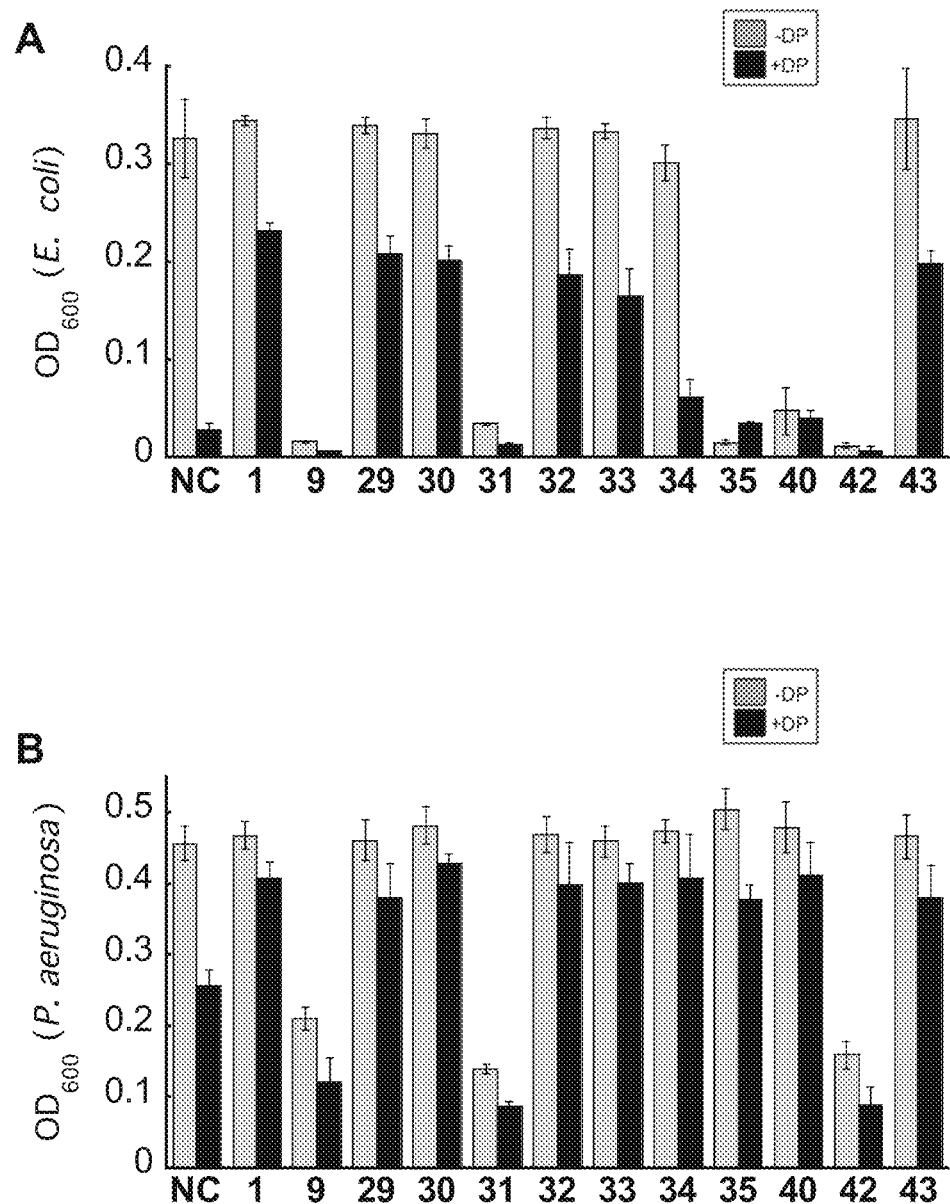
FIGS. 4A and 4B is an unlimited example. The comparative effects of enterobactin-cargo conjugates on bacterial cell growth. $E.$ $coli$ and $P.$ $aeruginosa$ were cultured in the presence of 10 µM of L-Ent 1, D-Ent 9 and the enterobactin-cargo conjugates 29-35, 40, 42, 43 in the absence (grey bars) and presence (black bars) of DP (50% MHB, T=30° C., t=19 h).
Figure 5:
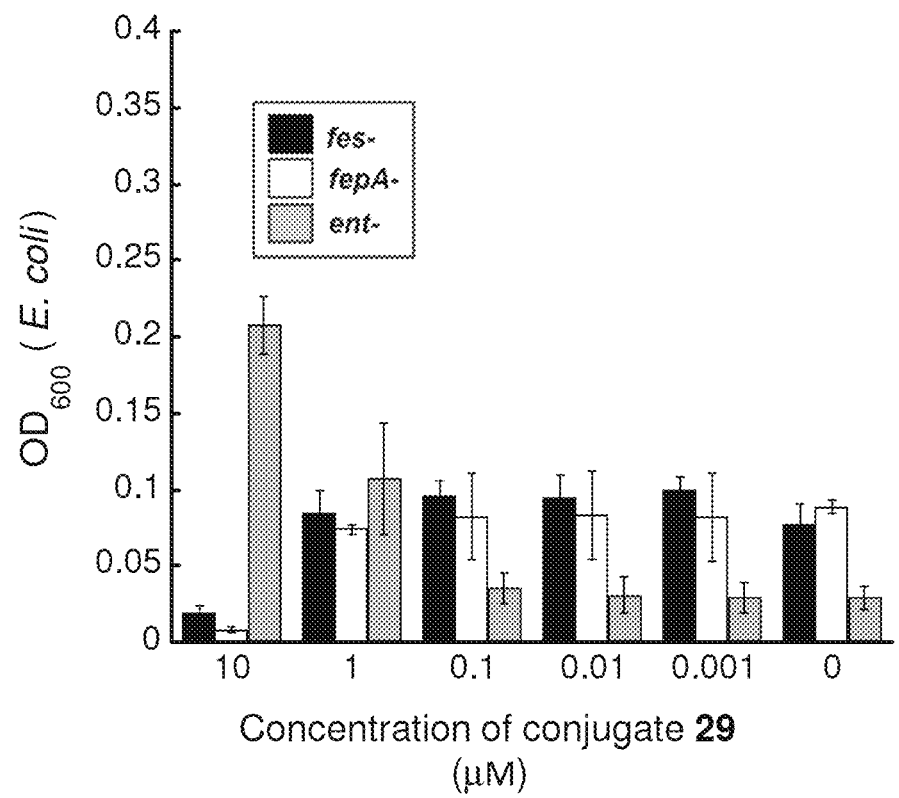
FIG. 5 is an unlimited example. Comparison of growth recovery for $E.$ $coli$ (ent-), $E.$ $coli$ (fepA-), and $E.$ $coli$ (fes-) with conjugate 29 in the presence of 200 µM DP. Black bars: $E.$ $coli$ (fes-) cultured with conjugate 29; white bars: $E.$ $coli$ (fepA-) cultured with conjugate 29; grey bars, $E.$ $coli$ (ent-) cultured with conjugate 29 in the presence of 200 µM DP.

It was first evaluated whether the enterobactin conjugates afforded growth recovery of *E. coli* (ent-) cultured under iron-deficient conditions (50% MHB, 200 µM DP). *E. coli* (ent-) grew to $OD_{600}$~0.35 in 50% MHB medium (30° C., t=19 h), and this value decreased to <0.05 when 200 µM DP was added to the media. Low-micromolar concentrations of L-Ent restored growth,[70] and the *E. coli* cultures reached $OD_{600}$~0.2 in the presence of 10 µM L-Ent (FIG. 3A). Likewise, low-micromolar concentrations of the enterobactin-cargo conjugates 29-33 and 43 exhibiting Boc (29, 43), cyclohexyl (30), napthyl (32), and phenylmethylbenzyl (33) cargos afforded growth recovery to similar levels (see, e.g., FIG. 3B). No growth restoration was observed when *E. coli* (fepA-) or *E. coli* (fes-) were cultured with 29 or 30 (see, e.g., FIG. 5), which supports the notion that the growth recovery of *E. coli* (ent-) results from FepA-mediated cytoplasmic transport and Fes-catalyzed hydrolysis of the enterobactin moiety to release iron. Moreover, the D-enantiomer of enterobactin, D-Ent 9, may be not a substrate for Fes and does not provide growth recovery (see, e.g., FIG. 4).[66] Indeed, no growth promotion occurred when *E. coli* (ent-) was treated with conjugate 31, the D-enantiomer of 30 (see, e.g., FIG. 4). Taken together, these results demonstrate that the enterobactin transport machinery has the capacity to recognize and transport cargo-derivatized enterobactin scaffolds to the *E. coli* cytoplasm, and that these molecules are substrates for the cytoplasmic esterase Fes.

Figure 3C:
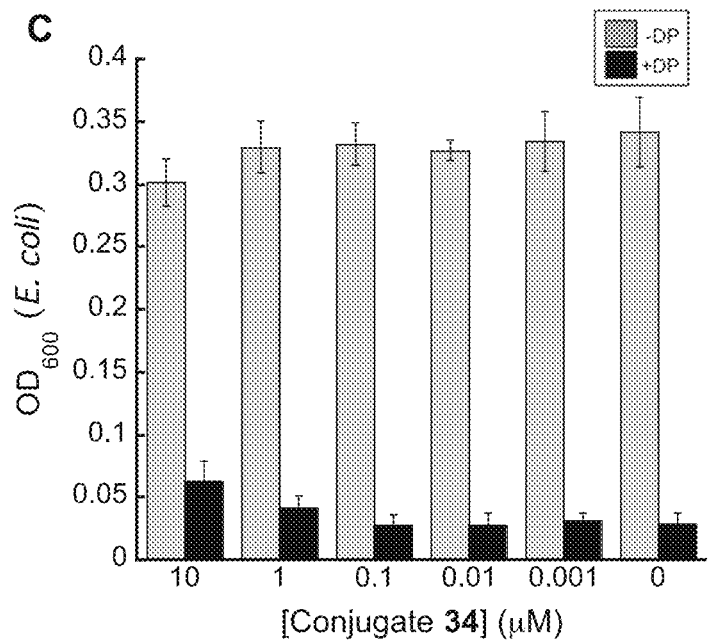

It was observed that there was no convincing evidence for marked uptake of larger cargos by *E. coli* ATCC 33475, which suggests that FepA of this *E. coli* strain has a cargo size limit. For instance, under iron limitation, negligible *E. coli* growth recovery and no toxicity was observed following treatment with the enterobactin-coumarin conjugate 34 (FIG. 3C), suggesting that *E. coli* (ent-) may not readily import 34. Moreover, no growth recovery occurred following treatment of *E. coli* with either ciprofloxacin 35 or 40 (see, e.g., FIG. 4). In the absence of DP, these conjugates afforded a concentration-dependent inhibition of *E. coli* growth. Likewise, 10 µM vancomycin 42 inhibited the growth of *E. coli* (+DP, see, e.g., FIG. 4). This behavior contrasts that of unmodified vancomycin, which is inactive against *E. coli* over the concentration range employed herein. Two possible origins for inhibitory activity of the ciprofloxacin and vancomycin conjugates are (i) enterobactin-antibiotic uptake and resulting antibacterial action or (ii) a lack of active transport into *E. coli*, resulting in extracellular iron chelation and hence nutrient deprivation. Taking all observations into account, including those for *P. aeruginosa* described below, it was contended that the latter option is the most probable explanation.

Example 6. Enterobactin-Cargo Conjugate Delivery to the *P. aeruginosa* Cytoplasm It was next sought to determine whether the enterobactin-cargo conjugates provided growth recovery for *Pseudomonas aeruginosa* PAO1. This Gram-negative opportunistic human pathogen synthesizes and exports two siderophores, pyoverdine (pvd) and pyochelin (pch), and employs multiple additional mechanisms for iron acquisition.[72,73] *P. aeruginosa* utilizes enterobactin as a xenosiderophore, and the genes pfeA[74,75] and pirA[76] encode outer membrane enterobactin transporters. Similar to the *E. coli* experiments, *P. aeruginosa* strains deficient in siderophore production or utilization were used in growth recovery assays. *P. aeruginosa* K648 (pvd-, pch-) is deficient in both pyoverdine and pyochelin biosynthesis, and shows attenuated growth in iron-deficient conditions, whereas *P. aeruginosa* K407 (pvd-, pFr-) is deficient in pyoverdine biosythesis and lacks the enterobactin transporter PfeA.[74]

Figure 3D:
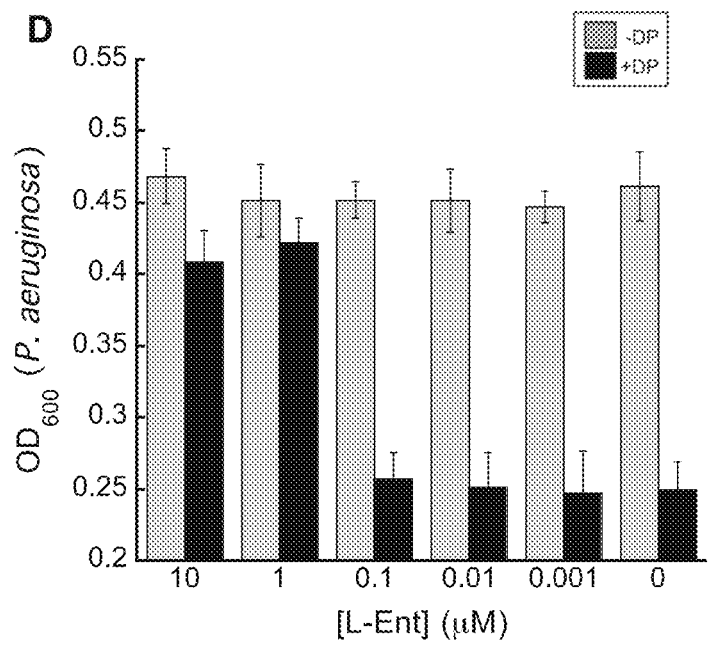
Figure 3E:
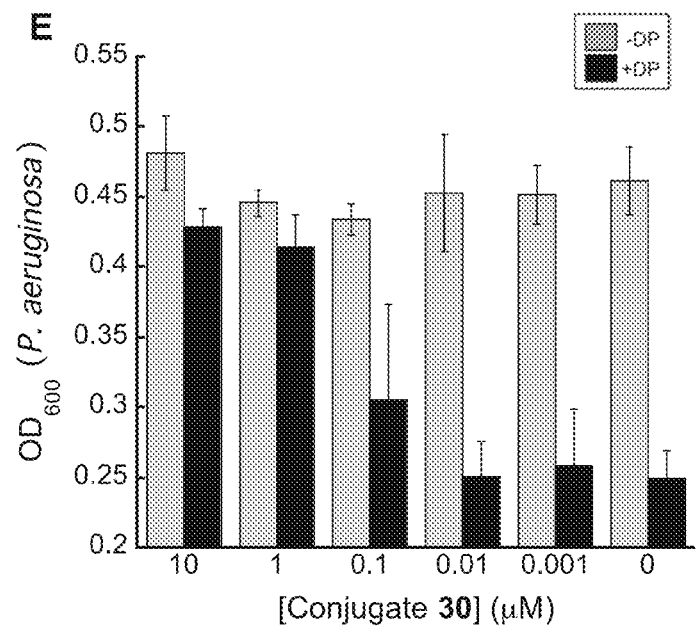
Figure 3F:
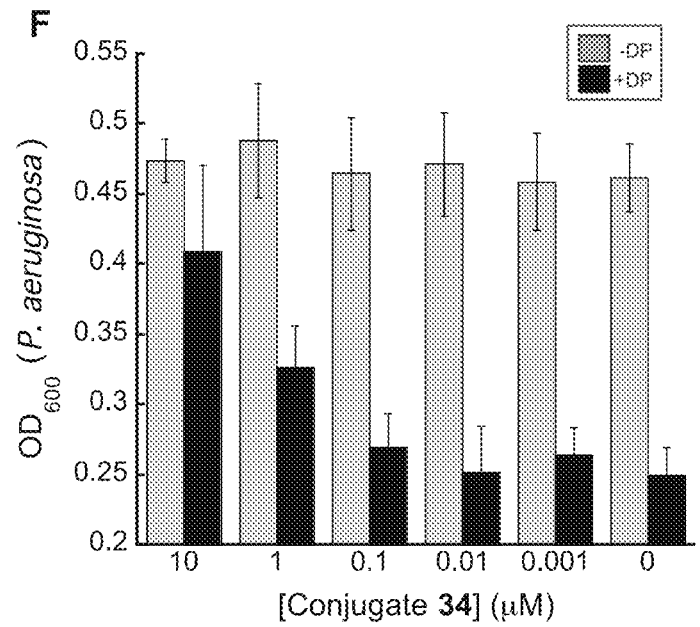

In 50% MHB medium, *P. aeruginosa* (pvd-, pch-) grew to $OD_{600}$~0.45 (30° C., t=19 h) and this value diminished to ca. 0.25 in the presence of 600 µM DP. Supplementation of the iron-limiting growth medium with low-micromolar concentrations of L-Ent resulted in the restoration of *P. aeruginosa* growth to $OD_{600}$~0.40 (FIG. 3D). Comparable growth recovery was observed for cultures treated with eight of the nine conjugates based on L-Ent (e.g., FIGS. 3E, 3F, and 4). Vancomycin 42, which exhibits the largest cargo, afforded a growth inhibitory effect (±DP) as observed for *E. coli* (ent-). In contrast to its L-Ent analog 30, conjugate 31 based on D-Ent was growth inhibitory as was D-Ent (see, e.g., FIG. 4). This result demonstrates that *P. aeruginosa* also requires the L-isomer for iron utilization. Lastly, no growth enhancement of *P. aeruginosa* (pfeA-) was observed in the presence of L-Ent or conjugate 30 (600 µM DP); instead, these siderophores caused growth inhibition at micromolar concentrations. These results demonstrate that PfeA is necessary for conjugate-mediated growth recovery, supporting its role as a transporter for the enterobactin conjugates. In total, these assays demonstrate that the enterobactin transport machinery of *P. aeruginosa*, and PfeA in particular, recognizes and delivers various cargo-modified enterobactin scaffolds to the cytoplasm.

Ciprofloxacin is a fluoroquinolone antibiotic that acts in the cytoplasm and inhibits DNA gyrase.[77] The fact that ciprofloxacin conjugates 35 and 40 each restored *P. aeruginosa* growth demonstrated that the cargo was successfully delivered to the cytoplasm of this microbe with negligible impact of the variable linker composition, and that conjugation of ciprofloxacin to enterobactin attenuated its antibacterial activity. This observation is in general agreement with reports of pyoverdine-fluoroquinoline[78] and pyochelin-fluoroquinoline[79,80] conjugates where the antibiotic was covalently attached to the siderophore and point to the need for appropriate linker design for fluoroquinolone delivery and release after cellular entry.[81] These pyoverdine/pyochelin-antibiotic conjugates afforded no antipseudomonal activity or diminished activity relative to the unmodified drug, and the pyoverdine-fluoroquinolone antibiotic exhibited decreased *E. coli* gyrase inhibitory activity in vitro.[78] A comparison of the enterobactin-cargo growth recovery profiles for *E. coli* and *P. aeruginosa* (see, e.g., FIG. 4) reveals that these particular microbes have different capacities for internalizing enterobactin-cargo conjugates, and that cargo size is an important factor. Vancomycin has a rigid dome-like structure and a molecular weight of ca. 1.45 kDa, and the assays presented herein suggest that this molecule is too big for enterobactin-mediated transport into *E. coli* or *P. aeruginosa*. In contrast, small and malleable cargos such as a Boc protecting group and cyclohexane afforded growth recovery comparable to that of L-Ent for both strains. A comparison of $OD_{600}$ values for bacterial cultures treated with such conjugates (e.g., 29, 30, 32, 34) shows that growth recovery to levels comparable to that of L-Ent occurs at a conjugate concentration of 1 µM for *P. aeruginosa* whereas 10 µM is required for *E. coli*. *P. aeruginosa* responds to lower Ent concentrations than *E. coli*, which indicates a higher uptake efficiency. Coumarin 343 is an example of a cargo that exhibits no signs of toxicity over the concentration range tested and affords markedly different results on microbial growth promotion for these two species. A comparison of the ciprofloxacin conjugate data for *E. coli* and *P. aeruginosa* also suggests differential uptake. For both the ciprofloxacin and coumarin cargo, the growth recovery assays indicate that the enterobactin transport machinery of *P. aeruginosa* imports these cargos whereas the *E. coli* system does not as readily do so. These observations suggest that species-selective targeting may be possible with strategic cargo choice even when a siderophore is utilized by multiple microbial species.

Figure 6A:
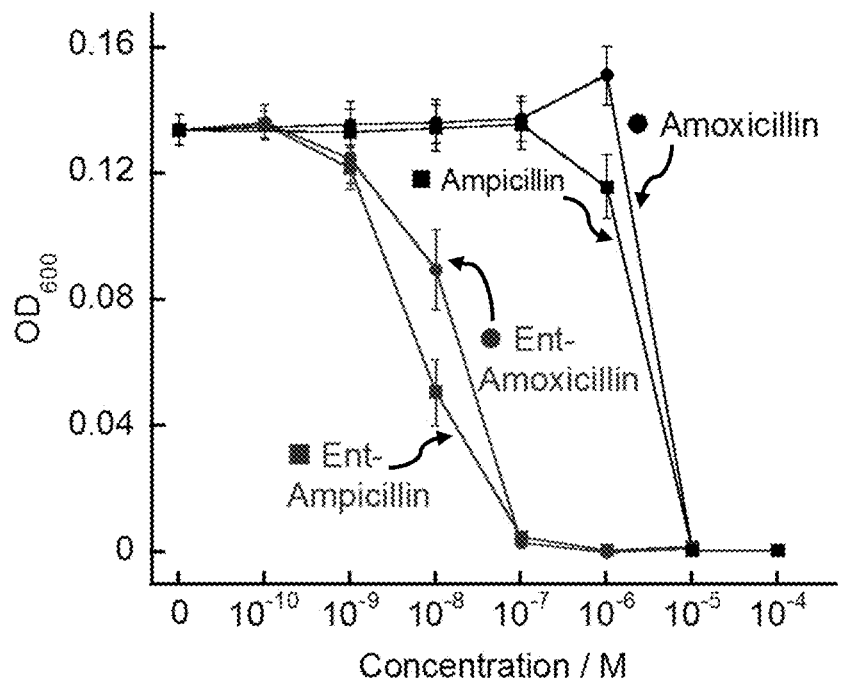
FIGS. 6A-6C is an unlimited example and shows the antibacterial activity of (L-Ent)-ampicillin conjugate 44 (Ent-ampicillin) and (L-Ent)-amoxicillin conjugate 45 (Ent-amoxicillin).
Figure 6B:
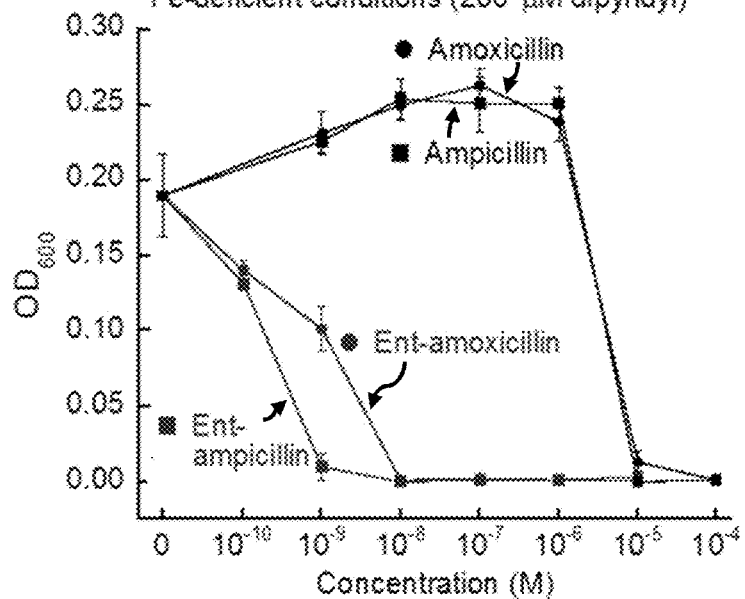
Figure 6C:
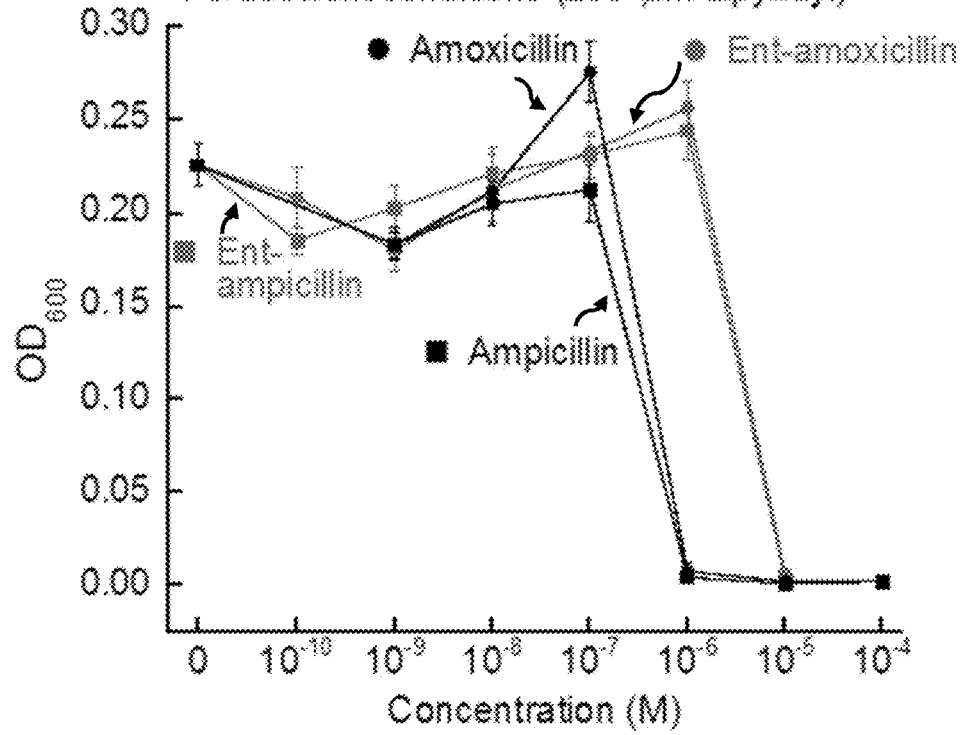

Example 7. Antibacterial Activity of Conjugates 44 and 45 In Vitro Against a Panel of Gram-Negative and Positive-Bacteria Ampicillin and amoxicillin are β-lactam antibiotics that have periplasmic targets in Gram-negative bacteria and inhibit cell wall biosynthesis. The antibacterial activity of Ent-ampicillin and Ent-amoxicillin conjugates 44 and 45 was evaluated in vitro against a panel of Gram-negative and positive-bacteria. FIG. 6 provides exemplary results from antibacterial activity assays against select bacterial species that include non-pathogenic and pathogenic *E. coli* strains and also *Staphylococcus aureus*. Under conditions of iron limitation (200 µM 2,2'-dipyridyl), the conjugates provide 100- to 1000-fold improved activity against various *E. coli* strains, including human pathogens, compared to the unmodified antibiotics. In contrast, no enhancement of activity is observed for Gram-positive *S. aureus*.

Example 8. DGE-Amp Selectively Inhibited *E. coli.* CFT073 Over *E. coli.* K12

Figure 11A:
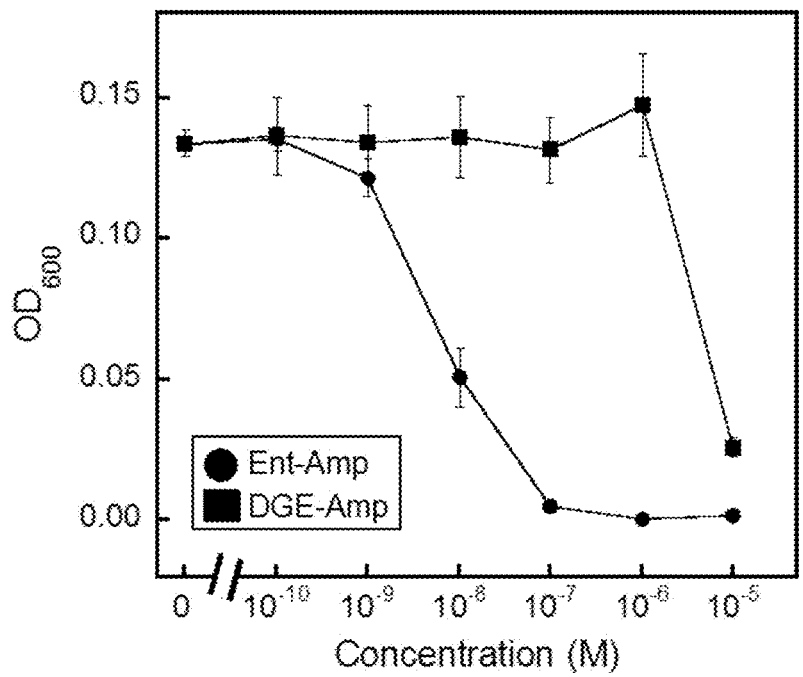
FIGS. 11A and 11B show exemplary antibacterial activities of Ent-ampicillin (Ent-Amp) and DGE-Amp against. $E.$ $coli.$ (50% MHB with 200 µM 2,2'-dipyridyl to provide conditions of iron limitation, 30° C., t=19 h).
Figure 11B:
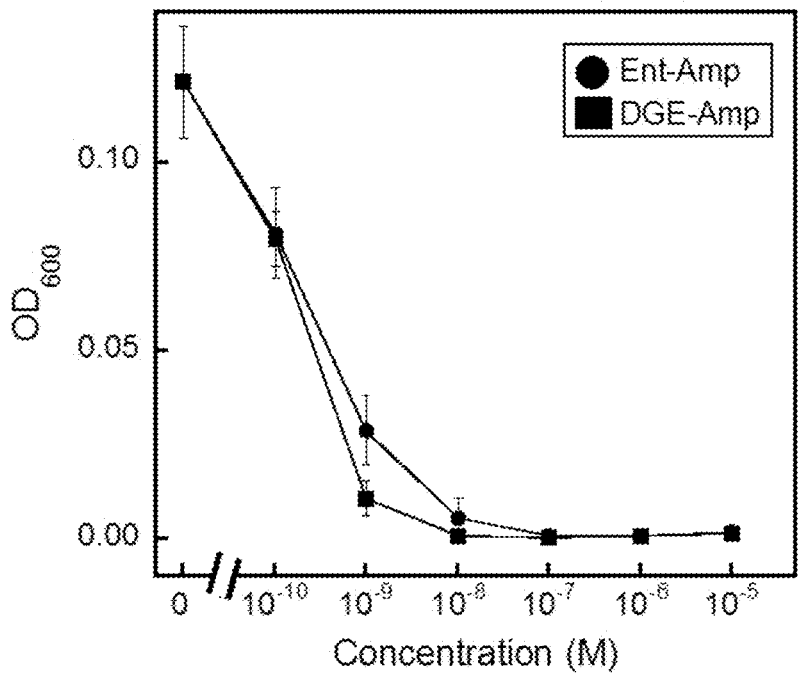
Figure 12A:
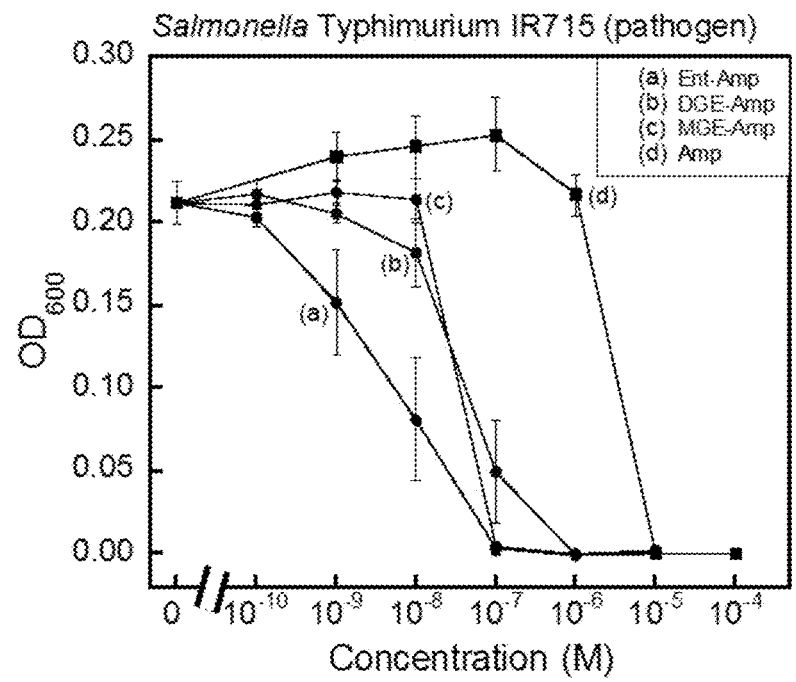
FIGS. 12A and 12B show exemplary antibacterial activities of Ent-Amp, Ent-Amx, MGE-Amp, MGE-Amx, DGE-Amp, and DGE-Amx against *Salmonella enterica* serovar Typhimurium (STM) IR715 (50% MHB with 100 µM 2,2'-dipyridyl to provide conditions of iron limitation, 30° C., t=19 h).
Figure 12B:
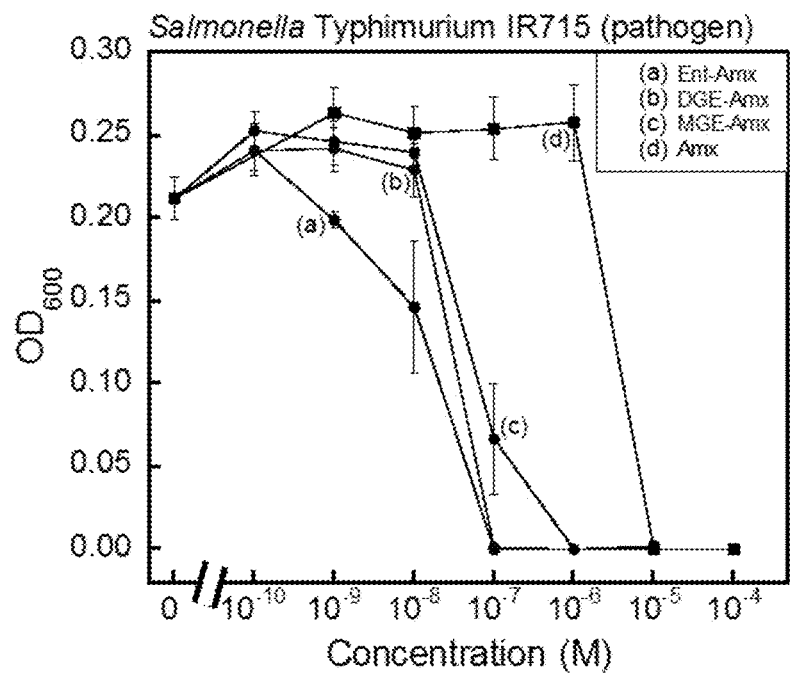
Figure 13:
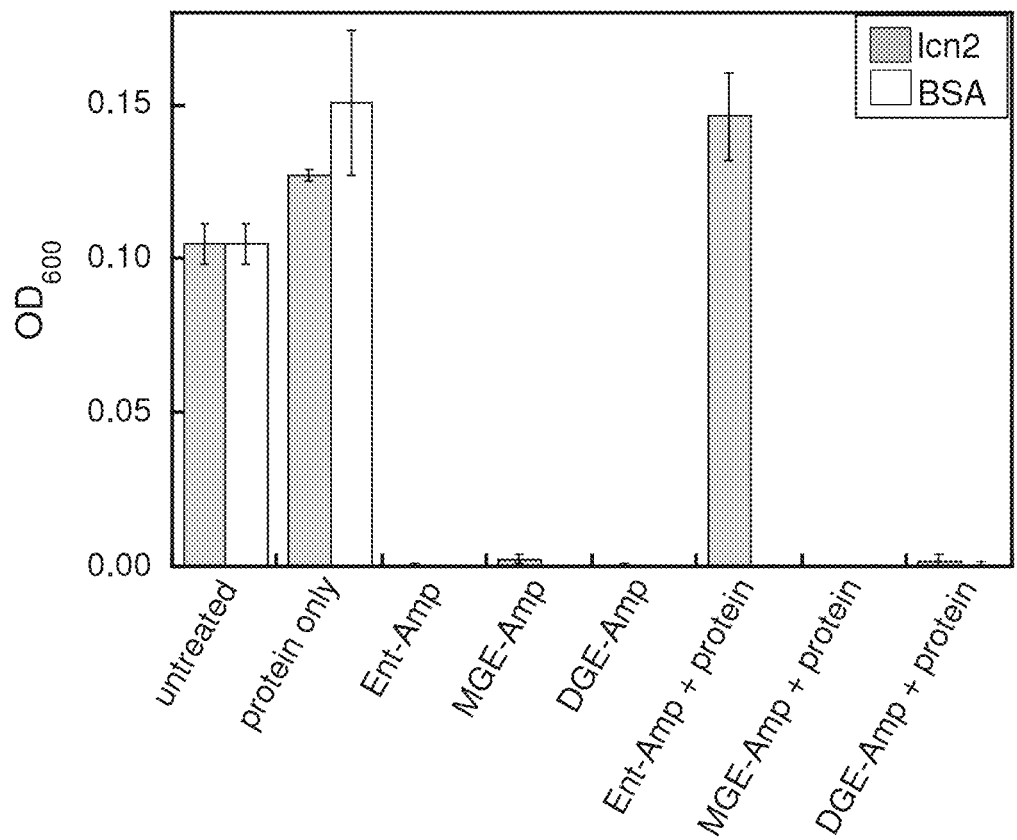
FIG. 13 shows exemplary effects of lipocalin-2 (lcn2) on the activity of Ent-Amp, MGE-Amp, and DGE-Amp against *E. coli* CFT073 in M9 minimal media (37° C., 24 h). The concentration of each one of the conjugates (Ent-Amp, MGE-Amp, and DGE-Amp) used in this assay was 100 nM, and the concentration of lcn2/BSA was 1.0 µM. The antibacterial activity of Ent-Amp was attenuated in the presence of lcn2. In contrast, lcn2 showed no effect on the antibacterial activity of MGE-Amp and DGE-Amp, indicating that lcn2 does not capture the MGE- or DGE-based conjugates.
Figures 14A, 14B:
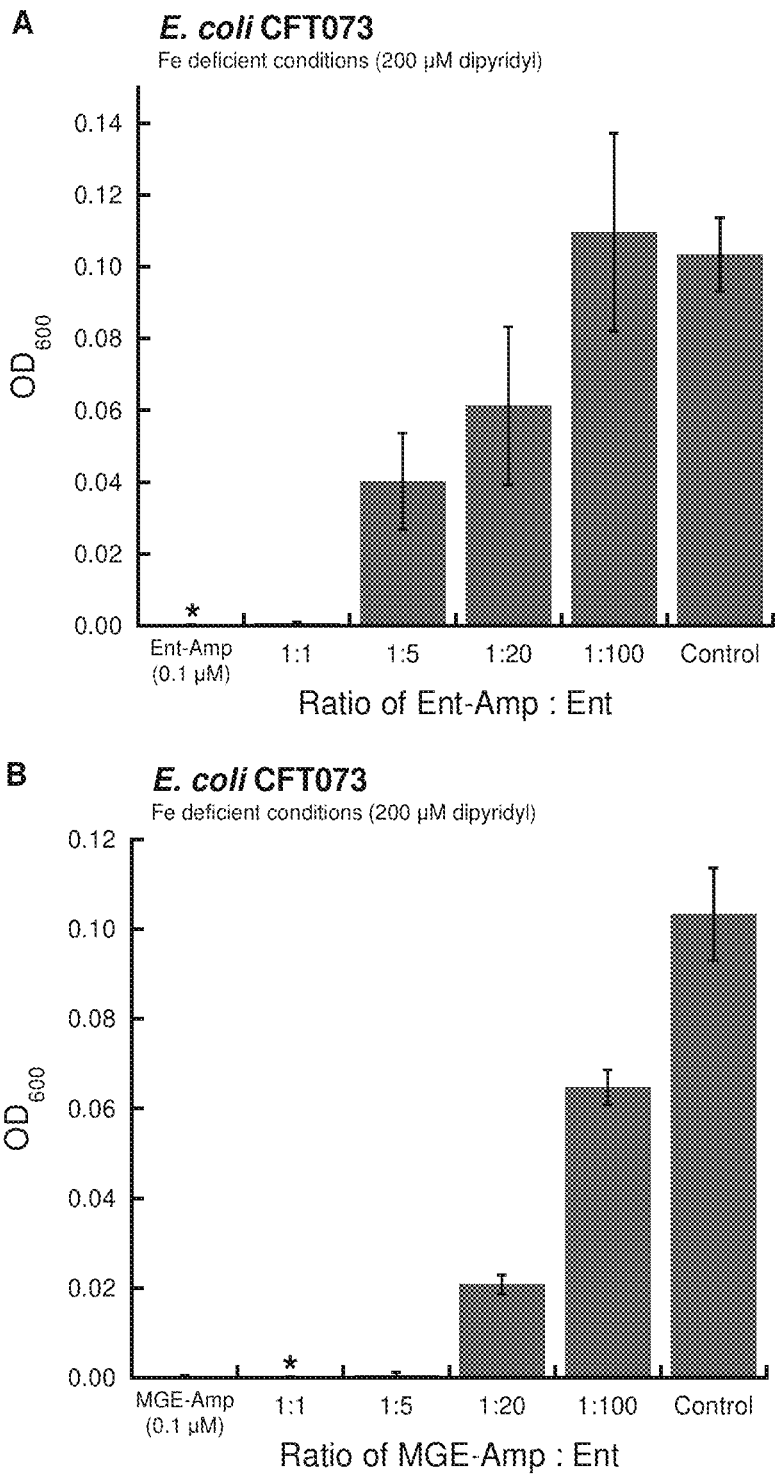
FIGS. 14A-14C show exemplary results of competition assays of Ent-Amp (FIG. 14A), MGE-Amp (FIG. 14B), and DGE-Amp (FIG. 14C) with Ent against *E. coli* CFT073. The concentration of each one of the conjugates (Ent-Amp, MGE-Amp, and DGE-Amp) was fixed at 0.1 µM, and the concentration of Ent varied as labeled. Error bars are the standard error of the mean for at least three independent repetitions. * The OD value is 0. These assays were performed with one synthetic batch of each conjugate.
Figure 14C:
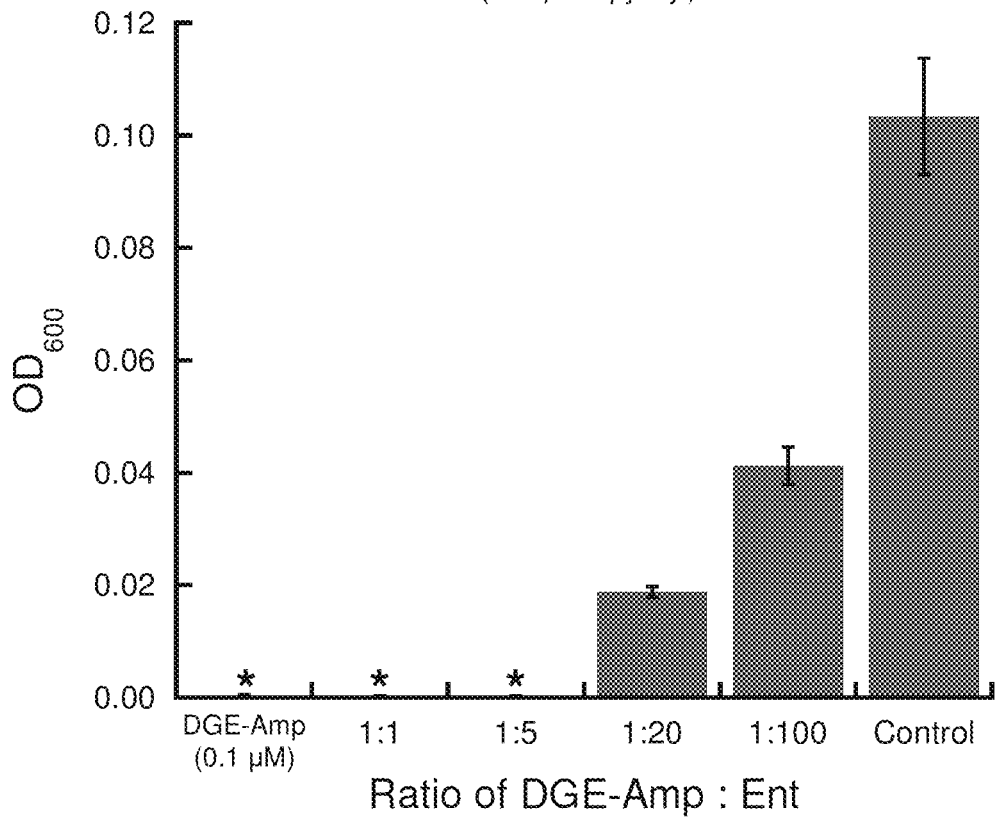
Figures 15A, 15B:
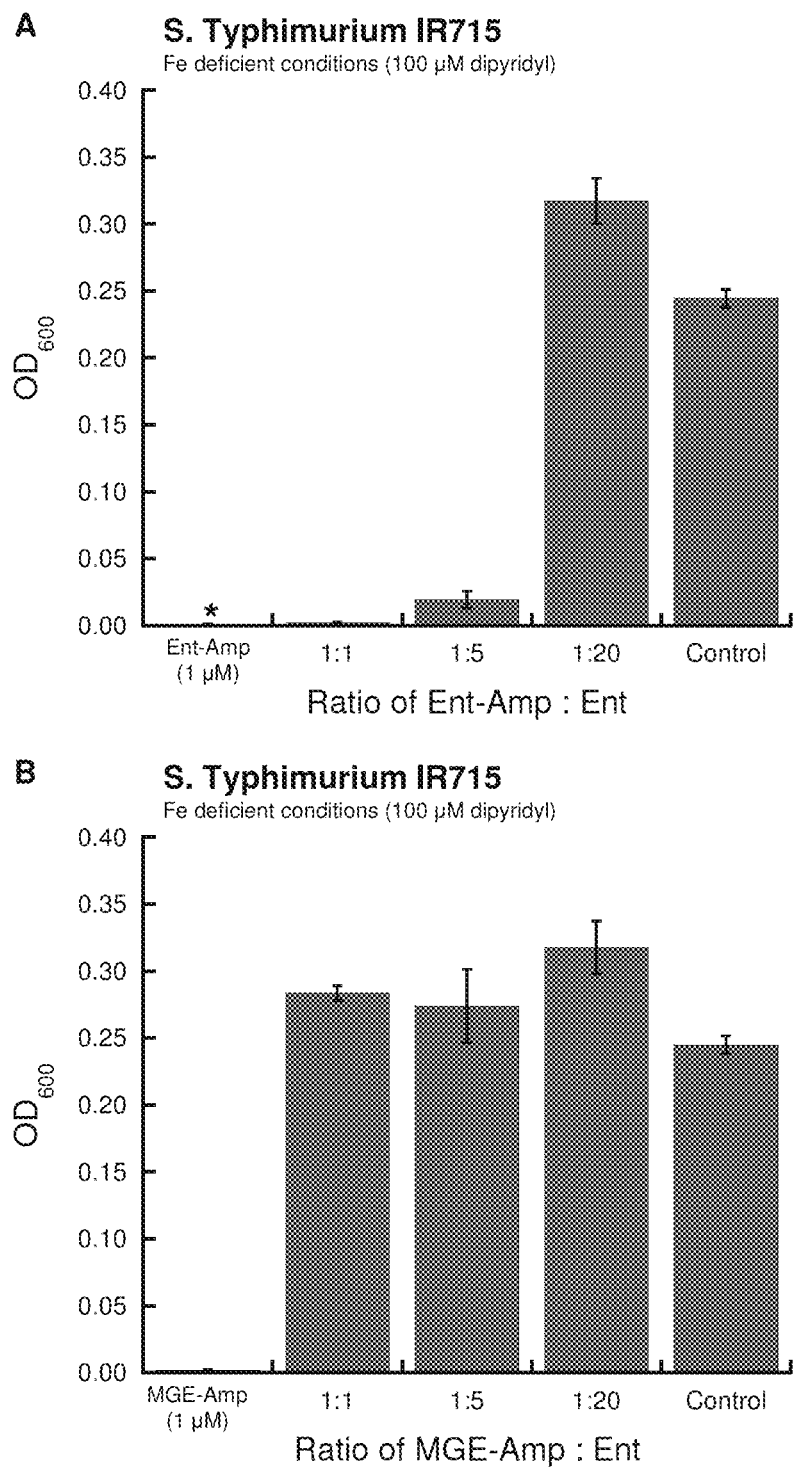
FIGS. 15A-15C show exemplary results of competition assays of Ent-Amp (FIG. 15A), MGE-Amp (FIG. 15B), and DGE-Amp (FIG. 15C) with Ent against STM IR715. The concentration of each one of the conjugates (Ent-Amp, MGE-Amp, and DGE-Amp) was fixed at 1 µM, and the concentration of Ent varied as labeled. Error bars are the standard error of the mean for at least three independent repetitions. * The OD value is 0. These assays were performed with one synthetic batch of each conjugate.
Figure 15C:
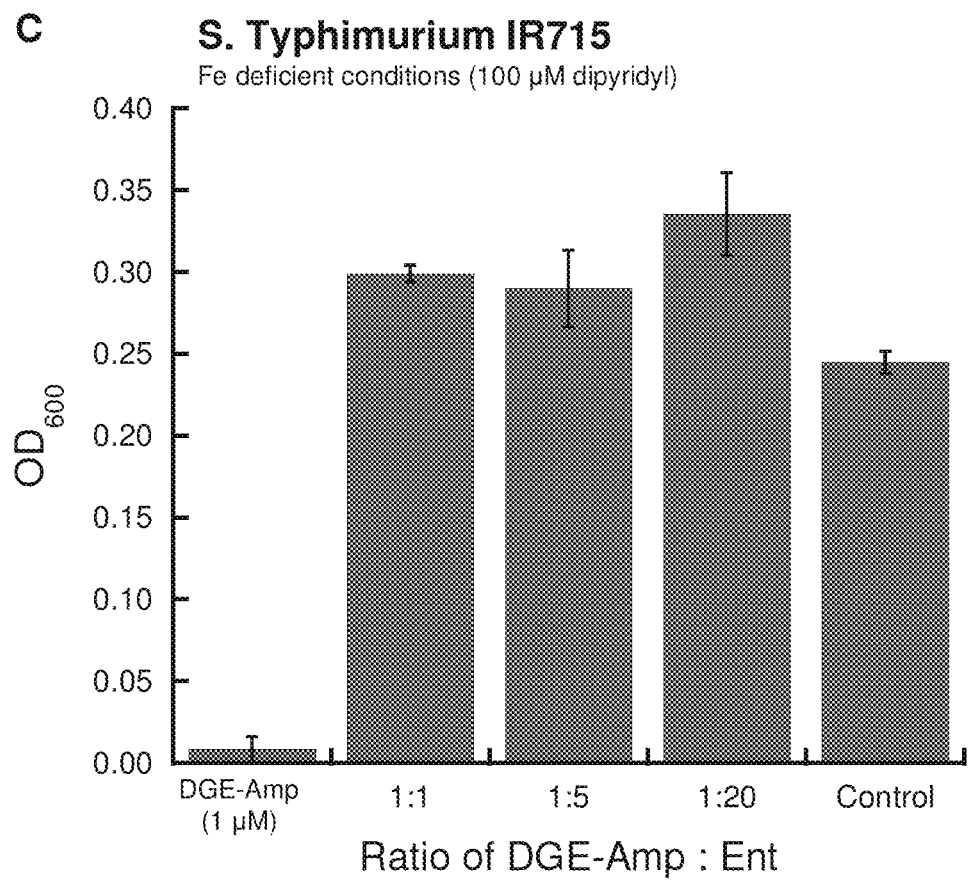
Figures 16A, 16B:
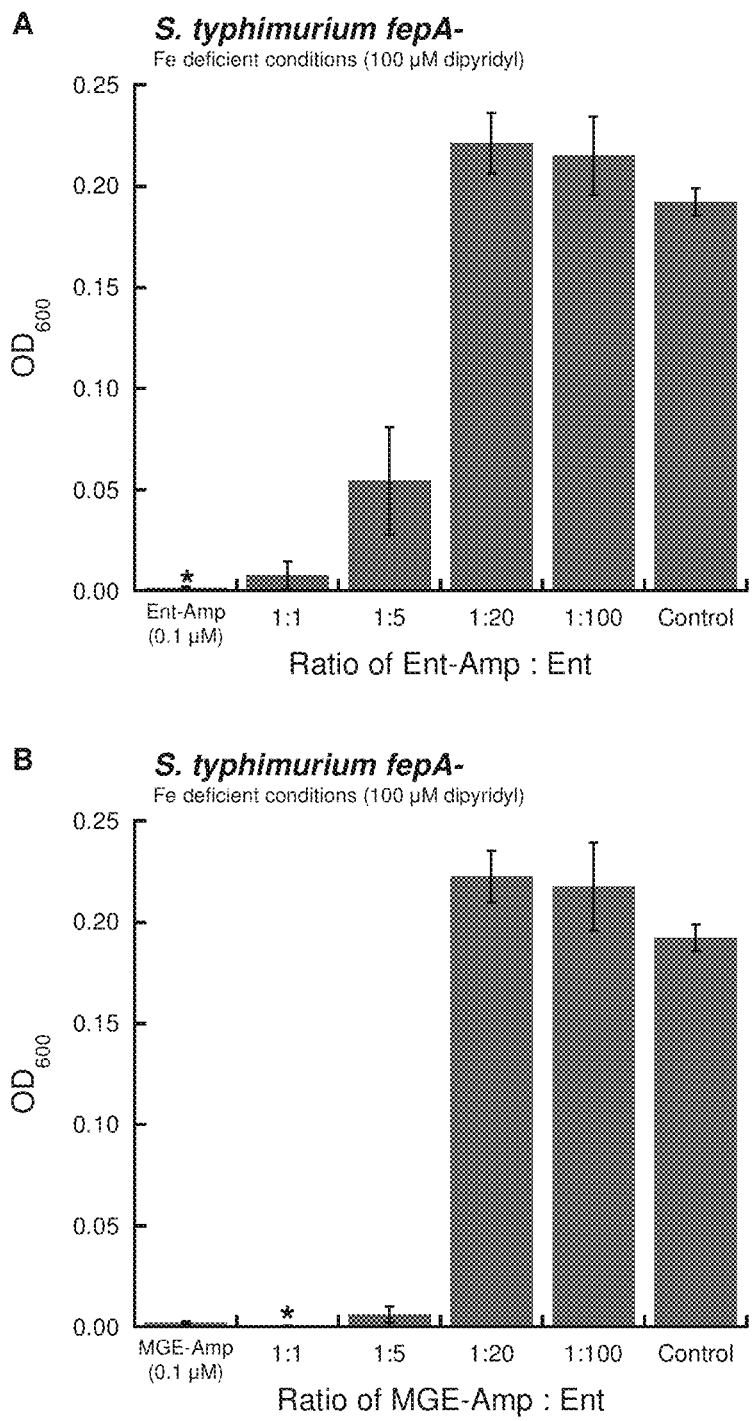
FIGS. 16A-16C show exemplary results of competition assays of Ent-Amp (FIG. 16A), MGE-Amp (FIG. 16B), and DGE-Amp (FIG. 16C) with Ent against STM fepA-. The concentration of each one of the conjugates (Ent-Amp, MGE-Amp, and DGE-Amp) was fixed at 0.1 µM, and the concentration of Ent varied as labeled. Error bars are the standard error of the mean for at least three independent repetitions. * The OD value is 0. These assays were performed with one synthetic batch of each conjugate.
Figure 16C:
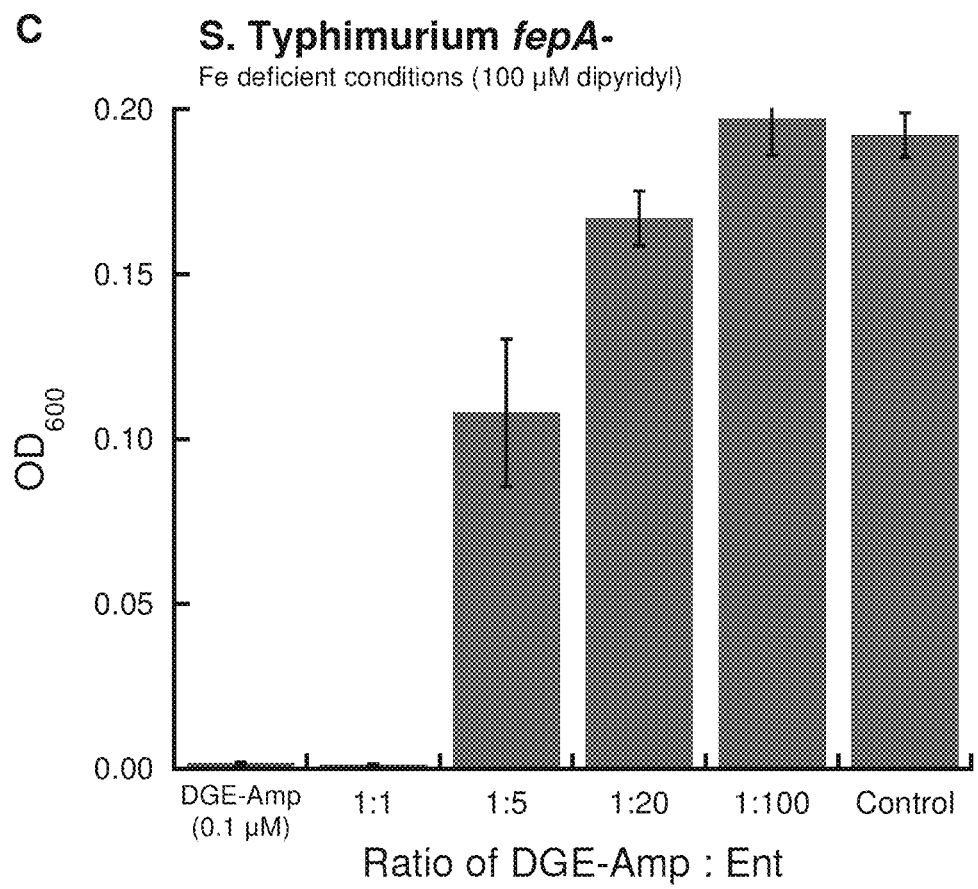
Figure 17A:
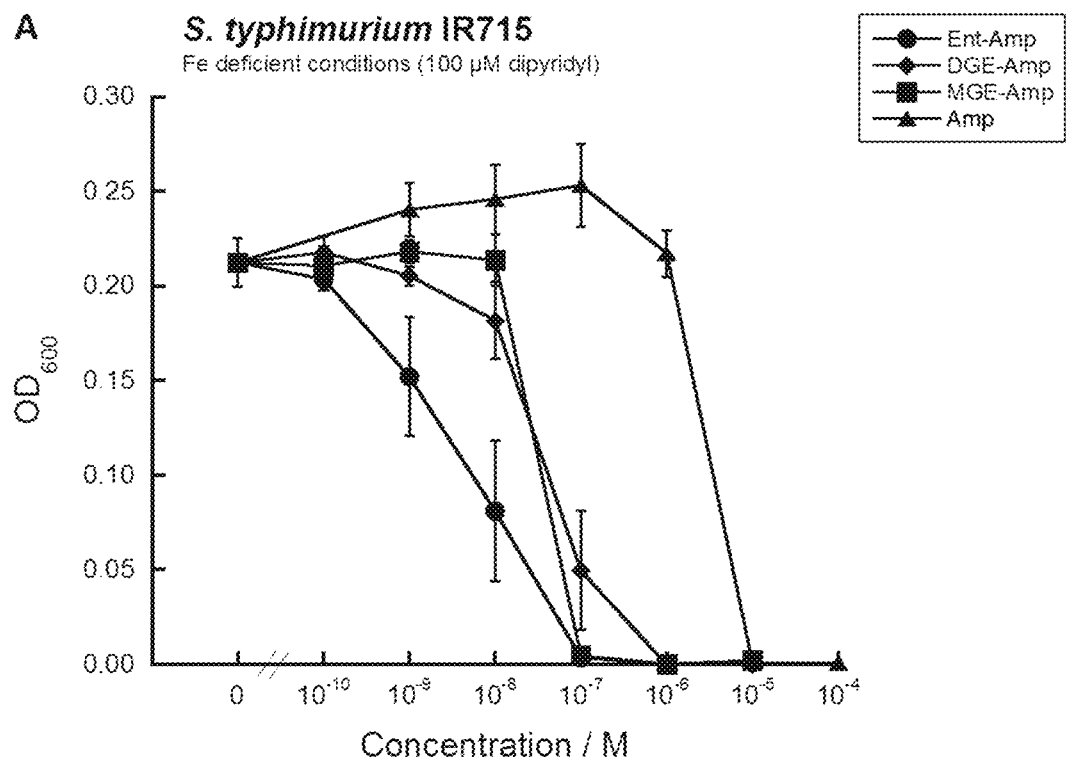
FIGS. 17A-17E show exemplary antimicrobial activities of Ent-Amp, MGE-Amp, DGE-Amp, and Amp against STM IR715 and its mutants. The bacterial growth is represented by $OD_{600}$ values. The bacterial cultures were grown in 96-well plates at 30° C. for 19 h. 2,2'-Dipyridyl (DP) (100 µM) was added to the growth media to afford iron limited condition. Error bars are the standard error of the mean for at least three independent repetitions. These assays were performed with one synthetic batch of each conjugate.
Figures 17B, 17C:
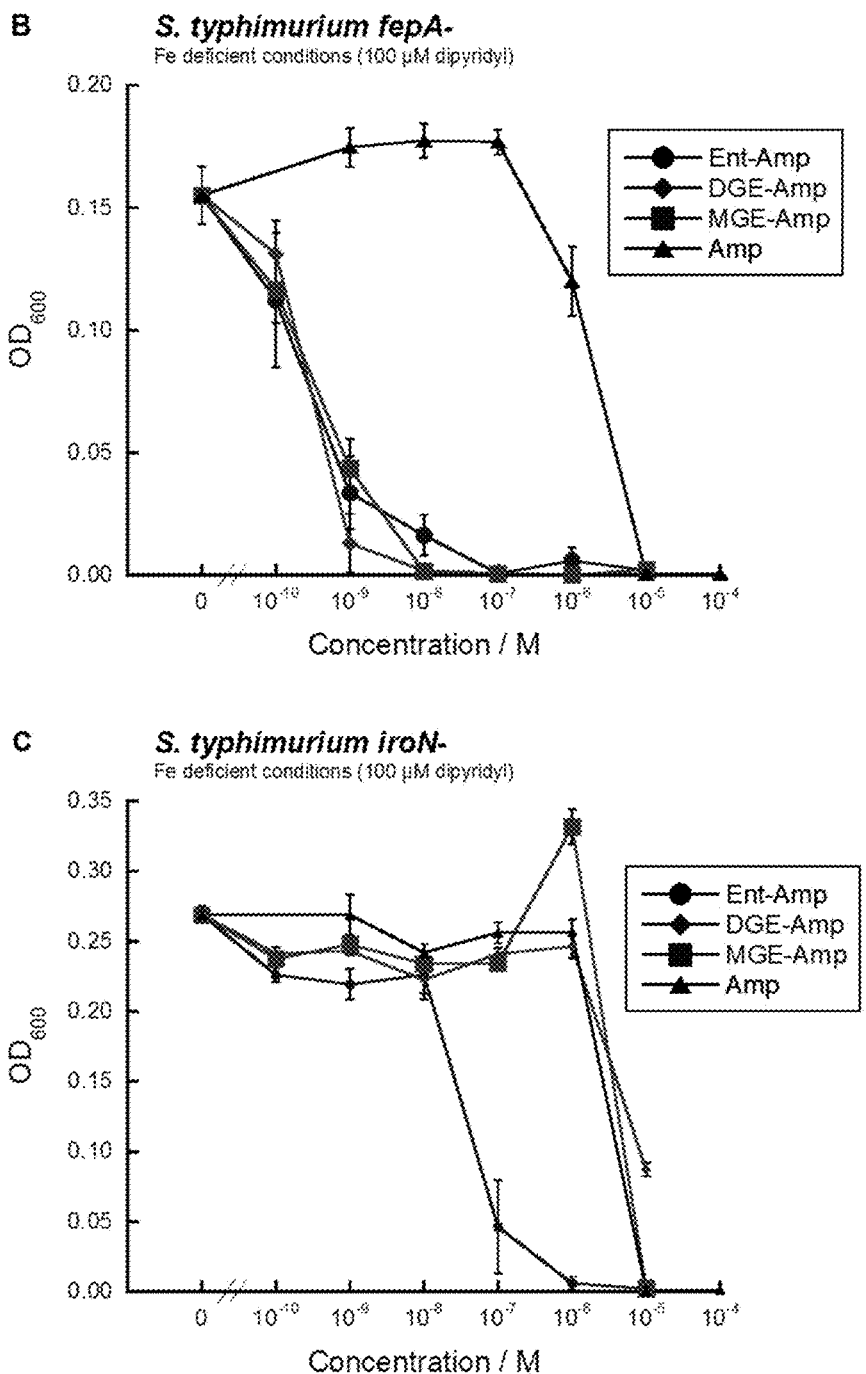
Figures 17D, 17E:
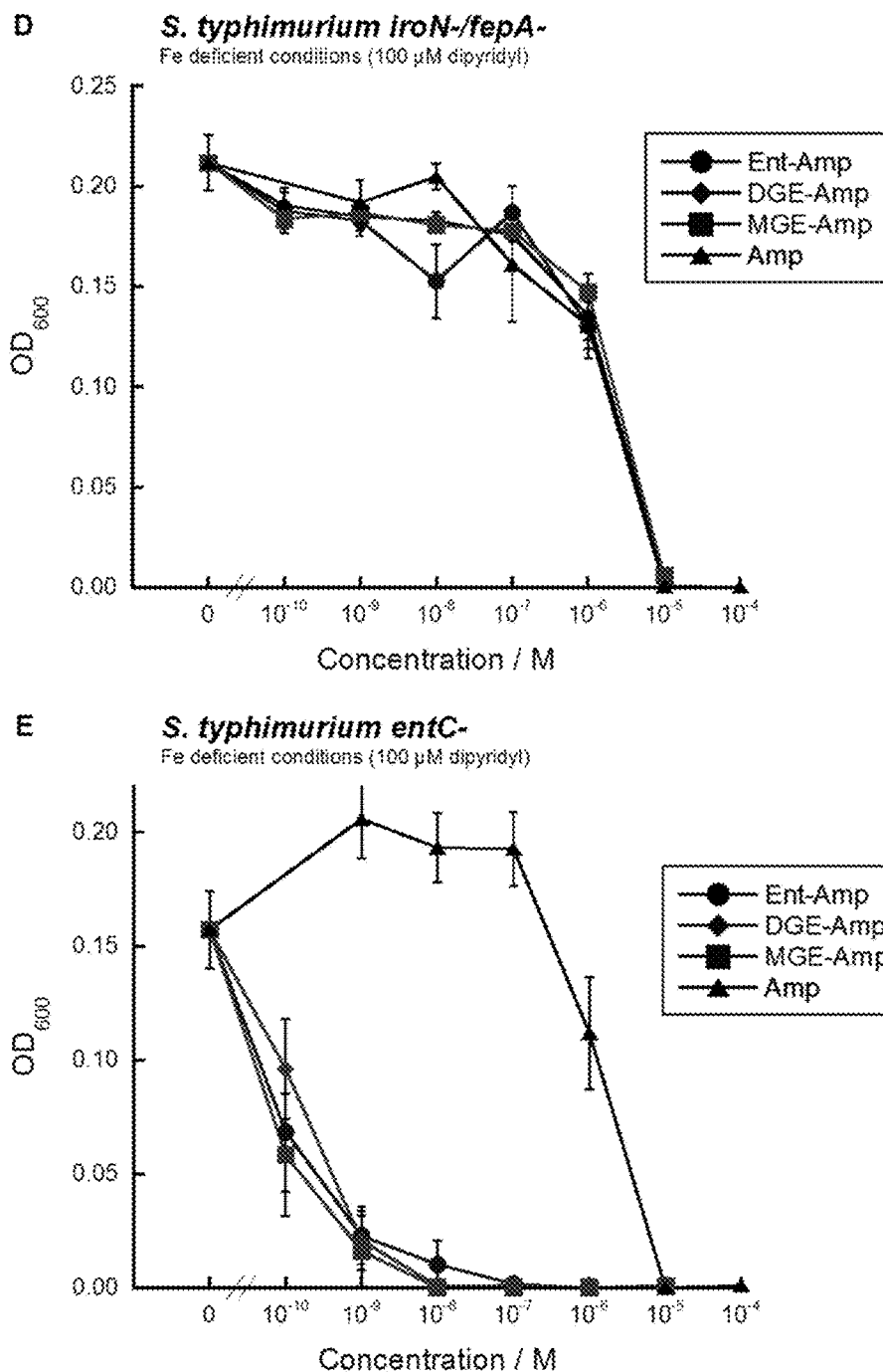
Figure 18A:
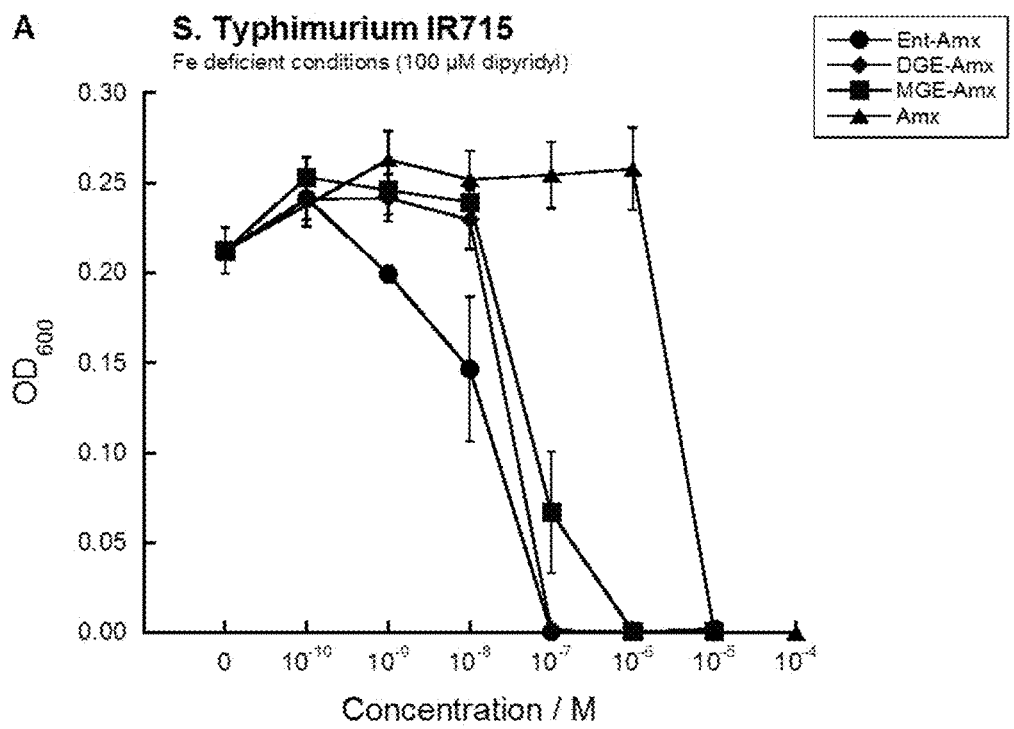
FIGS. 18A-18E show exemplary antimicrobial activities of Ent-Amx, MGE-Amx, DGE-Amx, and Amx against STM IR715 and its mutants. The bacterial growth is represented by $OD_{600}$ values. The bacterial cultures were grown in 96-well plates at 30° C. for 19 h. 2,2'-Dipyridyl (DP) (100 µM) was added to the growth media to afford iron limited condition. Error bars are the standard error of the mean for at least three independent repetitions. These assays were performed with one synthetic batch of each conjugate.
Figures 18B, 18C:
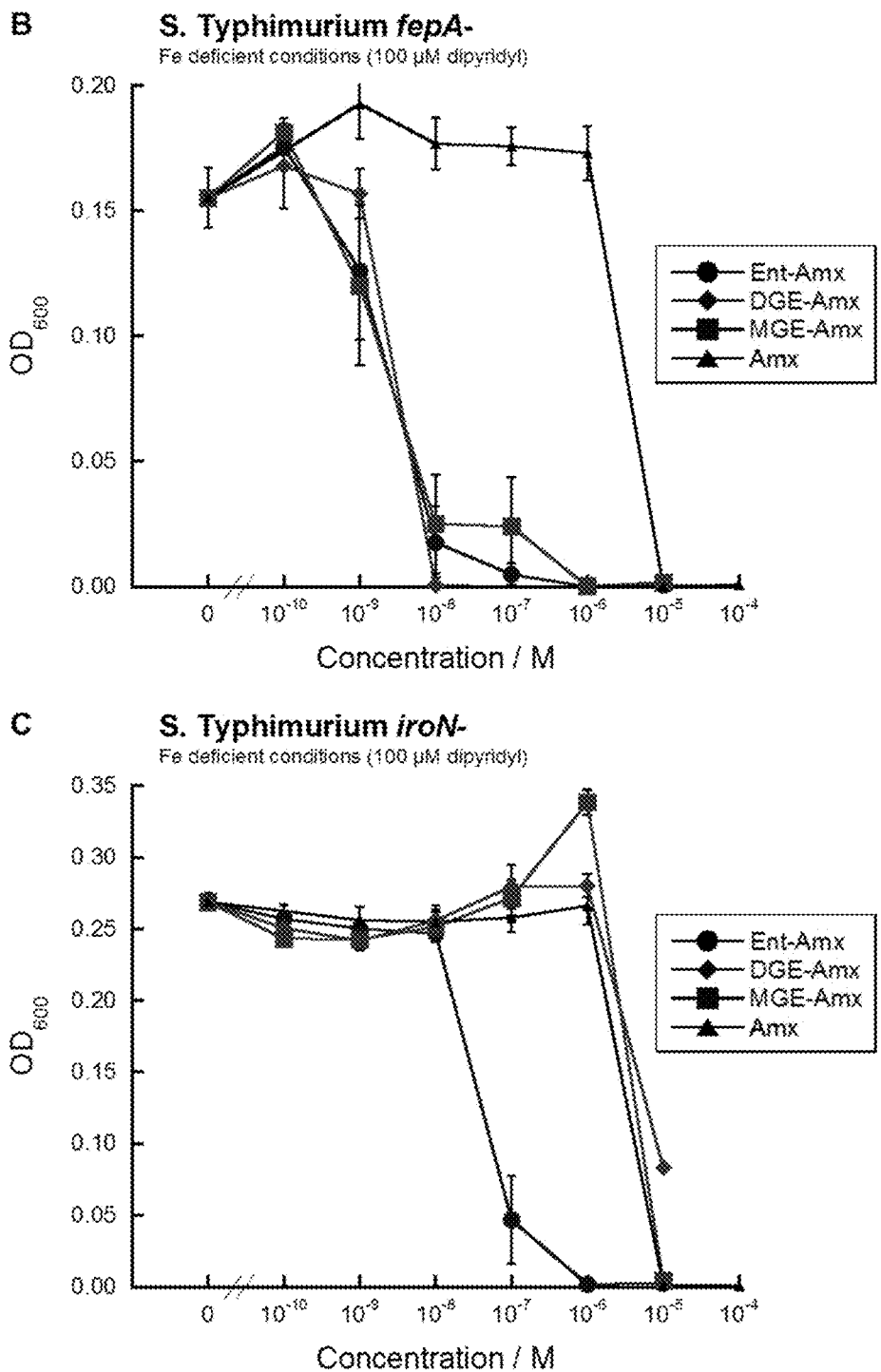
Figures 18D, 18E:
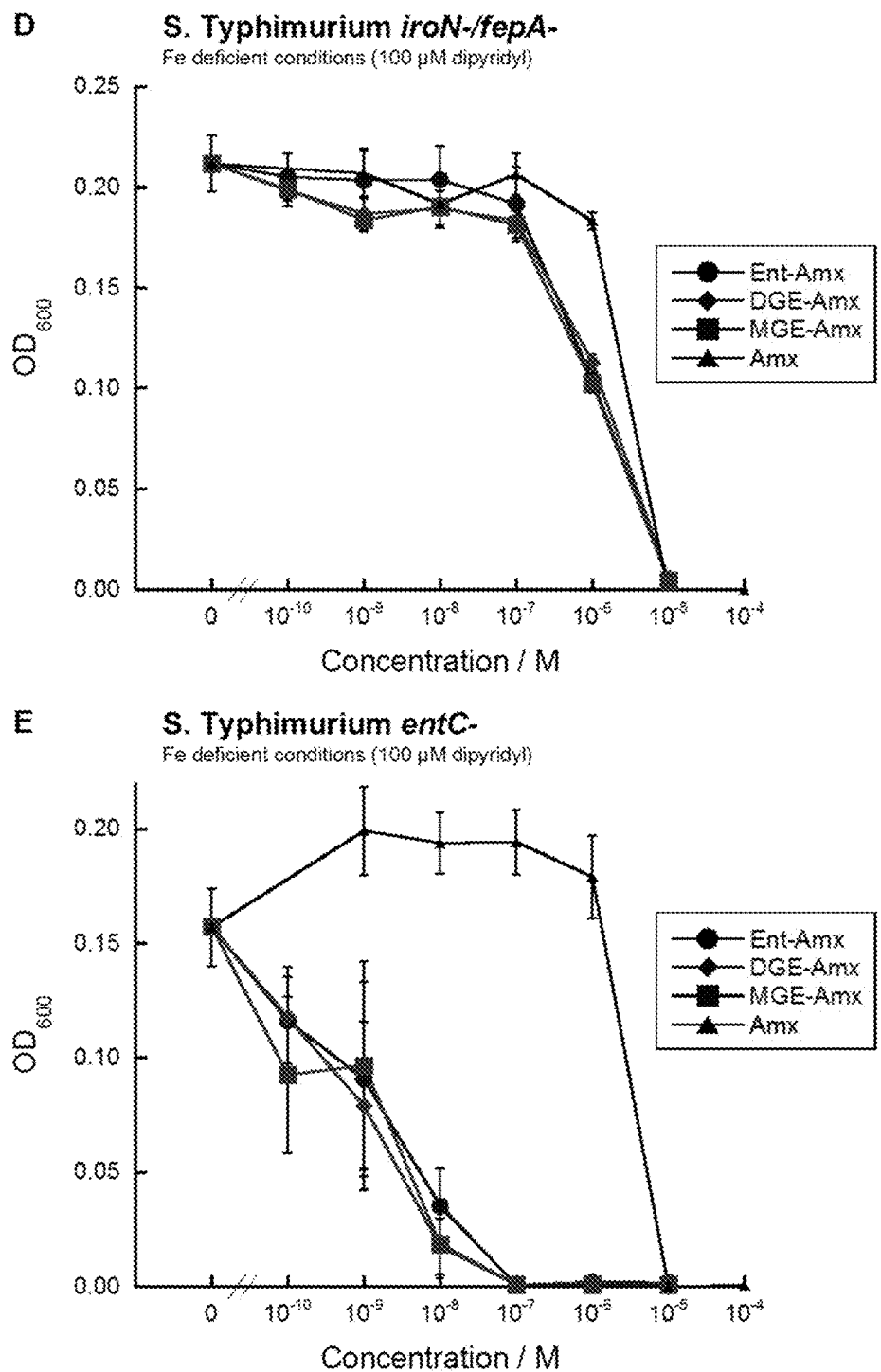

Exemplary results are shown in FIG. 11. DGE-Amp provided enhanced (e.g., 100-fold improved) antibacterial activity against uropathogenic *E. coli* CFT073, which utilizes salmochelins and IroN for iron acquisition, over the standard laboratory strain *E. coli* K-12, which lacks the iroA cluster and cannot utilize salmochelins. *E. coli* K-12 was only inhibited by MGE-Amp, MGE-Amx, DGE-Amp, or DGE-Amx at micromolar concentrations. This growth inhibition is attributed to iron deprivation resulting from having micromolar concentrations of the impermeable high-affinity iron chelators (MGE and DGE moieties of the conjugates) in the media. Moreover, the activity of MGE-Amp, MGE-Amx, DGE-Amp, or DGE-Amx against *E. coli* CFT073 is unaffected by the presence of lcn2, indicating that these conjugates are not bound by lcn2 and will not be compromised by the host innate immune response. See, e.g., FIG. 13.

Example 9. Antibacterial Activity of Enterobactin and Salmochelin Conjugates

Figures 20A, 20B:
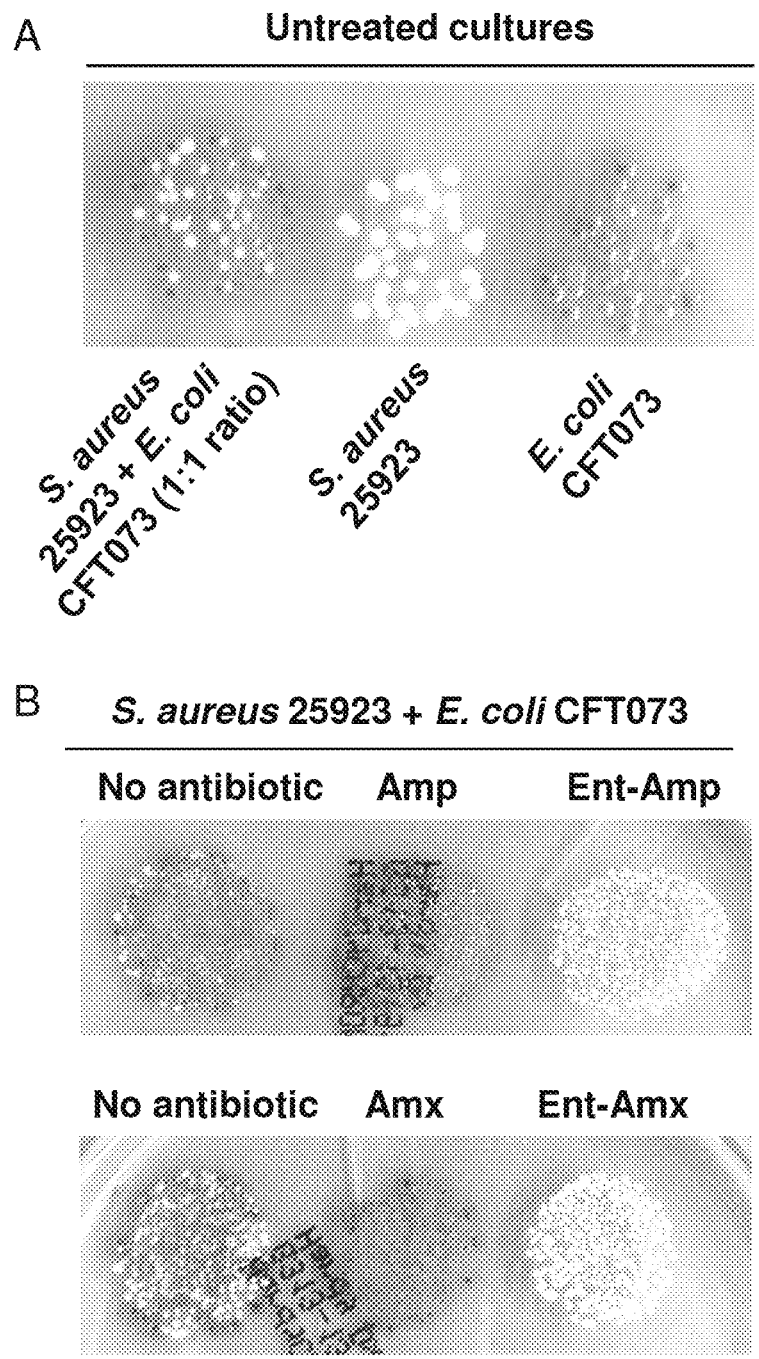
FIGS. 20A and 20B show that each of Ent-Amp and Ent-Amx killed *E. coli* CFT073 in the presence of *Staphylococcus aureus* (*S. aureus*) 25923.
Figures 21A, 21B:
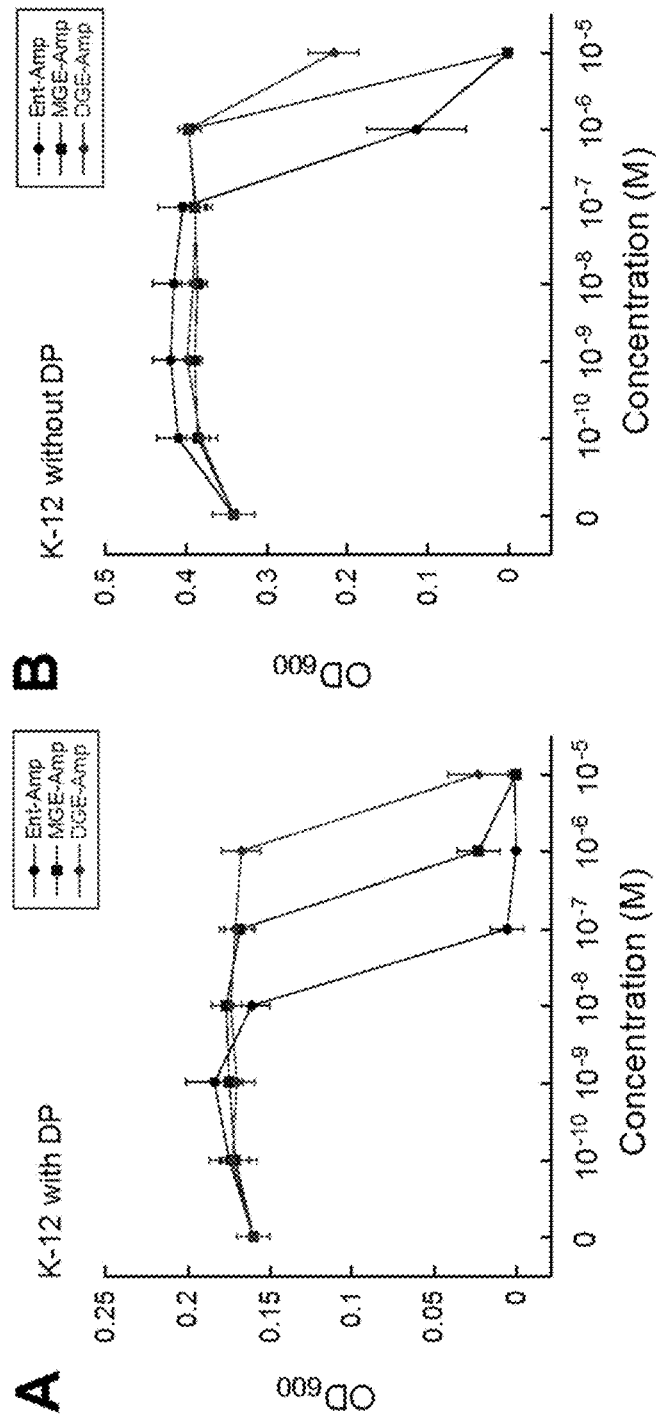
FIGS. 21A to 21D show exemplary antibacterial activities of select Ent-β-lactam conjugates (Ent-Amp and Ent-Amx) and their glucosylated derivatives (MGE-Amp, MGE-Amx, DGE-Amp, and DGE-Amx) against the non-pathogenic laboratory strain *E. coli* K-12.
Figures 21C, 21D:
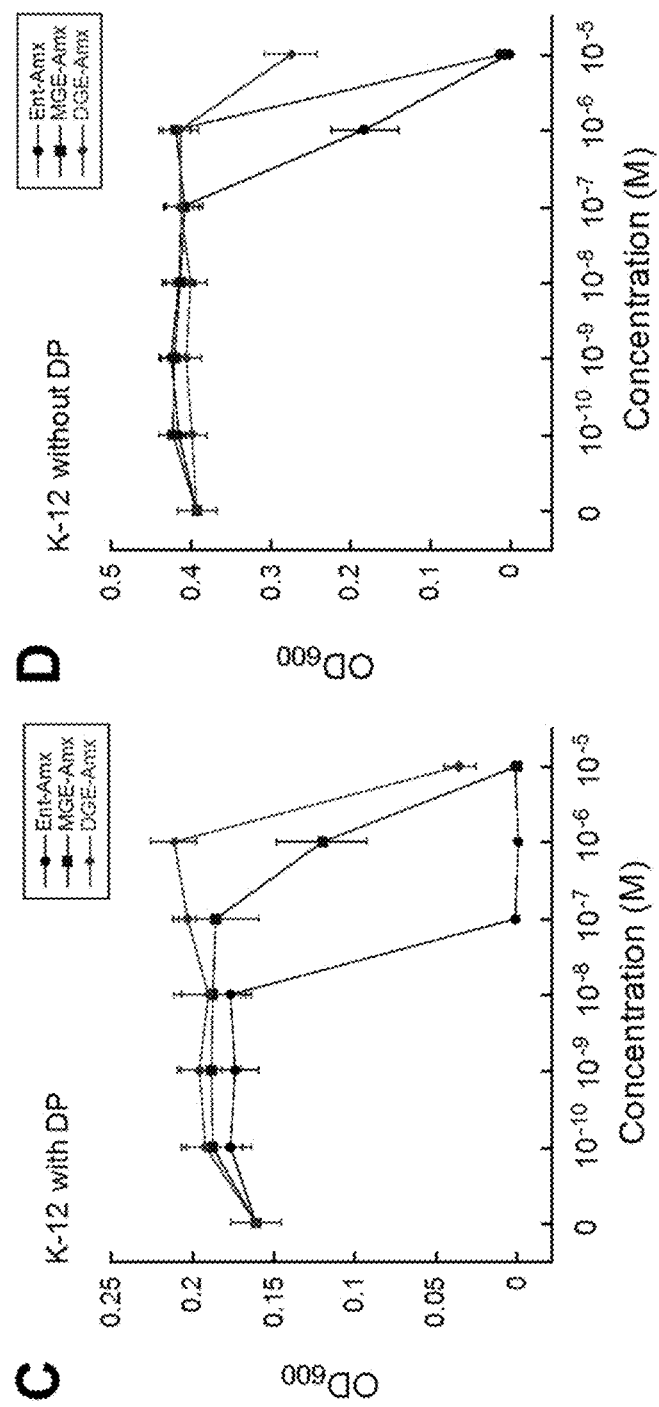
Figures 22A, 22B:
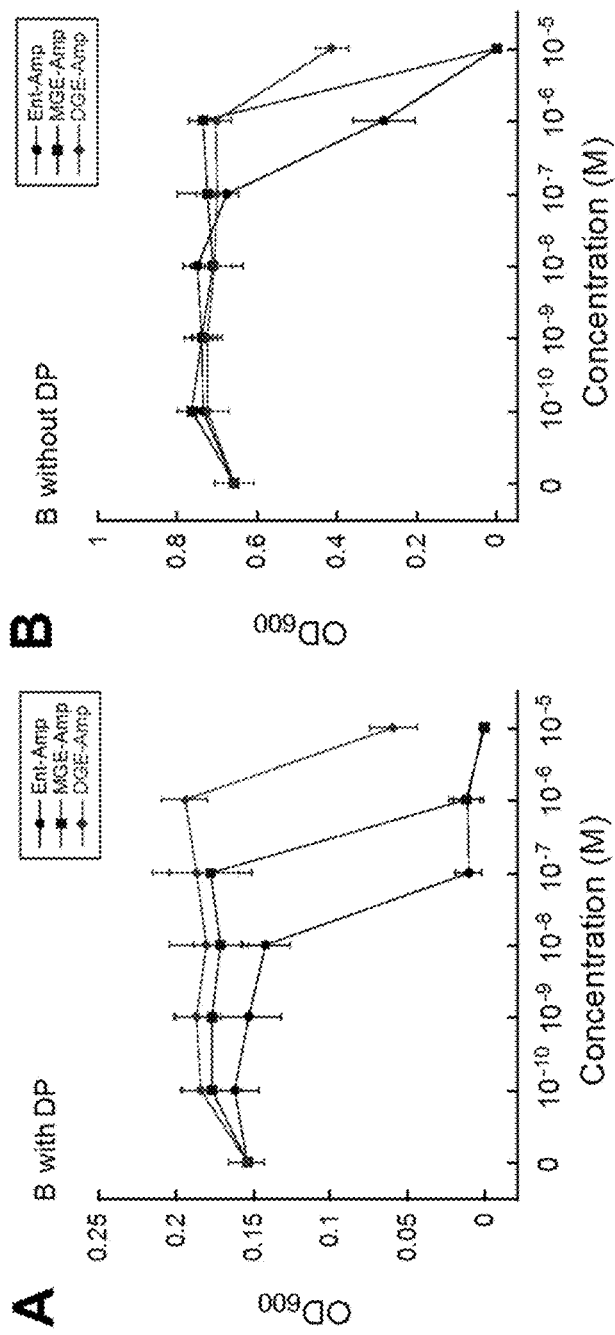
FIG. 22A to 22D show exemplary antibacterial activities of select Ent-β-lactam conjugates (Ent-Amp and Ent-Amx) and their glucosylated derivatives (MGE-Amp, MGE-Amx, DGE-Amp, and DGE-Amx) against the non-pathogenic laboratory strain *E. coli* B.
Figures 22C, 22D:
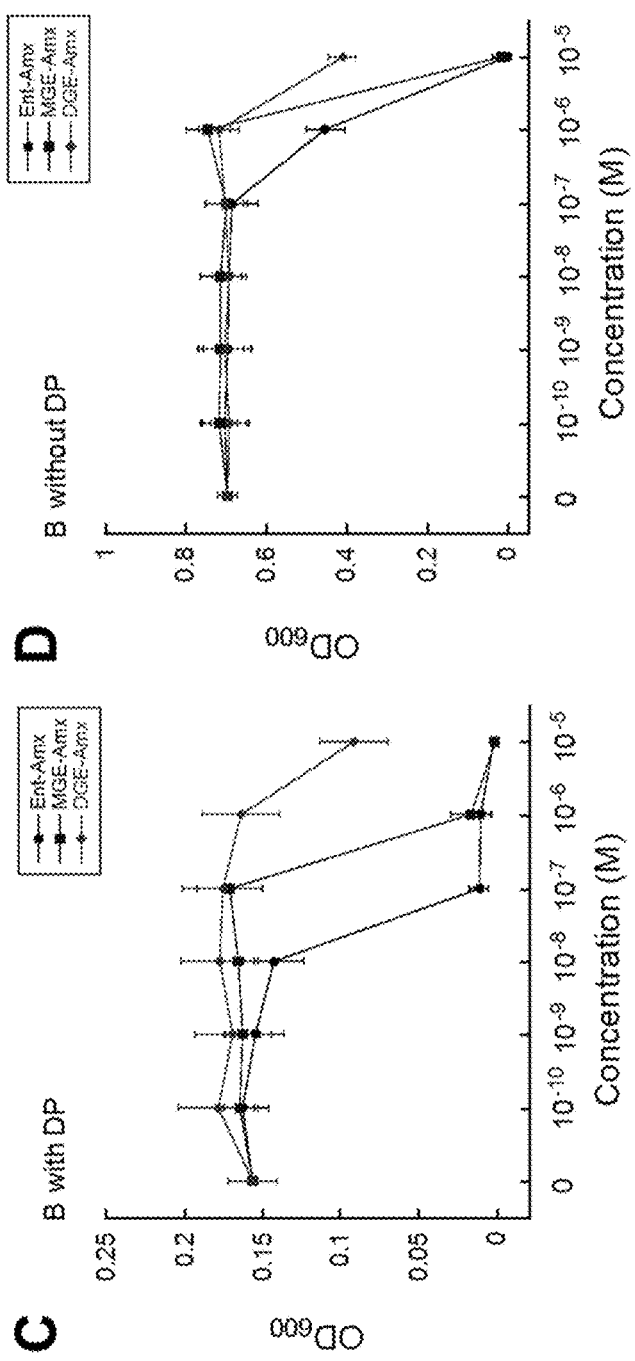
Figures 23A, 23B:
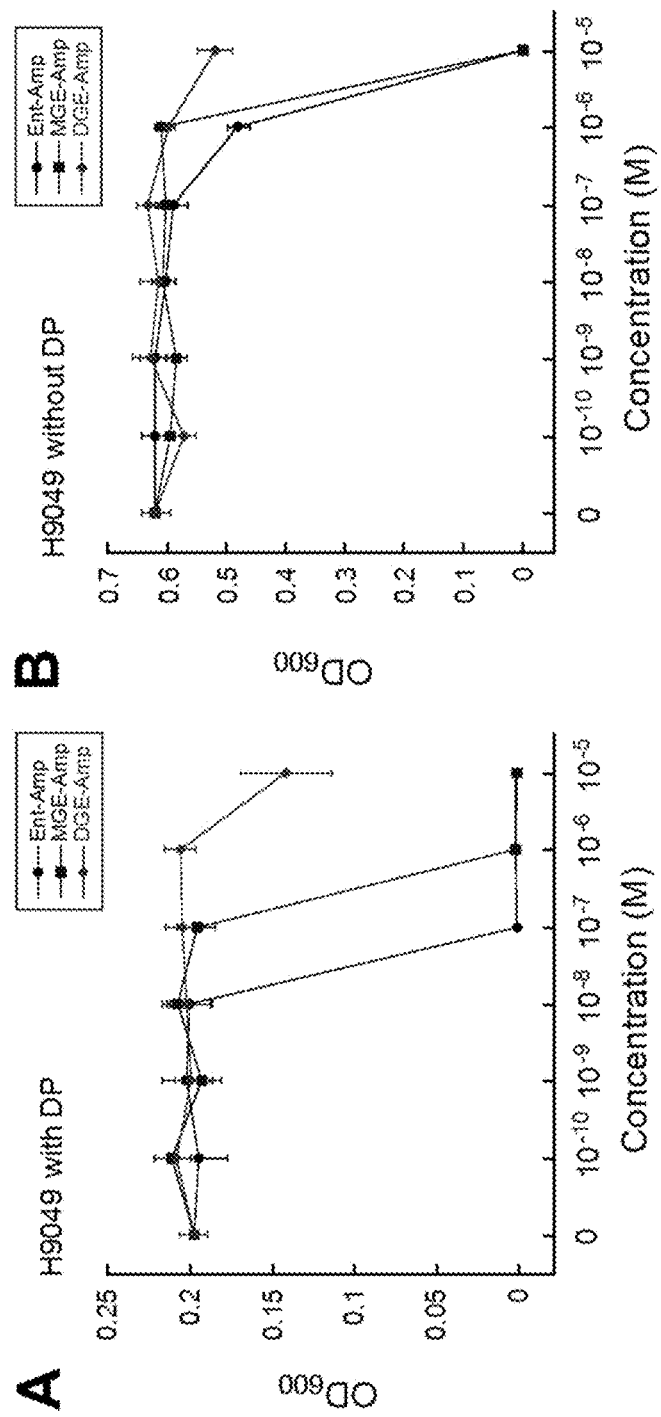
FIG. 23A to 23D show exemplary antibacterial activities of select Ent-β-lactam conjugates (Ent-Amp and Ent-Amx) and their glucosylated derivatives (MGE-Amp, MGE-Amx, DGE-Amp, and DGE-Amx) against the non-pathogenic clinical strain *E. coli* H9049.
Figures 23C, 23D:
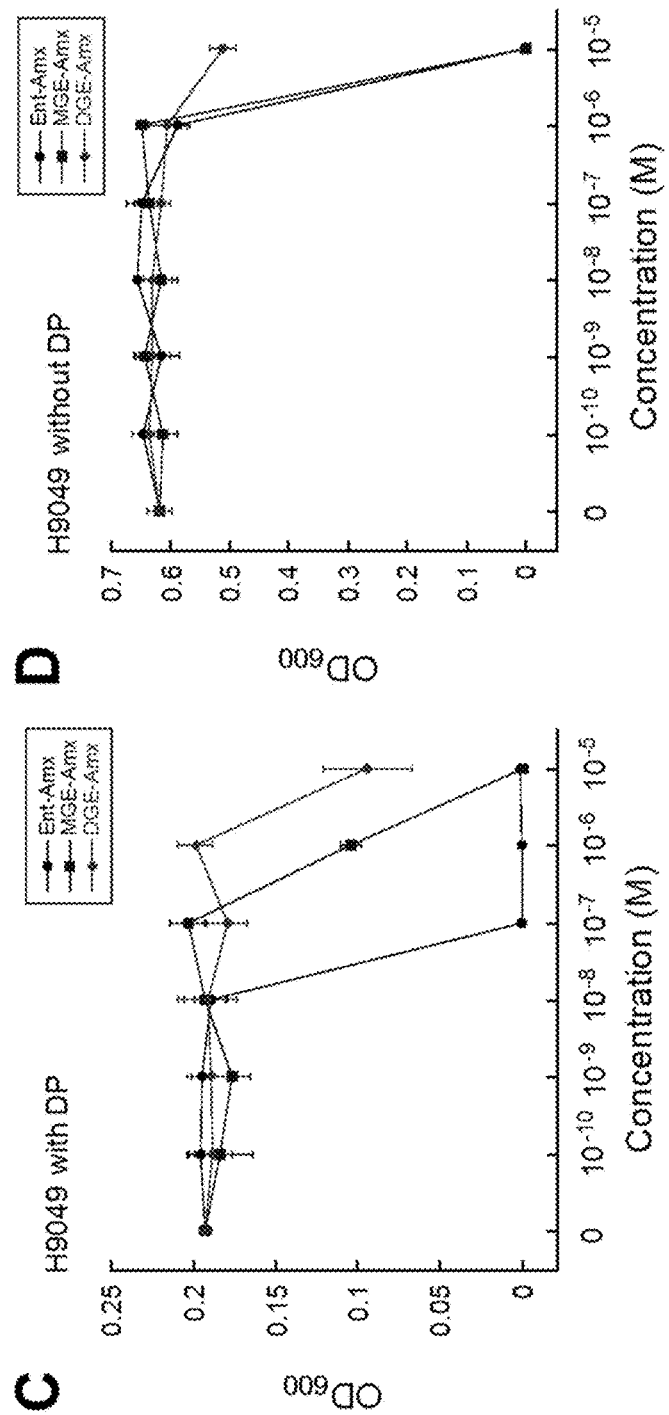
Figures 24A, 24B:
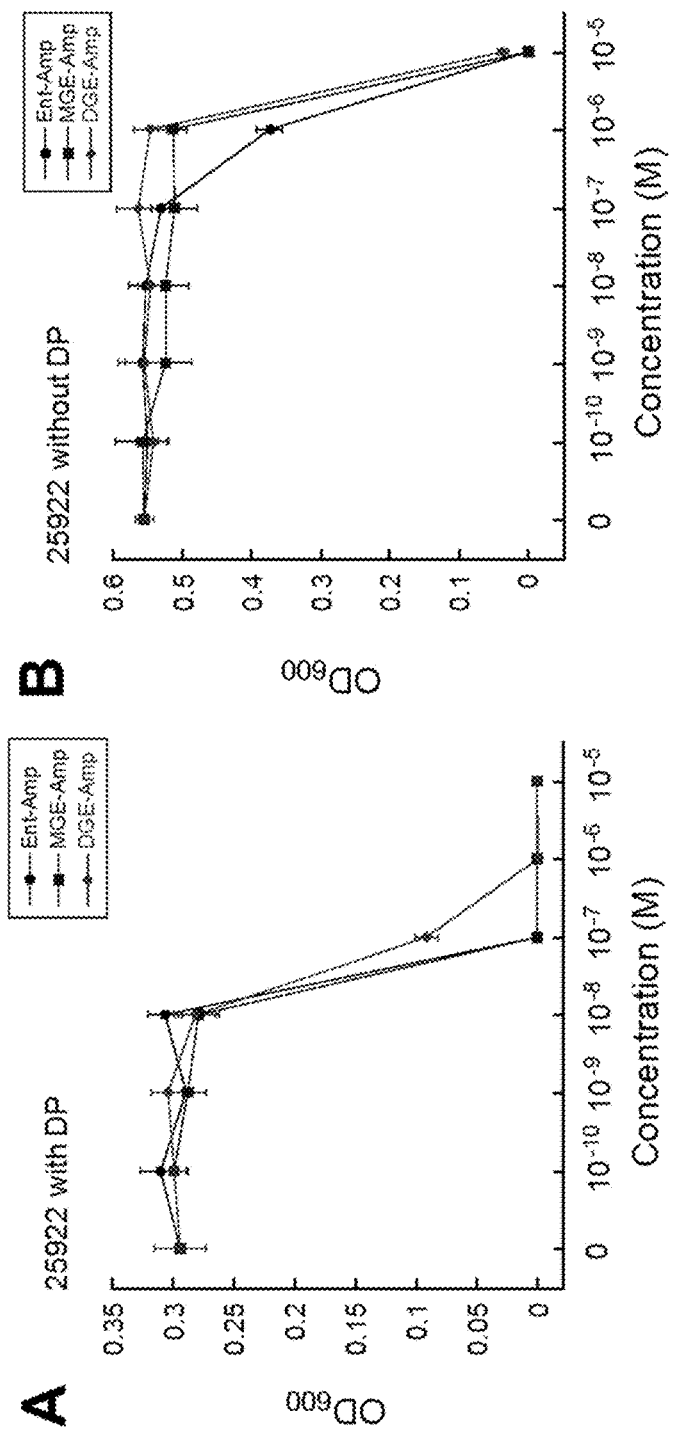
FIGS. 24A to 24D show exemplary antibacterial activities of select Ent-β-lactam conjugates (Ent-Amp and Ent-Amx) and their glucosylated derivatives (MGE-Amp, MGE-Amx, DGE-Amp, and DGE-Amx) against the non-pathogenic clinical strain *E. coli* 25922.
Figures 24C, 24D:
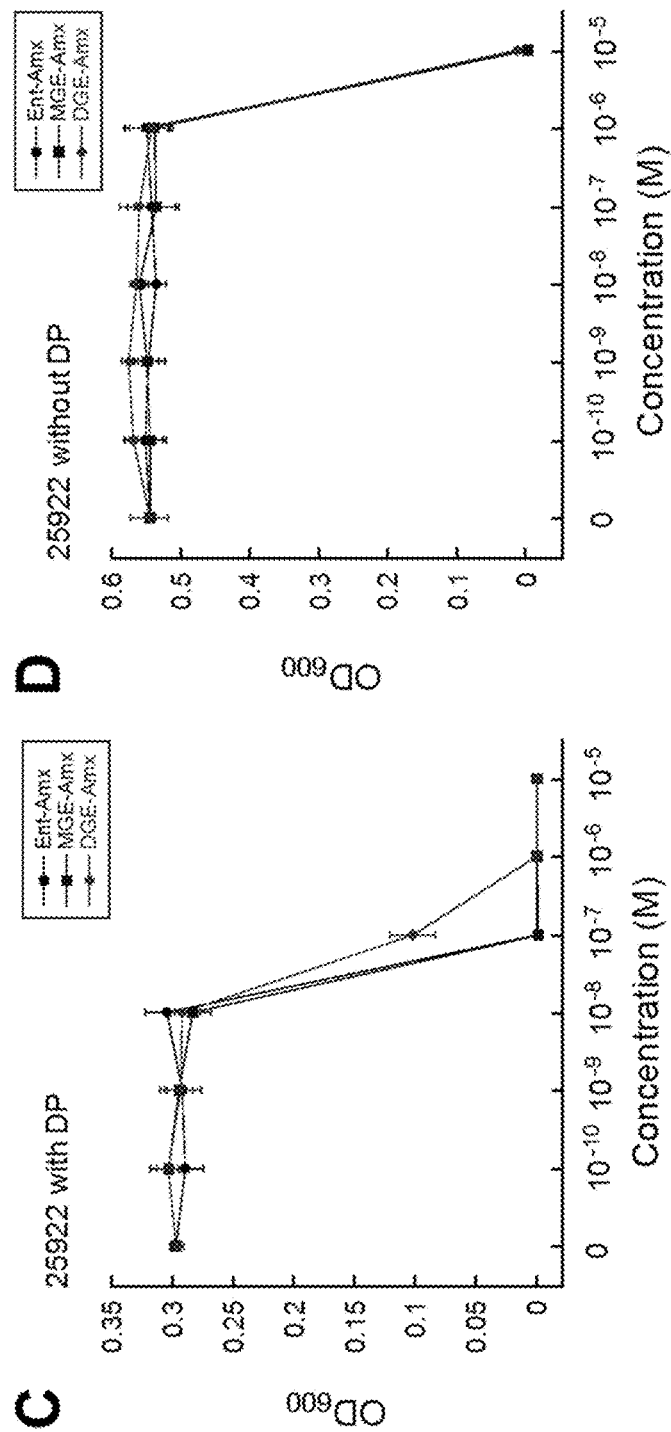
Figures 25A, 25B:
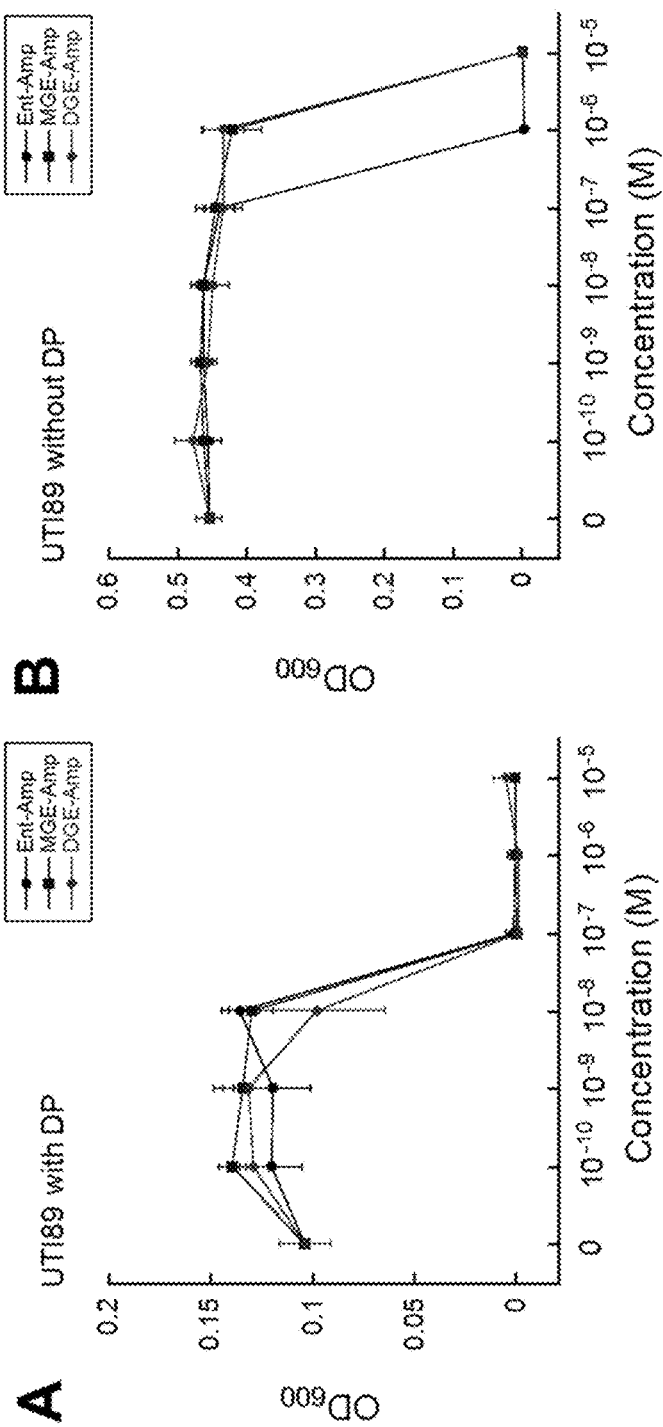
FIGS. 25A to 25D show exemplary antibacterial activities of select Ent-β-lactam conjugates (Ent-Amp and Ent-Amx) and their glucosylated derivatives (MGE-Amp, MGE-Amx, DGE-Amp, and DGE-Amx) against the uropathogenic strain *E. coli* UTI89.
Figures 25C, 25D:
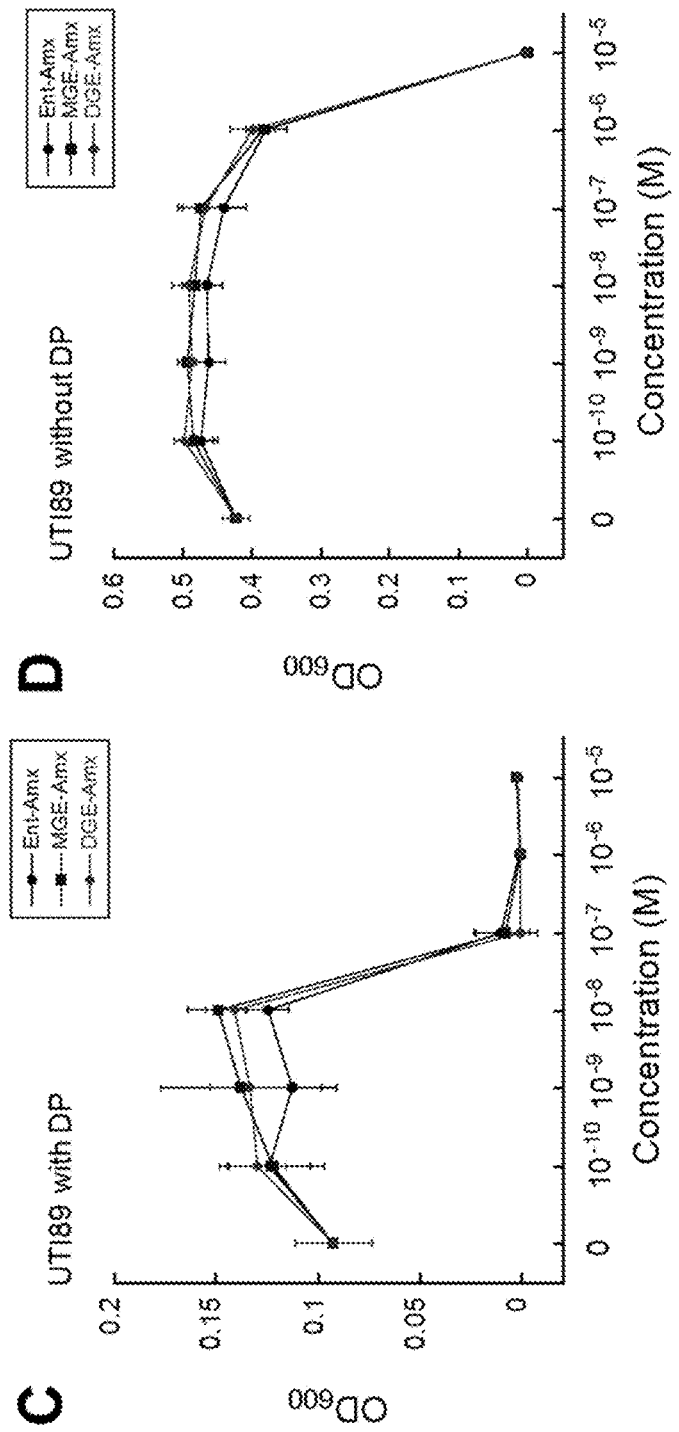
Figures 26A, 26B:
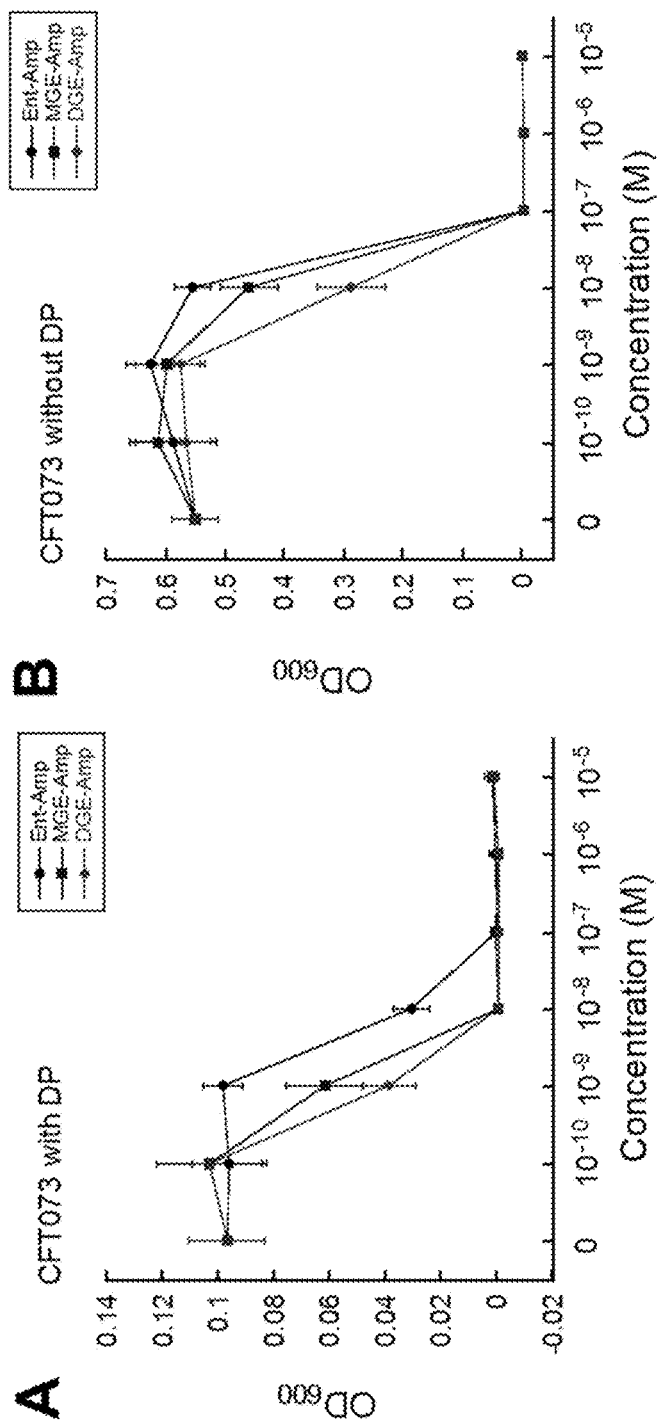
FIGS. 26A to 26D show exemplary antibacterial activities of select Ent-β-lactam conjugates (Ent-Amp and Ent-Amx) and their glucosylated derivatives (MGE-Amp, MGE-Amx, DGE-Amp, and DGE-Amx) against the uropathogenic strain *E. coli* CFT073.
Figures 26C, 26D:
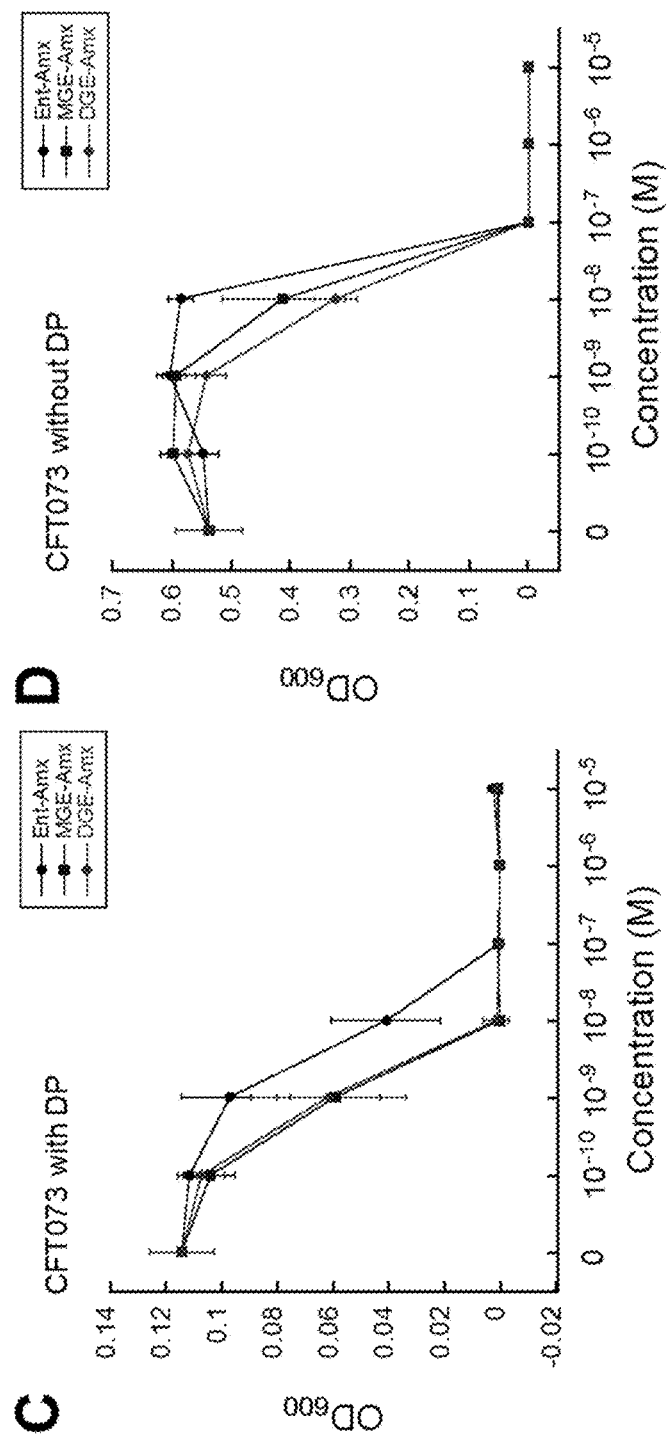
Figures 27A, 27B:
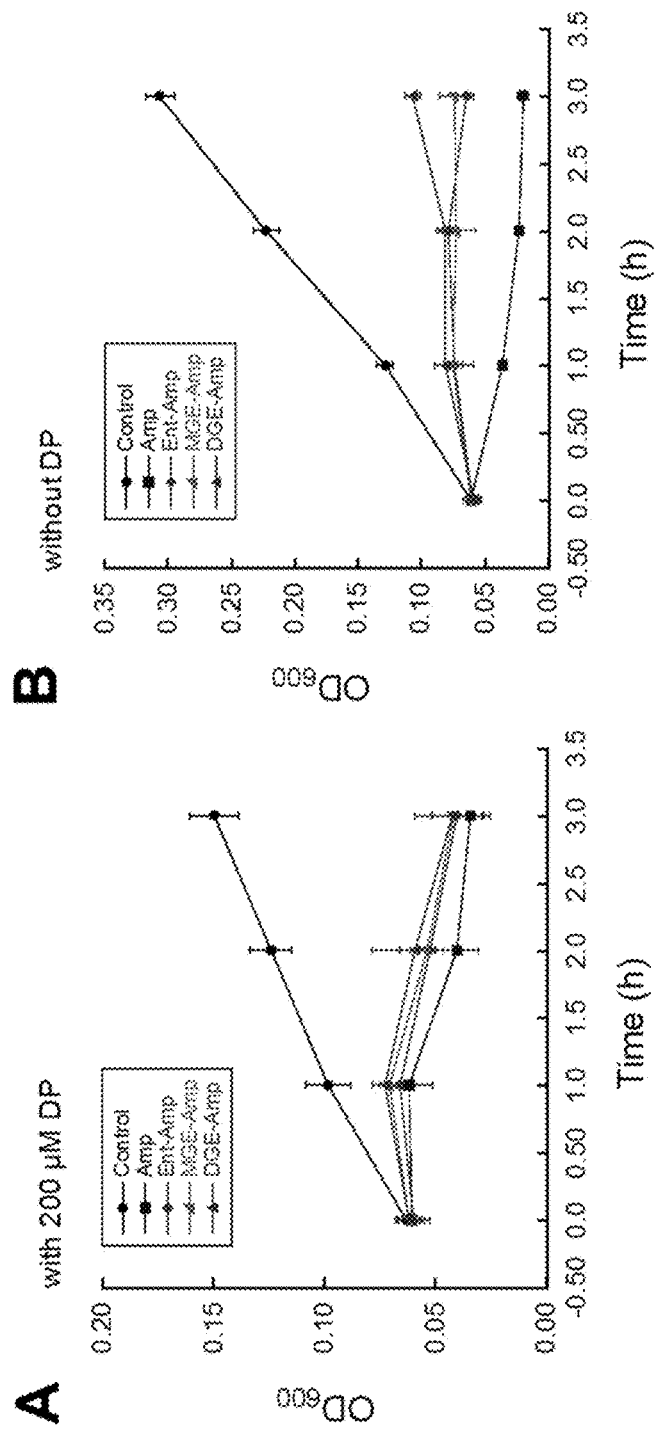
FIGS. 27A to 27D show exemplary $OD_{600}$ measurements of time-kill kinetic assays of select Ent-β-lactam conjugates (Ent-Amp and Ent-Amx) and their glucosylated derivatives (MGE-Amp, MGE-Amx, DGE-Amp, and DGE-Amx) against the uropathogenic strain *E. coli* UTI89 in 50% MHB at 37° C. 2,2'-dipyridyl (DP, 200 µM) was added to provide conditions of iron limitation.
Figures 27C, 27D:
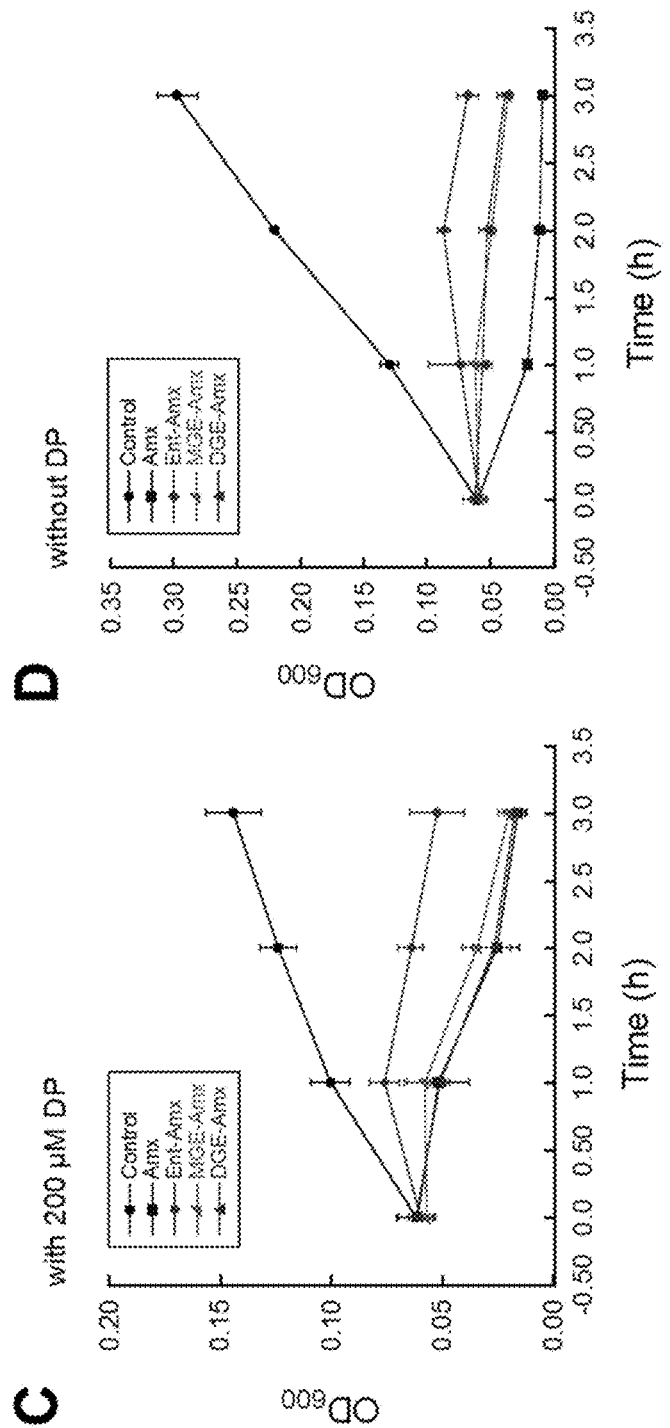
Figures 28A, 28B:
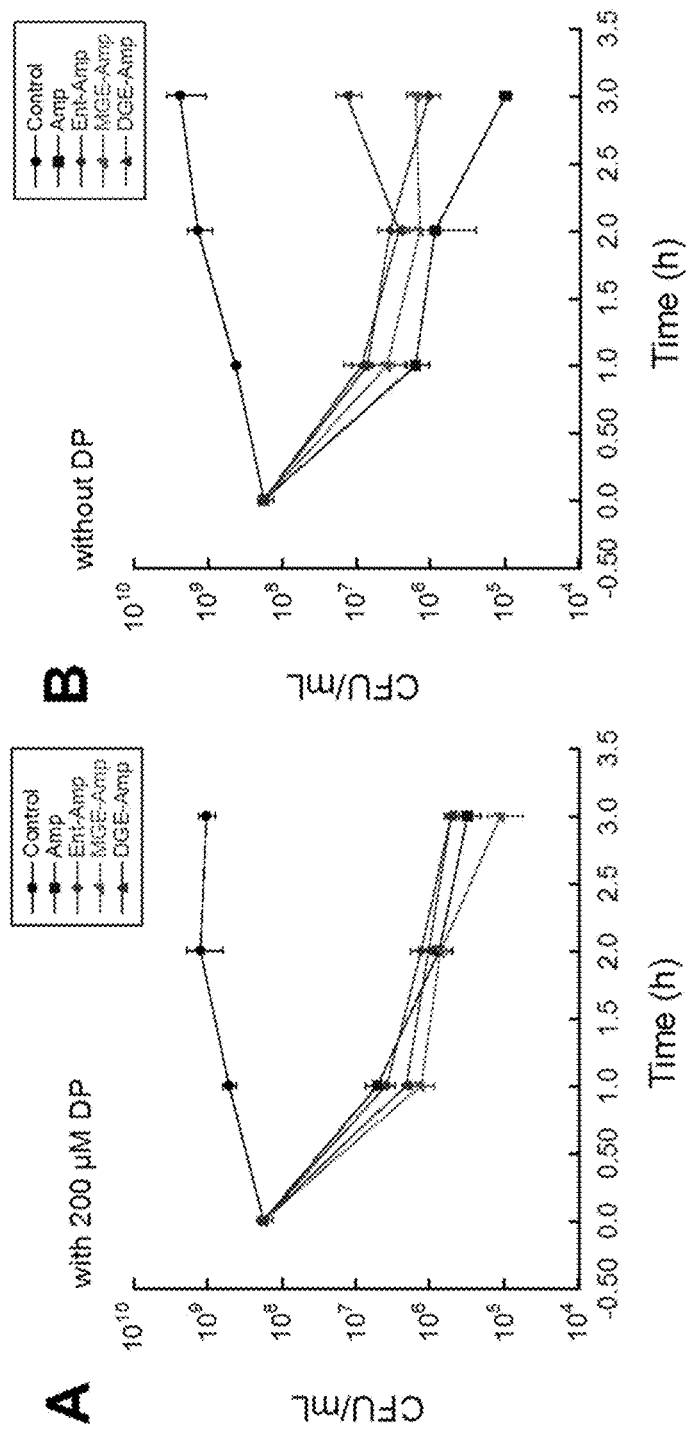
FIGS. 28A to 28D show the corresponding CFU of time-kill kinetic assays in FIGS. 27A to 27B of select Ent-β-lactam conjugates (Ent-Amp and Ent-Amx) and their glucosylated derivatives (MGE-Amp, MGE-Amx, DGE-Amp, and DGE-Amx) against the uropathogenic strain *E. coli* UTI89 in 50% MHB at 37° C. 2,2'-dipyridyl (DP, 200 µM) was added to provide conditions of iron limitation.
Figures 28C, 28D:
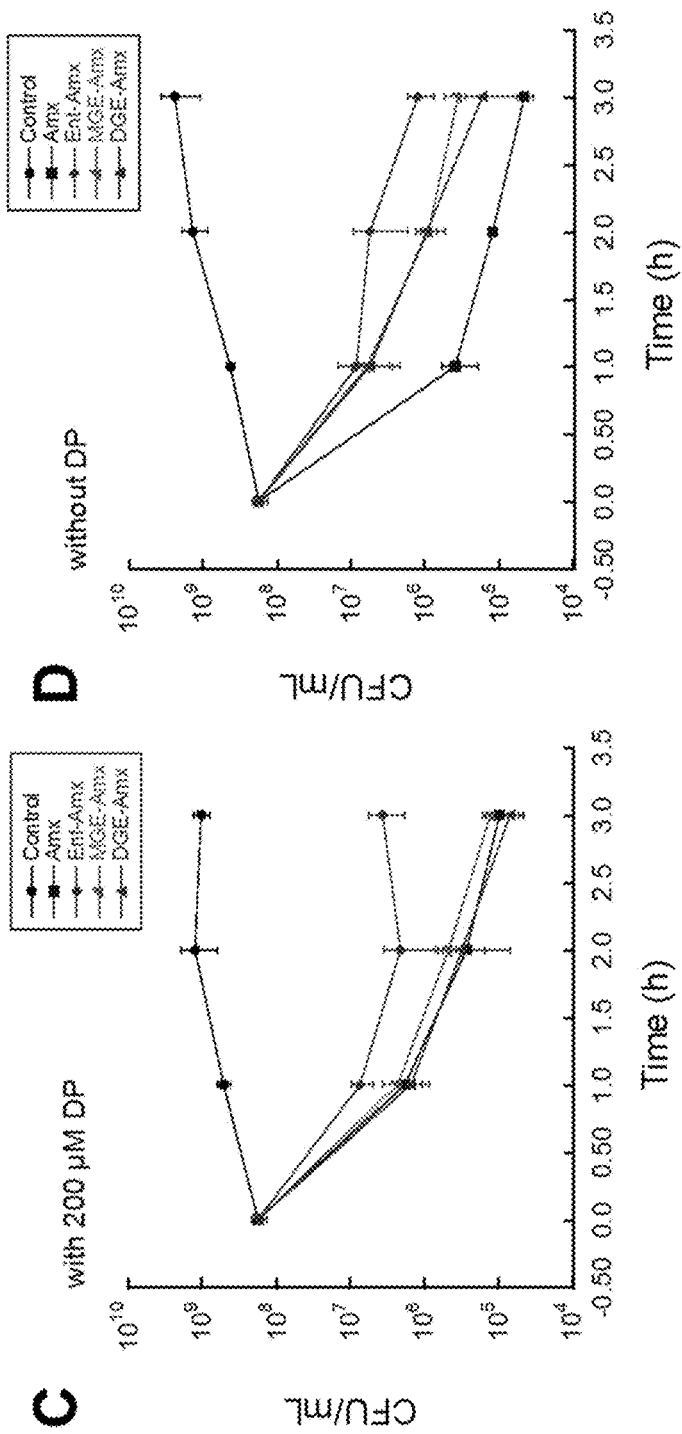
Figures 29A, 29B:
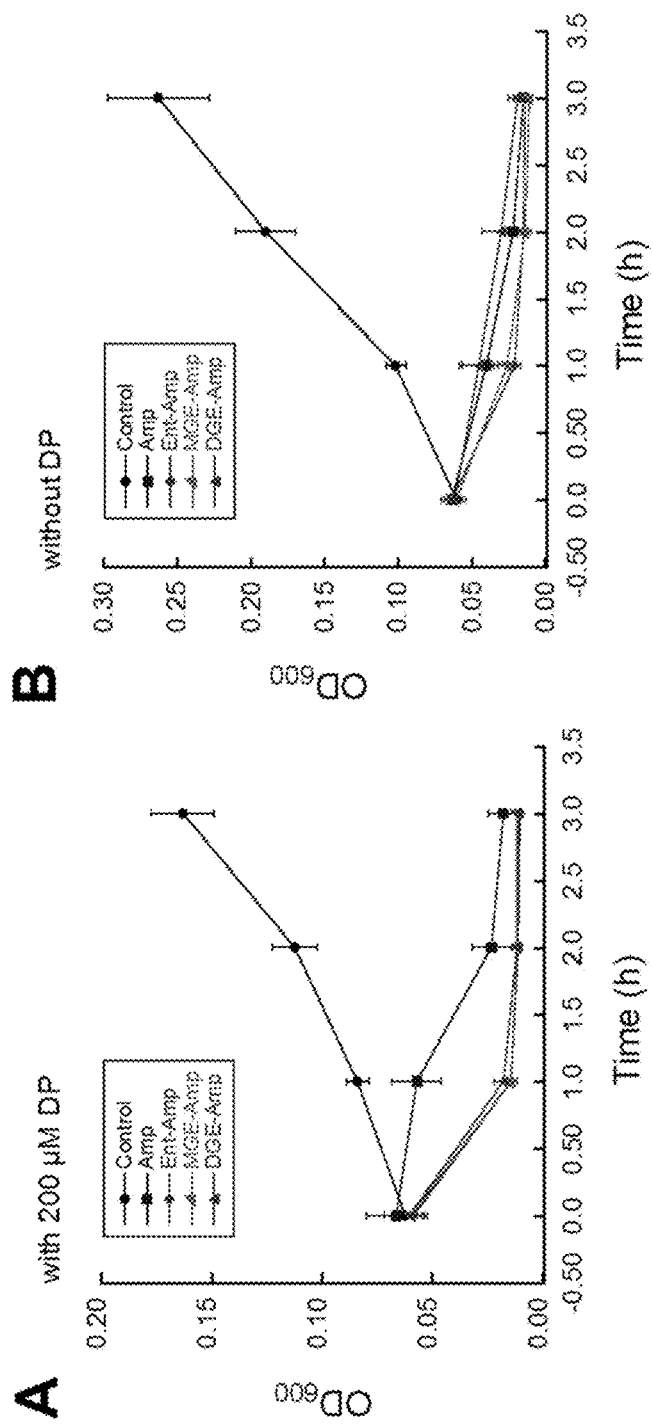
FIGS. 29A to 29D show exemplary $OD_{600}$ measurements of time-kill kinetic assays of select Ent-β-lactam conjugates (Ent-Amp and Ent-Amx) and their glucosylated derivatives (MGE-Amp, MGE-Amx, DGE-Amp, and DGE-Amx) against the uropathogenic strain *E. coli* CFT073 in 50% MHB at 37° C. 2,2'-dipyridyl (DP, 200 µM) was added to provide conditions of iron limitation.
Figures 29C, 29D:
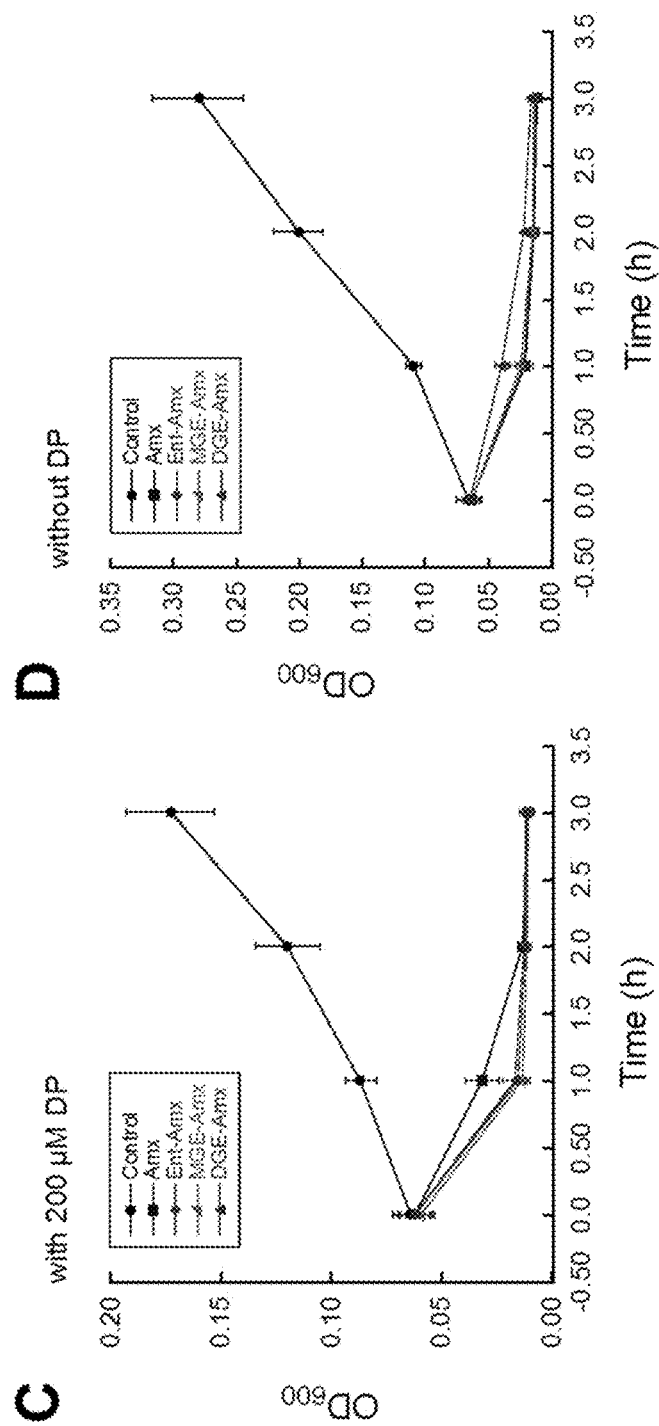
Figures 30A, 30B:
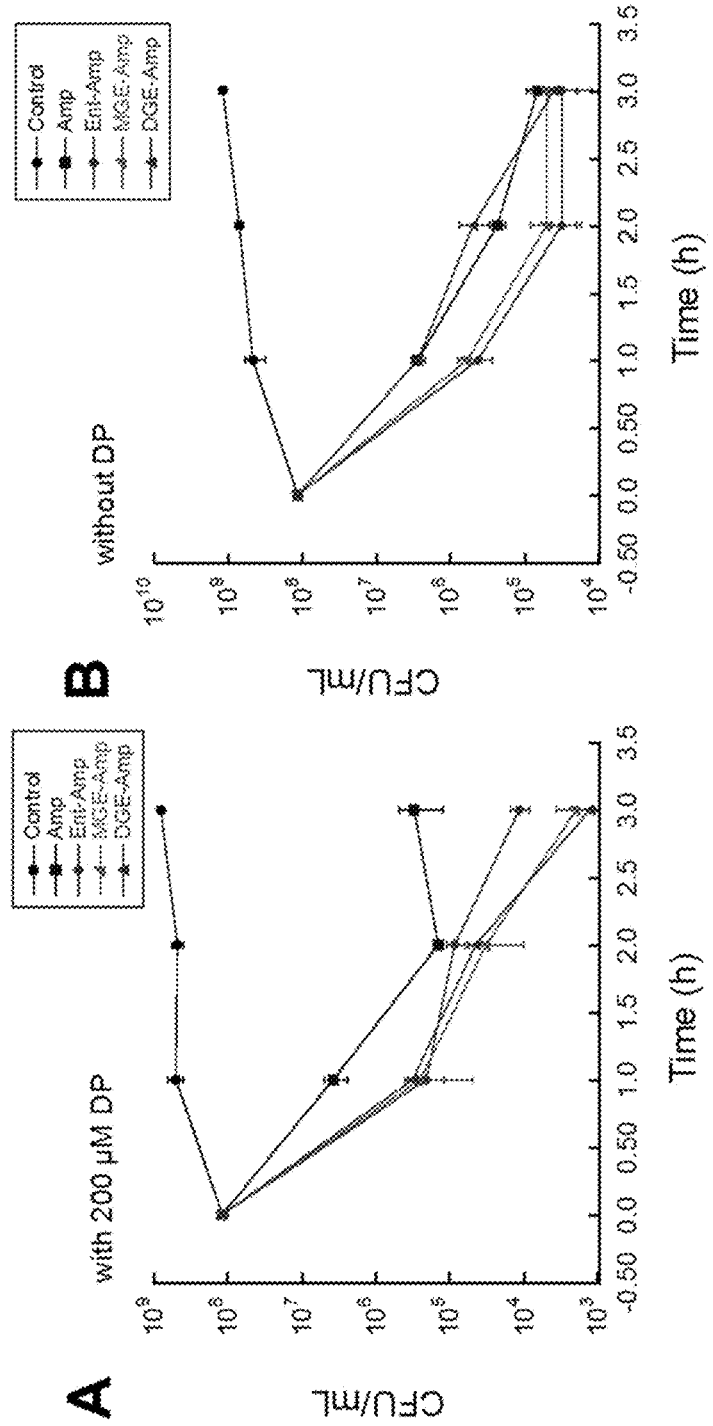
FIGS. 30A to 30D show the corresponding CFU of time-kill kinetic assays in FIGS. 29A to 29D of select Ent-β-lactam conjugates (Ent-Amp and Ent-Amx) and their glucosylated derivatives (MGE-Amp, MGE-Amx, DGE-Amp, and DGE-Amx) against the uropathogenic strain *E. coli* CFT073 in 50% MHB at 37° C. 2,2'-dipyridyl (DP, 200 µM) was added to provide conditions of iron limitation.
Figures 30C, 30D:
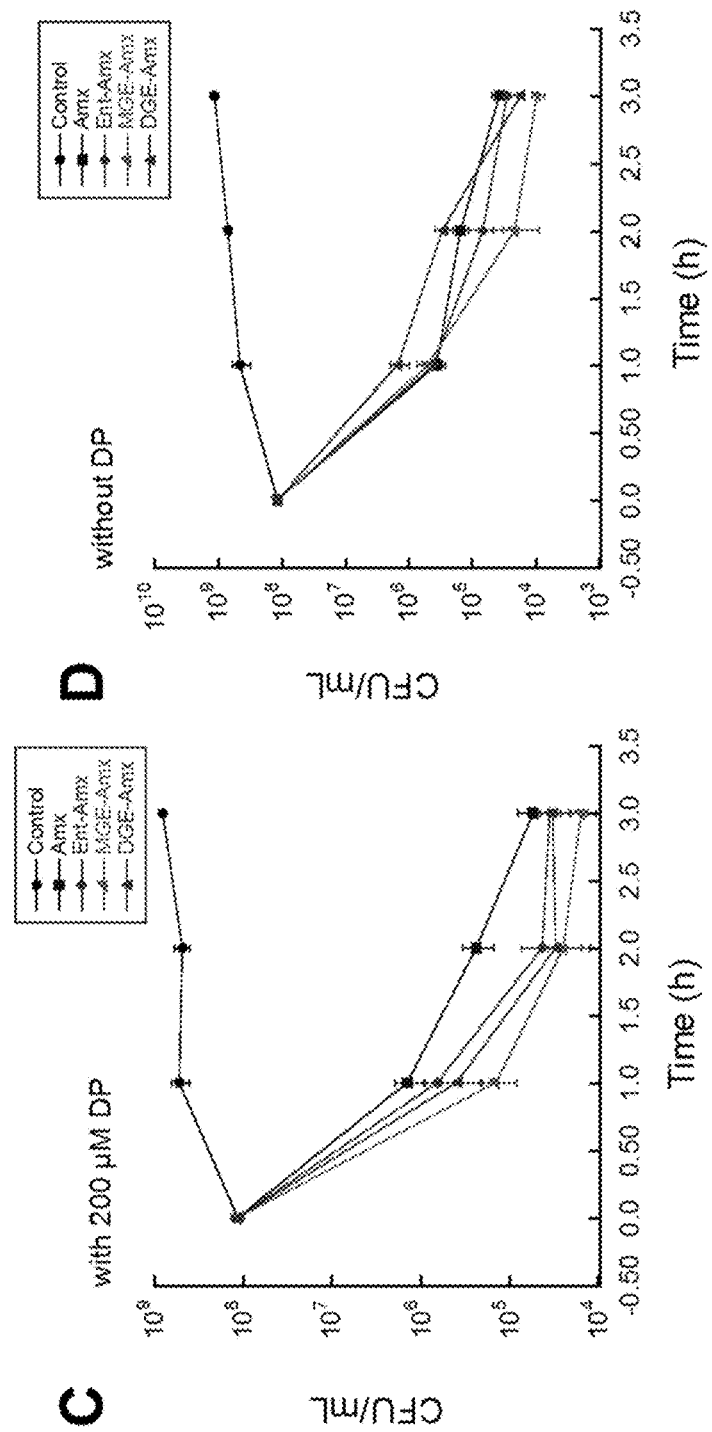

The antibacterial activity of Ent-ampicillin (Ent-Amp), Ent-amoxicillin (Ent-Amx), MGE-ampicillin (MGE-Amp), MGE-amoxicillin (MGE-Amx), DGE-ampicillin (DGE-Amp) and DGE-amoxicillin (DGE-Amx) conjugates was evaluated in vitro against *E. coli* and STM. FIGS. 12, 14-18, and 20 provide exemplary results from antibacterial activity assays, competition assays, and co-culture assays against select bacterial species and certain mutants thereof. The results as depicted in FIGS. 12, 14-18, and 20 show that the conjugates provide improved activity against various strains compared to the unmodified antibiotics. The data in FIG. 20 shows that Ent-Amp and Ent-Amx killed *E. coli* CFT073 that is co-cultured with *S. aureus* 25923.

Example 10. Cytotoxicity Studies Using MTT

Figure 19:
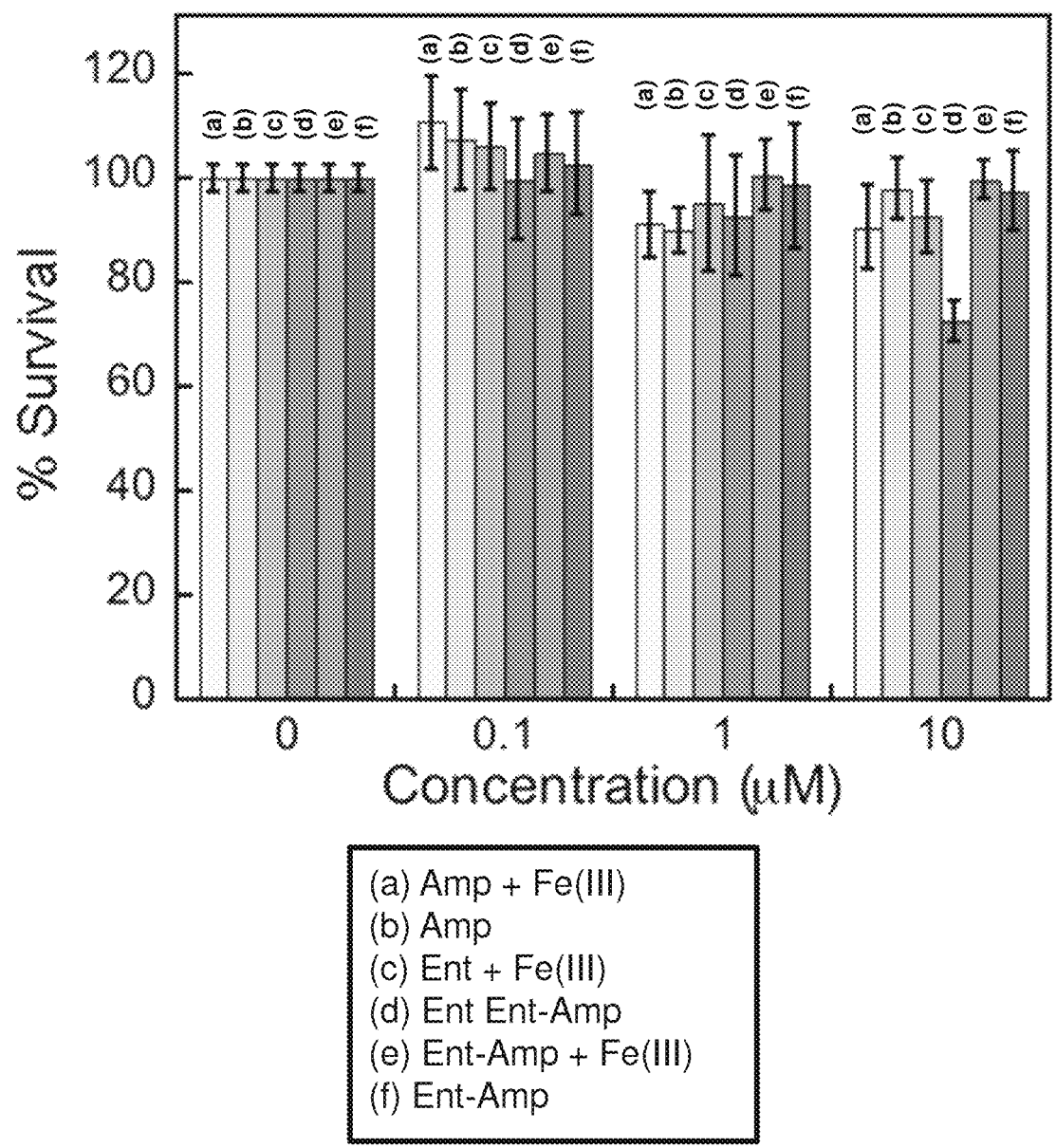
FIG. 19 shows that Ent-Amp exhibited negligible cytotoxicity in human T84 intestinal epithelial cells 24 hours post dose.

Colon epithelial T84 cell line (purchase from ATCC) were grown in DMEM/F12 medium containing penicillin (100 I.U./mL) and streptomycin (100 µg/mL). The cells were passed and plated in 96-well flat-bottom plates ~16 h before treatment. Each well contained 90 L of the cell culture at a density of $10^5$ cells/mL. Stock solutions of the tested conjugates (e.g., Ent-Amp) were prepared in sterile filtered 10% DMSO/water, and 10 µL of the each solution was added to each well. The plate was incubated at 37° C. and under 5% $CO_2$ for 24 h and 20 µL of MTT (5 mg/mL in sterile PBS) was added to each well. The plate was incubated at 37° C. for another 4 h, and the supernatant was removed from each well. DMSO (100 µL) was added to the wells to afford a purple solution, and the absorbance at 550 nm was recorded by using a plate reader. Blank readings were generated by wells that only contain the growth medium but no cells. The assay was repeated in three independent trials, and the resulting mean and standard errors are reported. The effect of DMSO on cell growth was also evaluated by performing the same assay with various DMSO concentrations to confirm that DMSO at the % (v/v) employed did not impact cell growth. Exemplary results are shown in FIG. 19. Ent-Amp, Ent, and Amp were incubated with human colon epithelial T84 cells for 24 h. Ent-Amp with concentrations up to 10 μM did not affect the viability of human cells significantly, neither did Amp. Ent with a 10 μM concentration decreased the percent survival of T84 cells by approximately 30%, which is likely due to iron deprivation because Ent with pre-loaded Fe did not exhibit this effect.

Figure 43A:
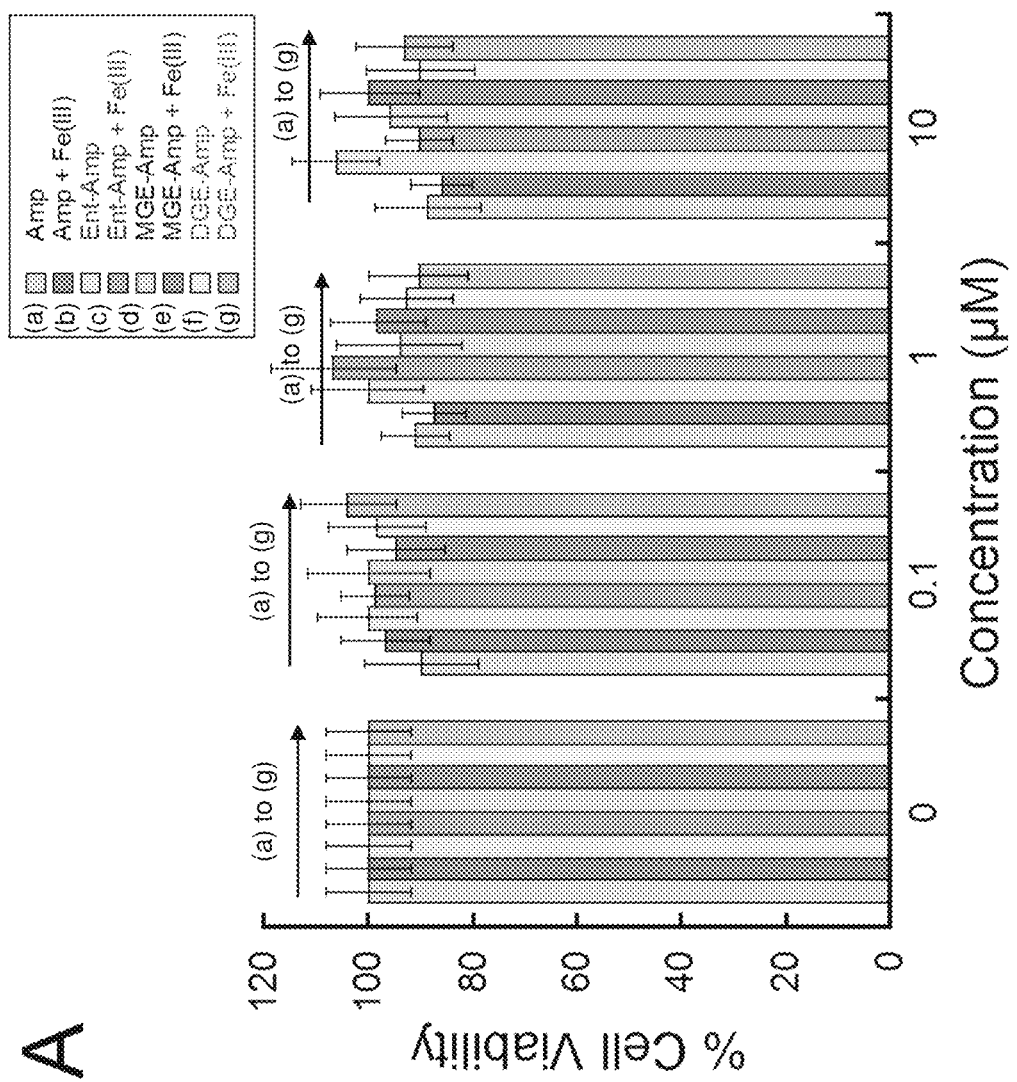
FIGS. 43A to 43B show exemplary cytotoxicity results of select Ent-β-lactam conjugates (Ent-Amp and Ent-Amx) and their glucosylated derivatives (MGE-Amp, MGE-Amx, DGE-Amp, and DGE-Amx) against human colonic epithelial cells (T84 cells).
Figure 43B:
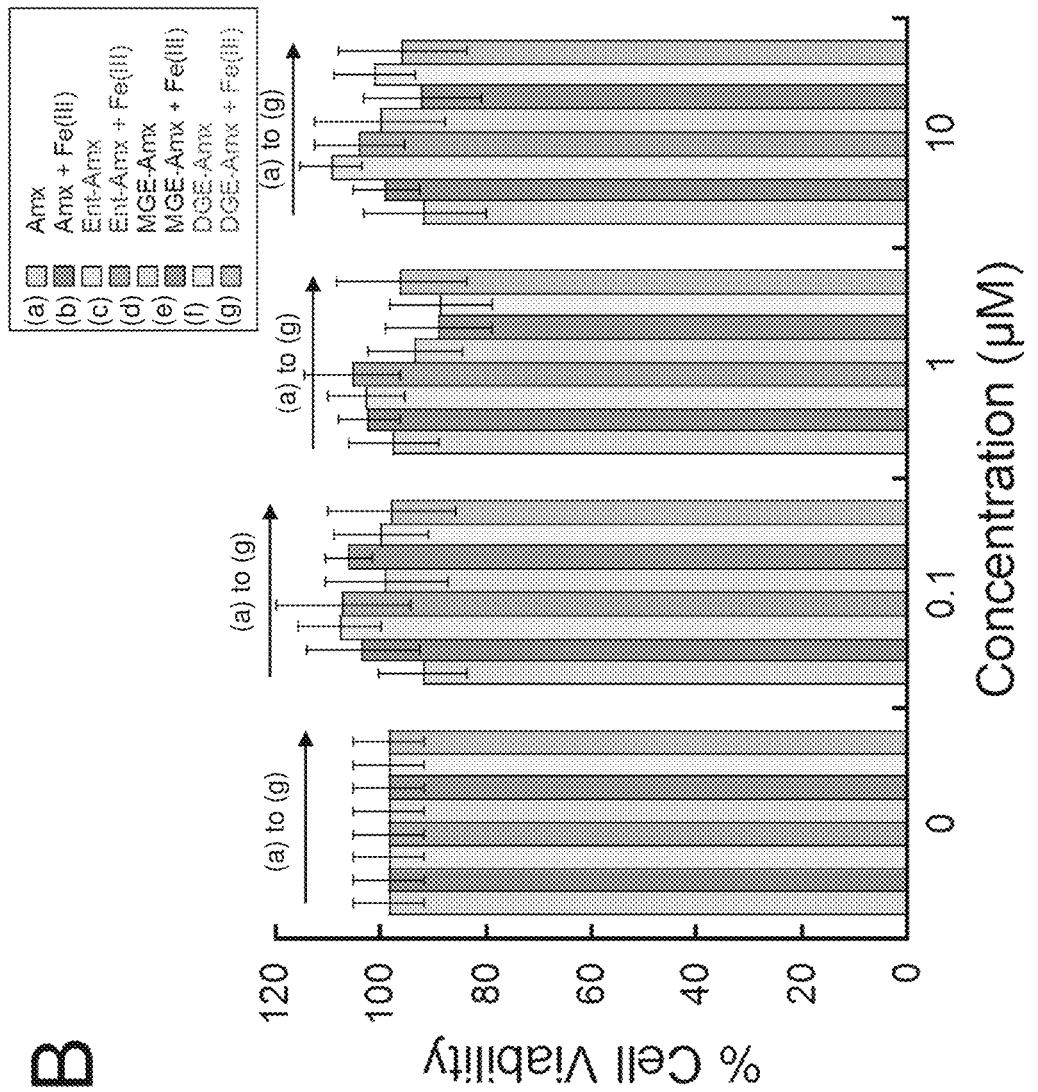

In another exemplary experiment, the human colon epithelial T84 cell line was purchased from ATCC and cultured in 1:1 DMEM/F12 medium with 10% fetal bovine serum, 1% penicillin, and streptomycin (v/v, ATCC). The cells were grown to approximately 95% confluency and treated with 3 mL of trypsin-EDTA (Corning). A 12-mL portion of fresh medium was added to the detached cells, and the T84 cell suspension was centrifuged (600 rpm×5 min, 37° C.). The supernatant was discarded, and the cell pellet was resuspended in 6 mL of the fresh culture media. The concentration of cells was quantified by using a manual hemocytometer (VWR International) and adjusted to $1\times10^5$ cells/mL. A 90-μL aliquot of T84 cells were then added to 96-well plates and incubated at 37° C. and 5% $CO_2$ for 24 h. Stock solutions (10×) of Amp, Amx, Ent-Amp, Ent-Amx, MGE-Amp, MGE-Amx, DGE-Amp, or DGE-Amx were prepared in sterile-filtered 10% DMSO/$H_2O$, and 10 μL of each solution was added to the appropriate well. The plate was incubated at 37° C. and 5% $CO_2$ for another 24 h. Then, a 20-μL aliquot of 3-[4,5-dimethylthiazol-2-yl]-2,5 diphenyl tetrazolium bromide (MTT, 5 mg/mL in sterile PBS) was added to each well. The plate was incubated at 37° C. and 5% $CO_2$ for 4 h and the supernatant was removed from each well. DMSO (100 μL) was added to each well and the absorbance at 550 nm was recorded by using a plate reader. Blank readings were recorded on wells that only contained the medium. The assay was repeated in triplicate on different days, and the mean and standard deviation were reported. Exemplary results are shown in FIGS. 43A to 43B. The data suggest that the conjugates, as well as the unmodified β-lactams, were non-toxic to T84 cells.

Example 11. Competition Assays of Ent-Amp, MGE-Amp, and DGE-Amp, in the Presence of ENT, MGE, or DGE These assays were performed following the general procedure described herein except that varying concentrations of Ent, MGE, or DGE, each of which was unmodified, were mixed with Ent-Amp, Ent-Amx, MGE-Amp, MGE-Amx, DGE-Amp, or DGE-Amx. Ent was synthesized following a literature procedure[55] and stored as DMSO stock solution at −20° C. MGE and DGE were prepared from Ent using McaC and IroB as described for MGE-$PEG_3$-$N_3$ and DGE-$PEG_3$-$N_3$.

Figure 32A:
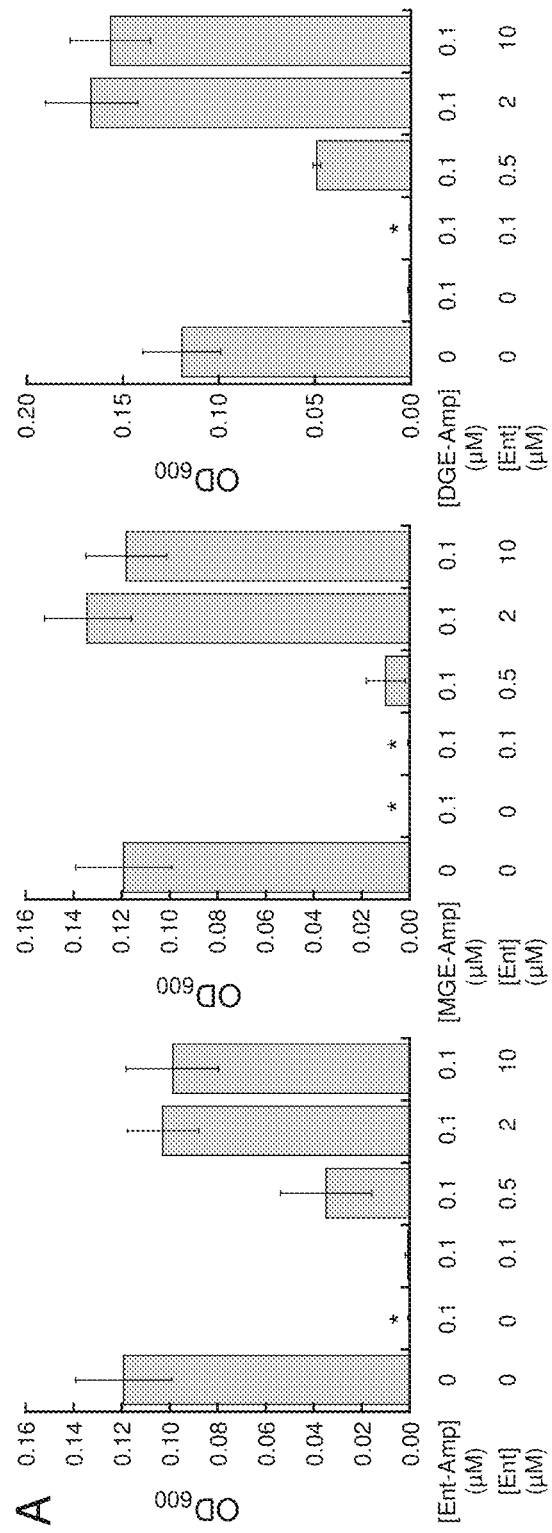
FIGS. 32A to 32C show exemplary competition assay results of select conjugates (Ent-Amp, MGE-Amp, and DGE-Amp) with select native siderophores (Ent, MGE, and DGE) against the uropathogenic strain *E. coli* UTI89. The asterisks indicate $OD_{600}$ was less than 0.001. The bacteria were treated with Ent-Amp (left panels), MGE-Amp (middle panels), or DGE-Amp (right panels) in the presence of Ent (FIG. 32A), MGE (FIG. 32B), or DGE (FIG. 32C).
Figure 32B:
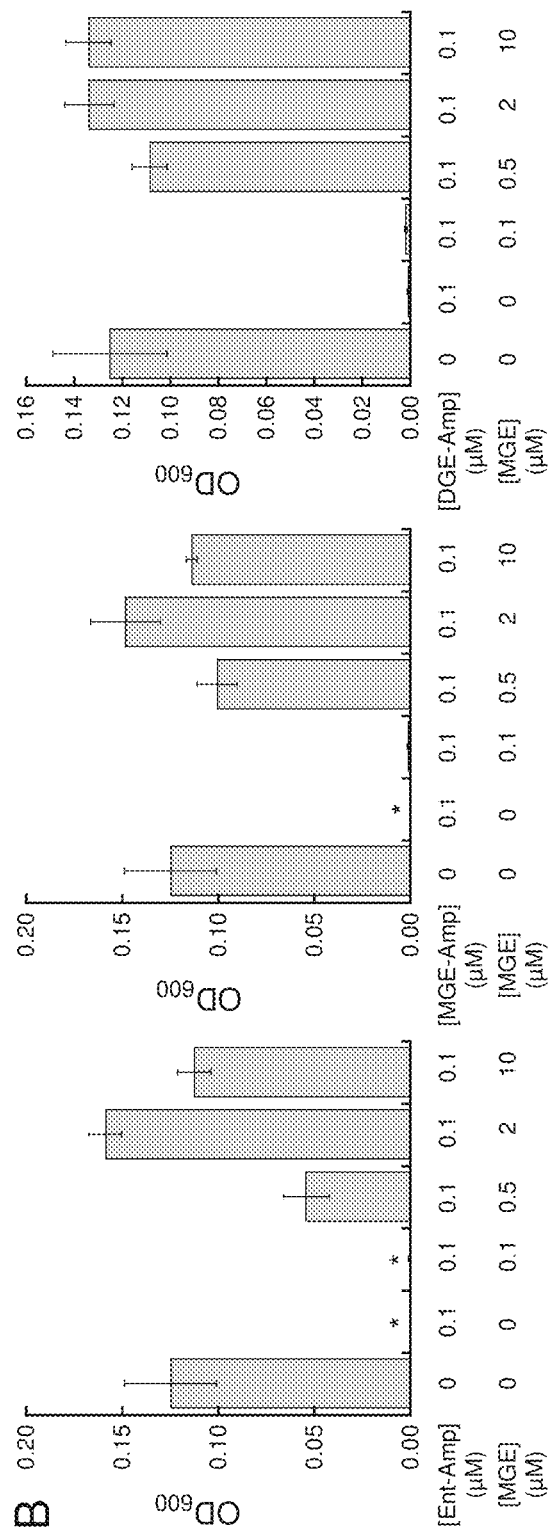
Figure 32C:
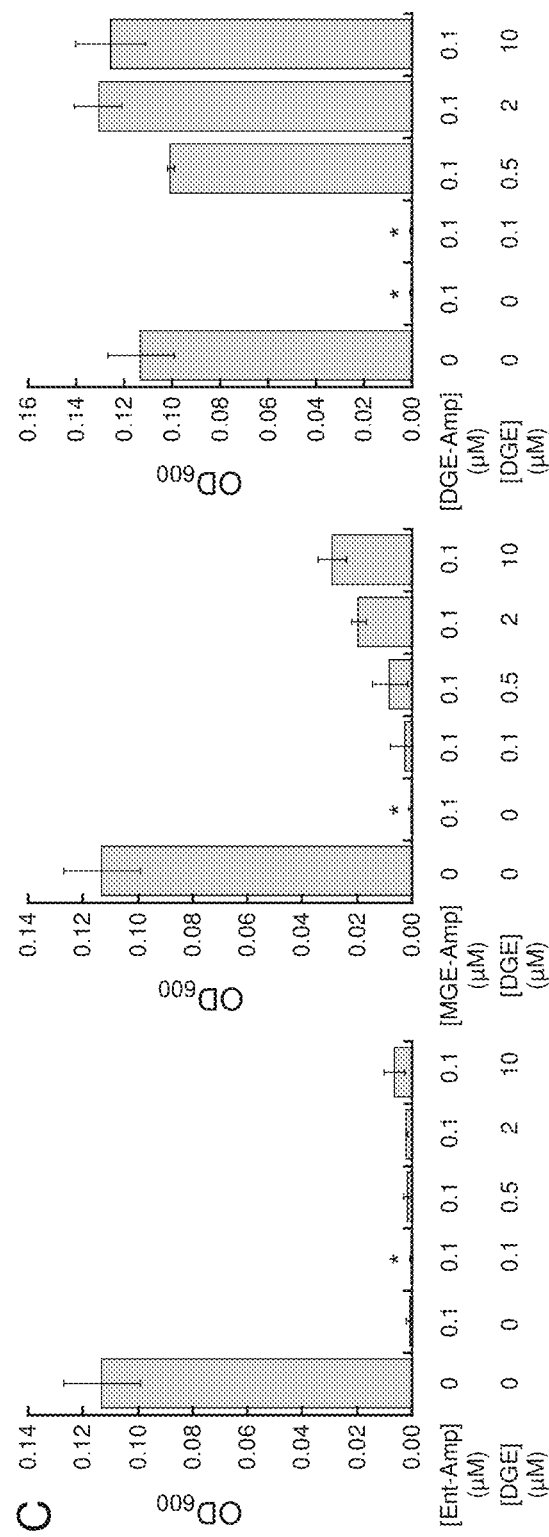

In an exemplary experiment, select conjugates (Ent-Amp, MGE-Amp, and DGE-Amp) with select native siderophores (Ent, MGE, and DGE) were tested against the uropathogenic strain E. coli UTI89 in 50% MHB, t=19 h, 30° C. 2,2'-dipyridyl (DP, 200 μM) was added to provide conditions of iron limitation. The concentration of the conjugates was fixed at 100 nM, and the concentration of the native siderophores was varied. Exemplary results are shown in FIGS. 32A to 32C. The antibacterial activity of Ent-Amp was only attenuated in the presence of Ent or MGE. However, the antibacterial activity of MGE-Amp and DGE-Amp was attenuated by Ent, MGE, or DGE. These observations indicate that Ent, MGE, Ent-Amp, and MGE-Amp may enter via both FepA and IroN with different efficiency, but DGE and DGE-Amp may only enter via IroN.

Figure 33A:
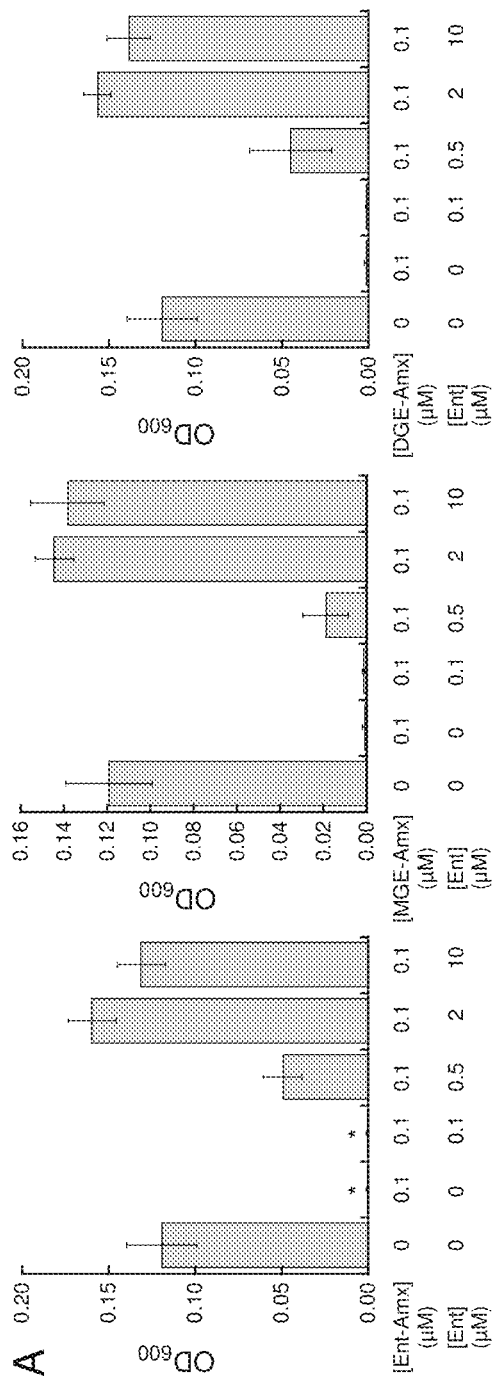
FIGS. 33A to 33C show exemplary competition assay results of select conjugates (Ent-Amx, MGE-Amx, and DGE-Amx) with select native siderophores (Ent, MGE, and DGE) against the uropathogenic strain *E. coli* UTI89. The asterisks indicate $OD_{600}$ was less than 0.001. The bacteria were treated with Ent-Amx (left panels), MGE-Amx (middle panels), or DGE-Amx (right panels) in the presence of Ent (FIG. 33A), MGE (FIG. 33B), or DGE (FIG. 33C).
Figure 33B:
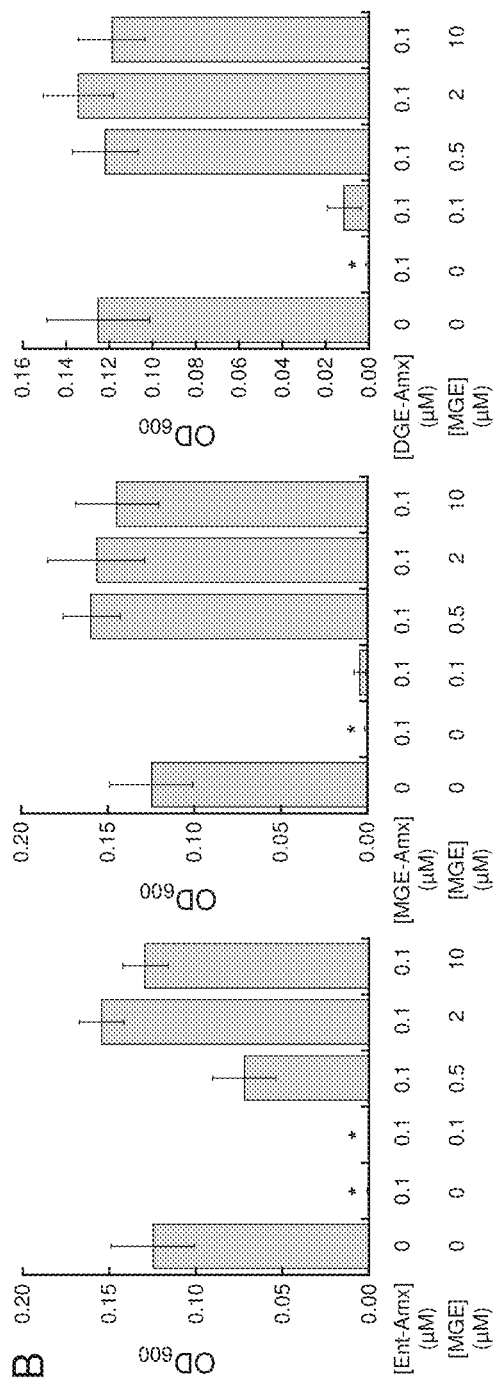
Figure 33C:
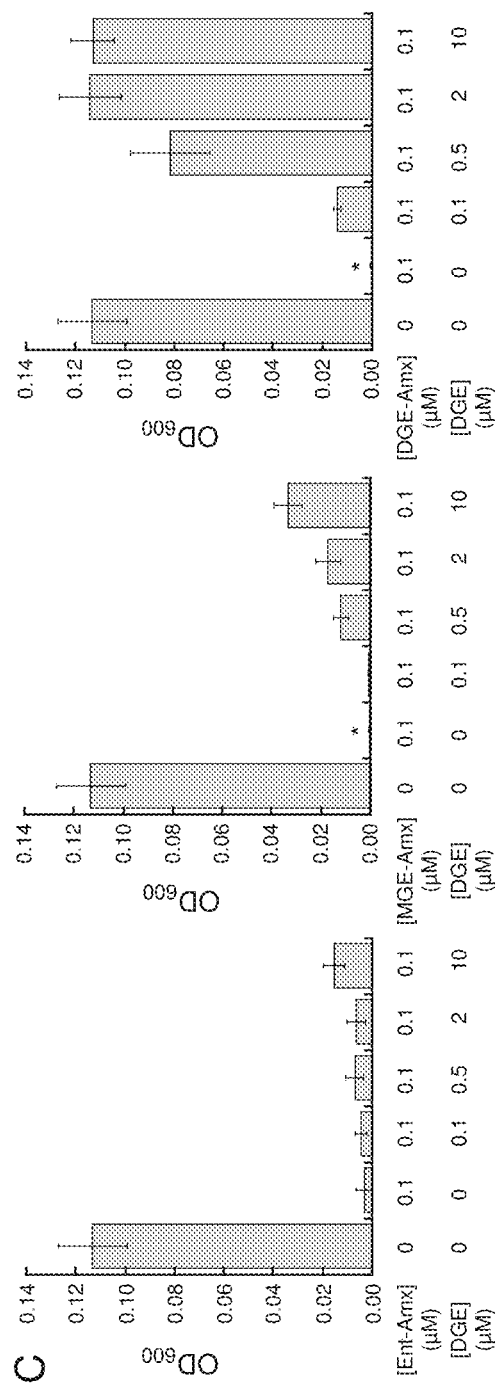

In another exemplary experiment, select conjugates (Ent-Amp, MGE-Amp, and DGE-Amp) with select native siderophores (Ent, MGE, and DGE) were tested against the uropathogenic strain E. coli UTI89 in 50% MHB, t=19 h, 30° C. 2,2'-dipyridyl (DP, 200 μM) was added to provide conditions of iron limitation. The concentration of the conjugates was fixed at 100 nM and the concentration of the native siderophores was varied. Exemplary results are shown in FIGS. 33A to 33C. The antibacterial activity of Ent-Amx was only attenuated in the presence of Ent or MGE. However, the antibacterial activity of MGE-Amx and DGE-Amx was attenuated by Ent, MGE, or DGE. These observations indicate that Ent, MGE, Ent-Amp, and MGE-Amp may enter via both FepA and IroN with different efficiency, but DGE and DGE-Amp may only enter via IroN.

Figure 34A:
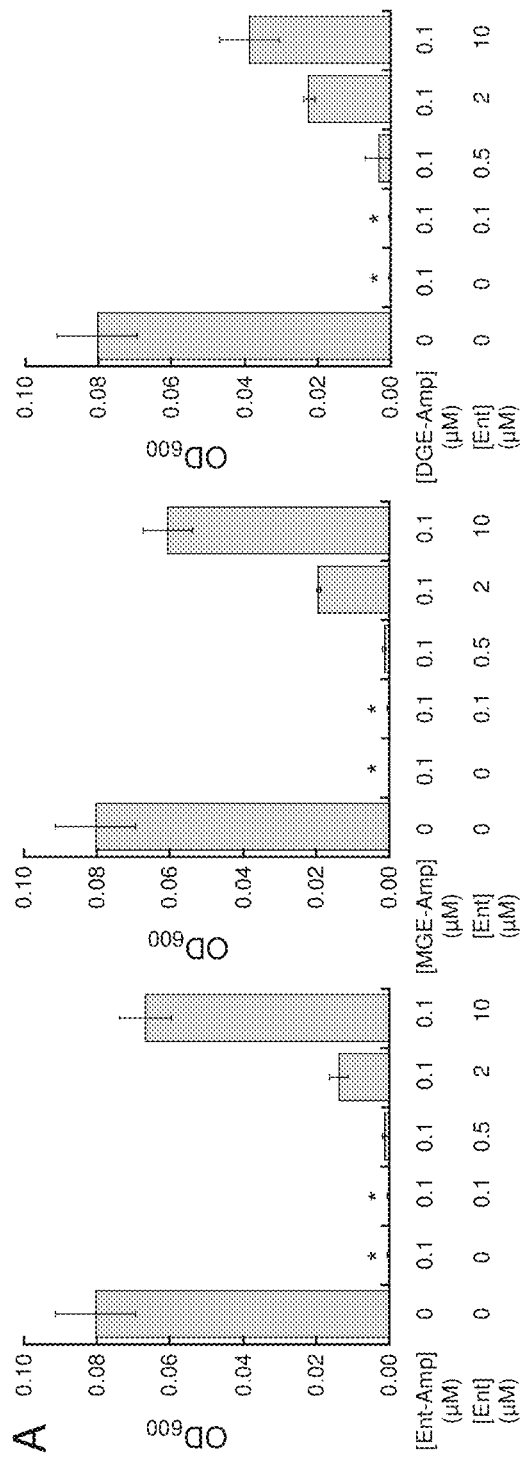
FIGS. 34A to 34C show exemplary competition assay results of select conjugates (Ent-Amp, MGE-Amp, and DGE-Amp) with select native siderophores (Ent, MGE, and DGE) against the uropathogenic strain *E. coli* CFT073. The asterisks indicate $OD_{600}$ was less than 0.001. The bacteria were treated with Ent-Amp (left panels), MGE-Amp (middle panels), or DGE-Amp (right panels) in the presence of Ent (FIG. 34A), MGE (FIG. 34B), or DGE (FIG. 34C).
Figure 34B:
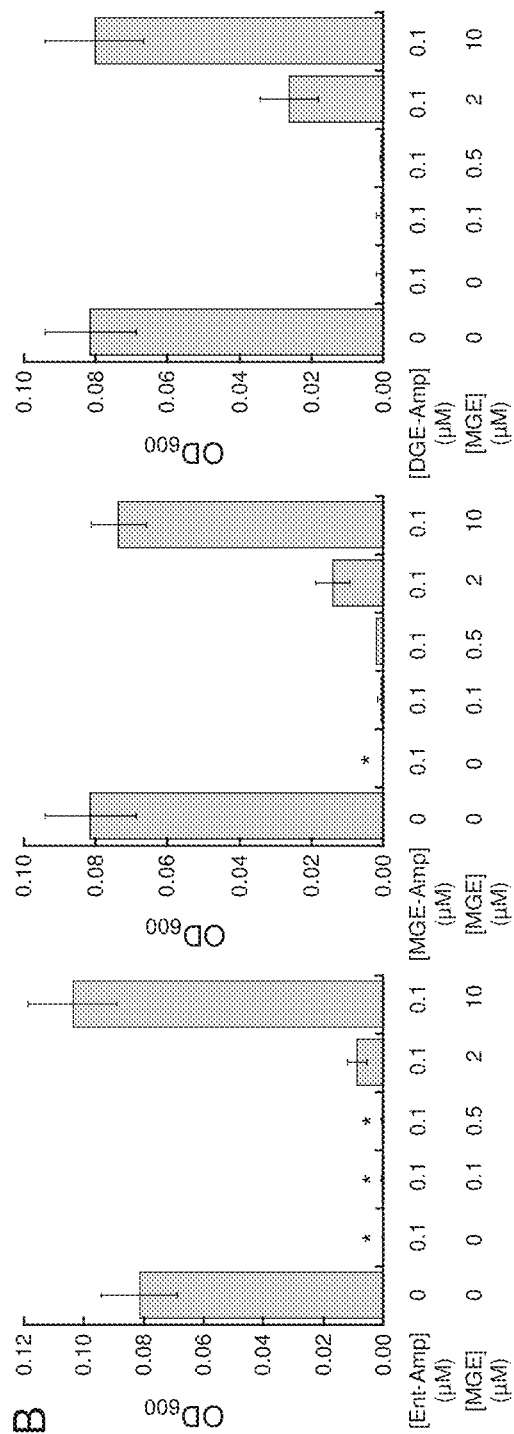
Figure 34C:
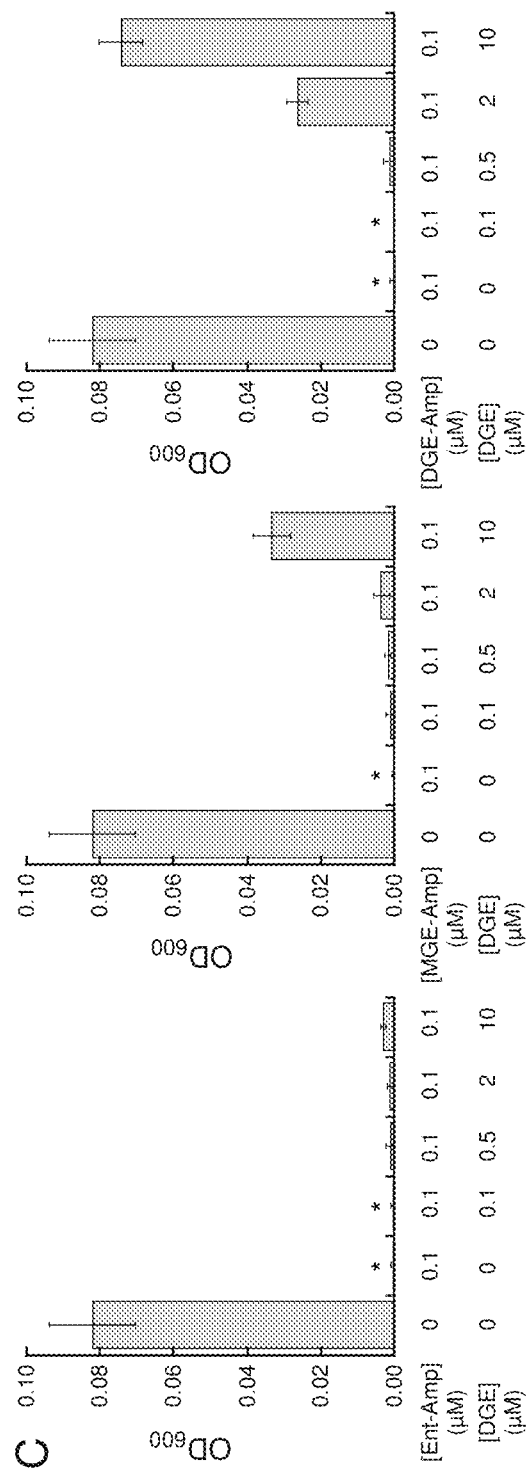

In another exemplary experiment, select conjugates (Ent-Amp, MGE-Amp, and DGE-Amp) with select native siderophores (Ent, MGE, and DGE) were tested against the uropathogenic strain E. coli CFT073 in 50% MHB, t=19 h, 30° C. 2,2'-dipyridyl (DP, 200 μM) was added to provide conditions of iron limitation. The concentration of the conjugates was fixed at 100 nM and the concentration of the native siderophores was varied. Exemplary results are shown in FIGS. 34A to 34C. The antibacterial activity of Ent-Amp was only attenuated in the presence of Ent and MGE. However, the antibacterial activity of MGE-Amp, DGE-Amp was attenuated by Ent, MGE, and DGE. These observations indicate that Ent, MGE, Ent-Amp, and MGE-Amp may enter via both FepA and IroN with different efficiency, but DGE, and DGE-Amp may only enter via IroN.

Figure 35A:
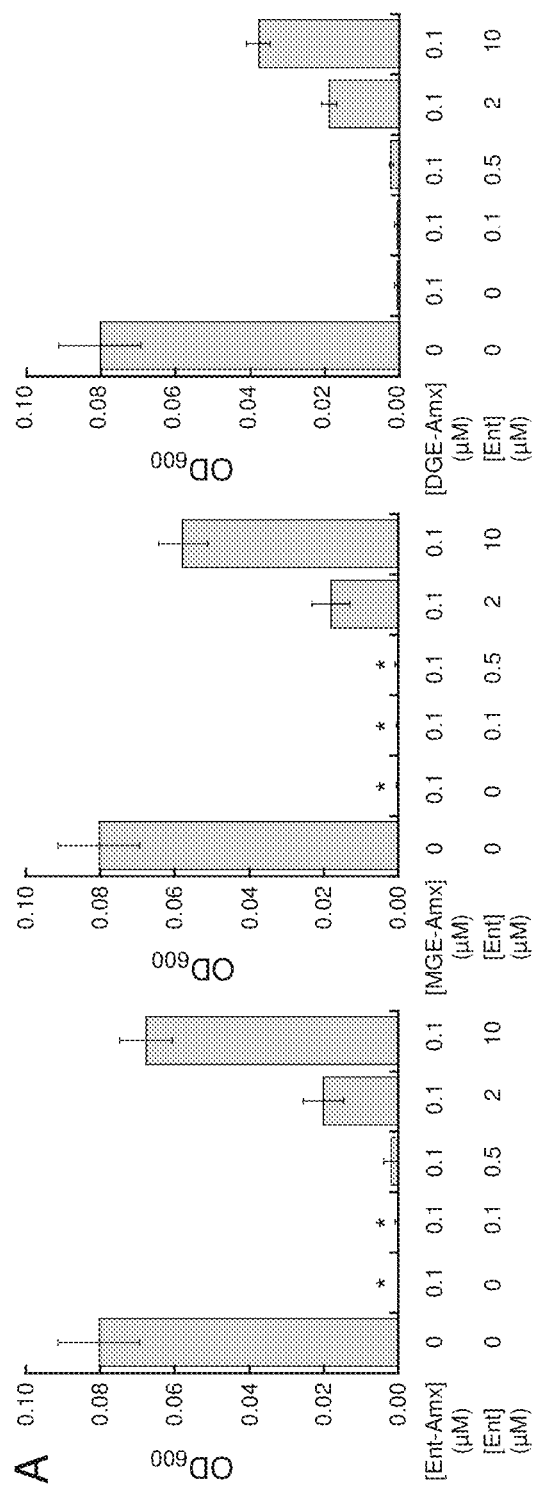
FIGS. 35A to 35C show exemplary competition assay results of select conjugates (Ent-Amx, MGE-Amx, and DGE-Amx) with select native siderophores (Ent, MGE, and DGE) against the uropathogenic strain *E. coli* CFT073. The asterisks indicate $OD_{600}$ was less than 0.001. The bacteria were treated with Ent-Amx (left panels), MGE-Amx (middle panels), or DGE-Amx (right panels) in the presence of Ent (FIG. 35A), MGE (FIG. 35B), or DGE (FIG. 35C).
Figure 35B:
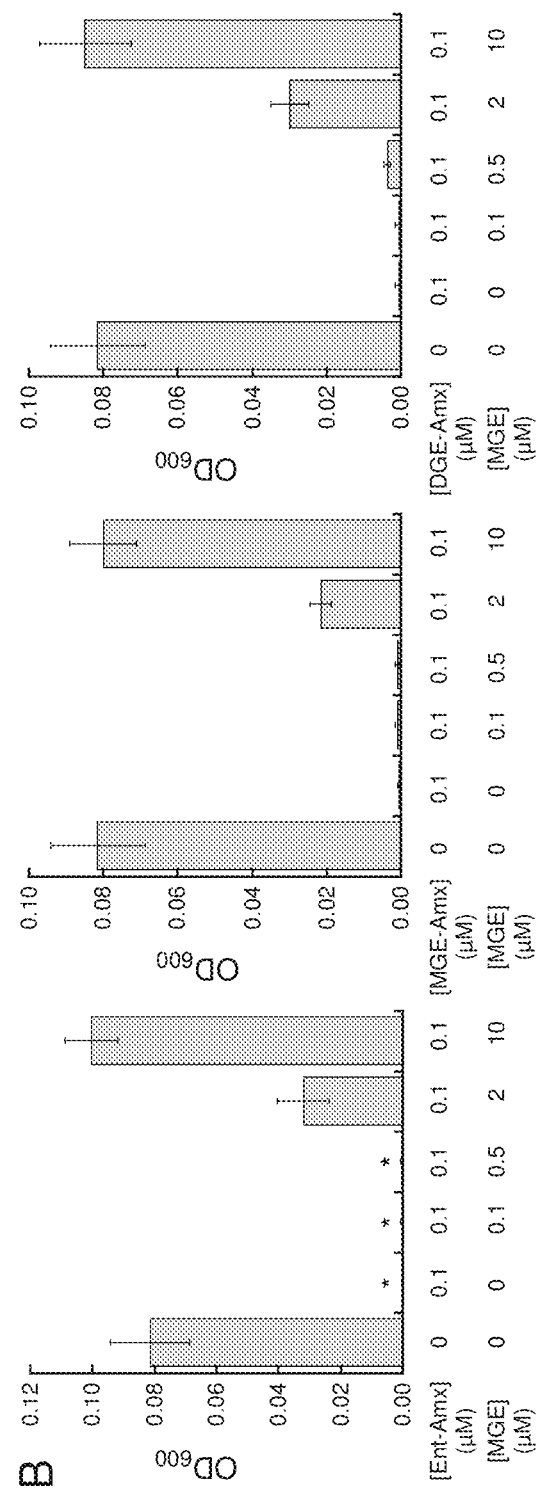
Figure 35C:
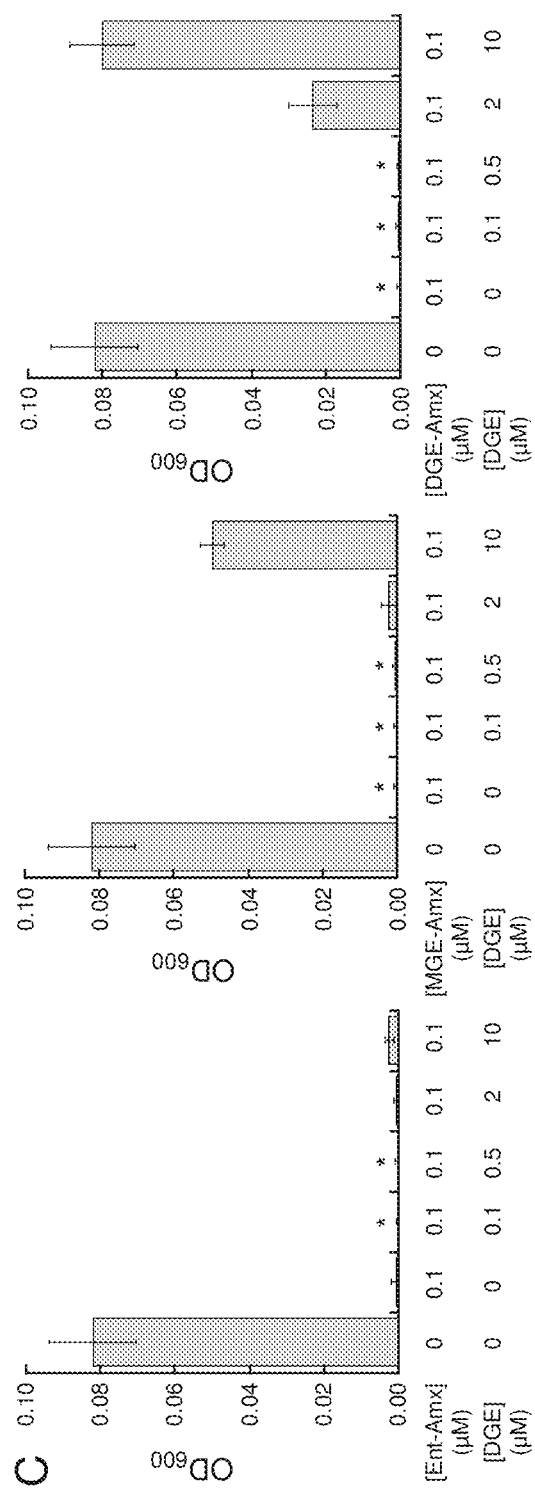
Figures 36A, 36B:
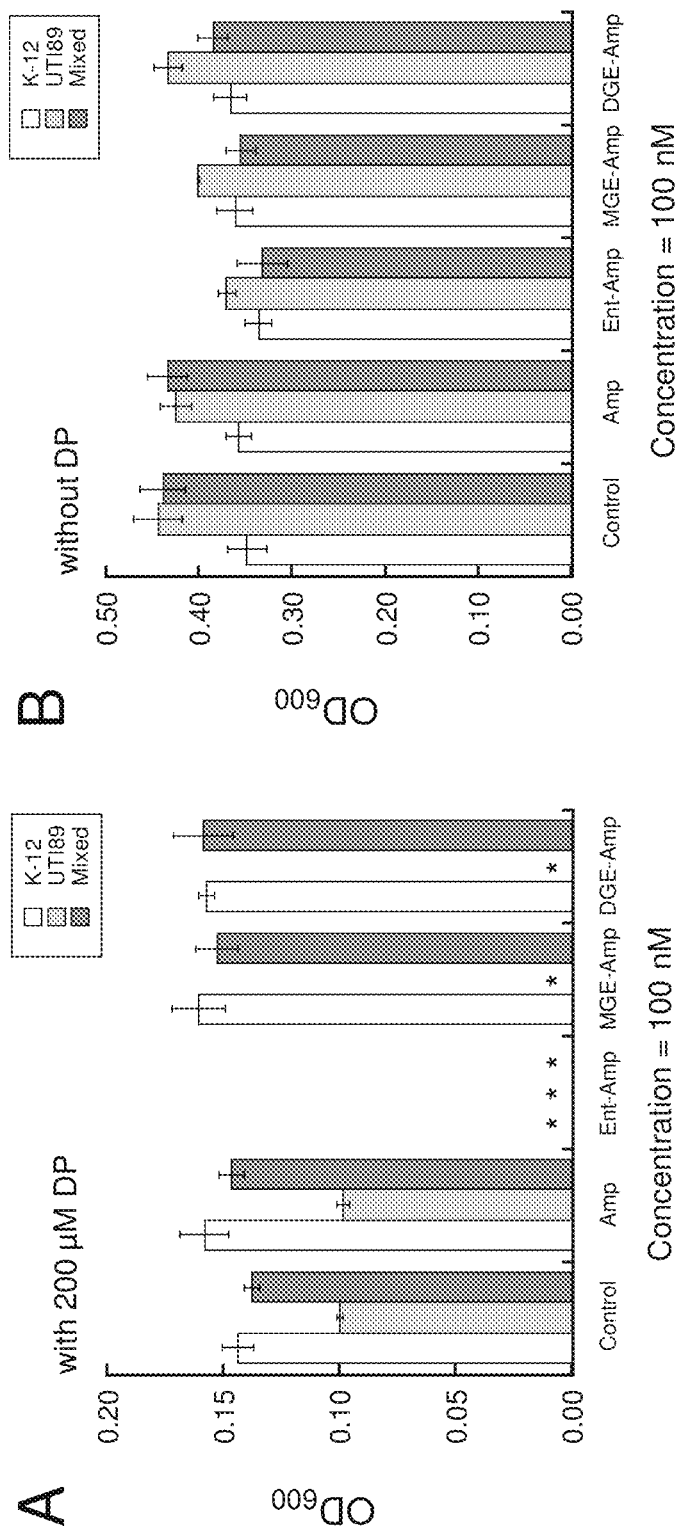
FIGS. 36A to 36D show exemplary $OD_{600}$ measurements of mixed culture assays of *E. coli* K-12 and *E. coli* UTI89 treated with select Ent-β-lactam conjugates (Ent-Amp and Ent-Amx) and their glucosylated derivatives (MGE-Amp, MGE-Amx, DGE-Amp, and DGE-Amx). The asterisks indicate $OD_{600}$ was less than 0.1.
Figures 36C, 36D:
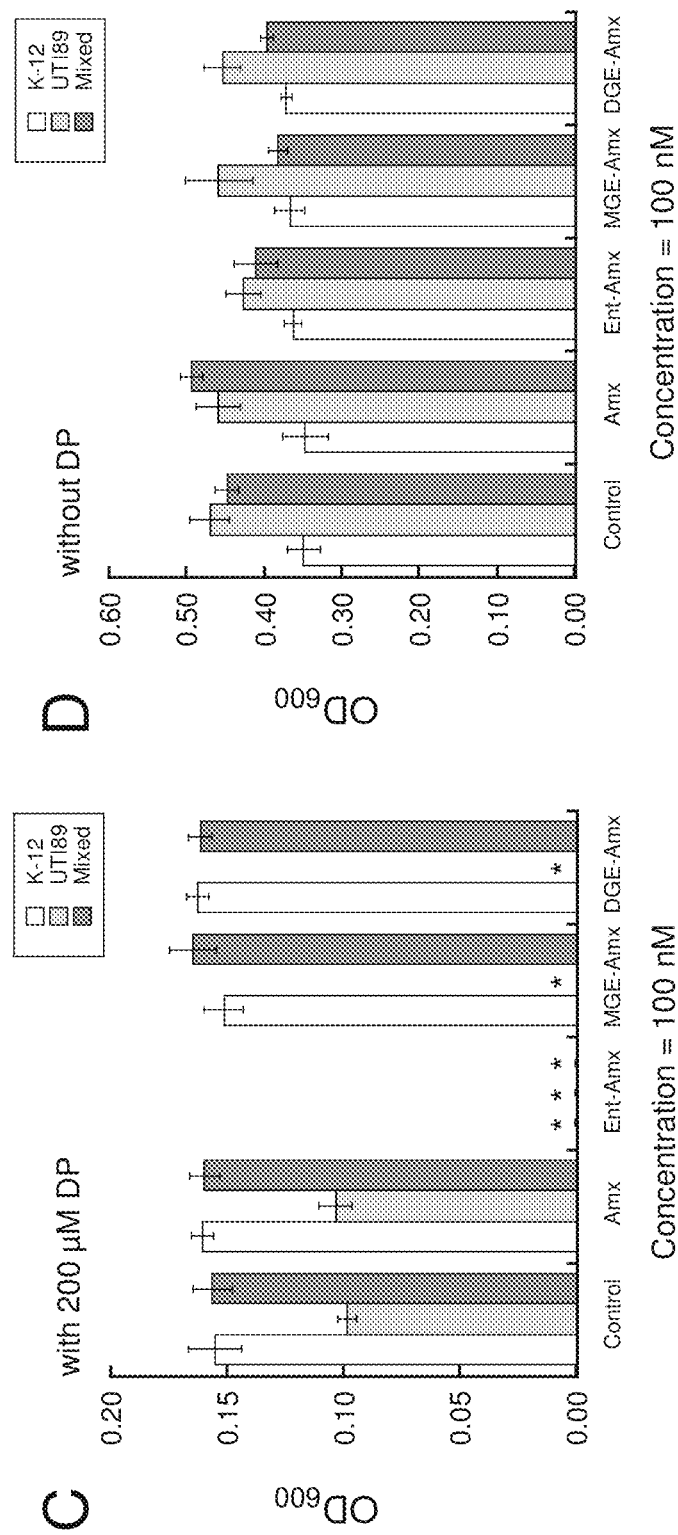
Figures 37A, 37B:
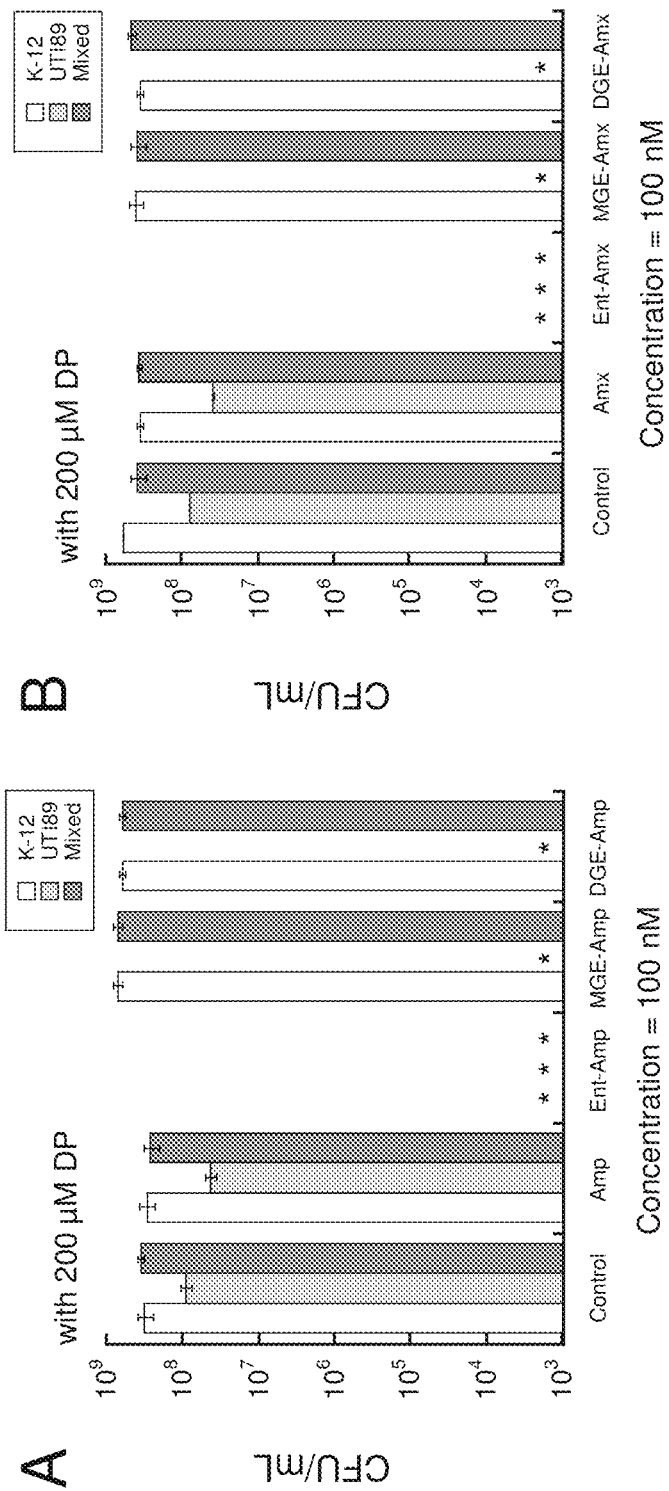
FIGS. 37A to 37B show the corresponding CFU of mixed culture assays in FIGS. 36A to 36D of *E. coli* K-12 and *E. coli* UTI89 treated with the select Ent-β-lactam conjugates and glucosylated derivatives in 50% MHB, 30° C., t=19 h. 2,2'-dipyridyl (DP, 200 µM) was added to provide conditions of iron limitation. The asterisks indicate no colony formation.
Figures 38A, 38B:
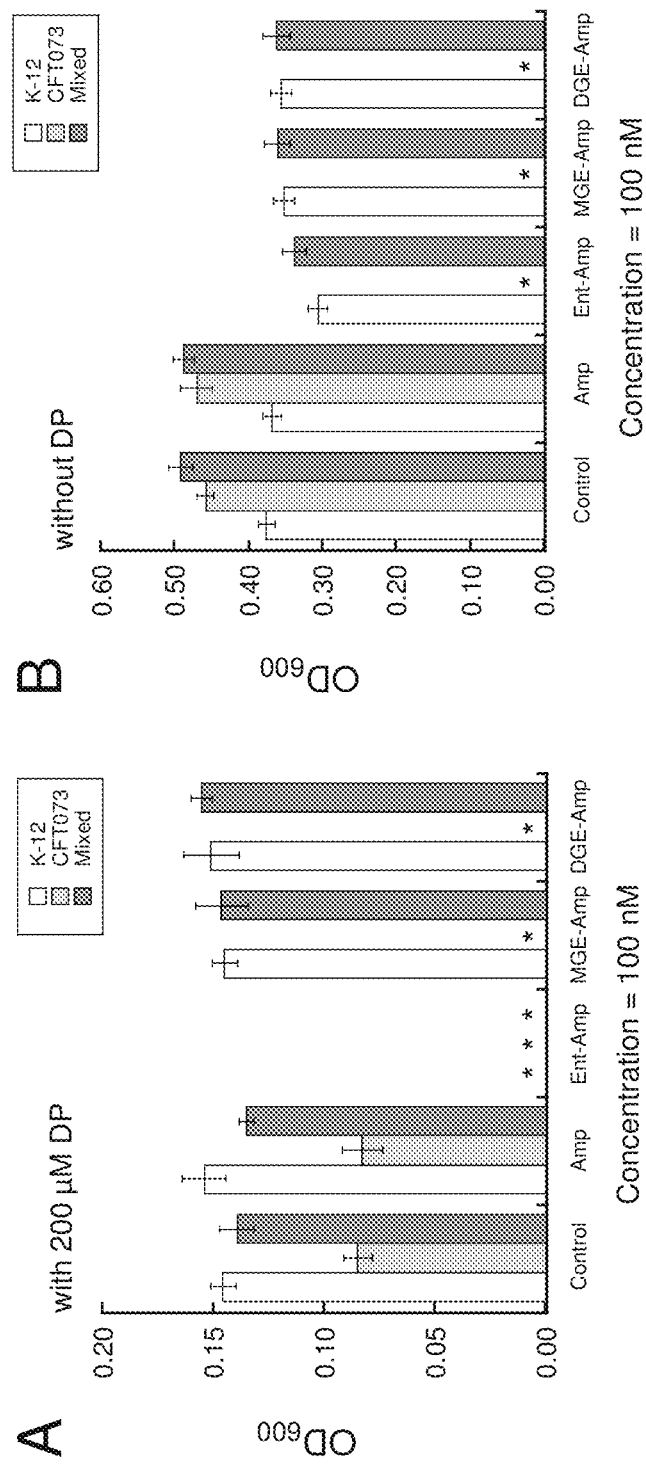
FIGS. 38A to 38D show exemplary $OD_{600}$ measurements of mixed culture assays of E. coli K-12 and E. coli CFT073 treated with select Ent-β-lactam conjugates (Ent-Amp and Ent-Amx) and their glucosylated derivatives (MGE-Amp, MGE-Amx, DGE-Amp, and DGE-Amx). The asterisks indicate $OD_{600}$ was less than 0.1.
Figures 38C, 38D:
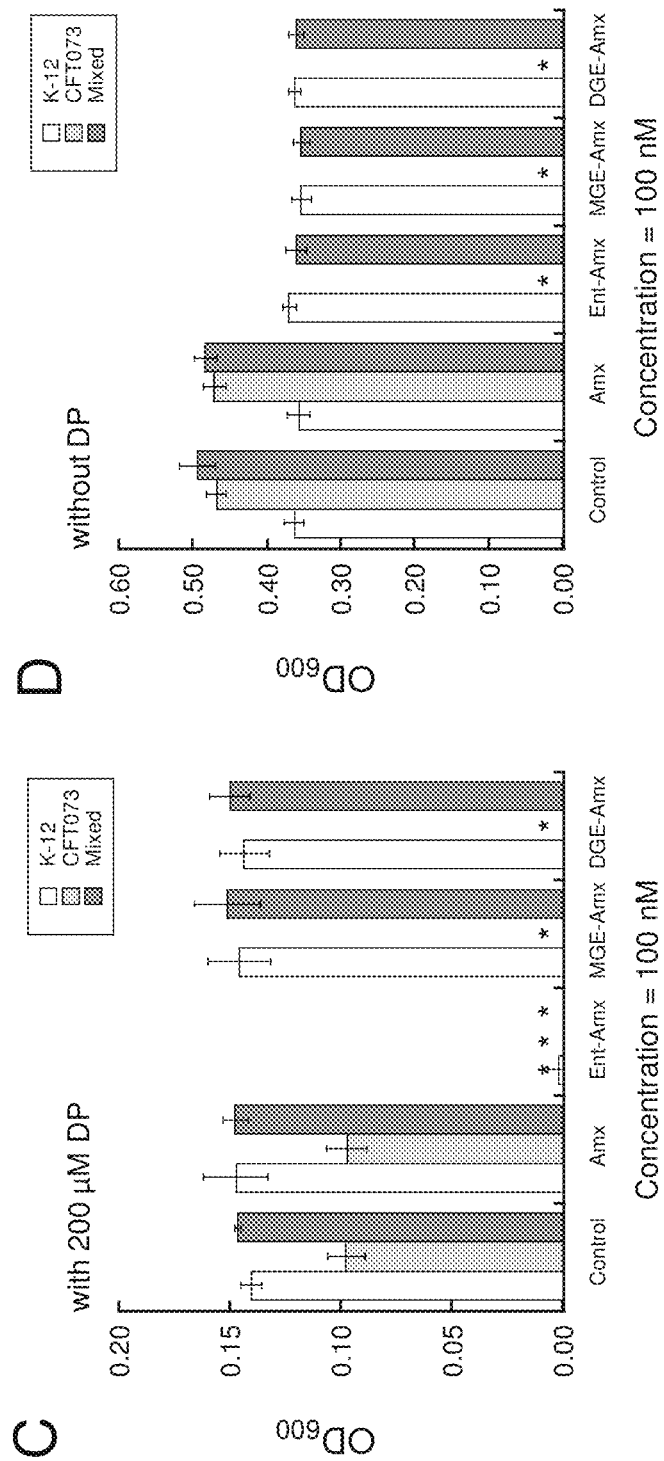
Figures 39A, 39B:
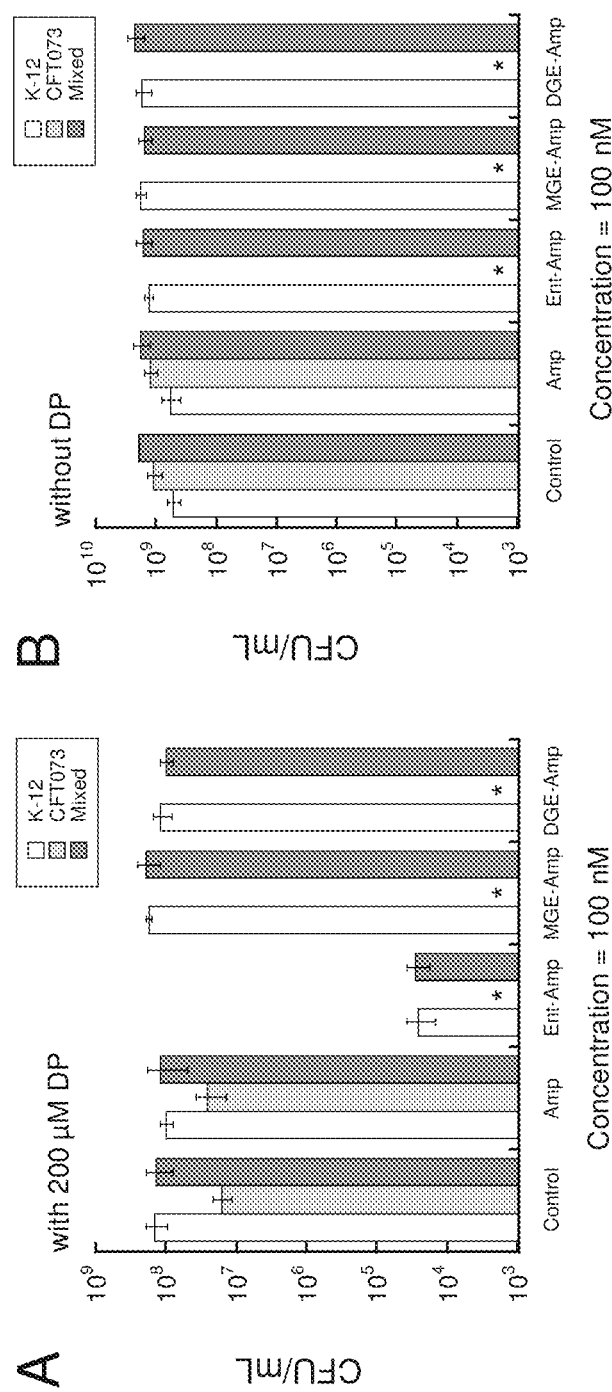
FIGS. 39A to 39D show the corresponding CFU of mixed culture assays in FIGS. 38A to 38D of E. coli K-12 and E. coli CFT073 treated with the select Ent-β-lactam conjugates and glucosylated derivatives in 50% MHB, 30° C., t=19 h. 2,2'-dipyridyl (DP, 200 μM) was added to provide conditions of iron limitation. The asterisks indicate no colony formation.
Figures 39C, 39D:
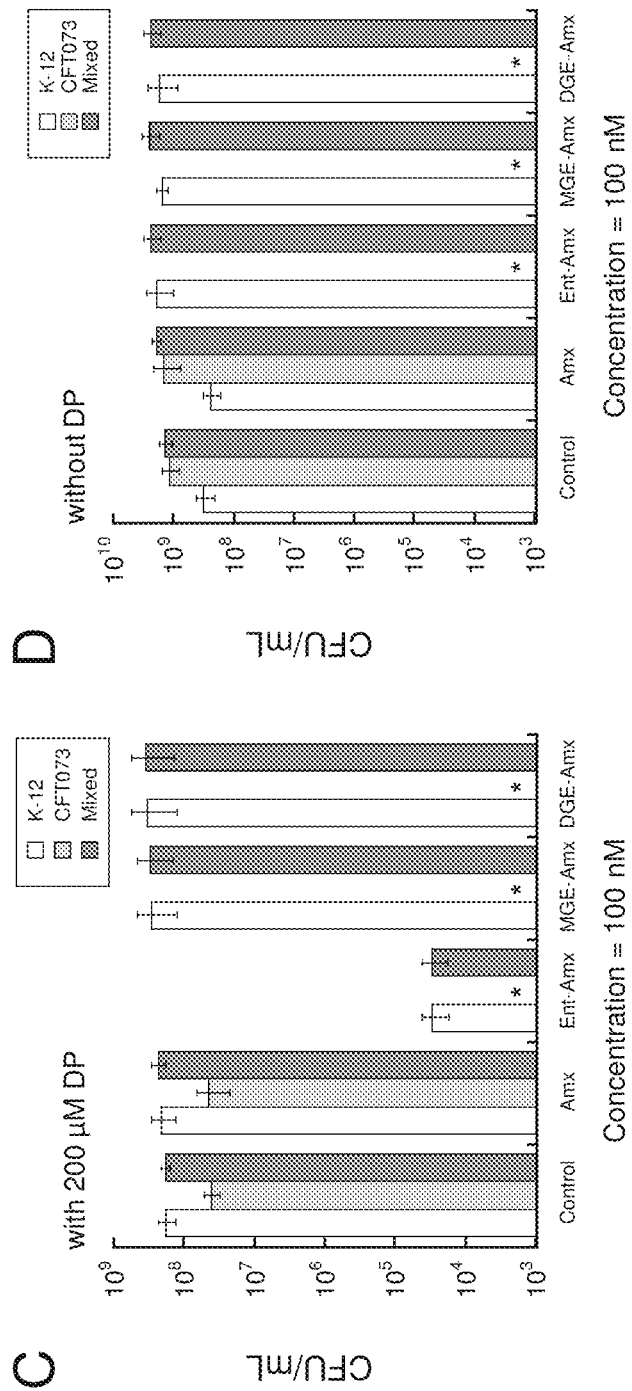
Figures 40A, 40B:
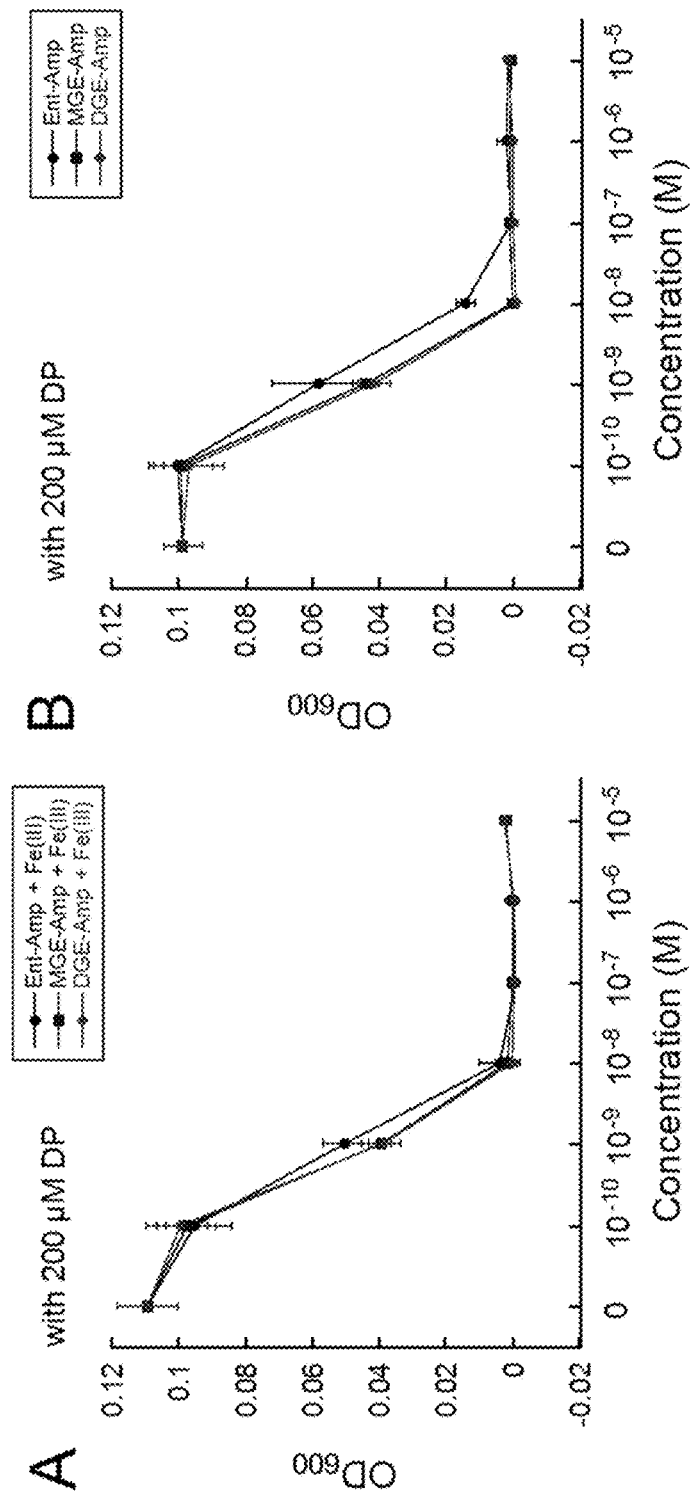
FIGS. 40A to 40D show exemplary antibacterial activities of (FIGS. 40A and 40C) Fe(III)-loaded or (FIGS. 40B and 40D) apo Ent-β-lactam conjugates (Ent-Amp and Ent-Amx) and their glucosylated derivatives (MGE-Amp, MGE-Amx, DGE-Amp, and DGE-Amx) against the uropathogenic strain E. coli CFT073.
Figures 40C, 40D:
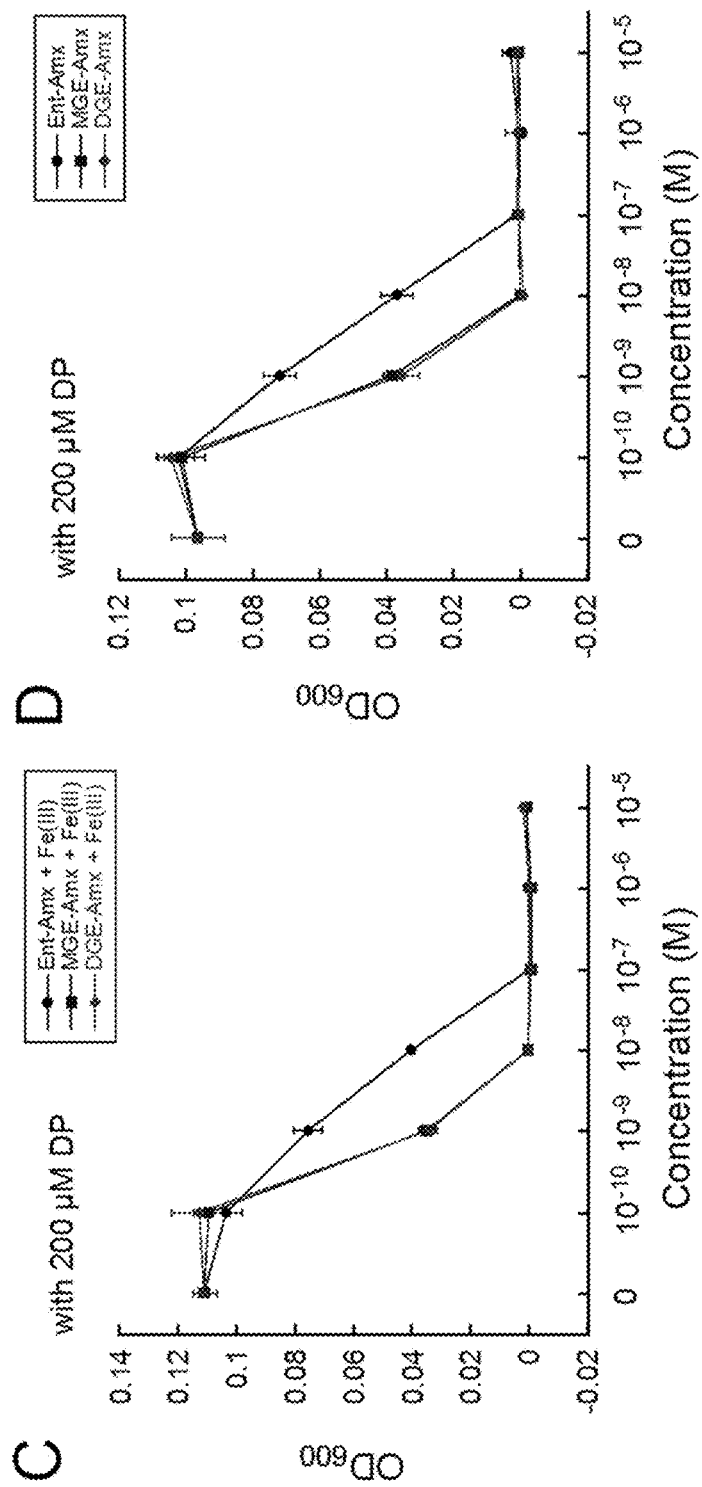
Figures 41A, 41B:
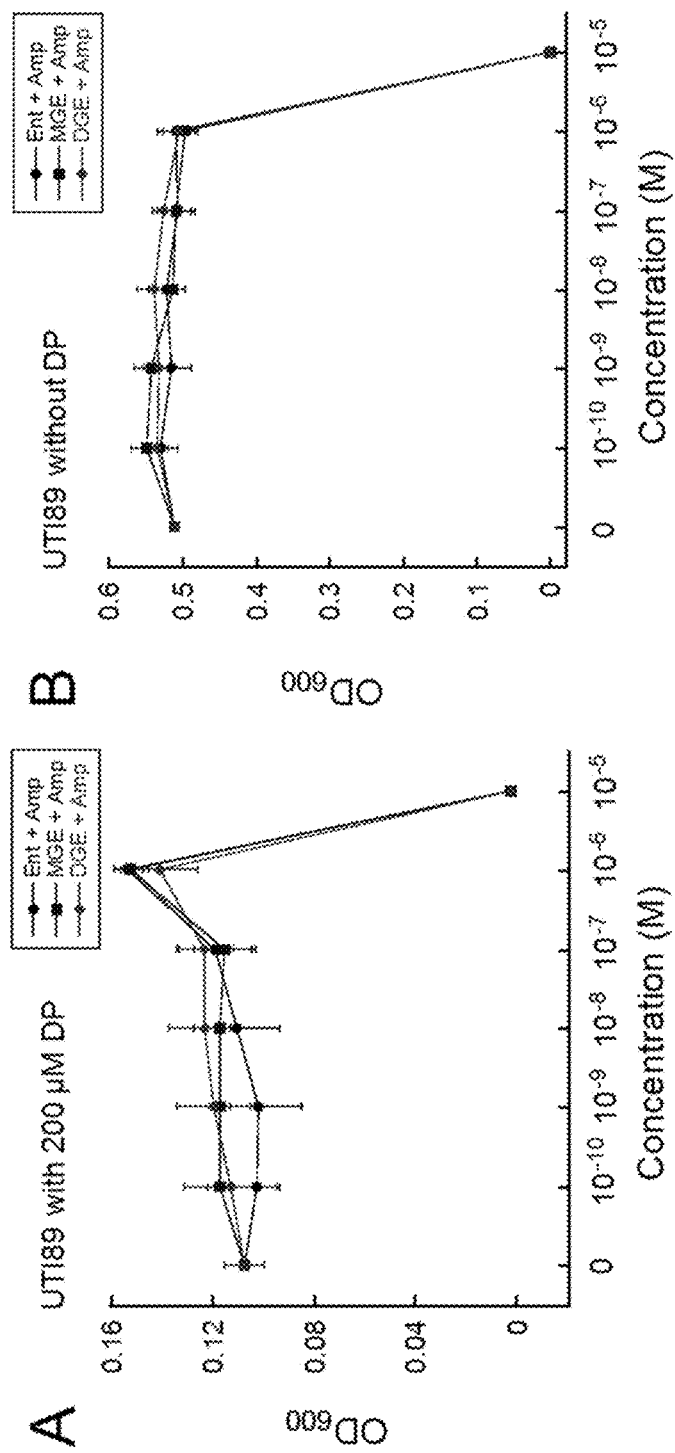
FIGS. 41A to 41D show exemplary antibacterial activities of Amp and Amx, in the presence of Ent, MGE, or DGE, against the uropathogenic strain E. coli UTI89.
Figures 41C, 41D:
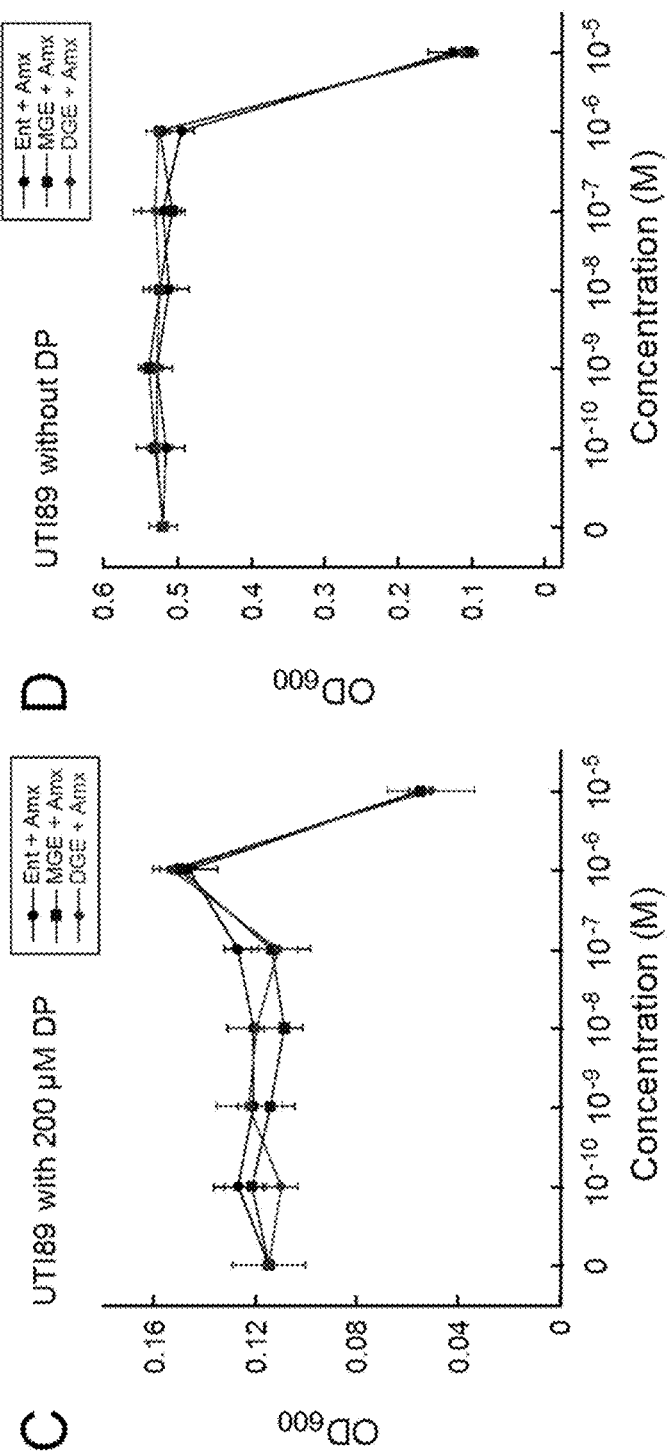
Figures 42A, 42B:
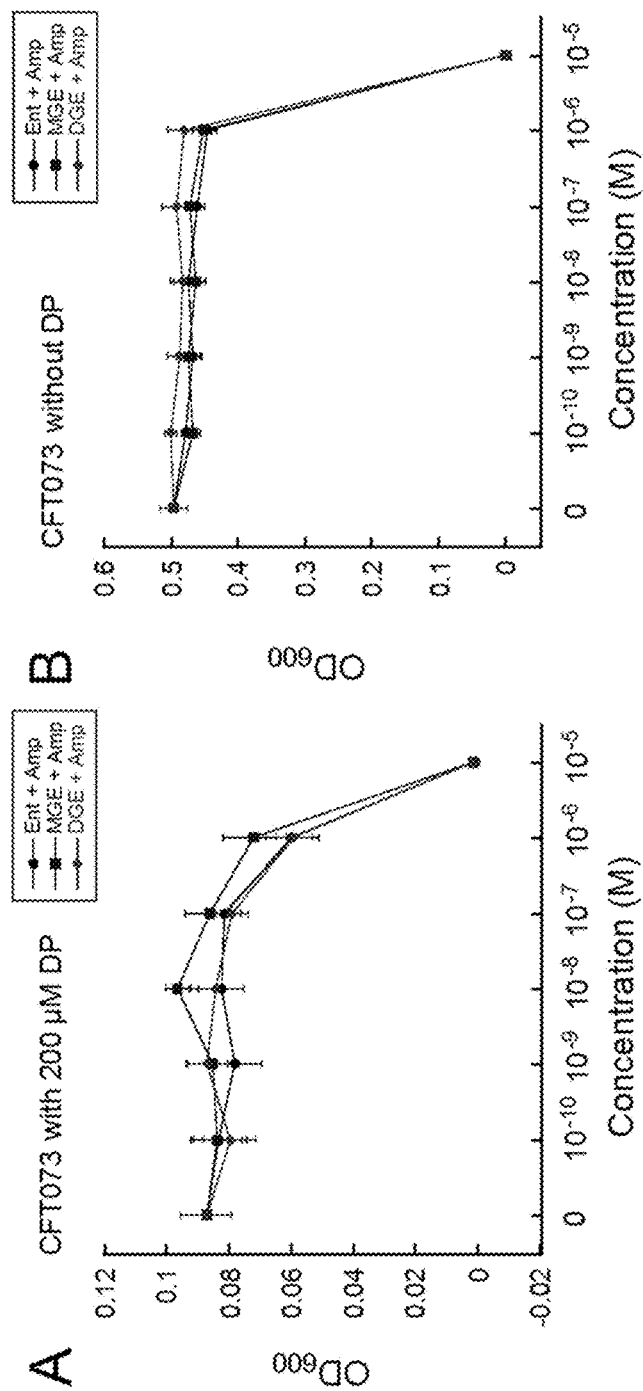
FIGS. 42A to 42D show exemplary antibacterial activities of Amp and Amx, in the presence of Ent, MGE, or DGE, against the uropathogenic strain E. coli CFT073.
Figures 42C, 42D:
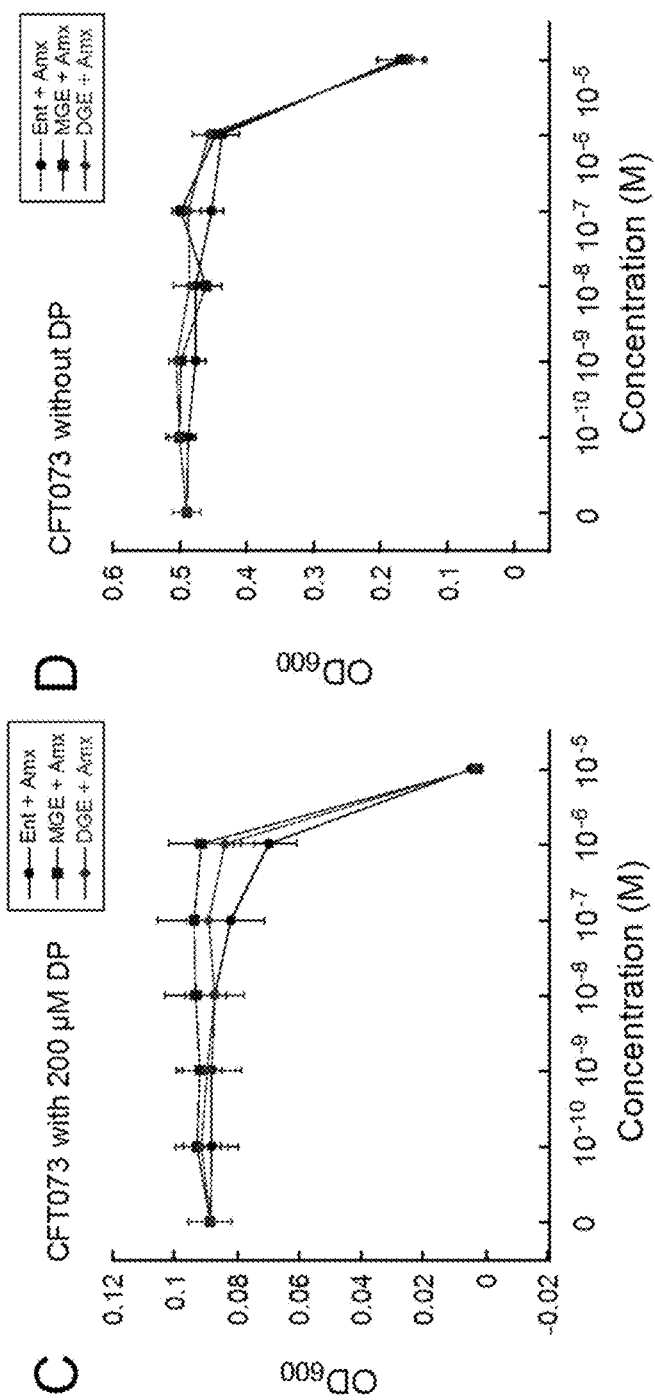

In another exemplary experiment, select conjugates (Ent-Amx, MGE-Amx, and DGE-Amx) with select native siderophores (Ent, MGE, and DGE) were tested against the uropathogenic strain E. coli CFT073 in 50% MHB, t=19 h, 30° C. DP (200 μM) was added to provide conditions of iron limitation. The concentration of the conjugates was fixed at 100 nM and the concentration of the native siderophores was varied. Exemplary results are shown in FIG. 35A to 35C. The antibacterial activity of Ent-Amx was only attenuated in the presence of Ent or MGE. However, the antibacterial activity of MGE-Amx and DGE-Amx was attenuated by Ent, MGE, or DGE. These observations indicate that Ent, MGE, Ent-Amp, and MGE-Amp may enter via both FepA and IroN with different efficiency, but DGE and DGE-Amp may only enter via IroN.

Example 12. Antimicrobial Activity Assays in the Presence of Lipocalin 2

Figures 31A, 31B:
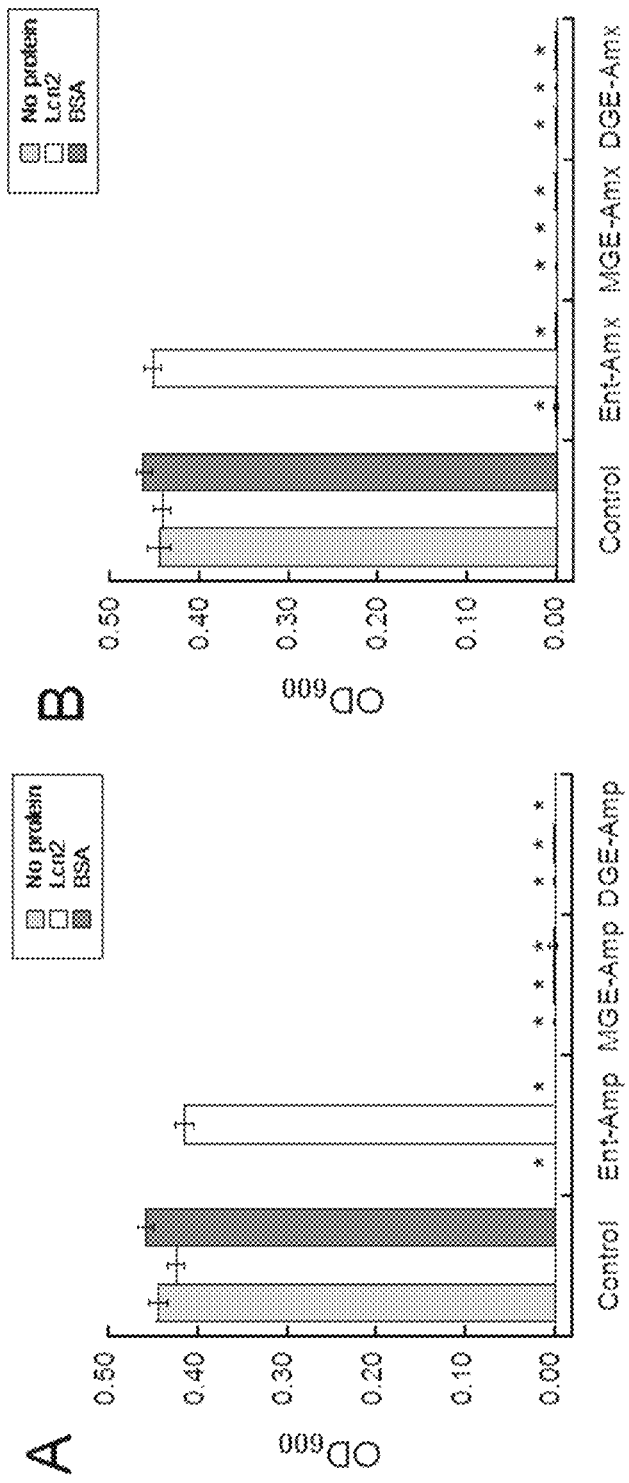
FIGS. 31A to 31B show exemplary effects of lipocalin-2 (Lcn2) on the antibacterial activity of select Ent-β-lactam conjugates (Ent-Amp and Ent-Amx) and their glucosylated derivatives (MGE-Amp, MGE-Amx, DGE-Amp, and DGE-Amx) against the uropathogenic strain *E. coli* CFT073 in modified M9 minimal media (6.8 g/L $Na_2HPO_4$, 3 g/L $KH_2PO_4$, 0.5 g/L NaCl, 1 g/L $NH_4Cl$, 2 mM $MgSO_4$, 0.1 mM $CaCl_2$, 0.4% glucose, 0.2% casein amino acids, and 16.5 g/mL thiamine), t=24 h, 37° C. The concentration of Lcn2 and BSA was 1 µM, and the concentration of the conjugates was 100 nM. The asterisks indicate $OD_{600}$ was less than 0.01.

The bacterial cultures were grown in modified M9 minimal medium (Blango, M. G.; Ott, E. M.; Erman, A.; Veranic, P.; Mulvey, M. A. Forced Resurgence and Targeting of Intracellular Uropathogenic Escherichia coli Reservoirs. PLoS One 2014, 9, e93327-e93335) ($Na_2HPO_4$ 6.8 g/L, $KH_2PO4$ 3 g/L, NaCl 0.5 g/L, $NH_4Cl$ 1 g/L, 0.4% glucose, 2 mM $MgSO_4$, 0.1 mM $CaCl_2$, 0.2% casein amino acids, and 16.5 μg/mL of thiamine) overnight. The overnight culture grew to saturation and was diluted 1:100 into 5 mL of fresh modified M9 minimal medium and incubated at 37° C. with shaking at 150 rpm until $OD_{600}$ reached 0.6. The cultures were serially diluted to an $OD_{600}$ value of 0.00001 in fresh modified M9 minimal medium. Lipocalin 2 (Lcn2) was diluted into PBS buffer to a concentration of 20 μM upon arrival and frozen at −20° C. until use. Bovine serum albumin (BSA, Sigma-Aldrich) was prepared in PBS buffer to achieve a concentration of 20 µM. A 90-µL aliquot of the diluted culture was combined with a 5-µL aliquot of a 20× solution of Ent-Amp, Ent-Amx, MGE-Amp, MGE-Amx, DGE-Amp, or DGE-Amx, and a 5-µL aliquot of Lcn2 or BSA, in a 96-well plate, which was wrapped in PARAFILM and incubated at 37° C. with shaking at 150 rpm for 24 h. The bacterial growth was determined by measuring $OD_{600}$ using the plate reader. Each well condition was repeated at least three times independently on different days. The resulting mean $OD_{600}$ was reported, and the error bars were the standard deviation. Exemplary results obtained from an optimized assay are shown in FIGS. 31A to 31B. The antibacterial activity of Ent-Amp and Ent-Amx was attenuated in the presence of Lcn2. In contrast, Lcn2 had no effect of the antibacterial activity of MGE-Amp, MGE-Amx, DGE-Amp, or DGE-Amx.

Example 13. Killing Kinetic Assays

A 5-mL overnight culture of E. coli UTI89 or E. coli CFT073 grown in LB was diluted 1:100 into 5 mL of fresh LB media with 200 µM DP and incubated at 37° C. with shaking at 150 rpm until $OD_{600}$ reached about 0.3. The culture was centrifuged (3000 rpm×10 min, rt), and the resulting pellet was resuspended in 50% MHB and centrifuged twice. The resulting pellet was resuspended in 50% MHB with or without DP (200 µM), and the $OD_{600}$ was adjusted to 0.3. A 90-µL aliquot of the resulting culture was combined with a 10-µL aliquot of a 10× solution of Amp, Amx, Ent-Amp, Ent-Amx, MGE-Amp, MGE-Amx, DGE-Amp, or DGE-Amx, in a 96-well plate, which was wrapped in PARAFILM and incubated at 37° C. with shaking at 150 rpm. The $OD_{600}$ values were recorded by using a plate reader at time (t)=0, 1, 2, 3 h. In a parallel experiment, a 10-µL aliquot of the culture was taken at t=0, 1, 2, 3 h and serially diluted by using sterile phosphate-buffered saline (PBS) and plated on LB agar to obtain colony forming units (CFU/mL). Each well condition was repeated at least three times independently on different days. The resulting mean $OD_{600}$ or CFU/mL was reported, and the error bars were the standard deviation. Exemplary results are shown in FIGS. 27A to 30D.

Example 14. Mixed-Species (Mixed Culture) Assays

The pET29a plasmid (kanamycin resistance) was transformed into E. coli K-12, and the pHSG398 plasmid (chloramphenicol resistance) was transformed into E. coli UTI89 and E. coli CFT073 via electroporation. Overnight cultures of the bacterial strains were prepared by inoculating 5 mL of LB containing the appropriate antibiotic with the bacterial freezer stocks, and the cultures were incubated at 37° C. in a tabletop incubator shaker set at 150 rpm. The final concentrations of the antibiotic markers used are as following: kanamycin, 50 µg/mL; chloramphenicol, 34 µg/mL. A 5-mL overnight culture of tested bacterial strain grown in LB was diluted 1:100 into 5 mL of fresh LB medium with 200 µM DP and incubated at 37° C. with shaking at 150 rpm until $OD_{600}$ reached 0.6. The cultures were diluted to an $OD_{600}$ value of 0.001 in 50% MHB separately or in a 1:1 mixture ($10^6$ CFU/mL for each strain), with or without 200 µM DP. No antibiotic marker was included in these cultures. These cultures were serially diluted by using sterile PBS and plated on LB agar plates with or without corresponding antibiotic to confirm the CFU of the starter culture. A 90-µL aliquot of these cultures was combined with a 10-µL aliquot of a 1-µM solution of Amp, Amx, Ent-Amp, Ent-Amx, MGE-Amp, MGE-Amx, DGE-Amp, or DGE-Amx, in a 96-well plate, which was wrapped in PARAFILM and incubated at 30° C. with shaking at 150 rpm for 19 h. Bacterial growth was assayed by both measuring $OD_{600}$ using the plate reader and plating on LB agar plates with or without corresponding antibiotic after serial dilutions. Each well condition was repeated at least three times independently on different days. The resulting mean $OD_{600}$ and CFU/mL values were reported, and the error bars were the standard deviation.

In an exemplary experiment, a mixed culture of E. coli K-12 and E. coli UTI89 was treated with select Ent-β-lactam conjugates (Ent-Amp and Ent-Amx) and their glucosylated derivatives (MGE-Amp, MGE-Amx, DGE-Amp, and DGE-Amx) in 50% MHB, 30° C., t=19 h. 2,2'-dipyridyl (DP, 200 µM) was added to provide conditions of iron limitation. Exemplary results are shown in FIGS. 36A to 37B. Under iron-deficient conditions, Ent-Amp provides a complete growth inhibition for both strains at 100 nM. In contrast, MGE-Amp and DGE-Amp only inhibited the growth of E. coli UTI89 at this concentration. Similar trends to the Amp conjugates were observed for the Amx conjugates. These observations indicate that MGE-Amp, MGE-Amx, DGE-Amp, and DGE-Amx can be used to target uropathogenic E. coli, which harbors IroN.

In another exemplary experiment, a mixed culture of E. coli K-12 and E. coli CFT073 was treated with select Ent-β-lactam conjugates (Ent-Amp and Ent-Amx) and their glucosylated derivatives (MGE-Amp, MGE-Amx, DGE-Amp, and DGE-Amx) in 50% MHB, 30° C., t=19 h. 2,2'-dipyridyl (DP, 200 µM) was added to provide conditions of iron limitation. Exemplary results are shown in FIGS. 38A to 39D. Under iron-deficient conditions, Ent-Amp provided a complete growth inhibition for both strains at 100 nM. In contrast, MGE-Amp and DGE-Amp only inhibited the growth of E. coli CFT073 at this concentration. Similar trends to the Amp conjugates were observed for the Amx conjugates. These observations indicate that MGE-Amp, MGE-Amx, DGE-Amp, and DGE-Amx can be used to target uropathogenic E. coli, which harbors IroN.

Example 15. Antibacterial Activities of Ent-Amp, Ent-Amx, MGE-Amp, MGE-Amx, DGE-Amp, and DGE-Amx Against Select Strains of E. coli Select Ent-β-lactam conjugates (Ent-Amp and Ent-Amx) and their glucosylated derivatives (MGE-Amp, MGE-Amx, DGE-Amp, and DGE-Amx) were tested against 6 strains of E. coli. Four of them are non-pathogenic strains, namely K-12, B, H9049, and 25922, and the other two are uropathogenic clinical isolates, namely UTI89 and CFT073. Overall, MGE-Amp, MGE-Amx, DGE-Amp, and DGE-Amx exhibited greater antibacterial activity against the uropathogenic E. coli compared to non-pathogenic E. coli. Moreover, in contrast to Ent-Amp and Ent-Amx, the antibacterial activity of MGE-Amp, MGE-Amx, DGE-Amp, and DGE-Amx was not attenuated in the presence of lipocalin-2 (Lcn-2), which is a mammalian antimicrobial protein and is known to bind to Fe(III)-Ent. Also demonstrate was that MGE-Amp, MGE-Amx, DGE-Amp, and DGE-Amx specifically inhibited the growth of the uropathogenic E. coli and left non-pathogenic E. coli unaffected in the mixed culture assays. It was also shown that preloading Fe(III) to Ent-Amp, Ent-Amx, MGE-Amp, MGE-Amx, DGE-Amp, and DGE-Amx had no effect on the antibacterial activity of the conjugates and that conjugation between the siderophores and the β-lactams was required for the enhanced antibacterial activity of the drugs. Furthermore, these conjugates were shown to be non-toxic to human colonic epithelial cells, T84 cells.

In an exemplary experiment, antibacterial activities of the conjugates were tested against *E. coli* K-12 in 50% MHB at 30° C., t=19 h. 2,2'-dipyridyl (DP, 200 μM) was added to provide conditions of iron limitation. Exemplary results are shown in FIGS. 21A to 21D. Under iron-deficient conditions, Ent-Amp provided a complete growth inhibition at 100 nM whereas MGE-Amp, and DGE-Amp are inactive at this concentration. However, MGE-Amp is more active against the bacteria than DGE-Amp. The growth inhibition observed for DGE-Amp at 10 μM may be attributed to iron deprivation by the conjugate. Similar trends to the Amp conjugates were observed for the Amx conjugates. These observations indicated that MGE-Amp and MGE-Amx may also enter via FepA, but the efficiency was lower than that of Ent-Amp and Ent-Amx.

In another exemplary experiment, antibacterial activities of the conjugates were tested against *E. coli* B in 50% MHB at 30° C., t=19 h. DP (200 μM) was added to provide conditions of iron limitation. Exemplary results are shown in FIGS. 22A to 22D. Under iron-deficient conditions, Ent-Amp provided a complete growth inhibition at 100 nM whereas MGE-Amp and DGE-Amp were inactive at this concentration. However, MGE-Amp was more active against the bacteria than DGE-Amp. The growth inhibition observed for DGE-Amp at 10 μM may be attributed to iron deprivation by the conjugate. Similar trends to the Amp conjugates were observed for the Amx conjugates. These observations indicated that MGE-Amp and MGE-Amx may also enter via FepA, but the efficiency was lower than that of Ent-Amp and Ent-Amx.

In another exemplary experiment, antibacterial activities of the conjugates were tested against *E. coli* H9049 in 50% MHB at 30° C., t=19 h. DP (200 μM) was added to provide conditions of iron limitation. Exemplary results are shown in FIGS. 23A to 23D. Under iron-deficient conditions, Ent-Amp provided a complete growth inhibition at 100 nM whereas MGE-Amp and DGE-Amp were inactive at this concentration. However, MGE-Amp was more active against the bacteria than DGE-Amp. The growth inhibition observed for DGE-Amp at 10 μM may be attributed to iron deprivation by the conjugate. Similar trends to the Amp conjugates were observed for the Amx conjugates. These observations indicated that MGE-Amp and MGE-Amx may also enter via FepA, but the efficiency was lower than that of Ent-Amp and Ent-Amx.

In another exemplary experiment, antibacterial activities of the conjugates were tested against *E. coli* 25922 in 50% MHB at 30° C., t=19 h. DP (200 μM) was added to provide conditions of iron limitation. Exemplary results are shown in FIGS. 24A to 24D. Under iron-deficient conditions, Ent-Amp and MGE-Amp provided a complete growth inhibition at 100 nM whereas 1 μM of DGE-Amp was required to provide a complete growth inhibition. Similar trends to the Amp conjugates were observed for the Amx conjugates.

In another exemplary experiment, antibacterial activities of the conjugates were tested against *E. coli* UTI89 in 50% MHB at 30° C., t=19 h. DP (200 μM) was added to provide conditions of iron limitation. Exemplary results are shown in FIGS. 25A to 25D. Under iron-deficient conditions, Ent-Amp, MGE-Amp, and DGE-Amp provided a complete growth inhibition at 100 nM. Similar trends to the Amp conjugates were observed for the Amx conjugates. When compared to those from nonpathogenic *E. coli* strains which harbor only FepA, these observations indicated that MGE-Amp and MGE-Amx may enter via both FepA and IroN, whereas DGE-Amp and DGE-Amx may only enter via IroN.

In another exemplary experiment, antibacterial activities of the conjugates were tested against *E. coli* CFT073 in 50% MHB at 30° C., t=19 h. DP (200 μM) was added to provide conditions of iron limitation. Exemplary results are shown in FIGS. 26A to 26D. Under iron-deficient conditions, MGE-Amp and DGE-Amp provided a complete growth inhibition at 10 nM, whereas Ent-Amp was slightly less active at this concentration. Similar trends to the Amp conjugates were observed for the Amx conjugates. When compared to those from nonpathogenic *E. coli* strains which harbor only FepA, these observations indicated that MGE-Amp and MGE-Amx may enter via both FepA and IroN, whereas DGE-Amp and DGE-Amx may only enter via IroN.

In another exemplary experiment, antibacterial activities of Fe(III)-loaded or apo Ent-β-lactam conjugates (Ent-Amp and Ent-Amx) and their glucosylated derivatives (MGE-Amp, MGE-Amx, DGE-Amp, and DGE-Amx) against the uropathogenic strain *E. coli* CFT073 were tested in 50% MHB, 30° C., t=19 h. 2,2'-dipyridyl (DP, 200 μM) was added to provide conditions of iron limitation. Exemplary results are shown in FIGS. 40A to 40D. Preloading Fe(III) to the conjugates had no effect on their antibacterial activity.

Example 16. Antibacterial Activities of Amp and Amx, in the Presence of Ent, MGE, or DGE, Against Select Strains of *E. coli*

In an exemplary experiment, antibacterial activities of Amp and Amx, in the presence of Ent, MGE, or DGE, were tested against the uropathogenic strain *E. coli* UTI89 in 50% MHB, 30° C., t=19 h. 2,2'-dipyridyl (DP, 200 μM) was added to provide conditions of iron limitation. Exemplary results are shown in FIGS. 41A to 41D. The data suggest that the PEG linker may be required for the increased antibacterial activity of Ent-β-lactam conjugates and their glucosylated derivatives.

In another exemplary experiment, antibacterial activities of Amp and Amx, in the presence of Ent, MGE, or DGE, were tested against the uropathogenic strain *E. coli* CFT073 in 50% MHB, 30° C., t=19 h. 2,2'-dipyridyl (DP, 200 μM) was added to provide conditions of iron limitation. Exemplary results are shown in FIGS. 42A to 42D. The data suggest that the PEG linker may be required for the increased antibacterial activity of Ent-β-lactam conjugates and their glucosylated derivatives.

CONCLUSION

A family of monofunctionalized enterobactin derivatives has been designed and prepared, and these scaffolds have been utilized for the preparation of enterobactin-cargo conjugates bearing cargos of varying size and complexity. Growth recovery assays employing *E. coli* and *P. aeruginosa* revealed that the enterobactin uptake machineries of these Gram-negative species recognize and transport enterobactin-cargo conjugates to the intracellular space (e.g., the cytoplasm or periplasm) of these Gram-negative bacteria. These results are surprisingly advantageous over what is known in the art in several respects. First, the notion of using siderophores for antibiotic delivery across the Gram-negative outer membrane, which serves as a permeability barrier, has achieved long-term interest.[6-8,13] Such "Trojan horse" antibiotics are largely inspired by the sideromycins,[11,12] a family of siderophore-antibiotic conjugates produced by the soil bacterium *Streptomyces*, and by early observations that catechol-modified β-lactams were recognized by the iron-uptake machinery of Gram-negative microbes.[43-46] Significant efforts have been made to prepare and characterize synthetic siderophore-antibiotic conjugates with the goal of targeting drug-resistant Gram-negative pathogens.[13,14] Timely examples of siderophore-antibiotic conjugates with antimicrobial activity include a mycobactin-artemisinin conjugate that kills *Mycobacterium tuberculosis* and *Plasmodium falciparum*,[82] and amoxicillin/ampicillin-appended tripodal triscatecholates that exhibit potent antipseudomonal activity relative to the parent β-lactam antibiotics.[49] One bottleneck with this general approach, and using siderophores in other applications, is that few synthetically tractable and modifiable native siderophores are available. DFO B and pyoverdine, which are readily obtained commercially (DFO B) or from bacterial cultures (pyoverdines), provide free amino groups useful for conjugation and are most commonly derivatized for application-based work.[18] Despite that syntheses of modified pyochelin,[15] petrobactin,[19] and mycobactin[82,83] platforms that house functional groups amenable to site-specific elaboration have been reported, the syntheses described herein provide enterobactin with a functional handle for versatile chemical modifications, and will allow strategic use of this canonical siderophore in a multitude of chemical biology and biotechnology initiatives.

Other unexpected advantages of the conjugates and methods of the invention over existing methods include: (1) compared to unmodified β-lactams, the conjugates of the invention showed 100- to 1000-fold greater activity against Gram-negative *Escherichia coli*, e.g., human pathogenic strains CFT073 (uropathogenic *E. coli*) and O157:H7 (enterohemorrhagic strain, food-borne illness); (2) a native siderophore platform is employed, which may provide enhanced recognition by the siderophore receptor compared to related strategies where siderophore-like ligands have been employed; (3) the synthetic approach is versatile so that many other cargos can be linked to the enterobactin platform via the route presented herein; and (4) the siderophore is enterobactin. This siderophore is by far the most well-studied siderophore from the perspectives of the molecule and its biology. The uptake system is well understood, which facilitates investigations of siderophore-antibiotic uptake and activity, including studies of mechanism. These aspects are important for guiding the design of future generations of molecules with improved characteristics.

Unanswered questions regarding the antibacterial activity and fate of reported synthetic siderophore-antibiotic conjugates exist. Whether a given conjugate is actively transported into the bacterial cell is oftentimes unclear. Because FepA recognizes relatively large biomolecules including MccE492m (84 amino acids) and colicin B (324 amino acids), it is tempting to predict that FepA may accommodate almost any cargo appended to an enterobactin or catecholate platform. The results presented herein challenge this notion and indicate that cargo size is an important and species-specific parameter. The assays indicate that *P. aeruginosa* PAO1 has a greater capacity to import enterobactin-cargo conjugates than *E. coli* ATCC 33475. It will be interesting to determine the cargo scope of other *E. coli* strains and bacterial species that utilize enterobactin for iron acquisition, and understand the molecular and physiological basis for such variations. Colicins are largely α-helical[40] and MccE492m shares some sequence homology with colicins.[84] It is likely that some enterobactin receptors have decreased propensity to transport synthetic small molecules or natural products with less structural malleability (i.e. vancomycin) than an α-helical peptide.

The mechanisms of iron release from siderophores, which vary tremendously for the myriad of siderophores produced by different bacterial species, are another important consideration in siderophore-cargo conjugate design. Studies of chiral recognition in enterobactin transport have demonstrated that D-Ent is transported into *E. coli* but cannot be hydrolyzed by Fes,[71] the monofunctionalized D-Ent scaffolds were designed to probe cytosolic delivery. This design feature prevents esterase-catalyzed iron release from enterobactin-based conjugates in the intracellular space and may have practical utility. From the standpoint of drug delivery, a tug-of-war may result from utilizing an iron-supplying siderophore that confers a growth advantage for delivering a toxic payload to a bacterial cell, and preventing iron release may be beneficial. In other applications, siderophore-fluorophore conjugates are of interest for bacterial detection and diagnostics, and Fe(III) binding to and release from the siderophore will likely influence the photophysical properties of such molecules.

In summary, the present invention provides, among other things, that the enterobactin transport machineries of *E. coli* (e.g., FepABCDG and TonB-ExbB-ExbD) and *P. aeruginosa* will deliver enterobactin-modified cargo to the intracellular space (e.g., cytoplasm or periplasm) of a Gram-negative bacterium. Moreover, the preparative work affords a new siderophore platform amenable to synthetic elaboration and an entry route for employing the native enterobactin scaffold in a multitude of application-based initiatives that include intracellular cargo delivery, iron sensing, gallium sensing, siderophore labeling, and therapeutic development. These conjugates can also be attached to peptides, proteins, and solid supports via Click chemistry (e.g., copper-catalyzed). A conjugate described herein (e.g., a salmochelin-cargo conjugate) may also allow the cargo to be targeted to pathogenic bacterium and leave the commensals unaffected. Furthermore, the native siderophore (e.g., enterobactin or salmochelin) platforms may provide enhanced recognition by the siderophore receptor compared to related strategies where non-native siderophore-like ligands have been employed. Last, the high-affinity Fe(III) binding exhibited by the native siderophores compared to siderophore-like ligands may be another advantage because any siderophore-cargo conjugate employed in vivo will need to compete for Fe(III) as the iron-bound forms are recognized by the receptors.

REFERENCES

1. Hider, R. C.; Kong, X. *Nat. Prod. Rep.* 2010, 27, 637-657.
2. Miethke, M.; Marahiel, M. A. Microbiol. *Mol. Biol. Rev.* 2007, 71, 413-451.
3. Rajkumar, M.; Ae, N.; Prasad, M. N. V.; Freitas, H. *TRENDS Biotechnol.* 2010, 28, 142-149.
4. Bernhardt, P. V. *Dalton Trans.* 2007, 3214-3220.
5. Manning, T.; Kean, G.; Thomas, J.; Thomas, K.; Corbitt, M.; Gosnell, D.; Ware, R.; Fulp, S.; Jarrard, J.; Phillips, D. *Curr. Med. Chem.* 2009, 16, 2416-2429.
6. Miller, M. J., *Chem. Rev.* 1989, 89, 1563-1579.
7. Roosenberg, J. M., II; Lin, Y.-M.; Lu, Y.; Miller, M. J. *Curr. Med. Chem.* 2000, 7, 159-197.
8. Budzikiewicz, H. *Curr. Top. Med. Chem.* 2001, 1, 73-82.
9. Ballouche, M.; Cornelis, P.; Baysse, C. *Recent Pat. Anti-infect. Drug Discovery* 2009, 4, 190-205.
10. Möllmann, U.; Heinisch, L.; Bauemfeind, A.; Köhler, T.; Ankel-Fuchs, D. *Biometals* 2009, 22, 615-624.

11. Braun, V.; Pramanik, A.; Gwinner, T.; Köberle, M.; Bohn, E. *Biometals* 2009, 22, 3-13.
12. Braun, V., *Drug Resist. Update* 1999, 2, 363-369.
13. Ji, C.; Juárez-Hernández, R. E.; Miller, M. J. *Future Med. Chem.* 2012, 4, 297-313.
14. Miller, M. J.; Zhu, H.; Xu, Y.; Wu, C.; Walz, A. J.; Vergne, A.; Roosenberg, J. M.; Moraski, G.; Minnick, A. A.; McKee-Dolence, J.; Hu, J.; Fennell, K.; Kurt Dolence, E.; Dong, L.; Franzblau, S.; Malouin, F.; Möllmann, U. *Biometals* 2009, 22, 61-75.
15. Nöel, S.; Guillon, L.; Schalk, I. J.; Mislin, G. L. A. *Org. Lett.* 2011, 13, 844-847.
16. Espósito, B. P.; Epsztejn, S.; Breuer, W.; Cabantchik, Z. I. *Anal. Biochem.* 2002, 304, 1-18.
17. Lam, C. K. S. C. C.; Jickells, T. D.; Richardson, D. J.; Russell, D. A. *Anal. Chem.* 2006, 78, 5040-5045.
18. Zheng, T.; Nolan, E. M. *Metallomics* 2012, 4, 866-880.
19. Bugdahn, N.; Peuckert, F.; Albrecht, A. G.; Miethke, M.; Marahiel, M. A.; Oberthür, M., *Angew. Chem. Int. Ed.* 2010, 49, 10210-10213.
20. Doorneweerd, D. D.; Henne, W. A.; Reifenberger, R. G.; Low, P. S. *Langmuir* 2010, 26, 15424-15429.
21. Kim, Y.; Lyvers, D. P.; Wei, A.; Reifenberger, R. G.; Low, P. S. *Lab Chip* 2012, 12, 971-976.
22. Raymond, K. N.; Dertz, E. A.; Kim, S. S. *Proc. Natl. Acad. Sci. U.S.A.* 2003, 100, 3584-3588.
23. Crosa, J. H.; Walsh, C. T. *Microbiol. Mol. Biol. Rev.* 2002, 66, 223-249.
24. Loomis, L. D.; Raymond, K. N. *Inorg. Chem.* 1991, 30, 906-911.
25. Buchanan, S. K.; Smith, B. S.; Venkatramani, L.; Xia, D.; Esser, L.; Palnitkar, M.; Chakraborty, R.; van der Helm, D.; Deisenhofer, J. *Nat. Struct. Biol.* 1999, 6, 56-63.
26. Newton, S. M. C.; Igo, J. D.; Scott, D. C.; Klebba, P. E. *Mol. Microbiol.* 1999, 32, 1153-1165.
27. Stephens, D. L.; Choe, M. D.; Earhart, C. F. *Microbiology-UK* 1995, 141, 1647-1654.
28. Chenault, S. S.; Earhart, C. F. *Mol. Microbiol.* 1991, 5, 1405-1413.
29. Shea, C. M.; Mcintosh, M. A. *Mol. Microbiol.* 1991, 5, 1415-1428.
30. Chakraborty, R.; Storey, E.; van der Helm, D. *Biometals* 2007, 20, 263-274.
31. Krewulak, K. D.; Vogel, H. J. *Biochim. Biophys. Acta.* 2008, 1778, 1781-1804.
32. Chu, B. C.; Garcia-Herrero, A.; Johanson, T. H.; Krewulak, K. D.; Lau, C. K.; Peacock, R. S.; Slavinskaya, Z.; Vogel, H. J. *Biometals* 2010, 23, 601-611.
33. Lin, H.; Fischbach, M. A.; Liu, D. R.; Walsh, C. T. *J. Am. Chem. Soc.* 2005, 127, 11075-11084.
34. Miethke, M.; Hou, J.; Marahiel, M. A. *Biochemistry* 2011, 50, 10951-10964.
35. Bäumler, A. J.; Norris, T. L.; Lasco, T.; Voigt, W.; Reissbrodt, R.; Rabsch, W.; Heffron, F., *J. Bacteriol.* 1998, 180, 1446-1453.
36. Lagos, R.; Baeza, M.; Corsini, G.; Hetz, C.; Strahsburger, E.; Castillo, J. A.; Vergara, C.; Monasterio, O. *Mol. Microbiol.* 2001, 42, 229-243.
37. Nolan, E. M.; Fischbach, M. A.; Koglin, A.; Walsh, C. T. *J. Am. Chem. Soc.* 2007, 129, 14336-14347.
38. Fischbach, M. A.; Lin, H. N.; Liu, D. R.; Walsh, C. T., *Proc. Natl. Acad. Sci. U.S.A.* 2005, 102, 571-576.
39. Müller, S.; Valdebenito, M.; Hantke, K. *Biometals* 2009, 22, 691-695.
40. Cao, Z.; Klebba, P. E. *Biochimie* 2002, 84, 399-412.
41. Lagos, R.; Tello, M.; Mercado, G.; Garcia, V.; Monasterio, O. *Curr. Pharm. Biotechnol.* 2009, 10, 74-85.
42. Rabsch, W.; Ma, L.; Wiley, G.; Najar, F. Z.; Kaserer, W.; Schuerch, D. W.; Klebba, J. E.; Roe, B. A.; Gomez, J. A. L.; Schallmey, M.; Newton, S. M. C.; Klebba, P. E. *J. Bacteriol.* 2007, 189, 5658-5674.
43. Katsu, K.; Kitoh, K.; Inoue, M.; Mitsuhashi, S. *Antimicrob. Agents Chemother.* 1982, 22, 181-185.
44. Watanabe, N.-A.; Nagasu, T.; Katsu, K.; Kitoh, K. *Antimicrob. Agents Chemother.* 1987, 31, 497-504.
45. Nakagawa, S.; Sanada, M.; Matsuda, K.; Hazumi, N.; Tanaka, N. *Antimicrob. Agents Chemother.* 1987, 31, 1100-1105.
46. Hashizume, T.; Sanada, M.; Nakagawa, S.; Tanaka, N. *J. Antibiot.* 1990, 43, 1617-1620.
47. Möllmann, U.; Ghosh, A.; Dolence, E. K.; Dolence, J. A.; Ghosh, M.; Miller, M. J.; Reissbrodt, R. *Biometals* 1998, 11, 1-12.
48. Mckee, J. A.; Sharma, S. K.; Miller, M. J. *Bioconjugate Chem.* 1991, 2, 281-291.
49. Ji, C.; Miller, P. A.; Miller, M. J. *J. Am. Chem. Soc.* 2012, 134, 9898-9901.
50. Diarra, M. S.; Lavoie, M. C.; Jacques, M.; Darwish, I.; Dolence, E. K.; Dolence, J. A.; Ghosh, A.; Ghosh, M.; Miller, M. J.; Malouin, F. *Antimicrob. Agents Chemother.* 1996, 40, 2610-2617.
51. Ghosh, A.; Ghosh, M.; Niu, C.; Malouin, F.; Möllmann, U.; Miller, M. J. *Chem. Biol.* 1996, 3, 1011-9.
52. Corey, E. J.; Bhattacharyya, S. *Tetrahedron Lett.* 1977, 45, 3919-3922.
53. Rastetter, W. H.; Erickson, T. J.; Venuti, M. C. *J. Org. Chem.* 1981, 46, 3579-3590.
54. Shanzer, A.; Libman, J. *J. Chem. Soc., Chem. Commun.* 1983, 15, 846-847.
55. Ramirez, R. J. A.; Karamanukyan, L.; Ortiz, S.; Gutierrez, C. G. *Tetrahedron Lett.* 1997, 38, 749-752.
56. Marinez, E. R.; Salmassian, E. K.; Lau, T. T.; Gutierrez, C. G. *J. Org. Chem.* 1996, 61, 3548-3550.
57. Rodgers, S. J.; Lee, C.-W.; Ng, C. Y.; Raymond, K. N. *Inorg. Chem.* 1987, 26, 1622-1625.
58. Tor, Y.; Libman, J.; Shanzer, A.; Felder, C. E.; Lifson, S. *J. Am. Chem. Soc.* 1992, 114, 6661-6671.
59. Ecker, D. J.; Loomis, L. D.; Cass, M. E.; Raymond, K. N. *J. Am. Chem. Soc.* 1988, 110, 2457-2464.
60. Stack, T. D. P.; Hou, Z.; Raymond, K. N. *J. Am. Chem. Soc.* 1993, 115, 6466-6467.
61. Yu, X.; Dai, Y.; Yang, T.; Gagné, M. R.; Gong, H. *Tetrahedron* 2011, 67, 144-151.
62. Gardner, R. A.; Kinkade, R.; Wang, C.; Phanstiel IV, O. *J. Org. Chem.* 2004, 69, 3530-3537.
63. Arnusch, C. J.; Bonvin, A. M. J. J.; Verel, A. M.; Jansen, W. T. M.; Liskamp, R. M. J.; de Kruijff, B.; Pieters, R. J.; Breukink, E. *Biochemistry* 2008, 47, 12661-12663.
64. Luo, M.; Lin, H.; Fischbach, M. A.; Liu, D. R.; Walsh, C. T.; Groves, J. T. *ACS Chem. Biol.* 2006, 1, 29-32.
65. Thomas, X.; Destoumieux-Garzón, D.; Peduzzi, J.; Afonso, C.; Blond, A.; Birlirakis, N.; Goulard, C.; Dubost, L.; Thai, R.; Tabet, J.-C.; Rebuffat, S., *J. Biol. Chem.* 2004, 279, 28233-28242.
66. Abergel, R. J.; Zawadzka, A. M.; Hoette, T. M.; Raymond, K. N. *J. Am. Chem. Soc.* 2009, 131, 12682-12692.
67. Zheng, T.; Nolan, E. *J. Am. Chem. Soc.* 2014, 136, 9677-9691.
68. Hubbard, B. K.; Walsh, C. T. *Angew. Chem. Int. Ed.* 2003, 42, 730-765.

69. Lawson, M. C.; Shoemaker, R.; Hoth, K. B.; Bowman, C. N.; Anseth, K. S. *Biomacromolecules* 2009, 10, 2221-2234.
70. Scarrow, R. C.; Ecker, D. J.; Ng, C.; Liu, S.; Raymond, K. N. *Inorg. Chem.* 1991, 30, 900-906.
71. Wayne, R.; Frick, K.; Neilands, J. B. *J. Bacteriol.* 1976, 126, 7-12.
72. Mossialos, D.; Amoutzias, G. D. *Future Microbiol.* 2007, 2, 387-395.
73. Cornelis, P. *App. Microbiol. Biotechnol.* 2010, 86, 1637-1645.
74. Poole, K.; Young, L.; Neshat, S. *J. Bacteriol.* 1990, 172, 6991-6996.
75. Dean, C. R.; Neshat, S.; Poole, K. *J. Bacteriol.* 1996, 178, 5361-5369.
76. Ghysels, B.; Ochsner, U.; Möllman, U.; Heinisch, L.; Vasil, M.; Cornelis, P.; Matthijs, S. *FEMS Microbiol. Lett.* 2005, 246 (2), 167-174.
77. Collin, F.; Karkare, S.; Maxwell, A. *App. Microbiol. Biotechnol.* 2011, 92, 479-497.
78. Hennard, C.; Truong, Q. C.; Desnottes, J.-F.; Paris, J. M.; Moreau, N. J.; Abdallah, M. A. *J. Med. Chem.* 2001, 44, 2139-2151.
79. Rivault, F.; Liebert, C.; Burger, A.; Hoegy, F.; Abdallah, M. A.; Schalk, I. J.; Mislin, G. L. A. *Bioorg. Med. Chem. Lett.* 2007, 17, 640-644.
80. Nöel, S.; Gasser, V.; Pesset, B.; Hoegy, F.; Rognan, D.; Schalk, I. J.; Mislin, G. L. A. *Org. Biomol. Chem.* 2011, 9 (24), 8288-8300.
81. Ji, C.; Miller, M. J. *Bioorg. Med. Chem.* 2012, 20, 3828-3836.
82. Miller, M. J.; Walz, A. J.; Zhu, H.; Wu, C.; Moraski, G.; Möllmann, U.; Tristani, E. M.; Crumbliss, A. L.; Ferdig, M. T.; Checkley, L.; Edwards, R. L.; Boshoff, H. I. *J. Am. Chem. Soc.* 2011, 133, 2076-2079.
83. Xu, Y.; Miller, M. J. *J. Org. Chem.* 1998, 63, 4314-4322.
84. Pons, A.-M.; Zorn, N.; Vignon, D.; Delalande, F.; Dorsselaer, A. V.; Cottenceau, G. *Antimicrob. Agents Chemother.* 2002, 46, 229-230.
85. Baba, T.; Ara, T.; Hasegawa, M.; Takai, Y.; Okumura, Y.; Baba, M.; Datsenko, K. A.; Tomita, M.; Wanner, B. L.; Mori, H., *Mol. Sys. Biol.* 2006, 2006.0008.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

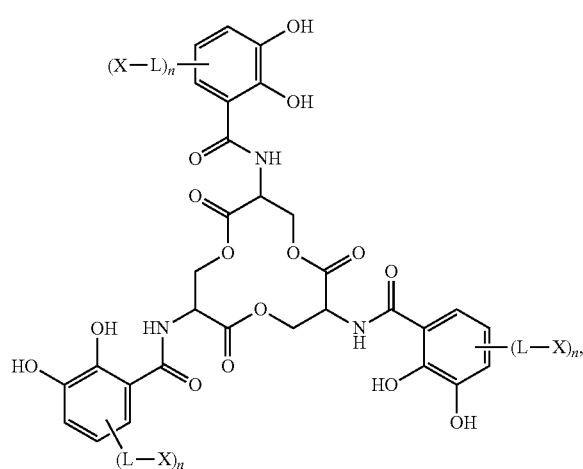

or a salt thereof, wherein:
    each instance of L is independently a bond or a divalent linker;
    one instance of X is:
        an antibiotic selected from the group consisting of β-lactam antibiotics, aminoglycoside antibiotics, ansamycin antibiotics, glycopeptide antibiotics, lincosamide antibiotics, lipopeptide antibiotics, macrolide antibiotics, nitrofuran antibiotics, oxazolidonone antibiotics, quinolone antibiotics, sulfonamide antibiotics, and tetracycline antibiotics; or
        a fluorophore selected from the group consisting of coumarin 343, coumarin 1, coumarin 6, coumarin 30, coumarin 153, coumarin 314, coumarin 334, coumarin 545t, 6,8-difluoro-7-hydroxy-4-methylcoumarin, 7-amino-4-methyl-6-sulfocoumarin-3-acetic acid, 7-methoxycoumarin-4-acetic acid, 7-hydroxy-4-methylcoumarin, rhodamine, Oregon green, eosin, Texas red, dansyl, cyanine, indocarbocyanine, oxacarbocyanine, thiacarbocyanine, merocyanine, pyridyloxazole, nitrobenzoxadiazole, benzoxadiazole, cascade blue, Nile red, Nile blue, cresyl violet, oxazine 170, proflavin, acridine orange, acridine yellow, auramine, crystal violet, malachite green, porphin, phthalocyanine, and bilirubin;
    all other instances of X are independently hydrogen, an antibiotic, a fluorophore, or a biotin moiety of the formula:

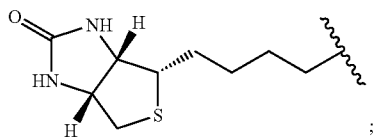 [SMILES: *CCCC[C@@H]1SC[C@@H]2NC(=O)N[C@@H]21]

one instance of n is 1, 2, or 3; and
the other two instances of n are independently 0, 1, 2, or 3;

provided that the molecular weight of each instance of X is less than 1,000 Da.

2. The compound of claim 1, wherein the compound is of the formula:

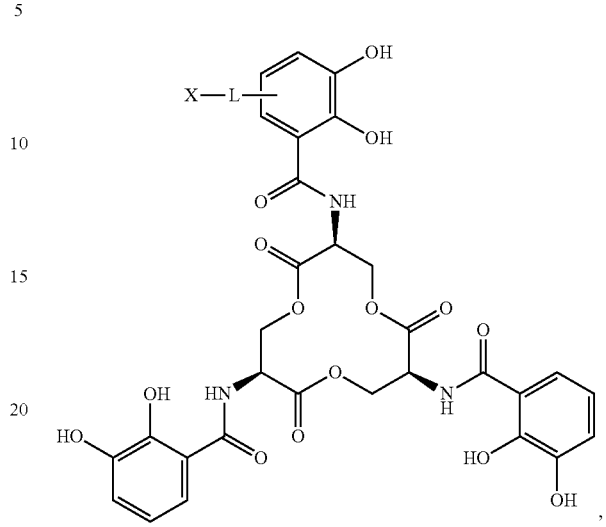

or a salt thereof.

3. The compound of claim 1, wherein the compound is of the formula:

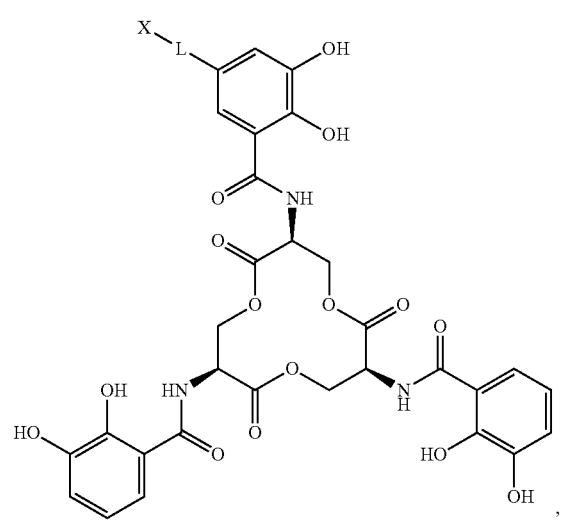

or a salt thereof.

4. The compound of claim 1, or a salt thereof, wherein at least one instance of L is hydrolytically stable under physiological conditions.

5. The compound of claim 1, or a salt thereof, wherein at least one instance of L is hydrolytically unstable under physiological conditions.

6. The compound of claim 1, or a salt thereof, wherein:
    each instance of L is independently a bond or a substituted or unsubstituted $C_{1-100}$ hydrocarbon chain, optionally wherein one or more carbon units of the hydrocarbon chain are independently replaced with —O—, —S—, —NR$^L$—, —S(=O)—, —S(=O)$_2$—, or substituted or unsubstituted heteroarylene; and
    each instance of $R^L$ is independently hydrogen, substituted or unsubstituted $C_{1-6}$ alkyl, or a nitrogen protecting group.

7. The compound of claim 6, or a salt thereof, wherein one carbon unit of at least one instance of L is replaced with unsubstituted heteroarylene of the formula:

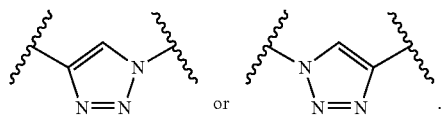 [SMILES: *c1cn(*)nn1 ; *c1cn(*)nn1]

8. A method of preparing a compound of claim 7, or a salt thereof, the method comprising:
contacting a compound of Formula (A1):

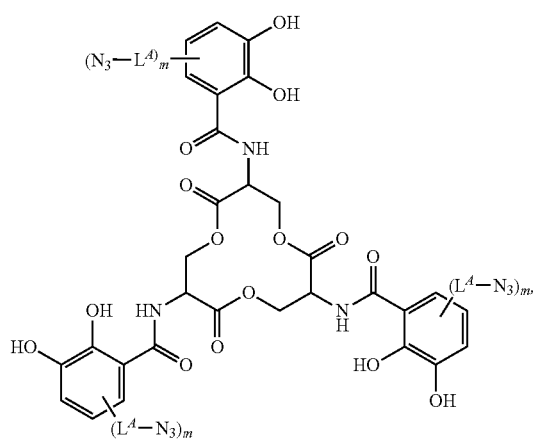

or a salt thereof, with a compound of Formula (B1):

$$X-L^B-C \equiv CH \quad (B1),$$

or a salt thereof, or contacting a compound of Formula (A2):

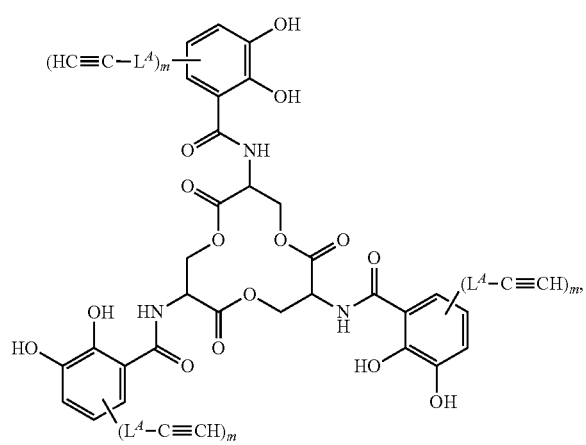

or a salt thereof, with a compound of Formula (B2):

$$X-L^B-N_3 \quad (B2),$$

or a salt thereof;
wherein:
each instance of $L^A$ is independently a bond or substituted or unsubstituted $C_{1-17}$ hydrocarbon chain, optionally wherein one or more carbon units of the hydrocarbon chain are independently replaced with —O—, —S—, —NR$^{LA}$—, —S(=O)—, or —S(=O)$_2$—;

each instance of $R^{LA}$ is independently hydrogen, unsubstituted $C_{1-6}$ alkyl, $C_{1-6}$ alkyl substituted with at least one halogen, or a nitrogen protecting group;

one instance of m is 1, 2, or 3;

two instances of m are independently 0, 1, 2, or 3;

each instance of $L^B$ is independently a bond or substituted or unsubstituted $C_{1-17}$ hydrocarbon chain, optionally wherein one or more carbon units of the hydrocarbon chain are independently replaced with —O—, —S—, —NR$^{LB}$—, —S(=O)—, or —S(=O)$_2$—; and each instance of $R^{LB}$ is independently hydrogen, unsubstituted $C_{1-6}$ alkyl, $C_{1-6}$ alkyl substituted with at least one halogen, or a nitrogen protecting group.

9. The compound of claim 6, or a salt thereof, wherein one carbon unit of each instance of L is replaced with unsubstituted heteroarylene of the formula:

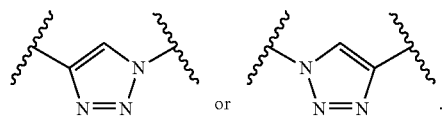

10. The compound of claim 6, or a salt thereof, wherein at least one instance of L is of the formula:

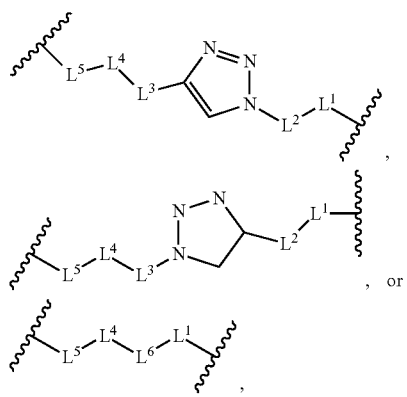

wherein:
$L^1$ and $L^4$ are independently —NR$^L$C(=O)— or —C(=O)NR$^L$—;

$L^2$ and $L^3$ are independently unsubstituted $C_{1-50}$ alkylene or $C_{1-50}$ alkylene substituted with at least one halogen, optionally wherein one to six carbon units of the $C_{1-50}$ alkylene are replaced with —O—;

$L^5$ is a bond, unsubstituted $C_{1-6}$ alkylene, or $C_{1-6}$ alkylene substituted with at least one halogen, optionally wherein one or two carbon units of the $C_{1-6}$ alkylene are replaced with —O—; and $L^6$ is unsubstituted $C_{2-90}$ alkylene, or $C_{2-90}$ alkylene substituted with at least one halogen, optionally wherein one to eight carbon units of the $C_{2-90}$ alkylene are replaced with —O—.

11. The compound of claim 10, wherein the compound is of the formula:

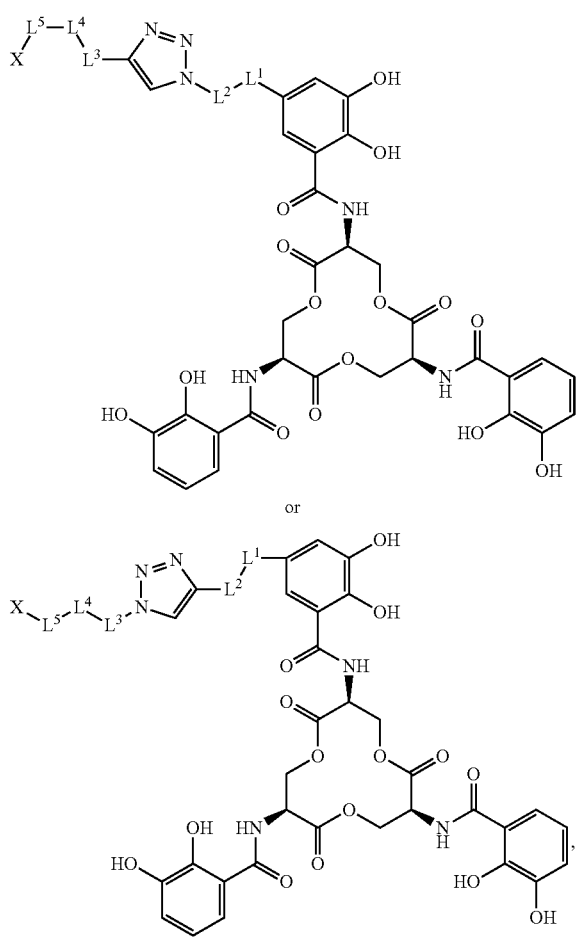

or a salt thereof.

12. The compound of claim 10, wherein the compound is of the formula:

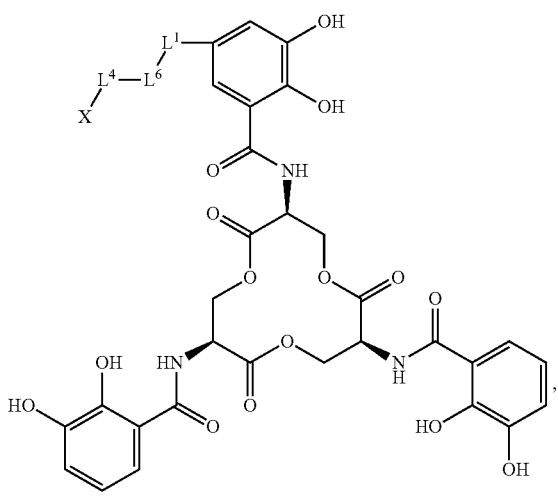

or a salt thereof.

13. The compound of claim 1, or a salt thereof, wherein the molecular weight of at least one instance of X is less than 300 Da.

14. The compound of claim 1, or a salt thereof, wherein the molecular weight of at least one instance of X is less than 600 Da.

15. The compound of claim 1, or a salt thereof, wherein at least one instance of X is an antibiotic selected from the group consisting of β-lactam antibiotics, aminoglycoside antibiotics, ansamycin antibiotics, glycopeptide antibiotics, lincosamide antibiotics, lipopeptide antibiotics, macrolide antibiotics, nitrofuran antibiotics, oxazolidonone antibiotics, quinolone antibiotics, sulfonamide antibiotics, and tetracycline antibiotics.

16. The compound of claim 15, or a salt thereof, wherein the antibiotic is effective against a Gram-negative bacterium.

17. The compound of claim 16, or a salt thereof, wherein the Gram-negative bacterium is an *Escherichia* species, a *Pseudomonas* species, a *Klebsiella* species, a *Salmonella* species, or an *Acinetobacter* species.

18. The compound of claim 17, or a salt thereof, wherein the Gram-negative bacterium is an *Escherichia coli* strain or a *Pseudomonas aeruginosa* strain.

19. The compound of claim 15, or a salt thereof, wherein the antibiotic is a β-lactam antibiotic.

20. A pharmaceutical composition comprising a compound of claim 15, or a pharmaceutically acceptable salt thereof, and optionally a pharmaceutically acceptable excipient.

21. The pharmaceutical composition of claim 20 further comprising an iron chelator.

22. The pharmaceutical composition of claim 20 further comprising Fe(III).

23. A method of treating a bacterial infection in a subject in need thereof, the method comprising administering to the subject a therapeutically effective amount of a compound of claim 15, or a pharmaceutical acceptable salt thereof.

24. The method of claim 23, wherein the bacterial infection is caused by a Gram-negative bacterium.

25. The method of claim 23, wherein the subject is a mammal.

26. The method of claim 23, wherein the subject is a human.

27. The compound of claim 1, or a salt thereof, wherein at least one instance of X is a fluorophore selected from the group consisting of coumarin 343, coumarin 1, coumarin 6, coumarin 30, coumarin 153, coumarin 314, coumarin 334, coumarin 545t, 6,8-difluoro-7-hydroxy-4-methylcoumarin, 7-amino-4-methyl-6-sulfocoumarin-3-acetic acid, 7-methoxycoumarin-4-acetic acid, 7-hydroxy-4-methylcoumarin, rhodamine, Oregon green, eosin, Texas red, dansyl, cyanine, indocarbocyanine, oxacarbocyanine, thiacarbocyanine, merocyanine, pyridyloxazole, nitrobenzoxadiazole, benzoxadiazole, cascade blue, Nile red, Nile blue, cresyl violet, oxazine 170, proflavin, acridine orange, acridine yellow, auramine, crystal violet, malachite green, porphin, phthalocyanine, and bilirubin.

28. A complex comprising a compound of claim 27, or a salt thereof, and Fe(III).

29. A composition comprising a compound of claim 27, or a salt thereof, and optionally an excipient.

30. The composition of claim 29 further comprising an iron chelator.

31. The composition of claim 29 further comprising Fe(III).

32. The compound of claim 1, or a salt thereof, wherein at least one instance of X is of the formula:

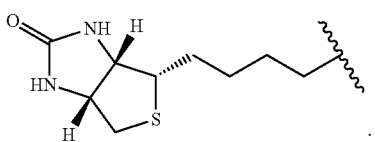

33. A complex comprising a compound of claim 1, or a salt thereof, and Fe(III).

34. A method of delivering an antibiotic or a fluorophore, and optionally a biotin moiety of the formula:

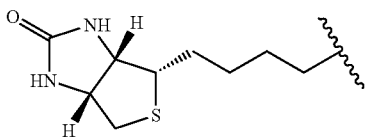 [SMILES: *CCCC[C@@H]1SC[C@@H]2NC(=O)N[C@@H]21]

to a bacterium, the method comprising contacting the bacterium with a compound of claim 1, or a salt thereof.

35. The method of claim 34, wherein the bacterium is a Gram-negative bacterium.

36. A kit comprising:
a compound of claim 1, or a salt thereof; and
instructions for using the compound or the salt.

37. The compound of claim 1, wherein the compound is of the formula:

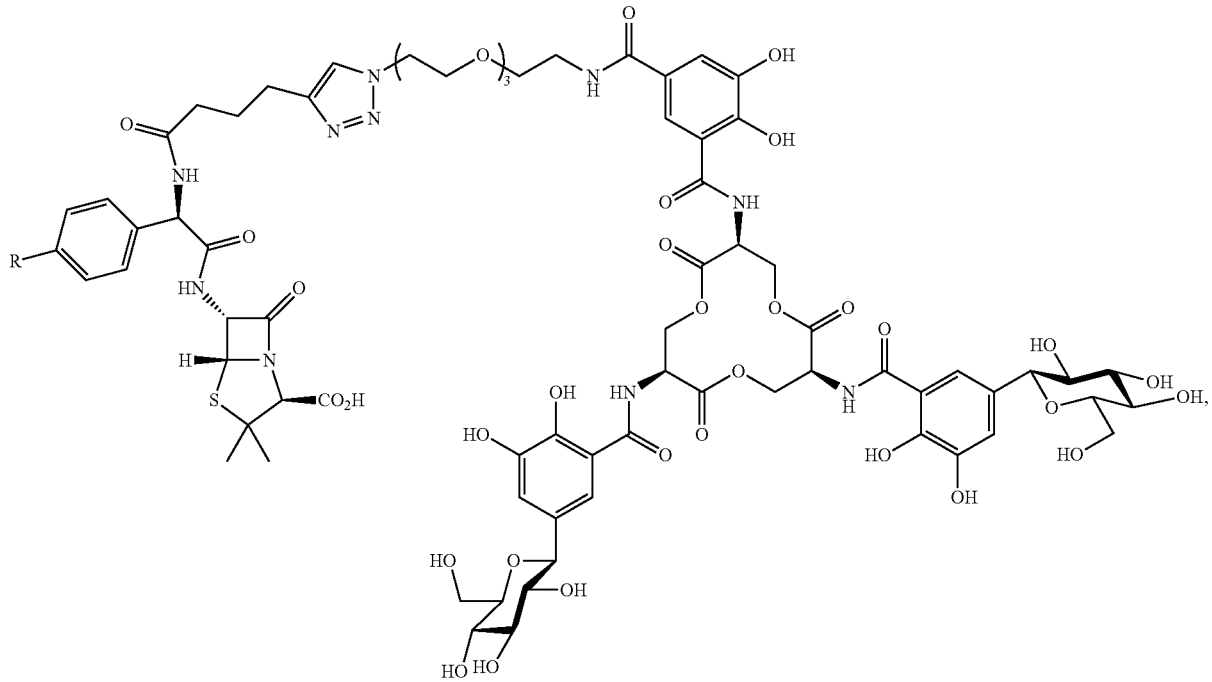

or a salt thereof, wherein R is hydrogen or —OH.

38. The compound of claim 1, or a salt thereof, wherein at least one instance of X is a penicillin.

39. The compound of claim 1, or a salt thereof, wherein each instance of the antibiotic is independently selected from the group consisting of β-lactam antibiotics, amino- glycoside antibiotics, ansamycin antibiotics, glycopeptide antibiotics, lincosamide antibiotics, lipopeptide antibiotics, macrolide antibiotics, nitrofuran antibiotics, oxazolidonone antibiotics, quinolone antibiotics, sulfonamide antibiotics, and tetracycline antibiotics.

40. The compound of claim 1, or a salt thereof, wherein at least one instance of X is amoxicillin or ampicillin.

41. The compound of claim 1, or a salt thereof, wherein each instance of the fluorophore is independently selected from the group consisting of coumarin 343, coumarin 1, coumarin 6, coumarin 30, coumarin 153, coumarin 314, coumarin 334, coumarin 545t, 6,8-difluoro-7-hydroxy-4-methylcoumarin, 7-amino-4-methyl-6-sulfocoumarin-3-acetic acid, 7-methoxycoumarin-4-acetic acid, 7-hydroxy-4-methylcoumarin, rhodamine, Oregon green, eosin, Texas red, dansyl, cyanine, indocarbocyanine, oxacarbocyanine, thiacarbocyanine, merocyanine, pyridyloxazole, nitrobenzoxadiazole, benzoxadiazole, cascade blue, Nile red, Nile blue, cresyl violet, oxazine 170, proflavin, acridine orange, acridine yellow, auramine, crystal violet, malachite green, porphin, phthalocyanine, and bilirubin.

42. The compound of claim 1, or a salt thereof, wherein at least one instance of X is hydrogen.

43. The compound of claim 1, or a salt therof, wherein the molecular weight of at least one instance of L is less than 200 Da.

44. The compound of claim 1, or a salt thereof, wherein all instances of n are 1.

45. The compound of claim 1, or a salt thereof, wherein one instance of n is 0; and the other two instances of n are 1.

* * * * *

UNITED STATES PATENT AND TRADEMARK OFFICE
CERTIFICATE OF CORRECTION

PATENT NO. : 9,902,986 B2
APPLICATION NO. : 14/516440
DATED : February 27, 2018
INVENTOR(S) : Elizabeth Marie Nolan et al.

Page 1 of 1

It is certified that error appears in the above-identified patent and that said Letters Patent is hereby corrected as shown below:

In the Claims

In Claim 10, at Column 138, Lines 39-43, the formula:

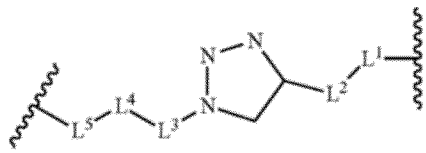

Should be replaced with the formula:

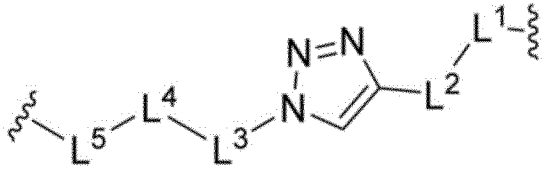

Signed and Sealed this
Ninth Day of July, 2019

Andrei Iancu
*Director of the United States Patent and Trademark Office*

SEQUENCE LISTING

```
<160> NUMBER OF SEQ ID NOS: 11

<210> SEQ ID NO 1
<211> LENGTH: 7
<212> TYPE: PRT
<213> ORGANISM: Artificial Sequence
<220> FEATURE:
<223> OTHER INFORMATION: Synthetic Polypeptide
```

```
<400> SEQUENCE: 1

Ser Ser Ser Gly Ser Gly Ser
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 2

Ser Ala Thr Ser Ser Ser Gly Ser Gly Ser
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 3

Gly Tyr Asn Ser Ala Thr Ser Ser Ser Gly Ser Gly Ser
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 4

Ser Ser Gly Tyr Asn Ser Ala Thr Ser Ser Ser Gly Ser Gly Ser
1               5                   10                  15

<210> SEQ ID NO 5
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 5

Ser Ala Thr Ser Ser Ser Gly Ser Gly Gly
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 6

Ser Ala Thr Ser Ser Ser Gly Ser Gly Ala
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Polypeptide
```

```
<400> SEQUENCE: 7

Ser Ala Thr Ser Ser Ser Gly Ser Gly Thr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 8

Ser Ala Ser Ser Ser Ala Gly Gly Gly Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 9

Ser Ser Thr Ser Ser Ala Val Ser Gly Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 10

Ser Ala Ser Ser Ser Ala Gly Ser Gly Ser
1               5                   10

<210> SEQ ID NO 11
<211> LENGTH: 84
<212> TYPE: PRT
<213> ORGANISM: Artificial Sequence
<220> FEATURE:
<223> OTHER INFORMATION: Synthetic Polypeptide

<400> SEQUENCE: 11

Gly Glu Thr Asp Pro Asn Thr Gln Leu Leu Asn Asp Leu Gly Asn Asn
1               5                   10                  15

Met Ala Trp Gly Ala Ala Leu Gly Ala Pro Gly Gly Leu Gly Ser Ala
                20                  25                  30

Ala Leu Gly Ala Ala Gly Gly Ala Leu Gln Thr Val Gly Gln Gly Leu
            35                  40                  45

Ile Asp His Gly Pro Val Asn Val Pro Ile Pro Val Leu Ile Gly Pro
        50                  55                  60

Ser Trp Asn Gly Ser Ser Ser Gly Tyr Asn Ser Ala Thr Ser Ser Ser
65                  70                  75                  80

Gly Ser Gly Ser
```